United States Patent
Yang et al.

(10) Patent No.: US 11,225,659 B2
(45) Date of Patent: Jan. 18, 2022

(54) TYPE VI-E AND TYPE VI-F CRISPR-CAS SYSTEM AND USES THEREOF

(71) Applicant: HuiGene Therapeutics Co., Ltd., Shanghai (CN)

(72) Inventors: Hui Yang, Shanghai (CN); Chunlong Xu, Shanghai (CN); Yingsi Zhou, Shanghai (CN); Qingquan Xiao, Shanghai (CN)

(73) Assignee: HuiGene Therapeutics Co., Ltd., Shanghai (CN)

( * ) Notice: Subject to any disclaimer, the term of this patent is extended or adjusted under 35 U.S.C. 154(b) by 60 days.

(21) Appl. No.: 16/864,982

(22) Filed: May 1, 2020

(65) Prior Publication Data
US 2021/0269795 A1    Sep. 2, 2021

Related U.S. Application Data

(63) Continuation of application No. PCT/CN2020/077211, filed on Feb. 28, 2020.

(51) Int. Cl.
| | | |
|---|---|---|
| *C12N 15/00* | (2006.01) | |
| *C12N 15/11* | (2006.01) | |
| *C12N 9/22* | (2006.01) | |
| *C12N 15/90* | (2006.01) | |

(52) U.S. Cl.
CPC ............... *C12N 15/11* (2013.01); *C12N 9/22* (2013.01); *C12N 15/907* (2013.01); *C12N 2310/20* (2017.05); *C12N 2800/80* (2013.01)

(58) Field of Classification Search
CPC ........ C12N 15/11; C12N 9/22; C12N 15/907; C12N 2310/20; C12N 2800/80
See application file for complete search history.

(56) References Cited

U.S. PATENT DOCUMENTS

| 10,266,886 B2 | 4/2019 | Abudayyeh | |
| 2020/0131488 A1* | 4/2020 | Cox | C12N 15/86 |

FOREIGN PATENT DOCUMENTS

| WO | 2020028555 A2 | 2/2020 | |
| WO | WO-2020028555 A2 * | 2/2020 | ............... C12N 9/22 |

OTHER PUBLICATIONS

Score result SEQ ID No. 3 for NA for WO-2020028555-A2 to Zhang et al. (aka Abudayyeh) (Year: 2020).*
Score result SEQ ID No. 3 for AA for WO-2020028555-A2 to Zhang et al. (aka Abudayyeh) (Year: 2020).*
"Novel miniature CRISPR-Cas13 systems from uncultivated microbes effective in degrading SARS-CoV-2 sequences and influenza viruses" (Research Square) published on May 21, 2020. (Year: 2020).*

* cited by examiner

*Primary Examiner* — Catherine S Hibbert
(74) *Attorney, Agent, or Firm* — McCarter & English, LLP; Yu Lu

(57) ABSTRACT

The invention provides novel CRISPR/Cas compositions and uses thereof for targeting nucleic acids. In particular, the invention provides non-naturally occurring or engineered RNA-targeting systems comprising a novel RNA-targeting Cas13e or Cas13f effector protein, and at least one targeting nucleic acid component such as a guide RNA (gRNA) or crRNA. The novel Cas effector proteins are among the smallest of the known Cas effector proteins, at about 800 amino acids in size, and are thus uniquely suitable for delivery using vectors of small capacity, such as an AAV vector.

30 Claims, 9 Drawing Sheets

Specification includes a Sequence Listing.

TYPE VI-E AND TYPE VI-F CRISPR-CAS SYSTEM AND USES THEREOF

CROSS-REFERENCE TO RELATED APPLICATIONS

This application is a continuation of International Patent Application No. PCT/CN2020/077211 filed Feb. 28, 2020, the disclosure of which is incorporated herein by reference in its entirety and for all purposes.

REFERENCE TO A SEQUENCE LISTING SUBMITTED VIA EFS-WEB

The content of the ASCII text file of the sequence listing named "132045-00101_SL.txt" which is 166,439 bytes in size was created on Sep. 20, 2021 and electronically submitted via EFS-Web herewith the application is incorporated herein by reference in its entirety.

BACKGROUND OF THE INVENTION

CRISPR (clustered regularly interspaced short palindromic repeats) is a family of DNA sequences found within the genomes of prokaryotic organisms such as bacteria and archaea. These sequences are understood to be derived from DNA fragments of bacteriophages that have previously infected the prokaryote, and are used to detect and destroy DNA from similar bacterialphages during subsequent infections of the prokaryotes.

CRISPR-associated systems is a set of homologous genes, or Cas genes, some of which encode Cas protein having helicase and nuclease activities. The Cas proteins are enzymes that utilize RNA derived form the CRISPR sequences (crRNA) as guide sequences to recognize and cleave specific strands of polynucleotide (e.g., DNA) that are complementary to the crRNA.

Together, the CRISPR-Cas system constitutes a primitive prokaryotic "immune system" that confers resistance or acquired immunity to foreign pathogenic genetic elements, such as those present within extrachromosomal DNA (e.g., plasmids) and bacterialphages, or foreign RNA encoded by foreign DNA.

In nature, the CRISPR/Cas system appears to be a widespread prokaryotic defense mechanism against foreign genetic materials, and is found in approximately 50% of sequenced bacterial genomes and nearly 90% of sequenced archaea. This prokaryotic system has since been developed to form the basis of a technology known as CRISPR-Cas that found extensive use in numerous eukaryotic organisms including human, in a wide variety of applications including basic biological research, development of biotechnology products, and disease treatment.

The prokaryotic CRISPR-Cas systems comprise an extremely diverse group of proteins effectors, non-coding elements, as well as loci architectures, some examples of which have been engineered and adapted to produce important biotechnologies.

The CRISPR locus structure has been studied in many systems. In these systems, the CRISPR array in the genomic DNA typically comprises an AT-rich leader sequence, followed by short DR sequences separated by unique spacer sequences. These CRISPR DR sequences typically range in size from 28 to 37 bps, though the range can be 23-55 bps. Some DR sequences show dyad symmetry, implying the formation of a secondary structure such as a stem-loop ("hairpin") in the RNA, while others appear unstructured. The size of spacers in different CRISPR arrays is typically 32-38 bps (with a range of 21-72 bps). There are usually fewer than 50 units of the repeat-spacer sequence in a CRISPR array.

Small clusters of cas genes are often found next to such CRISPR repeat-spacer arrays. So far, the 93 identified cas genes have been grouped into 35 families, based on sequence similarity of their encoded proteins. Eleven of the 35 families form the so-called cas core, which includes the protein families Cas1 through Cas9. A complete CRISPR-Cas locus has at least one gene belonging to the cas core.

CRISPR-Cas systems can be broadly divided into two classes—Class 1 systems use a complex of multiple Cas proteins to degrade foreign nucleic acids, while Class 2 systems use a single large Cas protein for the same purpose. The single-subunit effector compositions of the Class 2 systems provide a simpler component set for engineering and application translation, and has thus far been important sources of discovery, engineering, and optimization of novel powerful programmable technologies for genome engineering and beyond.

Class 1 system is further divided into types I, III, and IV; and Class 2 system is divided into types II, V, and VI. These 6 system types are additionally divided into 19 subtypes. Classification is also based on the complement of cas genes that are present. Most CRISPR-Cas systems have a Cas1 protein. Many prokaryotes contain multiple CRISPR-Cas systems, suggesting that they are compatible and may share components.

One of the first and best characterized Cas proteins—Cas9—is a prototypical member of Class 2, type II, and originates from *Streptococcus pyogenes* (SpCas9). Cas9 is a DNA endonuclease activated by a small crRNA molecule that complements a target DNA sequence, and a separate trans-activating CRISPR RNA (tracrRNA). The crRNA consists of a direct repeat (DR) sequence responsible for protein binding to the crRNA and a spacer sequence, which may be engineered to be complementary to any desired nucleic acid target sequence. In this way, CRISPR systems can be programmed to target DNA or RNA targets by modifying the spacer sequence of the crRNA. The crRNA and tracrRNA have been fused to form a single guide RNA (sgRNA) for better practical utility. When combined with Cas9, sgRNA hybridizes with its target DNA, and guides Cas9 to cut the target DNA. Other Cas9 effector protein from other species have also been identified and used similarly, including Cas9 from the *S. thermophilus* CRISPR system. These CRISPR/Cas9 systems have been widely used in numerous eukaryotic organisms, including baker's yeast (*Saccharomyces cerevisiae*), the opportunistic pathogen *Candida albicans*, zebrafish (*Danio rerio*), fruit flies (*Drosophila melanogaster*), ants (*Harpegnathos saltator* and *Ooceraea biroi*), mosquitoes (*Aedes aegypti*), nematodes (*Caenorhabditis elegans*), plants, mice, monkeys, and human embryos.

Another recently characterized Cas effector protein is Cas12a (formerly known as Cpf1). Cas12a, together with C2c1 and C2c3, are members belonging to Class 2, type V Cas proteins that lack HNH nuclease, but have RuvC nuclease activity. Cas12a which was initially characterized in the CRISPR/Cpf1 system of the bacterium *Francisella novicida*. Its original name reflects the prevalence of its CRISPR-Cas subtype in the *Prevotella* and *Francisella* lineages. Cas12a showed several key differences from Cas9, including: causing a "staggered" cut in double stranded DNA as opposed to the "blunt" cut produced by Cas9, relying on a "T rich" PAM sequence (which provides alternative targeting sites to Cas9) and requiring only a CRISPR RNA (crRNA) and no tracrRNA for successful targeting. Cas12a's small crRNAs are better suited than Cas9 for multiplexed genome editing, as more of them can be packaged in one vector than can Cas9's sgRNAs. Further, the sticky 5' overhangs left by Cas12a can be used for DNA assembly that is much more target-specific than traditional Restriction Enzyme cloning. Finally, Cas12a cleaves DNA 18-23 base pairs downstream from its PAM site, which means no disruption to the nuclease recognition sequence after DNA repair following the creation of double stranded break (DSB) by the NHEJ system, thus Cas12a enables multiple rounds of DNA cleavage, as opposed to the likely one round after Cas9 cleavage because the Cas9 cleavage sequence is only 3 base pairs upstream of the PAM site, and the NHEJ pathway typically results in indel mutations which destroy the recognition sequence, thereby preventing further rounds of cutting. In theory, repeated rounds of DNA cleavage is associated with an increased chance for the desired genomic editing to occur.

More recently, several Class 2, type VI Cas proteins, including Cas13 (also known as C2c2), Cas13b, Cas13c, and Cas13d have been identified, each is an RNA-guided RNase (i.e., these Cas proteins use their crRNA to recognize target RNA sequences, rather than target DNA sequences in Cas9 and Cas12a). Overall, the CRISPR/Cas13 systems can achieve higher RNA digestion efficiency compared to the traditional RNAi and CRISPRi technologies, while simultaneously exhibiting much less off-target cleavage compared to RNAi.

One drawback from these currently identified Cas13 proteins is their relatively large size. Each of Cas13a, Cas13b, and Cas13c has more than 1100 amino acid residues. Thus it is difficult, if possible at all, to package their coding sequence (about 3.3 kb) and sgRNA, plus any required promoter sequences and translation regulatory sequences, into certain small capacity gene therapy vectors, such as the current most efficient and safest gene therapy vector based on adeno associated virus (AAV), which has a package capacity of about 4.7 kb. Although Cas13d, the smallest Cas13 protein so far, only has about 920 amino acids (i.e., about 2.8 kb coding sequence), and can in theory be packaged into the AAV vector, it has limited use for single-base editing-based gene therapy that depends on using Cas13d-based fusion proteins with single-base editing functions, such as dCas13d-ADAR2DD (which has a coding sequence of about 3.9 kb).

Furthermore, the currently known Cas13 proteins/systems all have non-specific/collateral RNase activity upon activation by crRNA-based target sequence recognition. This activity is particularly strong in Cas13a and Cas13b, and still detectably exists in Cas13d. While this property can be advantageously used in nucleic acid detection methods, the non-specific/collateral RNase activity of these Cas13 proteins constitutes a tremendous potential danger for gene therapy use.

SUMMARY OF THE INVENTION

One aspect of the invention provides a Clustered Regularly Interspaced Short Palindromic Repeat (CRISPR)-Cas complex, comprising. (1) an RNA guide sequence comprising a spacer sequence capable of hybridizing to a target RNA, and a direct repeat (DR) sequence 3' to the spacer sequence; and, (2) a CRISPR-associated protein (Cas) having an amino acid sequence of any one of SEQ ID NOs: 1-7, or a derivative or functional fragment of said Cas; wherein the Cas, the derivative, and the functional fragment of said Cas, are capable of (i) binding to the RNA guide sequence and (ii) targeting the target RNA, with the proviso that the spacer sequence is not 100% complementary to a naturally-occurring bacterialphage nucleic acid when the complex comprises the Cas of any one of SEQ ID NOs: 1-7 or wherein the target RNA is encoded by a eukaryotic DNA.

In certain embodiments, the DR sequence has substantially the same secondary structure as the secondary structure of any one of SEQ ID NOs: 8-14.

In certain embodiments, the DR sequence is encoded by any one of SEQ ID NOs: 8-14.

In certain embodiments, the target RNA is encoded by a eukaryotic DNA.

In certain embodiments, the eukaryotic DNA is a non-human mammalian DNA, a non-human primate DNA, a human DNA, a plant DNA, an insect DNA, a bird DNA, a reptile DNA, a rodent DNA, a fish DNA, a worm/nematode DNA, a yeast DNA.

In certain embodiments, the target RNA is an mRNA.

In certain embodiments, the spacer sequence is between 15-55 nucleotides, between 25-35 nucleotides, or about 30 nucleotides.

In certain embodiments, the spacer sequence is 90-100% complementary to the target RNA.

In certain embodiments, the derivative comprises conserved amino acid substitutions of one or more residues of any one of SEQ ID NOs: 1-7.

In certain embodiments, the derivative comprises only conserved amino acid substitutions.

In certain embodiments, the derivative has identical sequence to wild-type Cas of any one of SEQ ID NOs: 1-7 in the HEPN domain or the RXXXXH motif.

In certain embodiments, the derivative is capable of binding to the RNA guide sequence hybridized to the target RNA, but has no RNase catalytic activity due to a mutation in the RNase catalytic site of the Cas.

In certain embodiments, the derivative has an N-terminal deletion of no more than 210 residues, and/or a C-terminal deletion of no more than 180 residues.

In certain embodiments, the derivative has an N-terminal deletion of about 180 residues, and/or a C-terminal deletion of about 150 residues.

In certain embodiments, the derivative further comprises an RNA base-editing domain.

In certain embodiments, the RNA base-editing domain is an adenosine deaminase, such as a double-stranded RNA-specific adenosine deaminase (e.g., ADAR1 or ADAR2); apolipoprotein B mRNA editing enzyme; catalytic polypeptide-like (APOBEC); or activation-induced cytidine deaminase (AID).

In certain embodiments, the ADAR has E488Q/T375G double mutation or is ADAR2DD.

In certain embodiments, the base-editing domain is further fused to an RNA-binding domain, such as MS2.

In certain embodiments, the derivative further comprises an RNA methyltransferase, a RNA demethylase, an RNA splicing modifier, a localization factor, or a translation modification factor.

In certain embodiments, the Cas, the derivative, or the functional fragment comprises a nuclear localization signal (NLS) sequence or a nuclear export signal (NES).

In certain embodiments, targeting of the target RNA results in a modification of the target RNA.

In certain embodiments, the modification of the target RNA is a cleavage of the target RNA.

In certain embodiments, the modification of the target RNA is deamination of an adenosine (A) to an inosine (I).

In certain embodiments, the CRISPR-Cas complex of the invention further comprises a target RNA comprising a sequence capable of hybridizing to the spacer sequence.

Another aspect of the invention provides a fusion protein, comprising (1) the Cas, the derivative thereof, or the functional fragment thereof, of the invention, and (2) a heterologous functional domain.

In certain embodiments, the heterologous functional domain comprises: a nuclear localization signal (NLS), a reporter protein or a detection label (e.g., GST, HRP, CAT, GFP, HcRed, DsRed, CFP, YFP, BFP), a localization signal, a protein targeting moiety, a DNA binding domain (e.g., MBP, Lex A DBD, Gal4 DBD), an epitope tag (e.g., His, myc, V5, FLAG, HA, VSV-G, Trx, etc), a transcription activation domain (e.g., VP64 or VPR), a transcription inhibition domain (e.g., KRAB moiety or SID moiety), a nuclease (e.g., FokI), a deamination domain (e.g., ADAR1, ADAR2, APOBEC, AID, or TAD), a methylase, a demethylase, a transcription release factor, an HDAC, a polypeptide having ssRNA cleavage activity, a polypeptide having dsRNA cleavage activity, a polypeptide having ssDNA cleavage activity, a polypeptide having dsDNA cleavage activity, a DNA or RNA ligase, or any combination thereof.

In certain embodiments, the heterologous functional domain is fused N-terminally, C-terminally, or internally in the fusion protein.

Another aspect of the invention provides a conjugate, comprising (1) the Cas, the derivative thereof, or the functional fragment thereof, of the invention, conjugated to (2) a heterologous functional moiety.

In certain embodiments, the heterologous functional moiety comprises: a nuclear localization signal (NLS), a reporter protein or a detection label (e.g., GST, HRP, CAT, GFP, HcRed, DsRed, CFP, YFP, BFP), a localization signal, a protein targeting moiety, a DNA binding domain (e.g., MBP, Lex A DBD, Gal4 DBD), an epitope tag (e.g., His, myc, V5, FLAG, HA, VSV-G, Trx, etc), a transcription activation domain (e.g., VP64 or VPR), a transcription inhibition domain (e.g., KRAB moiety or SID moiety), a nuclease (e.g., FokI), a deamination domain (e.g., ADAR1, ADAR2, APOBEC, AID, or TAD), a methylase, a demethylase, a transcription release factor, an HDAC, a polypeptide having ssRNA cleavage activity, a polypeptide having dsRNA cleavage activity, a polypeptide having ssDNA cleavage activity, a polypeptide having dsDNA cleavage activity, a DNA or RNA ligase, or any combination thereof.

In certain embodiments, the heterologous functional moiety is conjugated N-terminally, C-terminally, or internally with respect to the Cas, the derivative thereof, or the functional fragment thereof.

Another aspect of the invention provides a polynucleotide encoding any one of SEQ ID NOs: 1-7, or a derivative thereof, or a functional fragment thereof, or a fusion protein thereof, provided that the polynucleotide is not any one of SEQ ID NOs: 15-21.

In certain embodiments, the polynucleotide is codon-optimized for expression in a cell.

In certain embodiments, the cell is a eukaryotic cell.

Another aspect of the invention provides a non-naturally occurring polynucleotide comprising a derivative of any one of SEQ ID NOs: 8-14, wherein said derivative (i) has one or more (e.g., 1, 2, 3, 4, 5, 6, 7, 8, 9 or 10) nucleotides additions, deletions, or substitutions compared to any one of SEQ ID NOs: 8-14; (ii) has at least 20%, 30%, 40%, 50%, 60%, 70%, 80%, 90%, 95%, or 97% sequence identity to any one of SEQ ID NOs: 8-14; (iii) hybridize under stringent conditions with any one of SEQ ID NOs: 8-14 or any of (i) and (ii); or (iv) is a complement of any of (i)-(iii), provided that the derivative is not any one of SEQ ID NOs: 8-14, and that the derivative encodes an RNA (or is an RNA) that has maintained substantially the same secondary structure as any of the RNA encoded by SEQ ID NOs: 8-14.

In certain embodiments, the derivative functions as a DR sequence for any one of the Cas, the derivative thereof, or the functional fragment thereof, of the invention.

Another aspect of the invention provides a vector comprising the polynucleotide of the invention.

In certain embodiments, the polynucleotide is operably linked to a promoter and optionally an enhancer.

In certain embodiments, the promoter is a constitutive promoter, an inducible promoter, a ubiquitous promoter, or a tissue specific promoter.

In certain embodiments, the vector is a plasmid.

In certain embodiments, the vector is a retroviral vector, a phage vector, an adenoviral vector, a herpes simplex viral (HSV) vector, an AAV vector, or a lentiviral vector.

In certain embodiments, the AAV vector is a recombinant AAV vector of the serotype AAV1, AAV2, AAV4, AAV5, AAV6, AAV7, AAVrh74, AAV8, AAV9, AAV10, AAV 11, AAV 12, or AAV 13.

Another aspect of the invention provides a delivery system comprising (1) a delivery vehicle, and (2) the CRISPR-Cas complex of the invention, the fusion protein of the invention, the conjugate of the invention, the polynucleotide of the invention, or the vector of the invention.

In certain embodiments, the delivery vehicle is a nanoparticle, a liposome, an exosome, a microvesicle, or a gene-gun.

Another aspect of the invention provides a cell or a progeny thereof, comprising the CRISPR-Cas complex of the invention, the fusion protein of the invention, the conjugate of the invention, the polynucleotide of the invention, or the vector of the invention.

In certain embodiments, the cell or progeny thereof is a eukaryotic cell (e.g., a non-human mammalian cell, a human cell, or a plant cell) or a prokaryotic cell (e.g., a bacteria cell).

Another aspect of the invention provides a non-human multicellular eukaryote comprising the cell of the invention.

In certain embodiments, the non-human multicellular eukaryote is an animal (e.g., rodent or primate) model for a human genetic disorder.

Another aspect of the invention provides a method of modifying a target RNA, the method comprising contacting the target RNA with the CRISPR-Cas complex of the invention, wherein the spacer sequence is complementary to at least 15 nucleotides of the target RNA; wherein the Cas, the derivative, or the functional fragment associates with the RNA guide sequence to form the complex; wherein the complex binds to the target RNA; and wherein upon binding of the complex to the target RNA, the Cas, the derivative, or the functional fragment modifies the target RNA.

In certain embodiments, the target RNA is modified by cleavage by the Cas.

In certain embodiments, the target RNA is modified by deamination by a derivative comprising a Double-stranded RNA-specific adenosine deaminase.

In certain embodiments, the target RNA is an mRNA, a tRNA, an rRNA, a non-coding RNA, an lncRNA, or a nuclear RNA.

In certain embodiments, upon binding of the complex to the target RNA, the Cas, the derivative, and the functional fragment does not exhibit substantial (or detectable) collateral RNase activity.

In certain embodiments, the target RNA is within a cell.

In certain embodiments, the cell is a cancer cell.

In certain embodiments, the cell is infected with an infectious agent.

In certain embodiments, the infectious agent is a virus, a prion, a protozoan, a fungus, or a parasite.

In certain embodiments, the CRISPR-Cas complex is encoded by a first polynucleotide encoding any one of SEQ ID NOs: 1-7, or a derivative or functional fragment thereof, and a second polynucleotide comprising any one of SEQ ID NOs: 8-14 and a sequence encoding a spacer RNA capable of binding to the target RNA, wherein the first and the second polynucleotides are introduced into the cell.

In certain embodiments, the first and the second polynucleotides are introduced into the cell by the same vector.

In certain embodiments, the method causes one or more of: (i) in vitro or in vivo induction of cellular senescence; (ii) in vitro or in vivo cell cycle arrest; (iii) in vitro or in vivo cell growth inhibition and/or cell growth inhibition; (iv) in vitro or in vitro induction of anergy; (v) in vitro or in vitro induction of apoptosis; and (vi) in vitro or in vitro induction of necrosis.

Another aspect of the invention provides a method of treating a condition or disease in a subject in need thereof, the method comprising administering to the subject a composition comprising the CRISPR-Cas complex of the invention or a polynucleotide encoding the same; wherein the spacer sequence is complementary to at least 15 nucleotides of a target RNA associated with the condition or disease; wherein the Cas, the derivative, or the functional fragment associates with the RNA guide sequence to form the complex; wherein the complex binds to the target RNA; and wherein upon binding of the complex to the target RNA, the Cas, the derivative or the functional fragment cleaves the target RNA, thereby treating the condition or disease in the subject.

In certain embodiments, the condition or disease is a cancer or an infectious disease.

In certain embodiments, the cancer is Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, or urinary bladder cancer.

In certain embodiments, the method is an in vitro method, an in vivo method, or an ex vivo method.

Another aspect of the invention provides a cell or a progeny thereof, obtained by the method of the invention, wherein the cell and the progeny comprises a non-naturally existing modification (e.g., a non-naturally existing modification in a transcribed RNA of the cell/progeny).

Another aspect of the invention provides a method to detect the presence of a target RNA, the method comprising contacting the target RNA with a composition comprising a fusion protein of the invention, or a conjugate of the invention, or a polynucleotide encoding the fusion protein, wherein the fusion protein or the conjugate comprises a detectable label (e.g., one that can be detected by fluorescence, Northern blot, or FISH) and a complexed spacer sequence capable of binding to the target RNA.

Another aspect of the invention provides a eukaryotic cell comprising a Clustered Regularly Interspaced Short Palindromic Repeat (CRISPR)-Cas complex, said CRISPR-Cas complex comprising: (1) an RNA guide sequence comprising a spacer sequence capable of hybridizing to a target RNA, and a direct repeat (DR) sequence 3' to the spacer sequence; and, (2) a CRISPR-associated protein (Cas) having an amino acid sequence of any one of SEQ ID NOs: 1-7, or a derivative or functional fragment of said Cas; wherein the Cas, the derivative, and the functional fragment of said Cas, are capable of (i) binding to the RNA guide sequence and (ii) targeting the target RNA.

It should be understood that any one embodiment of the invention described herein, including those described only in the examples or claims, or only in one aspects/sections below, can be combined with any other one or more embodiments of the invention, unless explicitly disclaimed or improper.

BRIEF DESCRIPTION OF THE DRAWINGS

FIG. 14 discloses SEQ ID NOs: 64, 65, 64, 66, 64, and 65 respectively, in order of appearance.

DETAILED DESCRIPTION OF THE INVENTION

1. Overview

Figure 1:
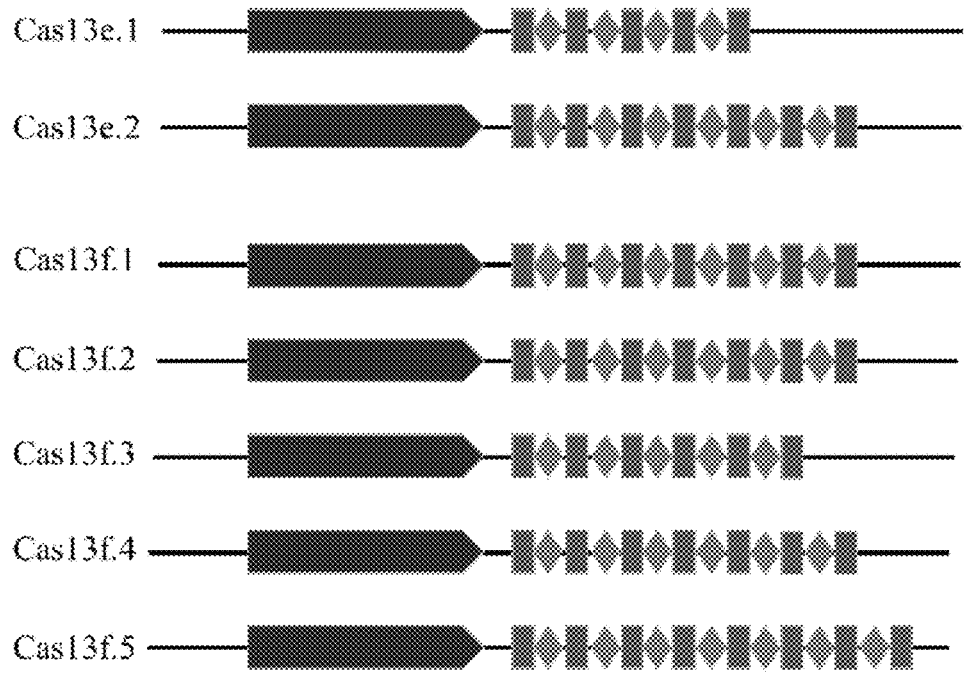
FIG. 1 is a schematic (not to scale) illustration of the genomic loci of the representative Cas13e and Cas13f families members. The Cas coding sequences (long bars with pointed end), followed by the multiple nearby direct repeat (DR) (short bars) and spacer sequences (diamonds) are shown.

The invention described herein provides novel Class 2, type VI Cas effector proteins, sometimes referred herein as Cas13e and Cas13f. The novel Cas13 proteins of the invention are much smaller than the previously discovered Cas13 effector proteins (Cas13a-Cas13d), such that they can be easily packaged with their crRNA coding sequences into small capacity gene therapy vectors, such as the AAV vectors. Further, the newly discovered Cas13e and Cas13f effector proteins are more potent in knocking down RNA target sequences, and more efficient in RNA single base editing, as compared to the Cas13a, Cas13b, and Cas13d effector proteins, while exhibiting negligible non-specific/collateral RNase activity upon activation by crRNA-based target recognition, except when the spacer sequence is within a specific narrow range (e.g., about 30 nucleotide). Thus these new Cas proteins are ideally suited for gene therapy.

Thus in the first aspect, the invention provides Cas13e and Cas13f effector proteins, such as those with amino acid sequences of SEQ ID NOs: 1-7, or orthologs, homologs, the various derivatives (described herein below), functional fragments thereof (described herein bellow), wherein said orthologs, homologs, derivatives and functional fragments have maintained at least one function of any one of the proteins of SEQ ID NOs: 1-7. Such functions include, but are not limited to, the ability to bind a guide RNA/crRNA of the invention (described herein below) to form a complex, the RNase activity, and the ability to bind to and cleave a target RNA at a specific site, under the guidance of the crRNA that is at least partially complementary to the target RNA.

In certain embodiments, the Cas13e or Cas13f effector proteins of the invention can be: (i) any one of SEQ ID NOs: 1-7; (ii) a derivative having one or more amino acids (e.g., 1, 2, 3, 4, 5, 6, 7, 8, 9, or 10 residues) of addition, deletion, and/or substitution (e.g., conserved substitution) of any one of SEQ ID NOs: 1-7; or (iii) a derivative having amino acid sequence identity of at least about 80%, 85%, 90%, 91%, 92%, 93%, 94%, 95%, 96%, 97%, 98%, or 99% compared to any one of SEQ ID NOs: 1-7.

In certain embodiments, the Cas13e and Cas13f effector proteins, orthologs, homologs, derivatives and functional fragments thereof are not naturally existing, e.g., having at least one amino acid difference compared to a naturally existing sequence.

In a related aspect, the invention provides additional derivatives Cas13e and Cas13f effector proteins based on any one of SEQ ID NOs: 1-7, or the above orthologs, homologs, derivatives and functional fragments thereof, which comprises another covalently or non-covalently linked protein or polypeptide or other molecules (such as detection reagents or drug/chemical moieties). Such other proteins/polypeptides/other molecules can be linked through, for example, chemical coupling, gene fusion, or other non-covalent linkage (such as biotin-streptavidin binding). Such derived proteins do not affect the function of the original protein, such as the ability to bind a guide RNA/crRNA of the invention (described herein below) to form a complex, the RNase activity, and the ability to bind to and cleave a target RNA at a specific site, under the guidance of the crRNA that is at least partially complementary to the target RNA.

Such derivation may be used, for example, to add a nuclear localization signal (NLS, such as SV40 large T antigen NLS) to enhance the ability of the subject Cas13e and Cas13f effector proteins to enter cell nucleus. Such derivation can also be used to add a targeting molecule or moiety to direct the subject Cas13e and Cas13f effector proteins to specific cellular or subcellular locations. Such derivation can also be used to add a detectable label to facilitate the detection, monitoring, or purification of the subject Cas13e and Cas13f effector proteins. Such derivation can further be used to add a deamination enzyme moiety (such as one with adenine or cytosine deamination activity) to facilitate RNA base editing.

The derivation can be through adding any of the additional moieties at the N- or C-terminal of the subject Cas13e and Cas13f effector proteins, or internally (e.g., internal fusion or linkage through side chains of internal amino acids).

In a related second aspect, the invention provides conjugates of the subject Cas13e and Cas13f effector proteins based on any one of SEQ ID NOs: 1-7, or the above orthologs, homologs, derivatives and functional fragments thereof, which are conjugated with moieties such as other proteins or polypeptides, detectable labels, or combinations thereof. Such conjugated moieties may include, without limitation, localization signals, reporter genes (e.g., GST, HRP, CAT, GFP, HcRed, DsRed, CFP, YFP, BFP), labels (e.g., fluorescent dye such as FITC, or DAPI), NLS, targeting moieties, DNA binding domains (e.g., MBP, Lex A DBD, Gal4 DBD), epitope tags (e.g., His, myc, V5, FLAG, HA, VSV-G, Trx, etc), transcription activation domains (e.g., VP64 or VPR), transcription inhibition domains (e.g., KRAB moiety or SID moiety), nucleases (e.g., FokI), deamination domain (e.g., ADAR1, ADAR2, APOBEC, AID, or TAD), methylase, demethylase, transcription release factor, HDAC, ssRNA cleavage activity, dsRNA cleavage activity, ssDNA cleavage activity, dsDNA cleavage activity, DNA or RNA ligase, any combination thereof, etc.

For example, the conjugate may include one or more NLSs, which can be located at or near N-terminal, C-terminal, internally, or combination thereof. The linkage can be through amino acids (such as D or E, or S or T), amino acid derivatives (such as Ahx, β-Ala, GABA or Ava), or PEG linkage.

In certain embodiments, conjugations do not affect the function of the original protein, such as the ability to bind a guide RNA/crRNA of the invention (described herein below) to form a complex, the RNase activity, and the ability to bind to and cleave a target RNA at a specific site, under the guidance of the crRNA that is at least partially complementary to the target RNA.

In a related third aspect, the invention provides fusions of the subject Cas13e and Cas13f effector proteins based on any one of SEQ ID NOs: 1-7, or the above orthologs, homologs, derivatives and functional fragments thereof, which fusions are with moieties such as localization signals, reporter genes (e.g., GST, HRP, CAT, GFP, HcRed, DsRed, CFP, YFP, BFP), NLS, protein targeting moieties, DNA binding domains (e.g., MBP, Lex A DBD, Gal4 DBD), epitope tags (e.g., His, myc, V5, FLAG, HA, VSV-G, Trx, etc), transcription activation domains (e.g., VP64 or VPR), transcription inhibition domains (e.g., KRAB moiety or SID moiety), nucleases (e.g., FokI), deamination domain (e.g., ADAR1, ADAR2, APOBEC, AID, or TAD), methylase, demethylase, transcription release factor, HDAC, ssRNA cleavage activity, dsRNA cleavage activity, ssDNA cleavage activity, dsDNA cleavage activity, DNA or RNA ligase, any combination thereof, etc.

For example, the fusion may include one or more NLSs, which can be located at or near N-terminal, C-terminal, internally, or combination thereof. In certain embodiments, conjugations do not affect the function of the original protein, such as the ability to bind a guide RNA/crRNA of the invention (described herein below) to form a complex, the RNase activity, and the ability to bind to and cleave a target RNA at a specific site, under the guidance of the crRNA that is at least partially complementary to the target RNA.

In a fourth aspect, the invention provides an isolated polynucleotide, comprising: (i) any one of SEQ ID NOs: 8-14; (ii) a polynucleotide having 1, 2, 3, 4, or 5 nucleotides of deletion, addition, and/or substitution compared to any one of SEQ ID NOs: 8-14; (iii) a polynucleotide sharing at least 80%, 85%, 90%, 95% sequence identity with any one of SEQ ID NOs: 8-14; (iv) a polynucleotide that hybridize under stringent condition with any one of the polynucleotide of (i)-(iii) or a complement thereof; (v) a complement sequence of any polynucleotide of (i)-(iii).

Any polynucleotide of (ii)-(iv) has maintained the function of the original SEQ ID NOs: 8-14, which is to encode a direct repeat (DR) sequence of a crRNA in the subject Cas13e or Cas13f system.

As used herein, "direct repeat sequence" may refer to the DNA coding sequence in the CRISPR locus, or to the RNA encoded by the same in crRNA. Thus when any of SEQ ID NOs: 8-14 is referred to in the context of an RNA molecule, such as crRNA, each T is understood to represent a U.

Thus in certain embodiments, the isolated polynucleotide is a DNA, which encodes a DR sequence for a crRNA of the subject Cas13e and Cas13f system.

In certain other embodiments, the isolated polynucleotide is an RNA, which is a DR sequence for a crRNA of the subject Cas13e and Cas13f system.

In a fifth aspect, the invention provides a complex comprising: (i) a protein composition that can be any one of the subject Cas13e or Cas13f effector protein, or orthologs, homologs, derivatives, conjugates, functional fragments thereof, conjugates thereof, or fusions thereof; and (ii) a polynucleotide composition, comprising an isolated polynucleotide described in the 4th aspect of the invention (e.g., a DR sequence), and a spacer sequence complementary to at least a portion of a target RNA. In certain embodiments, the DR sequence is at the 3' end of the spacer sequence.

In some embodiments, the polynucleotide composition is the guide RNA/crRNA of the subject Cas13e or Cas13f system, which does not include a tracrRNA.

In certain embodiments, for use with Cas13e and Cas13f effector proteins, homologs, orthologs, derivatives, fusions, conjugates, or functional fragments thereof having RNase activity, the spacer sequence is at least about 10 nucleotides, or between 10-60, 15-50, 20-50, 25-40, 25-50, or 19-50 nucleotides. In certain embodiments, for use with Cas13e and Cas13f effector proteins, homologs, orthologs, derivatives, fusion, conjugates, or functional fragments thereof having no RNase activity but ability to bind guide RNA and a target RNA complementary to the guide RNA, the spacer sequence is at least about 10 nucleotides, or between about 10-200, 15-180, 20-150, 25-125, 30-110, 35-100, 40-80, 45-60, 50-55, or about 50 nucleotides.

In certain embodiments, the DR sequence is between 15-36, 20-36, 22-36, or about 36 nucleotides. In certain embodiments, the DR sequence in the guide RNA has substantially the same secondary structure (including stems, bulges, and loop) as the RNA version of any one of SEQ ID NOs: 8-14.

In certain embodiments, the guide RNA is about 36 nucleotides longer than any of the spacer sequence lengths above, such as between 45-96, 55-86, 60-86, 62-86, or 63-86 nucleotides.

In a sixth aspect, the invention provides an isolated polynucleotide comprising: (i) a polynucleotide encoding any one of the Cas13e or Cas13f effector proteins of SEQ ID NOs: 1-7, or orthologs, homologs, derivatives, functional fragments, fusions thereof; (ii) a polynucleotide of any one of SEQ ID NOs: 8-14; or (iii) a polynucleotide comprising (i) and (ii).

In some embodiments, the polynucleotide is not naturally occurring/naturally existing, such as excluding SEQ ID NOs: 15-21.

In some embodiments, the polynucleotide is codon-optimized for expression in a prokaryote. In some embodiments, the polynucleotide is codon-optimized for expression in a eukaryote, such as in human or human cell.

In a seventh aspect, the invention provides a vector comprising or encompassing any of the polynucleotide of the sixth aspect. The vector can be a cloning vector, or an expression vector. The vector can be a plasmid, phagemid, or cosmid, just to name a few. In certain embodiments, the vector can be used to express the polynucleotide in a mammalian cell, such as a human cell, any one of the Cas13e or Cas13f effector proteins of SEQ ID NOs: 1-7, or orthologs, homologs, derivatives, functional fragments, fusions thereof; or any of the polynucleotide of the 4th aspect; or any of the complex of the 5th aspect.

In an eighth aspect, the invention provides a host cell comprising any of the polynucleotide of the 4th or 6th aspect, and/or the vector of the 7th aspect of the invention. The host cell can be a prokaryote such as *E. coli*, or a cell from a eukaryote such as yeast, insect, plant, animal (e.g., mammal including human and mouse). The host cell can be isolated primary cell (such as bone marrow cells for ex vivo therapy), or established cell lines such as tumor cell lines, 293T cells, or stem cells, iPCs, etc.

In a related aspect, the invention provides a eukaryotic cell comprising a Clustered Regularly Interspaced Short Palindromic Repeat (CRISPR)-Cas complex, said CRISPR-Cas complex comprising: (1) an RNA guide sequence comprising a spacer sequence capable of hybridizing to a target RNA, and a direct repeat (DR) sequence 3' to the spacer sequence; and, (2) a CRISPR-associated protein (Cas) having an amino acid sequence of any one of SEQ ID NOs: 1-7, or a derivative or functional fragment of said Cas; wherein the Cas, the derivative, and the functional fragment of said Cas, are capable of (i) binding to the RNA guide sequence and (ii) targeting the target RNA.

In a ninth aspect, the invention provides a composition comprising: (i) a first (protein) composition selected from any one of the Cas13e or Cas13f effector proteins of SEQ ID NOs: 1-7, or orthologs, homologs, derivatives, conjugates, functional fragments, fusions thereof; and (ii) a second (nucleotide) composition comprising an RNA encompassing a guide RNA/crRNA, particularly a spacer sequence, or a coding sequence for the same. The guide RNA may comprise a DR sequence, and a spacer sequence which can complement or hybridize with a target RNA. The guide RNA can form a complex with the first (protein) composition of (i). In some embodiment, the DR sequence can be the polynucleotide of the 4th aspect of the invention. In some embodiment, the DR sequence can be at the 3'-end of the guide RNA. In some embodiments, the composition (such as (i) and/or (ii)) is non-naturally occurring or modified from a naturally occurring composition. In some embodiments, at least a component of the composition is non-naturally occurring or modified from a naturally occurring component of the composition. In some embodiments, the target sequence is an RNA from a prokaryote or a eukaryote, such as a non-naturally existing RNA. The target RNA may be present inside a cell, such as in the cytosol or inside an organelle. In some embodiments, the protein composition may have an NLS that can be located at its N- or C-terminal, or internally.

In a tenth aspect, the invention provides a composition comprising one or more vectors of the 7th aspect of the invention, said one or more vectors comprise: (i) a first polynucleotide that encodes any one of the Cas13e or Cas13f effector proteins of SEQ ID NOs: 1-7, or orthologs, homologs, derivatives, functional fragments, fusions thereof; optionally operably linked to a first regulatory element; and (ii) a second polynucleotide that encodes a guide RNA of the invention; optionally operably linked to a second regulatory element. The first and the second polynucleotides can be on different vectors, or on the same vector. The guide RNA can form a complex with the protein product encoded by the first polynucleotide, and comprises a DR sequence (such as any one of the 4th aspect) and a spacer sequence that can bind to/complement with a target RNA. In some embodiments, the first regulatory element is a promoter, such as an inducible promoter. In some embodiments, the second regulatory element is a promoter, such as an inducible promoter. In some embodiments, the composition (such as (i) and/or (ii)) is non-naturally occurring or modified from a naturally occurring composition. In some embodiments, at least a component of the composition is non-naturally occurring or modified from a naturally occurring component of the composition. In some embodiments, the target sequence is an RNA from a prokaryote or a eukaryote, such as a non-naturally existing RNA. The target RNA may be present inside a cell, such as in the cytosol or inside an organelle. In some embodiments, the protein composition may have an NLS that can be located at its N- or C-terminal, or internally.

In some embodiments, the vector is a plasmid. In some embodiment, the vector is a viral vector based on a retrovirus, a replication incompetent retrovirus, adenovirus, replication incompetent adenovirus, or AAV. In some embodiments, the vector can self-replicate in a host cell (e.g., having a bacterial replication origin sequence). In some embodiments, the vector can integrate into a host genome and be replicated therewith. In some embodiment, the vector is a cloning vector. In some embodiment, the vector is an expression vector.

The invention further provides a delivery composition for delivering any of the Cas13e or Cas13f effector proteins of SEQ ID NOs: 1-7, or orthologs, homologs, derivatives, conjugates, functional fragments, fusions thereof of the 1st-3rd aspects of the invention; the polynucleotide of the 4th and/or 6th aspect of the invention; the complex of the 5th aspect of the invention; the vector of the 7th aspect of the invention; the cell of the 8th aspect of the invention, and the composition of the 9th and/or 10th aspects of the invention. The delivery can be through any one known in the art, such as transfection, lipofection, electroporation, gene gun, microinjection, sonication, calcium phosphate transfection, cation transfection, viral vector delivery, etc., using vehicles such as liposome(s), nanoparticle(s), exosome(s), microvesicle(s), a gene-gun or one or more viral vector(s).

The invention further provides a kit comprising any one or more of the following: any of the Cas13e or Cas13f effector proteins of SEQ ID NOs: 1-7, or orthologs, homologs, derivatives, conjugates, functional fragments, fusions thereof of the 1st-3rd aspects of the invention; the polynucleotide of the 4th and/or 6th aspect of the invention; the complex of the 5th aspect of the invention; the vector of the 7th aspect of the invention; the cell of the 8th aspect of the invention, and the composition of the 9th and/or 10th aspects of the invention. In some embodiments, the kit may further comprise an instruction for how to use the kit components, and/or how to obtain additional components from 3rd party for use with the kit components. Any component of the kit can be stored in any suitable container.

With the inventions generally described herein above, more detailed descriptions for the various aspects of the invention are provided in separate sections below. However, it should be understood that, for simplicity and to reduce redundancy, certain embodiments of the invention are only described under one section or only described in the claims or examples. Thus it should also be understood that any one embodiment of the invention, including those described only under one aspect, section, or only in the claims or examples, can be combined with any other embodiment of the invention, unless specifically disclaimed or the combination is improper.

2. Novel Class 2, Type VI CRISPR RNA-Guided RNases, and Derivatives Thereof

In one aspect, the invention described herein provides two novel families of CRISPR Class 2, type VI effectors having two strictly conserved RX4-6H (RXXXXH) motifs, characteristic of Higher Eukaryotes and Prokaryotes Nucleotide-binding (HEPN) domains. Similar CRISPR Class 2, type VI effectors that contain two HEPN domains have been previously characterized and include, for example, CRISPR Cas13a (C2c2), Cas13b, Cas13c, and Cas13d.

HEPN domains have been shown to be RNase domains and confer the ability to bind to and cleave target RNA molecule. The target RNA may be any suitable form of RNA, including but not limited to mRNA, tRNA, ribosomal RNA, non-coding RNA, lncRNA (long non-coding RNA), and nuclear RNA. For example, in some embodiments, the Cas proteins recognize and cleave RNA targets located on the coding strand of open reading frames (ORFs).

In one embodiment, the disclosure provides two families of CRISPR Class 2, type VI effectors, referred to herein generally as Type VI-E and VI-F CRISPR-Cas effector proteins, Cas13e or Cas13f. Direct comparison of the Type VI-E and VI-F CRISPR-Cas effector proteins with the effector of these other systems shows that Type VI-E and VI-F CRISPR-Cas effector proteins are significantly smaller (e.g., about 20% fewer amino acids) than even the smallest previously identified Type VI-D/Cas13d effectors (see FIG. 4), and have less than 30% sequence similarity in one to one sequence alignments to other previously described effector proteins, including the phylogenetically closest relatives Cas13b (see FIG. 3).

Figure 11:
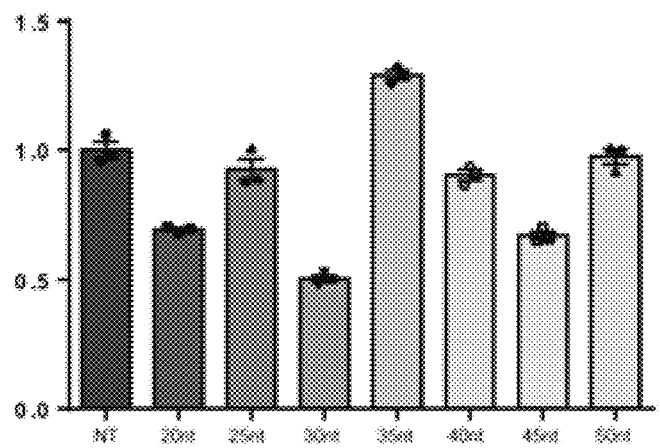
FIG. 11 shows the correlation between spacer sequence length and non-specific/collateral (guide RNA-independent) RNase activity against target RNAs relative to non-targeting (NT) control.

These two newly-identified families of CRISPR Class 2, type VI effectors can be used in a variety of applications, and are particularly suitable for therapeutic applications since they are significantly smaller than other effectors (e.g., CRISPR Cas13a, Cas13b, Cas13c, and Cas13d effectors) which allows for the packaging of the nucleic acids encoding the effectors and their guide RNA coding sequences into delivery systems having size limitations, such as the AAV vectors. Further, the lack of detectable collateral/non-specific RNase activity at selected range of spacer sequence lengths (such as about 30 nucleotides, see FIG. 11), upon activation of the specific RNase activity, makes these Cas effectors less prong to (if not immune from) potentially dangerous generalized off-target RNA digestion in target cells that are desirably not destroyed. On the other hand, at other selected spacer lengths such as about 30 nucleotides, significant collateral RNase activity exists for these Cas effectors, thus the subject Cas effectors can also be used in utilities depending on such collateral RNase activity.

Figure 2:
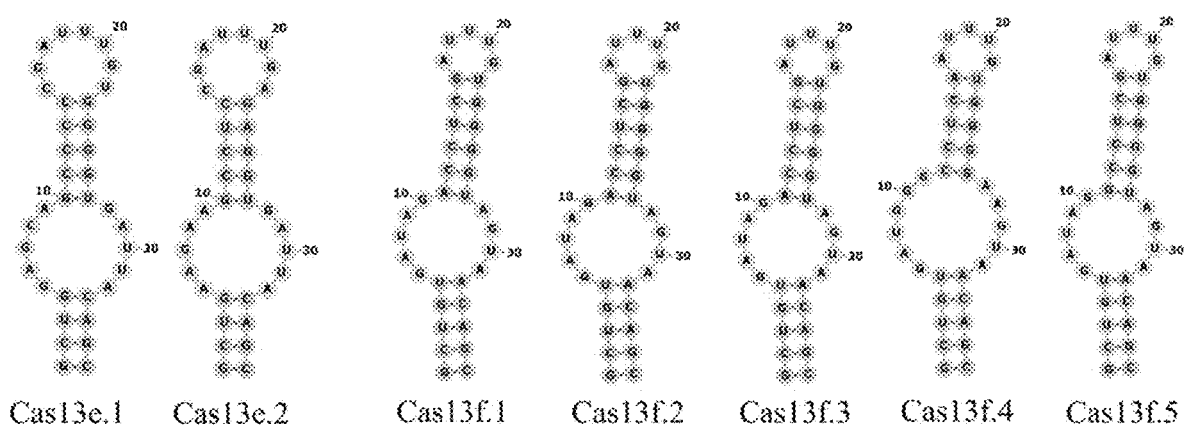
FIG. 2 shows putative secondary structures of the DR sequences associated with the respective Cas13e and Cas13f proteins (from left to right, SEQ ID NOs: 57-63, respectively). Their equivalent DNA sequences, from left to right, are represented by SEQ ID NOs: 8-14, respectively.

In bacteria, the Type VI-E and VI-F CRISPR-Cas systems include a single effector (approximately 775 residues and 790 residues, respectively) within close proximity to a CRISPR array (see FIG. 1). The CRISPR array includes direct repeat (DR) sequences typically 36 nucleotides in length, which are generally well conserved, both in sequences and secondary structures (see FIG. 2).

Data provided herein demonstrated that the crRNA is processed from the 5'-end, such that the DR sequences end up at the 3'-end of the mature crRNA.

The spacers contained in the Cas13e and Cas13f CRISPR arrays are most commonly 30 nucleotides in length, with the majority of variation in length contained in the range of 29 to 30 nucleotides. However, a wide range of spacer length may be tolerated. For example, for use in a functional Cas13e or Cas13f effector protein, or homologs, orthologs, derivatives, fusions, conjugates, or functional fragment thereof, the spacer can be between 10-60 nucleotides, 20-50 nucleotides, 25-45 nucleotides, 25-35 nucleotides, or about 27, 28, 29, 30, 31, 32, or 33 nucleotides. For use in dCas version of any of the above, however, the spacer can be between 10-200 nucleotides, 20-150 nucleotides, 25-100 nucleotides, 25-85 nucleotides, 35-75 nucleotides, 45-60 nucleotides, or about 46, 47, 48, 49, 50, 51, 52, 53, 54, or 55 nucleotides.

Exemplary Type VI-E and VI-F CRISPR-Cas effector proteins are provided in the table below.

```
Cas13e.1 MAQVSKQTSKKRELSIDEYQGARKWCFTIAFNKALVNRDKNDGLFVESLLRHEKYSKHDWY
         DEDTRALIKCSTQAANAKAEALRNYFSHYRHSPGCLIFTAEDELRTIMERAYERAIFECRR
         RETEVIIEFFSLFEGDRITTAGVVFFVSFFVERRVLDRLYGAVSGLKKNEGQYKLIRKALS
         MYCLKDSRFTKAWDKRVLLFRDILAQLGRIPAEAYEYYHGEQGDKKRANDNEGINPKRHKD
         KPIEFALHYLEAQHSEICFGRRHIVREEAGAGDEHKKHRTKGKVVVDFSKKDEDQSYYISK
         NNVIVRIDKNAGPRSYRMGLNELKYLVLLSLQGKGDDAIAKLYRYRQHVENILDVVKVIDK
         DNHVFLPREVLEQHGIGRKAFKQRIDGRVKHVRGVWEKKKAATNEMILHEKARDILQYVNE
         NCIRSFNPGEYNRLLVCLVGKDVENFQAGLKRLQLAERIDGRVYSIPAQTSTINEMHQVVC
         DQILNRLCRIGDQKLYDYVGLGKKDEIDYKQKVAWFKEHISIRRGFLRKKFWYDSKKGFAK
         LVEEHLESGGGQRDVGLDKKYYHIDAIGRFEGANPALYETLARDRLCLMMAQYFLGSVRKE
         LGNKIVWSNDSIELPVEGSVGNEKSIVFSVSDYGKLYVLDDAEFLGRICEYFMPHEKGKIR
         YHTVYEKGFRAYNDLQKKCVEAVLAFEEKVVKAKKMSEKEGAHYIDFREILAQTMCKEAEK
         TAVNKVRRAFFHHHLKEVIDEFGLFSDVMKKYGIEKEWKFPVK* (SEQ ID NO: 1)

Cas13e.2 MKVENIKEKSKKAMYLINHYEGPKKWCFAIVLNRACDNYEDNPHLFSKSLLEFEKTSRKDW
         FDEETRELVEQADTEIQPNPNLKPNTTANRKLKDIRNYFSHHYHKNECLYFKNDDPIRCIM
         EAAYEKSKIYIKGKQIEQSDIPLPELFESSGWITPAGILLLASFFVERGILHRLMGNIGGF
         KDNRGEYGLTHDIFTTYCLKGSYSIRAQDHDAVMFRDILGYLSRVPTESFQRIKQPQIRKE
         GQLSERKTDKFITFALNYLEDYGLKDLEGCKACFARSKIVREQENVESINDKEYKPHENKK
         KVEIHEDQSKEDRFYINRNNVILKIQKKDGHSNIVRMGVYELKYLVLMSLVGKAKEAVEKI
         DNYIQDLRDQLPYIEGKNKEEIKEYVRFFPRFIRSHLGLLQINDEEKIKARLDYVKTKWLD
         KKEKSKELELHKKGRDILRYINERCDRELNRNVYNRILELLVSKDLTGFYRELEELKRTRR
```

```
           IDKNIVQNLSGQKTINALHEKVCDLVLKEIESLDTENLRKYLGLIPKEEKEVTFKEKVDRI
           LKQPVIYKGFLRYQFFKDDKKSFVLLVEDALKEKGGGCDVPLGKEYYKIVSLDKYDKENKT
           LCETLAMDRLCLMMARQYYLSLNAKLAQEAQQIEWKKEDSIELIIFTLKNPDQSKQSFSIR
           FSVRDFTKLYVTDDPEFLARLCSYFFPVEKEIEYHKLYSEGINKYTNLQKEGIEAILELEK
           KLIERNRIQSAKNYLSFNEIMNKSGYNKDEQDDLKKVRNSLLHYKLIFEKEHLKKEYEVMR
           GEGIEKKWSLIV* (SEQ ID NO: 2)

Cas13f.1   MNGIELKKEEAAFYFNQAELNLKAIEDNIFDKERRKILLNNPQILAKMENFIENFRDVTKN
           AKGEIDCLLLKLRELRNFYSHVHKRDVRELSKGEKPILEKYYQFAIESTGSENVKLEIIE
           NDAWLADAGVLFFLCIFLKKSQANKLISGISGFKRNDDTGQPRRNLFTYFSIREGYKVVPE
           MQKHFLLFSLVNHLSNQDDYIEKAHQPYDIGEGLFFHRIASTFLNISGILRNMKFYTYQSK
           RLVEQRGELKREKDIFAWEEPFQGNSYFEINGHKGVIGEDELKELCYAFLIGNQDANKVEG
           RITQFLEKFRNANSVQQVKDDEMLKPEYFPANYFAESGVGRIKDRVLNRLNKAIKSNKAKK
           GEIIAYDKMREVMAFINNSLPVDEKLKPKDYKRYLGMVRENDREKDNIKREFETKEWSKYL
           PSNFWTAKNLERVYGLAREKNAELFNKLKADVEKMDERELEKYQKINDAKDLANLRRLASD
           FGVKWEEKDWDEYSGQIKKQITDSQKLTIMKQRITAGLKKKHGIENLNLRITIDINKSRKA
           VLNRIAIPRGFVKRHILGWQESEKVSKKIREAECEILLSKEYEELSKQFFQSKDYDKMTRI
           NGLYEKNKLIALMAVYLMGQLRILFKEHTKLDDITKTTVDFKISDKVTVKIPFSNYPSLVY
           TMSSKYVDNIGNYGFSNKDKDKPILGKIDVIEKQRMEFIKEVLGFEKYLFDDKIIDKSKFA
           DTATHISFAEIVEELVEKGWDKDRLTKLKDARNKALHGEILTGTSFDETKSLINELKK*
           (SEQ ID NO: 3)

Cas13f.2   MSPDFIKLEKEQAAFYFNQTELNLKAIESNILDKQQRMILLNNPRILAKVGNFIFNFRDVT
           KNAKGEIDCLLFKLEELRNFYSHVHTDNVKELSNGEKPLLERYYQIAIQATRSEDVKFEL
           FETRNENKITDAGVLFFLCMFLKKSQANKLISGISGFKRNDPTGQPRRNLFTYFSAREGYK
           ALPDMQKHFLLFTLVNYLSNQDEYISELKQYGEIGQGAFFNRIASTFLNISGISGNTKFYS
           YQSKRIKEQRGELNSEKDSFEWIEPFQGNSYFEINGHKGVIGEDELKELCYALLVAKQDIN
           AVEGKIMQFLKKFRNTGNLQQVKDDEMLEIEYFPASYFNESKKEDIKKEILGRLDKKIRSC
           SAKAEKAYDKMKEVMEFINNSLPAEEKLKRKDYRRYLKMVREWSREKGNIEREFRTKEWSK
           YFSSDFWRKNNLEDVYKLATQKNAELFKNLKAAAEKMGETEFEKYQQINDVKDLASLRRLT
           QDFGLKWEEKDWEEYSEQIKKQITDRQKLTIMKQRVTAELKKKHGIENLNLRITIDSNKSR
           KAVLNRIAIPRGFVKKHILGWQGSEKISKNIREAECKILLSKKYEELSRQFFEAGNEDKLT
           QINGLYEKNKLTAFMSVYLMGRLNIQLNKHTELGNLKKTEVDFKISDKVTEKIPFSQYPSL
           VYAMSRKYVDNVDKYKFSHQDKKKPFLGKIDSIEKERIEFIKEVLDFEEYLFKNKVIDKSK
           FSDTATHISFKEICDEMGKKGCNRNKLTELNNARNAALHGEIPSETSFREAKPLINELKK*
           (SEQ ID NO: 4)

Cas13f.3   MSPDFIKLEKEQAAFYFNQTELNLKAIESNIFDKQQRVILLNNPQILAKVGDFIFNFRDVT
           KNAKGEIDCLLLKLRELRNFYSHVVYTDDVKILSNGERPLLEKYYQFAIEATGSENVKLEI
           IESNNRLTEAGVLFFLCMFLKKSQANKLISGISGFKRNDPTGQPRRNLFTYFSVREGYKVV
           PDMQKHFLLFVLVNHLSGQDDYIEKAQKPYDIGEGLFFHRIASTFLNISGILRNMEFYIYQ
           SKRLKEQQGELKREKDIFPWIEPFQGNSYFEINGNKGIIGEDELKELCYALLVAGKDVRAV
           EGKITQFLEKEKNADNAQQVEKDEMLDRNNFPANYFAESNIGSIKEKILNRLGKTDDSYNK
           TGTKIKPYDMMKEVMEFINNSLPADEKLKRKDYRRYLKMVRIWDSEKDNIKREFESKEWSK
           YFSSDFWMAKNLERVYGLAREKNAELFNKLKAVVEKMDEREFEKYRLINSAEDLASLRRLA
           KDFGLKWEEKDWQEYSGQIKKQISDRQKLTIMKQRITAELKKKHGIENLNLRITIDSNKSR
           KAVLNRIAVPRGFVKEHILGWQGSEKVSKKTREAKCKILLSKEYEELSKQFFQTRNYDKMT
           QVNGLYEKNKLLAFMVVYLMERLNILLNKFTELNELEKAEVDFKISDKVMAKIPFSQYPSL
           VYAMSSKYADSVGSYKFENDEKNKPFLGKIDTIEKQRMEFIKEVLGFEEYLFEKKIIDKSE
           FADTATHISFDEICNELIKKGWDKDKLIKLKDARNAALHGEIPAETSFREAKPLINGLKK*
           (SEQ ID NO: 5)

Cas13f.4   MNIIKLKKEEAAFYFNQTILNLSGLDEIIEKQIPHIISNKENAKKVIDKIFNNRLLLKSVE
           NYIYNFKDVAKNARTEIEAILLKLVELRNFYSHVHNDTVKILSNGEKPILEKYYQIAIEA
           TGSKNVKLVIIENNNCLIDSGVLFLLCMFLKKSQANKLISSVSGFKRNDKEGQPRRNLFTY
           YSVREGYKVVPDMQKHFLLFALVNHLSEQDDHIEKQQQSDELGKGLFFHRIASTFLNESGI
           FNKMQFYTYQSNRLKEKRGELKHEKDIFTWIEPFQGNSYFTLNGHKGVISEDQLKELCYTI
           LIEKQNVDSLEGKIIQFLKKFQNVSSKQQVDEDELLKREYFPANYFGRAGIGILKEKILNR
           LDKRMDPISKVIDKAYDKMIEVMEFINMCLPSDEKLRQKDYRRYLKMVREWNKEKHNIKRE
           FDSKKWIRFLPTELWNKRNLEEAYQLARKENKKKLEDMRNQVRSLKENDLEKYQQINYVND
           LENLRLLSQELGVKWQEKDWVEYSGQIKKQISDNQKLTIMKQRITAELKKMHGIENLNLRI
           SIDINKSRQTVMNRIALPKGFVKNHIQQNSSEKISKRIREDYCKIELSGKYEELSRQFFDK
           KNEDKMTLINGLCEKNKLIAFMVIYLLERLGFELKEKTKLGELKQTRMTYKISDKVKEDIP
           LSYYPKLVYAMNRKYVDNIDSYAFAAYESKKAILDKVDIIEKQRMEFIKQVLCFEEYIFEN
           RIIEKSKENDEETHISFIQIHDELIKKGRDTEKLSKLKHARNKALHGEIPDGISFEKAKLL
           INEIKK* (SEQ ID NO: 6)

Cas13f5    MNAIELKKEEAAFYFNQARLNISGLDEIIEKQLPHIGSNRENAKKTVDMILDNPEVLKKME
           NYVFNSRDIAKNARGELEALLLKLVELRNFYSHVHKDDVKILSYGEKPLLDKYYEIAIEA
           TGSKDVRLEIIDDKNKLIDAGVLFLLCMFLKKSEANKLISSIRGFKRNDKEGQPRRNLFTY
           YSVREGYKVVPDMQKHFLLFTLVNHLSNQDEYISNLRPNQEIGQGGFFHRIASKFLSDSGI
           LHSMKFYTYRSKRLTEQRGELKPKKDHFTWIEPFQGNSYFSVQGQKGVIGEEQLKELCYVL
           LVAREDFRAVEGKVTQFLKKFQNANNVQQVEKDEVLKEYFPANYFENRDVGRVKDKILNR
           LKKITESYKAKGREVKAYDKMKEVMEFINNCLPTDENLKLKDYRRYLKMVRFWGREKENIK
           REFDSKKWERFLPRELWQKRNLEDAYQLAKEKNTELENKLKTIVERMNELEFEKYQQINDA
           KDLANLRQLARDFGVKWEEKDWQEYSGQIKKQITDRQKLTIMKQRITAALKKKQGIENLNL
           RITTDINKSRKVVLNRIALPKGFVRKHILKTDIKISKQIRQSQCPIILSNNYMKLAKEFFE
           ERNFDKMIQINGLFEKNVLIAFMIVYLMEQLNLRLGKNTELSNLKKTEVNFTITDKVIEKV
           QISQYPSLVFAINREYVDGISGYKLPPKKPKEPPYIFFEKIDAIEKERMEFIKQVLGFEEH
```

```
LFEKNVIDKIRFIDTATHISFNEICDELIKKGWDENKIIKLKDARNAALHGKIPEDISFDE
AKVLINELKK* (SEQ ID NO: 7)
```

In the sequences above, the two RX4-6H (RXXXXH) motifs in each effector are double-underlined. In Cas3e.1, the C-terminal motif may have two possibilities due to the RR and HH sequences flanking the motif. Mutations atone or both such domains may create an RNase dead version (or "dCas) of the Cas13e and Cas13f effector proteins, homologs, orthologs, fusions, conjugates, derivatives, or functional fragments thereof, while substantially maintaining their ability to bind the guide RNA and the target RNA complementary to the guide RNA.

The corresponding DR coding sequences for the Cas effectors are listed below:

```
Cas13e.1   GCTGGAGCAGCCCCCGATTTGTGGGGTGATTACAGC   (SEQ ID NO: 8)
Cas13e.2   GCTGAAGAAGCCTCCGATTTGAGAGGTGATTACAGC   (SEQ ID NO: 9)
Cas13f.1   GCTGTGATAGACCTCGATTTGTGGGGTAGTAACAGC   (SEQ ID NO: 10)
Cas13f.2   GCTGTGATAGACCTCGATTTGTGGGGTAGTAACAGC   (SEQ ID NO: 11)
Cas13f.3   GCTGTGATAGACCTCGATTTGTGGGGTAGTAACAGC   (SEQ ID NO: 12)
Cas13f.4   GCTGTGATGGGCCTCAATTTGTGGGAAGTAACAGC    (SEQ ID NO: 13)
Cas13f.5   GCTGTGATAGGCCTCGATTTGTGGGGTAGTAACAGC   (SEQ ID NO: 14)
```

Since the secondary structures of the DR sequences, including the location and size of the step, bulge, and loop structures, are likely more important than the specific nucleotide sequences that form such secondary structures, alternative or derivative DR sequences can also be used in the systems and methods of the invention, so long as these derivative or alternative DR sequences have a secondary structure that substantially resembles the secondary structure of an RNA encoded by any one of SEQ ID NO: 8-14. For example, the derivative DR sequence may have ±1 or 2 base pair(s) in one or both stems (see FIG. 2), have ±1, 2, or 3 bases in either or both of the single strands in the bulge, and/or have ±1, 2, 3, or 4 bases in the loop region.

In some embodiments, a Type VI-E and VI-F CRISPR-Cas effector proteins include a "derivative" having an amino acid sequence with at least about 80% sequence identity to the amino acid sequence of any one of SEQ ID NOs: 1-7 above (e.g., 81%, 82%, 83%, 84%, 85%, 86%, 87% 88%, 89%, 90%, 91%, 92%, 93%, 94%, 95%, 96%, 97%, 98%, 99%, or 100%). Such derivative Cas effectors sharing significant protein sequence identity to any one of SEQ ID NOs: 1-7 have retained at least one of the functions of the Cas of SEQ ID NOs: 1-7 (see below), such as the ability to bind to and form a complex with a crRNA comprising at least one of the DR sequences of SEQ ID NOs: 8-14. For example, a Cas13e.1 derivative may share 85% amino acid sequence identity to SEQ ID NO: 1, 2, 3, 4, 5, 6, or 7 respectively, and retains the ability to bind to and form a complex with a crRNA having a DR sequence of SEQ ID NO: 8, 9, 10, 11, 12, 13, or 14, respectively.

In some embodiments, the derivative comprises conserved amino acid residue substitutions. In some embodiments, the derivative comprises only conserved amino acid residue substitutions (i.e., all amino acid substitutions in the derivative are conserved substitutions, and there is no substitution that is not conserved).

In some embodiments, the derivative comprises no more than 1, 2, 3, 4, 5, 6, 7, 8, 9, or 10 amino acid insertions or deletions into any one of the wild-type sequences of SEQ ID NOs: 1-7. The insertion and/or deletion maybe clustered together, or separated throughout the entire length of the sequences, so long as at least one of the functions of the wild-type sequence is preserved. Such functions may include the ability to bind the guide/crRNA, the RNase activity, the ability to bind to and/or cleave the target RNA complementary to the guide/crRNA. In some embodiments, the insertions and/or deletions are not present in the RXXXXH motifs, or within 5, 10, 15, or 20 residues from the RXXXXH motifs.

In some embodiments, the derivative has retained the ability to bind guide RNA/crRNA.

In some embodiments, the derivative has retained the guide/crRNA-activated RNase activity.

In some embodiments, the derivative has retained the ability to bind target RNA and/or cleave the target RNA in the presence of the bound guide/crRNA that is complementary in sequence to at least a portion of the target RNA.

In other embodiments, the derivative has completely or partially lost the guide/crRNA-activated RNase activity, due to, for example, mutations in one or more catalytic residues of the RNA-guided RNase. Such derivatives are sometimes referred to as dCas, such as dCas13e.1, etc.

Thus in certain embodiments, the derivative may be modified to have diminished nuclease/RNase activity, e.g., nuclease inactivation of at least 50%, at least 60%, at least 70%, at least 80%, at least 90%, at least 95%, at least 97%, or 100% as compared with the counterpart wild type proteins. The nuclease activity can be diminished by several methods known in the art, e.g., introducing mutations into the nuclease (catalytic) domains of the proteins. In some embodiments, catalytic residues for the nuclease activities are identified, and these amino acid residues can be substituted by different amino acid residues (e.g., glycine or alanine) to diminish the nuclease activity. In some embodiments, the amino acid substitution is a conservative amino acid substitution. In some embodiments, the amino acid substitution is a non-conservative amino acid substitution.

In some embodiments, the modification comprises one or more mutations (e.g., amino acid deletions, insertions, or substitutions) in at least one HEPN domain. In some embodiments, there is one, two, three, four, five, six, seven, eight, nine, or more amino acid substitutions in at least one HEPN domain. For example, in some embodiments, the one or more mutations comprise a substitution (e.g., an alanine substitution) at an amino acid residue corresponding to R84, H89, R739, H744, R740, H745 of SEQ ID NO: 1, or R97, H102, R770, H775 of SEQ ID NO: 2, or R77, H82, R764, H769 of SEQ ID NO: 3, or R79, H84, R766A, H771 of SEQ ID NO: 4, or R79, H84, R766, H771 of SEQ ID NO: 5, or R89, H94, R773, H778 of SEQ ID NO: 6, or R89, H94, R777, H782 of SEQ ID NO: 7.

In certain embodiments, the one or more mutations or the two or more mutations may be in a catalytically active domain of the effector protein comprising a HEPN domain, or a catalytically active domain which is homologous to a HEPN domain. In certain embodiments, the effector protein comprises one or more of the following mutations: R84A, H89A, R739A, H744A, R740A, H745A (wherein amino acid positions correspond to amino acid positions of Cas13e.1). The skilled person will understand that corresponding amino acid positions in different Cas13e and Cas13f proteins may be mutated to the same effect. In certain embodiments, one or more mutations abolish catalytic activity of the protein completely or partially (e.g. altered cleavage rate, altered specificity, etc.).

Other exemplary (catalytic) residue mutations include: R97A, H102A, R770A, H775A of Cas13e.2, or R77A, H82A, R764A, H769A of Cas13f.1, or R79A, H84A, R766A, H771A of Cas13f.2, or R79A, H84A, R766A, H771A of Cas13f.3, or R89A, H94A, R773A, H778A of Cas13f.4, or R89A, H94A, R777A, H782A of Cas13f.5. In certain embodiments, any of the R and/or H residues herein may be replaced not be A but by G, V, or I.

The presence of at least one of these mutations results in a derivative having reduced or diminished RNase activity as compared to the corresponding wild-type protein lacking the mutations.

In certain embodiments, the effector protein as described herein is a "dead" effector protein, such as a dead Cas13e or Cas13f effector protein (i.e. dCas13e and dCas13f). In certain embodiments, the effector protein has one or more mutations in HEPN domain 1 (N-terminal). In certain embodiments, the effector protein has one or more mutations in HEPN domain 2 (C-terminal). In certain embodiments, the effector protein has one or more mutations in HEPN domain 1 and HEPN domain 2.

The inactivated Cas or derivative or functional fragment thereof can be fused or associated with one or more heterologous/functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, base-editing activity, and switch activity (e.g., light inducible). In some embodiments, the functional domains are Krüppel associated box (KRAB), SID (e.g. SID4X), VP64, VPR, VP16, FokI, P65, HSF1, MyoD1, Adenosine Deaminase Acting on RNA such as ADAR1, ADAR2, APOBEC, cytidine deaminase (AID), TAD, mini-SOG, APEX, and biotin-APEX.

In some embodiments, the functional domain is a base editing domain, e.g., ADAR1 (including wild-type or ADAR1DD version thereof, with or without the E1008Q), ADAR2 (including wild-type or ADAR2DD version thereof, with or without the E488Q mutation(s)), APOBEC, or AID.

In some embodiments, the functional domain may comprise one or more nuclear localization signal (NLS) domains. The one or more heterologous functional domains may comprise at least two or more NLS domains. The one or more NLS domain(s) may be positioned at or near or in proximity to a terminus of the effector protein (e.g., Cas13e/Cas13f effector proteins) and if two or more NLSs, each of the two may be positioned at or near or in proximity to a terminus of the effector protein (e.g., Cas13e/Cas13f effector proteins).

In some embodiments, at least one or more heterologous functional domains may be at or near the amino-terminus of the effector protein and/or wherein at least one or more heterologous functional domains is at or near the carboxy-terminus of the effector protein. The one or more heterologous functional domains may be fused to the effector protein. The one or more heterologous functional domains may be tethered to the effector protein. The one or more heterologous functional domains may be linked to the effector protein by a linker moiety.

In some embodiments, multiple (e.g., two, three, four, five, six, seven, eight, or more) identical or different functional domains are present.

In some embodiments, the functional domain (e.g., a base editing domain) is further fused to an RNA-binding domain (e.g., MS2).

In some embodiments, the functional domain is associated to or fused via a linker sequence (e.g., a flexible linker sequence or a rigid linker sequence). Exemplary linker sequences and functional domain sequences are provided in table below.

Amino Acid Sequences of Motifs and Functional Domains in Engineered Variants of Type VI-E and VI-F CRISPR Cas Effectors

| | |
|---|---|
| Linker 1 | GS (SEQ ID NO: 67) |
| Linker 2 | GSGGGGS (SEQ ID NO: 68) |
| Linker 3 | GGGGSGGGGSGGGGS (SEQ ID NO: 69) |
| ADAR1DD-WT | SLGTGNRCVKGDSLSLKGETVNDCHAEIISRRGFIRFLYSELMKYNSQTAKDSIFEPAKGG EKLQIKKTVSFHLYISTAPCGDGALFDKSCSDRAMESTESRHYPVFENPKQGKLRTKVENG EGTIPVESSDIVPTWDGIRLGERLRTMSCSDKILRWNVLGLQGALLTHFLQPIYLKSVTLG YLFSQGHLTRAICCRVIRDGSAFEDGLRHPFIVNHPKVGRVSIYDSKRQSGKIKETSVNWC LADGYDLEILDGTRGTVDGPRNELSRVSKKNIFLLFKKLCSFRYRRDLLRLSYGEAKKAAR DYETAKNYFKKGLKDMGYGNWISKPQEEKNF (SEQ ID NO: 70) |
| ADAR1DD-E1008Q | SLGTGNRCVKGDSLSLKGETVNDCHAEIISRRGFIRFLYSELMKYNSQTAKDSIFEPAKGG EKLQIKKTVSFHLYISTAPCGDGALFDKSCSDRAMESTESRHYPVFENPKQGKLRTKVENG QGTIPVESSDIVPTWDGIRLGERLRTMSCSDKILRWNVLGLQGALLTHFLQPIYLKSVTLG |

Amino Acid Sequences of Motifs and Functional Domains in Engineered Variants
of Type VI-E and VI-F CRISPR Cas Effectors

|  |  |
|---|---|
|  | YLFSQGHLTRAICCRVIRDGSAFEDGLRHPFIVNHPKVGRVSIYDSKRQSGKIKETSVNWC<br>LADGYDLEILDGTRGTVDGPRNELSRVSKKNIFLLFKKLCSFRYRRDLLRLSYGEAKKAAR<br>DYETAKNYFKKGLKDMGYGNWISKPQEEKNF (SEQ ID NO: 71) |
| ADAR2DD-<br>WT | QLHLPQVLADAVSRLVLGKFGDLTDNFSSPHARRKVLAGVVMTTGTDVKDAKVISVSTGTK<br>CINGEYMSDRGLALNDCHAEIISRRSLLRFLYTQLELYLNNKDDQKRSIFQKSERGGFRLK<br>ENVQFHLYISTSPCGDARIFSPHEPILEEPADRHPNRKARGQLRTKIESGEGTIPVRSNAS<br>IQTWDGVLQGERLLTMSCSDKIARWNVVGIQGSLLSIFVEPIYFSSIILGSLYHGDHLSRA<br>MYQRISNIEDLPPLYTLNKPLLSGISNAEARQPGKAPNFSVNWTVGDSAIEVINATTGKDE<br>LGRASRLCKHALYCRWMRVHGKVPSHLLRSKITKPNVYHESKLAAKEYQAAKARLFTAFIK<br>AGLGAWVEKPTEQDQFSLT (SEQ ID NO: 72) |
| ADAR2DD-<br>E488Q | QLHLPQVLADAVSRLVLGKFGDLTDNFSSPHARRKVLAGVVMTTGTDVKDAKVISVSTGTK<br>CINGEYMSDRGLALNDCHAEIISRRSLLRFLYTQLELYLNNKDDQKRSIFQKSERGGFRLK<br>ENVQFHLYISTSPCGDARIFSPHEPILEEPADRHPNRKARGQLRTKIESGQGTIPVRSNAS<br>IQTWDGVLQGERLLTMSCSDKIARWNVVGIQGSLLSIFVEPIYFSSIILGSLYHGDHLSRA<br>MYQRISNIEDLPPLYTLNKPLLSGISNAEARQPGKAPNFSVNWTVGDSAIEVINATTGKDE<br>LGRASRLCKHALYCRWMRVHGKVPSHLLRSKITKPNVYHESKLAAKEYQAAKARLFTAFIK<br>AGLGAWVEKPTEQDQFSLT (SEQ ID NO: 73) |
| AID-<br>APOBEC1 | MDSLLMNRRKFLYQFKNVRWAKGRRETYLCYVVKRRDSATSFSLDFGYLRNKNGCHVELLF<br>LRYISDWDLDPGRCYRVTWFTSWSPCYDCARHVADFLRGNPNLSLRIFTARLYFCEDRKAE<br>PEGLRRLHRAGVQIAIMTFKDYFYCWNTFVENHERTFKAWEGLHENSVRLSRQLRRILLPL<br>YEVDDLRDAFRTLGL (SEQ ID NO: 74) |
| Lamprey_<br>AID-<br>APOBEC1 | MTDAEYVRIHEKLDIYTFKKQFNNKKSVSHRCYVLFELKRRGERRACFWGYAVNKPQSGT<br>ERGIHAEIFSIRKVEEYLRDNPGQFTINWYSSWSPCADCAEKILEWYNQELRGNGHTLKIW<br>ACKLYYEKNARNQIGLWNLRDNGVGLNVMVSEHYQCCRKIFIQSSHNQLNENRWLEKTLKR<br>AEKRRSELSIMIQVKILHTTKSPAV (SEQ ID NO: 75) |
| APOBEC1_<br>BE1 | MSSETGPVAVDPTLRRRIEPHEFEVFFDPRELRKETCLLYEINWGGRHSIWRHTSQNTNKH<br>VEVNFIEKFTTERYFCPNTRCSITWFLSWSPCGECSRAITEFLSRYPHVTLFIYIARLYHH<br>ADPRNRQGLRDLISSGVTIQIMTEQESGYCWRNFVNYSPSNEAHWPRYPHLWVRLYVLELY<br>CIILGLPPCLNILRRKQPQLTFFTIALQSCHYQRLPPHILTATATGLK (SEQ ID NO: 76) |

The positioning of the one or more functional domains on the inactivated Cas proteins is one that allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., FokI) is positioned to cleave or partially cleave the target. In some embodiments, the functional domain is positioned at the N-terminus of the Cas/dCas. In some embodiments, the functional domain is positioned at the C-terminus of the Cas/dCas. In some embodiments, the inactivated CRISPR-associated protein (dCas) is modified to comprise a first functional domain at the N-terminus and a second functional domain at the C-terminus.

Various examples of inactivated CRISPR-associated proteins fused with one or more functional domains and methods of using the same are described, e.g., in International Publication No. WO 2017/219027, which is incorporated herein by reference in its entirety, and in particular with respect to the features described herein.

In some embodiments, a Type VI-E and VI-F CRISPR-Cas effector proteins includes the amino acid sequence of any one of SEQ ID NOs: 1-7 above. In some embodiments, a Type VI-E and VI-F CRISPR-Cas effector proteins excludes the naturally occurring amino acid sequence of any one of SEQ ID NOs: 1-7 above.

In some embodiments, instead of using full-length wild-type (SEQ ID NOs: 1-7) or derivative Type VI-E and VI-F Cas effectors, "functional fragments" thereof can be used.

A "functional fragment," as used herein, refers to a fragment of a wild-type protein of any one of SEQ ID NOs: 1-7, or a derivative thereof, that has less-than full-length sequence. The deleted residues in the functional fragment can be at the N-terminus, the C-terminus, and/or internally. The functional fragment retains at least one function of the wild-type VI-E or VI-F Cas, or at least one function of its derivative. Thus a functional fragment is defined specifically with respect to the function at issue. For example, a functional fragment, wherein the function is the ability to bind crRNA and target RNA, may not be a functional fragment with respect to the RNase function, because losing the RXXXXH motifs at both ends of the Cas may not affect its ability to bind a crRNA and target RNA, but may eliminate destroy the RNase activity.

In some embodiments, compared to full-length sequences SEQ ID NOs: 1-7, the Type VI-E or VI-F CRISPR-Cas effector proteins or derivatives thereof or functional fragments thereof lacks about 30, 60, 90, 120, 150, or about 180 residues from the N-terminus.

In some embodiments, compared to full-length sequences SEQ ID NOs: 1-7, the Type VI-E or VI-F CRISPR-Cas effector proteins or derivatives thereof or functional fragments thereof lacks about 30, 60, 90, 120, or about 150 residues from the C-terminus.

In some embodiments, compared to full-length sequences SEQ ID NOs: 1-7, the Type VI-E or VI-F CRISPR-Cas effector proteins or derivatives thereof or functional fragments thereof lacks about 30, 60, 90, 120, 150, or about 180 residues from the N-terminus, and lacks about 30, 60, 90, 120, or about 150 residues from the C-terminus.

In some embodiments, the Type VI-E or VI-F CRISPR-Cas effector proteins or derivatives thereof or functional fragments thereof have RNase activity, e.g., guide/crRNA-activated specific RNase activity.

In some embodiments, the Type VI-E or VI-F CRISPR-Cas effector proteins or derivatives thereof or functional fragments thereof have no substantial/detectable collateral RNase activity.

Here, "collateral RNase activity" refers to the non-specific RNase activity observed in certain other Class 2, type VI RNA-guided RNases, such as Cas13a. A complex comprising Cas13a, for example, upon activation by binding to a target nucleic acid (e.g., a target RNA), a conformational change results, which in turn causes the complex to act as a non-specific RNase, cleaving and/or degrading nearby RNA molecules (e.g., ssRNA or dsRNA molecules)(i.e., "collateral" effects).

In certain embodiments, a complex comprised of (but not limited to) the Type VI-E or VI-F CRISPR-Cas effector proteins or derivatives thereof or functional fragments thereof and a crRNA does not exhibit collateral RNase activity subsequent to target recognition. This "collateral-free" embodiment may comprise wild-type, engineered/derivative effector proteins, or functional fragments thereof.

In some embodiments, the Type VI-E or VI-F CRISPR-Cas effector proteins or derivatives thereof or functional fragments thereof recognizes and cleaves the target RNA without any additional requirements adjacent to or flanking the protospacer (i.e., protospacer adjacent motif "PAM" or protospacer flanking sequence "PFS" requirements).

The present disclosure also provides a split version of the CRISPR-associated proteins described herein (e.g., a Type VI-E or VI-F CRISPR-Cas effector protein). The split version of the CRISPR-associated protein may be advantageous for delivery. In some embodiments, the CRISPR-associated proteins are split into two parts of the enzyme, which together substantially comprise a functioning CRISPR-associated protein.

The split can be done in a way that the catalytic domain(s) are unaffected. The CRISPR-associated protein may function as a nuclease or may be an inactivated enzyme, which is essentially a RNA-binding protein with very little or no catalytic activity (e.g., due to mutation(s) in its catalytic domains). Split enzymes are described, e.g., in Wright et al., "Rational design of a split-Cas9 enzyme complex," *Proc. Natl. Acad. Sci.* 112(10): 2984-2989, 2015, which is incorporated herein by reference in its entirety.

For example, in some embodiments, the nuclease lobe and α-helical lobe are expressed as separate polypeptides. Although the lobes do not interact on their own, the crRNA recruits them into a ternary complex that recapitulates the activity of full-length CRISPR-associated proteins and catalyzes site-specific DNA cleavage. The use of a modified crRNA abrogates split-enzyme activity by preventing dimerization, allowing for the development of an inducible dimerization system.

In some embodiments, the split CRISPR-associated protein can be fused to a dimerization partner, e.g., by employing rapamycin sensitive dimerization domains. This allows the generation of a chemically inducible CRISPR-associated protein for temporal control of the activity of the protein. The CRISPR-associated protein can thus be rendered chemically inducible by being split into two fragments and rapamycin-sensitive dimerization domains can be used for controlled re-assembly of the protein.

The split point is typically designed in silico and cloned into the constructs. During this process, mutations can be introduced to the split CRISPR-associated protein and non-functional domains can be removed.

In some embodiments, the two parts or fragments of the split CRISPR-associated protein (i.e., the N-terminal and C-terminal fragments), can form a full CRISPR-associated protein, comprising, e.g., at least 70%, at least 80%, at least 90%, at least 95%, or at least 99% of the sequence of the wild-type CRISPR-associated protein.

The CRISPR-associated proteins described herein (e.g., a Type VI-E or VI-F CRISPR-Cas effector protein) can be designed to be self-activating or self-inactivating. For example, the target sequence can be introduced into the coding construct of the CRISPR-associated protein. Thus, the CRISPR-associated protein can cleave the target sequence, as well as the construct encoding the protein thereby self-inactivating their expression. Methods of constructing a self-inactivating CRISPR system are described, e.g., in Epstein and Schaffer, *Mol. Ther.* 24: S50, 2016, which is incorporated herein by reference in its entirety.

In some other embodiments, an additional crRNA, expressed under the control of a weak promoter (e.g., 7SK promoter), can target the nucleic acid sequence encoding the CRISPR-associated protein to prevent and/or block its expression (e.g., by preventing the transcription and/or translation of the nucleic acid). The transfection of cells with vectors expressing the CRISPR-associated protein, the crRNAs, and crRNAs that target the nucleic acid encoding the CRISPR-associated protein can lead to efficient disruption of the nucleic acid encoding the CRISPR-associated protein and decrease the levels of CRISPR-associated protein, thereby limiting the genome editing activity.

In some embodiments, the genome editing activity of the CRISPR-associated protein can be modulated through endogenous RNA signatures (e.g., miRNA) in mammalian cells. A CRISPR-associated protein switch can be made by using a miRNA-complementary sequence in the 5'-UTR of mRNA encoding the CRISPR-associated protein. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (see, e.g., Hirosawa el al., *Nucl. Acids Res.* 45(13): el 18, 2017).

The CRISPR-associated proteins (e.g., Type VI-E and VI-F CRISPR-Cas effector proteins) can be inducibly expressed, e.g., their expression can be light-induced or chemically-induced. This mechanism allows for activation of the functional domain in the CRISPR-associated proteins. Light inducibility can be achieved by various methods known in the art, e.g., by designing a fusion complex wherein CRY2 PHR/CIBN pairing is used in split CRISPR-associated proteins (see, e.g., Konermann et al., "Optical control of mammalian endogenous transcription and epigenetic states," *Nature* 500:7463, 2013.

Chemical inducibility can be achieved, e.g., by designing a fusion complex wherein FKBP/FRB (FK506 binding protein/FKBP rapamycin binding domain) pairing is used in split CRISPR-associated proteins. Rapamycin is required for forming the fusion complex, thereby activating the CRISPR-associated proteins (see, e.g., Zetsche et al., "A split-Cas9 architecture for inducible genome editing and transcription modulation," *Nature Biotech.* 33:2:139-42, 2015).

Furthermore, expression of the CRISPR-associated proteins can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless et al., "Direct and specific chemical control of eukaryotic translation with a synthetic RNA-protein interaction," Nucl. Acids Res. 40:9: e64-e64, 2012).

Various embodiments of inducible CRISPR-associated proteins and inducible CRISPR systems are described, e.g., in U.S. Pat. No. 8,871,445, US Publication No. 2016/0208243, and International Publication No. WO 2016/205764, each of which is incorporated herein by reference in its entirety.

In some embodiments, the CRISPR-associated proteins include at least one (e.g., 1, 2, 3, 4, 5, 6, 7, 8, 9, or 10) Nuclear Localization Signal (NLS) attached to the N-terminal or C-terminal of the protein. Non-limiting examples of NLSs include an NLS sequence derived from: the NLS of the SV40 virus large T-antigen, having the amino acid sequence PKKKRKV (SEQ ID NO: 77); the NLS from nucleoplasmin (e.g., the nucleoplasmin bipartite NLS with the sequence KRPAATKKAGQAKKKK (SEQ ID NO. 78)); the c-myc NLS having the amino acid sequence PAAKRVKLD (SEQ ID NO: 79) or RQRRNELKRSP (SEQ ID NO: 80); the hRNPA1 M9 NLS having the sequence NQSSNFGPMKGGNFGGRSS GPYGGGGQYFAK-PRNQGGY (SEQ ID NO: 81); the sequence RMRIZFKNKGKDTAELRRRRVEVSVELRK AKKD-EQILKRRNV (SEQ ID NO: 82) of the IBB domain from importin-alpha; the sequences VSRKRPRP (SEQ ID NO: 83) and PPKKARED (SEQ ID NO: 84) of the myoma T protein; the sequence PQPKKKPL (SEQ ID NO: 85) of human p53; the sequence SALIKKKKKMAP (SEQ ID NO: 86) of mouse c-abl IV; the sequences DRLRR (SEQ ID NO: 87) and PKQKKRK (SEQ ID NO: 88) of the influenza virus NSI; the sequence RKLKKKIKKL (SEQ ID NO: 89) of the Hepatitis virus delta antigen; the sequence REKKKFLKRR (SEQ ID NO: 90) of the mouse Mx1 protein; the sequence KRKGDEVDGVDEVAKKKSKK (SEQ ID NO: 91) of the human poly(ADP-ribose) polymerase; and the sequence RKCLQAGMNLEARKTKK (SEQ ID NO: 92) of the human glucocorticoid receptor. In some embodiments, the CRISPR-associated protein comprises at least one (e.g., 1, 2, 3, 4, 5, 6, 7, 8, 9, or 10) Nuclear Export Signal (NES) attached the N-terminal or C-terminal of the protein. In a preferred embodiment a C-terminal and/or N-terminal NLS or NES is attached for optimal expression and nuclear targeting in eukaryotic cells, e.g., human cells.

In some embodiments, the CRISPR-associated proteins described herein are mutated at one or more amino acid residues to alter one or more functional activities.

For example, in some embodiments, the CRISPR-associated protein is mutated at one or more amino acid residues to alter its helicase activity.

In some embodiments, the CRISPR-associated protein is mutated at one or more amino acid residues to alter its nuclease activity (e.g., endonuclease activity or exonuclease activity).

In some embodiments, the CRISPR-associated protein is mutated at one or more amino acid residues to alter its ability to functionally associate with a guide RNA.

In some embodiments, the CRISPR-associated protein is mutated at one or more amino acid residues to alter its ability to functionally associate with a target nucleic acid.

In some embodiments, the CRISPR-associated proteins described herein are capable of cleaving a target RNA molecule.

In some embodiments, the CRISPR-associated protein is mutated at one or more amino acid residues to alter its cleaving activity. For example, in some embodiments, the CRISPR-associated protein may comprise one or more mutations that render the enzyme incapable of cleaving a target nucleic acid.

In some embodiments, the CRISPR-associated protein is capable of cleaving the strand of the target nucleic acid that is complementary to the strand to which the guide RNA hybridizes.

In some embodiments, a CRISPR-associated protein described herein can be engineered to have a deletion in one or more amino acid residues to reduce the size of the enzyme while retaining one or more desired functional activities (e.g., nuclease activity and the ability to interact functionally with a guide RNA). The truncated CRISPR-associated protein can be advantageously used in combination with delivery systems having load limitations.

In some embodiments, the CRISPR-associated proteins described herein can be fused to one or more peptide tags, including a His-tag, GST-tag, a V5-tag, FLAG-tag, HA-tag, VSV-G-tag, Trx-tag, or myc-tag.

In some embodiments, the CRISPR-associated proteins described herein can be fused to a detectable moiety such as GST, a fluorescent protein (e.g., GFP, HcRed, DsRed, CFP, YFP, or BFP), or an enzyme (such as HRP or CAT).

In some embodiments, the CRISPR-associated proteins described herein can be fused to MBP, LexA DNA binding domain, or Gal4 DNA-binding domain.

In some embodiments, the CRISPR-associated proteins described herein can be linked to or conjugated with a detectable label such as a fluorescent dye, including FITC and DAPI.

In any of the embodiments herein, the linkage between the CRISPR-associated proteins described herein and the other moiety can be at the N- or C-terminal of the CRISPR-associated proteins, and sometimes even internally via covalent chemical bonds. The linkage can be effected by any chemical linkage known in the art, such as peptide linkage, linkage through the side chain of amino acids such as D, E, S, T, or amino acid derivatives (Ahx, β-Ala, GABA or Ava), or PEG linkage.

3. Polynucleotides

The invention also provides nucleic acids encoding the proteins and guide RNAs (e.g., a crRNA) described herein (e.g., a CRISPR-associated protein or an accessory protein).

In some embodiments, the nucleic acid is a synthetic nucleic acid. In some embodiments, the nucleic acid is a DNA molecule. In some embodiments, the nucleic acid is an RNA molecule (e.g., an mRNA molecule encoding the Cas, derivative or functional fragment thereof). In some embodiments, the mRNA is capped, polyadenylated, substituted with 5-methyl cytidine, substituted with pseudouridine, or a combination thereof.

In some embodiments, the nucleic acid (e.g., DNA) is operably linked to a regulatory element (e.g., a promoter) in order to control the expression of the nucleic acid. In some embodiments, the promoter is a constitutive promoter. In some embodiments, the promoter is an inducible promoter. In some embodiments, the promoter is a cell-specific promoter. In some embodiments, the promoter is an organism-specific promoter.

Suitable promoters are known in the art and include, for example, a pol I promoter, a pol II promoter, a pol III promoter, a T7 promoter, a U6 promoter, a H1 promoter, retroviral Rous sarcoma virus LTR promoter, a cytomegalovirus (CMV) promoter, a SV40 promoter, a dihydrofolate reductase promoter, and a β-actin promoter. For example, a U6 promoter can be used to regulate the expression of a guide RNA molecule described herein.

In some embodiments, the nucleic acid(s) are present in a vector (e.g., a viral vector or a phage). The vector can be a cloning vector, or an expression vector. The vectors can be plasmids, phagemids, Cosmids, etc. The vectors may include one or more regulatory elements that allow for the propagation of the vector in a cell of interest (e.g., a bacterial cell or a mammalian cell). In some embodiments, the vector includes a nucleic acid encoding a single component of a CRISPR-associated (Cas) system described herein. In some embodiments, the vector includes multiple nucleic acids, each encoding a component of a CRISPR-associated (Cas) system described herein.

In one aspect, the present disclosure provides nucleic acid sequences that are at least 50%, 55%, 60%, 65%, 70%, 75%, 80%, 85%, 90%, 91%, 92%, 93%, 94%, 95%, 96%, 97%, 98%, 99%, or 100% identical to the nucleic acid sequences described herein, i.e., nucleic acid sequences encoding the Cas proteins, derivatives, functional fragments, or guide/crRNA, including the DR sequences of SEQ ID NOs: 8-14.

In another aspect, the present disclosure also provides nucleic acid sequences encoding amino acid sequences that are at least 50%, 55%, 60%, 65%, 70%, 75%, 80%, 85%, 90%, 91%, 92%, 93%, 94%, 95%, 96%, 97%, 98%, 99%, or 100% identical to the amino acid sequences described herein, such as SEQ ID NOs: 1-7.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In related embodiments, the invention provides amino acid sequences having at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The proteins described herein (e.g., CRISPR-associated proteins or accessory proteins) can be delivered or used as either nucleic acid molecules or polypeptides.

In certain embodiments, the nucleic acid molecule encoding the CRISPR-associated proteins, derivatives or functional fragments thereof are codon-optimized for expression in a host cell or organism. The host cell may include established cell lines (such as 293T cells) or isolated primary cells. The nucleic acid can be codon optimized for use in any organism of interest, in particular human cells or bacteria. For example, the nucleic acid can be codon-optimized for any prokaryotes (such as E. coli), or any eukaryotes such as human and other non-human eukaryotes including yeast, worm, insect, plants and algae (including food crop, rice, corn, vegetables, fruits, trees, grasses), vertebrate, fish, non-human mammal (e.g., mice, rats, rabbits, dogs, birds (such as chicken), livestock (cow or cattle, pig, horse, sheep, goat etc.), or non-human primates). Codon usage tables are readily available, for example, at the "Codon Usage Database" available at www.kazusa.orjp/codon/, and these tables can be adapted in a number of ways. See Nakamura et al., Nucl. Acids Res. 28:292, 2000 (incorporated herein by reference in its entirety). Computer algorithms for codon optimizing a particular sequence for expression in a particular host cell are also available, such as Gene Forge (Aptagen; Jacobus, Pa.).

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at http://www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a Cas correspond to the most frequently used codon for a particular amino acid.

4. RNA Guides or crRNA

In some embodiments, the CRISPR systems described herein include at least RNA guide (e.g., a gRNA or a crRNA).

The architecture of multiple RNA guides is known in the art (see, e.g., International Publication Nos. WO 2014/093622 and WO 2015/070083, the entire contents of each of which are incorporated herein by reference).

In some embodiments, the CRISPR systems described herein include multiple RNA guides (e.g., one, two, three, four, five, six, seven, eight, or more RNA guides).

In some embodiments, the RNA guide includes a crRNA. In some embodiments, the RNA guide includes a crRNA but not a tracrRNA.

Sequences for guide RNAs from multiple CRISPR systems are generally known in the art, see, for example, Grissa et al. (*Nucleic Acids Res.* 35 (web server issue): W52-7, 2007; Grissa et al., BMC Bioinformatics 8:172, 2007; Grissa el al., Nucleic Acids Res. 36 (web server issue): W145-8, 2008; and Moller and Liang, PeerJ 5: e3788, 2017; the CRISPR database at: crispr.i2bc.paris-saclayfr/crispr/BLAST/CRISPRsBlast.php; and MetaCRAST available at: github.com/molleraj/MetaCRAST). All incorporated herein by reference.

In some embodiments, the crRNA includes a direct repeat (DR) sequence and a spacer sequence. In certain embodiments, the crRNA comprises, consists essentially of, or consists of a direct repeat sequence linked to a guide sequence or spacer sequence, preferably at the 3'-end of the spacer sequence.

In general, the Cas protein forms a complex with the mature crRNA, which spacer sequence directs the complex to a sequence-specific binding with the target RNA that is complementary to the spacer sequence, and/or hybridizes to the spacer sequence. The resulting complex comprises the Cas protein and the mature crRNA bound to the target RNA.

The direct repeat sequences for the Cas13e and Cas13f systems are generally well conserved, especially at the ends, with a GCTG for Cas13e and GCTGT for Cas13f at the 5'-end, reverse complementary to a CAGC for Cas13e and ACAGC for Cas13f at the 3' end. This conservation suggests strong base pairing for an RNA stem-loop structure that potentially interacts with the protein(s) in the locus.

In some embodiments, the direct repeat sequence, when in RNA, comprises the general secondary structure of 5'-S1a-Ba-S2a-L-S2b-Bb-S1b-3', wherein segments S1a and S1b are reverse complement sequences and form a first stem (S1) having 4 nucleotides in Cas13e and 5 nucleotides in Cas13f; segments Ba and Bb do not base pair with each other and form a symmetrical or nearly symmetrical bulge (B), and have 5 nucleotides each in Cas13e, and 5 (Ba) and 4 (Bb) or 6 (Ba) and 5 (Bb) nucleotides respectively in Cas13f; segments S2a and S2b are reverse complement sequences and form a second stem (S2) having 5 base pairs in Cas13e and either 6 or 5 base pairs in Cas13f; and L is an 8-nucleotide loop in Cas13e and a 5-nucleotide loop in Cas13f. See FIG. 2.

In certain embodiments, S1a has a sequence of GCUG in Cas13e and GCUGU in Cas13f.

In certain embodiments, S2a has a sequence of GCCCC in Cas13e and A/G CCUC G/A in Cas13f (wherein the first A or G may be absent).

In some embodiments, the direct repeat sequence comprises or consists of a nucleic acid sequence of SEQ ID NOs: 8-14.

As used herein, "direct repeat sequence" may refer to the DNA coding sequence in the CRISPR locus, or to the RNA encoded by the same in crRNA. Thus when any of SEQ ID NOs: 8-14 is referred to in the context of an RNA molecule, such as crRNA, each T is understood to represent a U.

In some embodiments, the direct repeat sequence comprises or consists of a nucleic acid sequence having up to 1, 2, 3, 4, 5, 6, 7, or 8 nucleotides of deletion, insertion, or substitution of SEQ ID NOs: 8-14. In some embodiments, the direct repeat sequence comprises or consists of a nucleic acid sequence having at least 80%, 85%, 90%, 95%, or 97% of sequence identity with SEQ ID NOs: 8-14 (e.g., due to deletion, insertion, or substitution of nucleotides in SEQ ID NOs: 8-14). In some embodiments, the direct repeat sequence comprises or consists of a nucleic acid sequence that is not identical to any one of SEQ ID NOs: 8-14, but can hybridize with a complement of any one of SEQ ID NOs: 8-14 under stringent hybridization conditions, or can bind to a complement of any one of SEQ ID NOs: 8-14 under physiological conditions.

In certain embodiments, the deletion, insertion, or substitution does not change the overall secondary structure of that of SEQ ID NOs: 8-14 (e.g., the relative locations and/or sizes of the stems and bulges and loop do not significantly deviate from that of the original stems, bulges, and loop). For example, the deletion, insert, or substitution may be in the bulge or loop region so that the overall symmetry of the bulge remains largely the same. The deletion, insertion, or substitution may be in the stems so that the length of the stems do not significantly deviate from that of the original stems (e.g., adding or deleting one base pair in each of the two stems correspond to 4 total base changes).

In certain embodiments, the deletion, insertion, or substitution results in a derivative DR sequence that may have ±1 or 2 base pair(s) in one or both stems (see FIG. 2), have 1, 2, or 3 bases in either or both of the single strands in the bulge, and/or have ±1, 2, 3, or 4 bases in the loop region.

In certain embodiments, any of the above direct repeat sequences that is different from any one of SEQ ID NOs: 8-14 retains the ability to function as a direct repeat sequence in the Cas13e or Cas13f proteins, as the DR sequence of SEQ ID NOs: 8-14.

In some embodiments, the direct repeat sequence comprises or consists of a nucleic acid having a nucleic acid sequence of any one of SEQ ID NOs: 8-14, with a truncation of the initial three, four, five, six, seven, or eight 3' nucleotides.

In some embodiments, the Cas protein comprises the amino acid sequence of SEQ ID NO: 1 and the crRNA comprises a direct repeat sequence, wherein the direct repeat sequence comprises or consists of the nucleic acid sequence of SEQ ID NO: 8.

In some embodiments, the Cas protein comprises the amino acid sequence of SEQ ID NO: 2 and the crRNA comprises a direct repeat sequence, wherein the direct repeat sequence comprises or consists of the nucleic acid sequence of SEQ ID NO: 9.

In some embodiments, the Cas protein comprises the amino acid sequence of SEQ ID NO: 3 and the crRNA comprises a direct repeat sequence, wherein the direct repeat sequence comprises or consists of the nucleic acid sequence of SEQ ID NO: 10.

In some embodiments, the Cas protein comprises the amino acid sequence of SEQ ID NO: 4 and the crRNA comprises a direct repeat sequence, wherein the direct repeat sequence comprises or consists of the nucleic acid sequence of SEQ ID NO: 11.

In some embodiments, the Cas protein comprises the amino acid sequence of SEQ ID NO: 5 and the crRNA comprises a direct repeat sequence, wherein the direct repeat sequence comprises or consists of the nucleic acid sequence of SEQ ID NO: 12.

In some embodiments, the Cas protein comprises the amino acid sequence of SEQ ID NO: 6 and the crRNA comprises a direct repeat sequence, wherein the direct repeat sequence comprises or consists of the nucleic acid sequence of SEQ ID NO: 13.

In some embodiments, the Cas protein comprises the amino acid sequence of SEQ ID NO: 7 and the crRNA comprises a direct repeat sequence, wherein the direct repeat sequence comprises or consists of the nucleic acid sequence of SEQ ID NO: 14.

In classic CRISPR systems, the degree of complementarity between a guide sequence (e.g., a crRNA) and its corresponding target sequence can be about 50%, 60%, 75%, 80%, 85%, 90%, 95%, 97.5%, 99%, or 100%. In some embodiments, the degree of complementarity is 90-100%.

The guide RNAs can be about 5, 10, 11, 12, 13, 14, 15, 16, 17, 18, 19, 20, 21, 22, 23, 24, 25, 26, 27, 28, 29, 30, 35, 40, 45, 50, 75, 100, 125, 150, 175, 200 or more nucleotides in length. For example, for use in a functional Cas13e or Cas13f effector protein, or homologs, orthologs, derivatives, fusions, conjugates, or functional fragment thereof, the spacer can be between 10-60 nucleotides, 20-50 nucleotides, 25-45 nucleotides, 25-35 nucleotides, or about 27, 28, 29, 30, 31, 32, or 33 nucleotides. For use in dCas version of any of the above, however, the spacer can be between 10-200 nucleotides, 20-150 nucleotides, 25-100 nucleotides, 25-85 nucleotides, 35-75 nucleotides, 45-60 nucleotides, or about 46, 47, 48, 49, 50, 51, 52, 53, 54, or 55 nucleotides.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required, provided there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5'-ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Type VI CRISPR-Cas effectors have been demonstrated to employ more than one RNA guide, thus enabling the ability of these effectors, and systems and complexes that include them, to target multiple nucleic acids. In some embodiments, the CRISPR systems described herein include multiple RNA guides (e.g., two, three, four, five, six, seven, eight, nine, ten, fifteen, twenty, thirty, forty, or more) RNA guides. In some embodiments, the CRISPR systems described herein include a single RNA strand or a nucleic acid encoding a single RNA strand, wherein the RNA guides are arranged in tandem. The single RNA strand can include multiple copies of the same RNA guide, multiple copies of distinct RNA guides, or combinations thereof. The processing capability of the Type VI-E and VI-F CRISPR-Cas effector proteins described herein enables these effectors to be able to target multiple target nucleic acids (e.g., target RNAs) without a loss of activity. In some embodiments, the Type VI-E and VI-F CRISPR-Cas effector proteins may be delivered in complex with multiple RNA guides directed to different target RNA. In some embodiments, the Type VI-E and VI-F CRISPR-Cas effector proteins may be co-delivered with multiple RNA guides, each specific for a different target nucleic acid. Methods of multiplexing using CRISPR-associated proteins are described, for example, in U.S. Pat. No. 9,790,490 B2, and EP 3009511 B1, the entire contents of each of which are expressly incorporated herein by reference.

The spacer length of crRNAs can range from about 10-60 nucleotides, such as 15-50 nucleotides, 20-50 nucleotides, 25-50 nucleotide, or 19-50 nucleotides. In some embodiments, the spacer length of a guide RNA is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides (e.g., 15, 16, or 17 nucleotides), from 17 to 20 nucleotides (e.g., 17, 18, 19, or 20 nucleotides), from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 36, 37, 38, 39, 40, 41, 42, 43, 44, or 45 nucleotides), from 30 or 35 to 40 nucleotides, from 41 to 45 nucleotides, from 45 to 50 nucleotides (e.g., 45, 46, 47, 48, 49, or 50 nucleotides), or longer. In some embodiments, the spacer length is from about 15 to about 42 nucleotides.

In some embodiments, the direct repeat length of the guide RNA is 15-36 nucleotides, is at least 16 nucleotides, is from 16 to 20 nucleotides (e.g., 16, 17, 18, 19, or 20 nucleotides), is from 20-30 nucleotides (e.g., 20, 21, 22, 23, 24, 25, 26, 27, 28, 29, or 30 nucleotides), is from 30-40 nucleotides (e.g., 30, 31, 32, 33, 34, 35, 36, 37, 38, 39, or 40 nucleotides), or is about 36 nucleotides (e.g., 33, 34, 35, 36, 37, 38, or 39 nucleotides). In some embodiments, the direct repeat length of the guide RNA is 36 nucleotides.

In some embodiments, the overall length of the crRNA/guide RNA is about 36 nucleotides longer than any one of the spacer sequence length described herein above. For example, the overall length of the crRNA/guide RNA may be between 45-86 nucleotides, or 60-86 nucleotides, 62-86 nucleotides, or 63-86 nucleotides.

The crRNA sequences can be modified in a manner that allows for formation of a complex between the crRNA and CRISPR-associated protein and successful binding to the target, while at the same time not allowing for successful nuclease activity (i.e., without nuclease activity/without causing indels). These modified guide sequences are referred to as "dead crRNAs," "dead guides," or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50%, shorter than respective guide RNAs that have nuclease activity. Dead guide sequences of guide RNAs can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR-associated protein as described herein, and a crRNA, wherein the crRNA comprises a dead crRNA sequence whereby the crRNA is capable of hybridizing to a target sequence such that the CRISPR system is directed to a genomic locus of interest in a cell without detectable nuclease activity (e.g., RNase activity).

A detailed description of dead guides is described, e.g., in International Publication No. WO 2016/094872, which is incorporated herein by reference in its entirety.

Guide RNAs (e.g., crRNAs) can be generated as components of inducible systems. The inducible nature of the systems allows for spatio-temporal control of gene editing or gene expression. In some embodiments, the stimuli for the inducible systems include, e.g., electromagnetic radiation, sound energy, chemical energy, and/or thermal energy.

In some embodiments, the transcription of guide RNA (e.g., crRNA) can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in the entirety.

Chemical modifications can be applied to the crRNA's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.*, 24, pp. 374-387, 2014); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," *J. Med. Chem.* 48.4: 901-904, 2005). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," Front. Genet., 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized crRNA molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the crRNA includes one or more phosphorothioate modifications. In some embodiments, the crRNA includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biolechnol.* 233:74-83, 2016; WO 2016205764; and U.S. Pat. No. 8,795,965 B2; each which is incorporated by reference in its entirety.

The sequences and the lengths of the RNA guides (e.g., crRNAs) described herein can be optimized. In some embodiments, the optimized length of an RNA guide can be determined by identifying the processed form of crRNA (i.e., a mature crRNA), or by empirical length studies for crRNA tetraloops.

The crRNAs can also include one or more aptamer sequences. Aptamers are oligonucleotide or peptide molecules have a specific three-dimensional structure and can bind to a specific target molecule. The aptamers can be specific to gene effectors, gene activators, or gene repressors. In some embodiments, the aptamers can be specific to a protein, which in turn is specific to and recruits and/or binds to specific gene effectors, gene activators, or gene repressors. The effectors, activators, or repressors can be present in the form of fusion proteins. In some embodiments, the guide RNA has two or more aptamer sequences that are specific to the same adaptor proteins. In some embodiments, the two or more aptamer sequences are specific to different adaptor proteins. The adaptor proteins can include, e.g., MS2, PP7, Q0, F2, GA, fr, JP501, M12, R17, BZ13, JP34, JP500, KU1, M11, MX1, TW18, VK, SP, FI, ID2, NL95, TW19, AP205, φkCb5, φkCb8r, φkCb12r, φkCb23r, 7s, and PRR1. Accordingly, in some embodiments, the aptamer is selected from binding proteins specifically binding any one of the adaptor proteins as described herein. In some embodiments, the aptamer sequence is a MS2 binding loop (5'-ggcccAACAUGAGGAUCACC-CAUGUCUGCAGgggcc-3' (SEQ ID NO: 93)). In some embodiments, the aptamer sequence is a QBeta binding loop (5'-ggcccAUGCUGUCUAAGACAGCAUgggcc-3' (SEQ ID NO: 94)). In some embodiments, the aptamer sequence is a PP7 binding loop (5'-ggcccUAAGGGUUUAUAUG-GAAACCCUUAgggcc-3' (SEQ ID NO: 95). A detailed description of aptamers can be found, e.g., in Nowak et al., "Guide RNA engineering for versatile Cas9 functionality," *Nucl. Acid. Res.*, 44(20):9555-9564, 2016; and WO 2016205764, which are incorporated herein by reference in their entirety.

In certain embodiments, the methods make use of chemically modified guide RNAs. Examples of guide RNA chemical modifications include, without limitation, incorporation of 2'-O-methyl (M), 2'-O-methyl 3'-phosphorothioate (MS), or 2'-O-methyl 3'-thioPACE (MSP) at one or more terminal nucleotides. Such chemically modified guide RNAs can comprise increased stability and increased activity as compared to unmodified guide RNAs, though on-target vs. off-target specificity is not predictable. See, Hendel, *Nat Biotechnol.* 33(9):985-9, 2015, incorporated by reference). Chemically modified guide RNAs may further include, without limitation, RNAs with phosphorothioate linkages and locked nucleic acid (LNA) nucleotides comprising a methylene bridge between the 2' and 4' carbons of the ribose ring.

The invention also encompasses methods for delivering multiple nucleic acid components, wherein each nucleic acid component is specific for a different target locus of interest thereby modifying multiple target loci of interest. The nucleic acid component of the complex may comprise one or more protein-binding RNA aptamers. The one or more aptamers may be capable of binding a bacteriophage coat protein. The bacteriophage coat protein may be selected from the group comprising Qβ, F2, GA, fr, JP501, MS2, M12, R17, BZ13, JP34, JP500, KU1, M11, MX1, TW18, VK, SP, F1, ID2, NL95, TW19, AP205, φCb5, φCb8r, φCb12r, φCb23r, 7s and PRR1. In certain embodiments, the bacteriophage coat protein is MS2.

5. Target RNA

The target RNA can be any RNA molecule of interest, including naturally-occurring and engineered RNA molecules. The target RNA can be an mRNA, a tRNA, a ribosomal RNA (rRNA), a microRNA (miRNA), an interfering RNA (siRNA), a ribozyme, a riboswitch, a satellite RNA, a microswitch, a microzyme, or a viral RNA.

In some embodiments, the target nucleic acid is associated with a condition or disease (e.g., an infectious disease or a cancer).

Thus, in some embodiments, the systems described herein can be used to treat a condition or disease by targeting these nucleic acids. For instance, the target nucleic acid associated with a condition or disease may be an RNA molecule that is overexpressed in a diseased cell (e.g., a cancer or tumor cell). The target nucleic acid may also be a toxic RNA and/or a mutated RNA (e.g., an mRNA molecule having a splicing defect or a mutation). The target nucleic acid may also be an RNA that is specific for a particular microorganism (e.g., a pathogenic bacteria).

6. Complex and Cell

One aspect of the invention provides a CRISPR/Cas13e or CRISPR/Cas13f complex comprising (1) any of the Cas13e/Cas13f effector proteins, homologs, orthologs, fusions, derivative, conjugates, or functional fragments thereof as described herein, and (2) any of the guide RNA described herein, each including a spacer sequence designed to be at least partially complementary to a target RNA, and a DR sequence compatible with the Cas13e/Cas13f effector proteins, homologs, orthologs, fusions, derivatives, conjugates, or functional fragments thereof.

In certain embodiments, the complex further comprises the target RNA bound by the guide RNA.

In certain embodiments, the complex is not naturally existing/occurring. For example, at least one of the components of the complex is not naturally existing/occurring. In certain embodiments, the Cas13e/Cas13f effector protein, homolog, ortholog, fusion, derivative, conjugate, or functional fragment thereof is not naturally occurring/existing due to, for example, the existence of at least one amino acid mutation (deletion, insertion, and/or substitution) as compared to a wild-type protein. In certain embodiments, the DR sequence is not naturally occurring/existing, i.e., not any one of SEQ ID NOs. 8-14, due to, for example, addition, deletion, and/or substitution of at least one nucleotide base in the wild-type sequence. In certain embodiments, the spacer sequence is not naturally occurring, in that it is not present or encoded by any spacer sequences present in the wild-type CRISPR locus of a prokaryote in which the subject Cas13e or Cas13f exists. The spacer sequence may be not naturally existing when it is not 100% complementary to a naturally-occurring bacterialphage nucleic acid.

In a related aspect, the invention also provides a cell comprising any of the complex of the invention.

In certain embodiments, the cell is a prokaryote.

In certain embodiments, the cell is a eukaryote. When the cell is a eukaryote, the complex in the eukaryotic cell can be a naturally existing Cas13e/Cas13f complex in a prokaryote from which the Cas13e/Cas13f is isolated.

7. Methods of Using CRISPR Systems

The CRISPR systems described herein have a wide variety of utilities including modifying (e.g., deleting, inserting, translocating, inactivating, or activating) a target polynucleotide or nucleic acid in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), controlling interfering RNA or miRNA, detecting circulating tumor DNA, preparing next generation library, drug screening, disease diagnosis and prognosis, and treating various genetic disorders.

DNA/RNA Detection

In one aspect, the CRISPR systems described herein can be used in DNA or RNA detection. As shown in the examples, the Cas13e and Cas13f proteins of the invention exhibit non-specific/collateral RNase activity upon activation of its guide RNA-dependent specific RNase activity when the spacer sequence is about 30 nucleotides. Thus the CRISPR-associated proteins of the invention can be reprogrammed with CRISPR RNAs (crRNAs) to provide a platform for specific RNA sensing. By choosing specific spacer sequence length, and upon recognition of its RNA target, activated CRISPR-associated proteins engage in "collateral" cleavage of nearby non-targeted RNAs. This crRNA-programmed collateral cleavage activity allows the CRISPR systems to detect the presence of a specific RNA by triggering programmed cell death or by nonspecific degradation of labeled RNA.

The SHERLOCK method (Specific High Sensitivity Enzymatic Reporter UnLOCKing) provides an in vitro nucleic acid detection platform with attomolar sensitivity based on nucleic acid amplification and collateral cleavage of a reporter RNA, allowing for real-time detection of the target. To achieve signal detection, the detection can be combined with different isothermal amplification steps. For example, recombinase polymerase amplification (RPA) can be coupled with T7 transcription to convert amplified DNA to RNA for subsequent detection. The combination of amplification by RPA, T7 RNA polymerase transcription of amplified DNA to RNA, and detection of target RNA by collateral RNA cleavage-mediated release of reporter signal is referred as SHERLOCK. Methods of using CRISPR in SHERLOCK are described in detail, e.g., in Gootenberg, et al. "Nucleic acid detection with CRISPR-Cas13a/C2c2," Science, 2017 Apr. 28; 356(6336):438-442, which is incorporated herein by reference in its entirety.

The CRISPR-associated proteins can be used in Northern blot assays, which use electrophoresis to separate RNA samples by size. The CRISPR-associated proteins can be used to specifically bind and detect the target RNA sequence. The CRISPR-associated proteins can also be fused to a fluorescent protein (e.g., GFP) and used to track RNA localization in living cells. More particularly, the CRISPR-associated proteins can be inactivated in that they no longer cleave RNAs as described above. Thus, CRISPR-associated proteins can be used to determine the localization of the RNA or specific splice variants, the level of mRNA transcripts, up- or down-regulation of transcripts and disease-specific diagnosis. The CRISPR-associated proteins can be used for visualization of RNA in (living) cells using, for example, fluorescent microscopy or flow cytometry, such as fluorescence-activated cell sorting (FACS), which allows for high-throughput screening of cells and recovery of living cells following cell sorting. A detailed description regarding how to detect DNA and RNA can be found, e.g., in International Publication No. WO 2017/070605, which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," Science, 2015 Apr. 24; 348(6233):aaa6090, which is incorporated herein by reference herein in its entirety.

In some embodiments, the CRISPR systems described herein can be used to detect a target RNA in a sample (e.g., a clinical sample, a cell, or a cell lysate). The collateral RNase activity of the Type VI-E and/or VI-F CRISPR-Cas effector proteins described herein is activated when the effector proteins bind to a target nucleic acid when the spacer sequence is of a specific chosen length (such as about 30 nucleotides). Upon binding to the target RNA of interest, the effector protein cleaves a labeled detector RNA to generate a signal (e.g., an increased signal or a decreased signal) thereby allowing for the qualitative and quantitative detection of the target RNA in the sample. The specific detection and quantification of RNA in the sample allows for a multitude of applications including diagnostics. In some embodiments, the methods include contacting a sample with: i) an RNA guide (e.g., crRNA) and/or a nucleic acid encoding the RNA guide, wherein the RNA guide consists of a direct repeat sequence and a spacer sequence capable of hybridizing to the target RNA; (ii) a Type VI-E or VI-F CRISPR-Cas effector protein (Cas13e or Cas13f) and/or a nucleic acid encoding the effector protein; and (iii) a labeled detector RNA; wherein the effector protein associates with the RNA guide to form a complex; wherein the RNA guide hybridizes to the target RNA; and wherein upon binding of the complex to the target RNA, the effector protein exhibits collateral RNase activity and cleaves the labeled detector RNA; and b) measuring a detectable signal produced by cleavage of the labeled detector RNA, wherein said measuring provides for detection of the single-stranded target RNA in the sample. In some embodiments, the methods further comprise comparing the detectable signal with a reference signal and determining the amount of target RNA in the sample. In some embodiments, the measuring is performed using gold nanoparticle detection, fluorescence polarization, colloid phase transition/dispersion, electrochemical detection, and semiconductor based-sensing. In some embodiments, the labeled detector RNA includes a fluorescence-emitting dye pair, a fluorescence resonance energy transfer (FRET) pair, or a quencher/fluor pair. In some embodiments, upon cleavage of the labeled detector RNA by the effector protein, an amount of detectable signal produced by the labeled detector RNA is decreased or increased. In some embodiments, the labeled detector RNA produces a first detectable signal prior to cleavage by the effector protein and a second detectable signal after cleavage by the effector protein. In some embodiments, a detectable signal is produced when the labeled detector RNA is cleaved by the effector protein. In some embodiments, the labeled detector RNA comprises a modified nucleobase, a modified sugar moiety, a modified nucleic acid linkage, or a combination thereof. In some embodiments, the methods include the multi-channel detection of multiple independent target RNAs in a sample (e.g., two, three, four, five, six, seven, eight, nine, ten, fifteen, twenty, thirty, forty, or more target RNAs) by using multiple Type VI-E and/or VI-F CRISPR-Cas (Cas13e and/or Cas13f) systems, each including a distinct orthologous effector protein and corresponding RNA guides, allowing for the differentiation of multiple target RNAs in the sample. In some embodiments, the methods include the multi-channel detection of multiple independent target RNAs in a sample, with the use of multiple instances of Type VI-E and/or VI-F CRISPR-Cas systems, each containing an orthologous effector protein with differentiable collateral RNase substrates. Methods of detecting an RNA in a sample using CRISPR-associated proteins are described, for example, in U.S. Patent Publication No. 2017/0362644, the entire contents of which are incorporated herein by reference.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The CRISPR-associated proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965, WO 2016205764, and WO 2017070605; each of which is incorporated herein by reference herein in its entirety.

RNA Isolation, Purification, Enrichment, and/or Depletion

The CRISPR systems (e.g., CRISPR-associated proteins) described herein can be used to isolate and/or purify the RNA. The CRISPR-associated proteins can be fused to an affinity tag that can be used to isolate and/or purify the RNA-CRISPR-associated protein complex. These applications are useful, e.g., for the analysis of gene expression profiles in cells.

In some embodiments, the CRISPR-associated proteins can be used to target a specific noncoding RNA (ncRNA) thereby blocking its activity. In some embodiments, the CRISPR-associated proteins can be used to specifically enrich a particular RNA (including but not limited to increasing stability, etc.), or alternatively, to specifically deplete a particular RNA (e.g., particular splice variants, isoforms, etc.).

These methods are described, e.g., in U.S. Pat. No. 8,795,965, WO 2016205764, and WO 2017070605; each of which is incorporated herein by reference herein in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR-associated protein transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," BMC Genomics, 15.1 (2014): 1002, which is incorporated herein by reference in its entirety.

Engineered Microorganisms

Microorganisms (e.g., E. coli, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with, e.g., fusion complexes with the appropriate effectors such as kinases or enzymes.

In some embodiments, crRNAs that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of Saccharomyces cerevisiae," Yeast doi: 10.1002/yea.3278, 2017; and Hlavova et al., "Improving microalgae for biotechnology-from genetics to synthetic biology," Biotechnol. Adv., 33:1194-203, 2015, both of which are incorporated herein by reference in the entirety.

In some embodiments, the CRISPR systems provided herein can be used to induce death or dormancy of a cell (e.g., a microorganism such as an engineered microorganism). These methods can be used to induce dormancy or death of a multitude of cell types including prokaryotic and eukaryotic cells, including, but not limited to mammalian cells (e.g., cancer cells, or tissue culture cells), protozoans, fungal cells, cells infected with a virus, cells infected with an intracellular bacteria, cells infected with an intracellular protozoan, cells infected with a prion, bacteria (e.g., pathogenic and non-pathogenic bacteria), protozoans, and unicellular and multicellular parasites. For instance, in the field of synthetic biology it is highly desirable to have mechanisms of controlling engineered microorganisms (e.g., bacteria) in order to prevent their propagation or dissemination. The systems described herein can be used as "kill-switches" to regulate and/or prevent the propagation or dissemination of an engineered microorganism. Further, there is a need in the art for alternatives to current antibiotic treatments. The systems described herein can also be used in applications where it is desirable to kill or control a specific microbial population (e.g., a bacterial population). For example, the systems described herein may include an RNA guide (e.g., a crRNA) that targets a nucleic acid (e.g., an RNA) that is genus-, species-, or strain-specific, and can be delivered to the cell. Upon complexing and binding to the target nucleic acid, the collateral RNase activity of the Type VI-E and/or VI-F CRISPR-Cas effector proteins is activated leading to the cleavage of non-target RNA within the microorganisms, ultimately resulting in dormancy or death. In some embodiments, the methods comprise contacting the cell with a system described herein including a Type VI-E and/or VI-F CRISPR-Cas effector proteins or a nucleic acid encoding the effector protein, and a RNA guide (e.g., a crRNA) or a nucleic acid encoding the RNA guide, wherein the spacer sequence is complementary to at least 15 nucleotides (e.g., 16, 17, 18, 19, 20, 21, 22, 23, 24, 25, 26, 27, 28, 29, 30, 35, 40, 45, 50 or more nucleotides) of a target nucleic acid (e.g., a genus-, strain-, or species-specific RNA guide). Without wishing to be bound by any particular theory, the cleavage of non-target RNA by the Type VI-E and/or VI-F CRISPR-Cas effector proteins may induce programmed cell death, cell toxicity, apoptosis, necrosis, necroptosis, cell death, cell cycle arrest, cell anergy, a reduction of cell growth, or a reduction in cell proliferation. For example, in bacteria, the cleavage of non-target RNA by the Type VI-E and/or VI-F CRISPR-Cas effector proteins may be bacteriostatic or bactericidal.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," Curr. Opin. Allergy Clin. Immunol. 11(3): 222-8, 2011, and WO 2016205764 A1; both of which are incorporated herein by reference in the entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae*," *Nat. Biotechnol.* 34(1):78-83, 2016, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of guide RNA (gRNA)-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.* 14(3):297-301, 2017, which is incorporated herein by reference in its entirety.

Saturation Mutagenesis (Bashing)

The CRISPR systems described herein can be used for in situ saturating mutagenesis. In some embodiments, a pooled guide RNA library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature* 527(7577): 192-7, 2015, which is incorporated herein by reference in its entirety.

RNA-Related Applications

The CRISPR systems described herein can have various RNA-related applications, e.g., modulating gene expression, degrading a RNA molecule, inhibiting RNA expression, screening RNA or RNA products, determining functions of lincRNA or non-coding RNA, inducing cell dormancy, inducing cell cycle arrest, reducing cell growth and/or cell proliferation, inducing cell anergy, inducing cell apoptosis, inducing cell necrosis, inducing cell death, and/or inducing programmed cell death. A detailed description of these applications can be found, e.g., in WO 2016/205764 A1, which is incorporated herein by reference in its entirety. In different embodiments, the methods described herein can be performed in vitro, in vivo, or ex vivo.

For example, the CRISPR systems described herein can be administered to a subject having a disease or disorder to target and induce cell death in a cell in a diseased state (e.g., cancer cells or cells infected with an infectious agent). For instance, in some embodiments, the CRISPR systems described herein can be used to target and induce cell death in a cancer cell, wherein the cancer cell is from a subject having a Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, or urinary bladder cancer.

Modulating Gene Expression

The CRISPR systems described herein can be used to modulate gene expression. The CRISPR systems can be used, together with suitable guide RNAs, to target gene expression, via control of RNA processing. The control of RNA processing can include, e.g., RNA processing reactions such as RNA splicing (e.g., alternative splicing), viral replication, and tRNA biosynthesis. The RNA targeting proteins in combination with suitable guide RNAs can also be used to control RNA activation (RNAa). RNA activation is a small RNA-guided and Argonaute (Ago)-dependent gene regulation phenomenon in which promoter-targeted short double-stranded RNAs (dsRNAs) induce target gene expression at the transcriptional/epigenetic level. RNAa leads to the promotion of gene expression, so control of gene expression may be achieved that way through disruption or reduction of RNAa. In some embodiments, the methods include the use of the RNA targeting CRISPR as substitutes for e.g., interfering ribonucleic acids (such as siRNAs, shRNAs, or dsRNAs). The methods of modulating gene expression are described, e.g., in WO 2016205764, which is incorporated herein by reference in its entirety.

Controlling RNA Interference

Control over interfering RNAs or microRNAs (miRNA) can help reduce off-target effects by reducing the longevity of the interfering RNAs or miRNAs in vivo or in vitro. In some embodiments, the target RNAs can include interfering RNAs, i.e., RNAs involved in the RNA interference pathway, such as small hairpin RNAs (shRNAs), small interfering (siRNAs), etc. In some embodiments, the target RNAs include, e.g., miRNAs or double stranded RN As (dsRNA).

In some embodiments, if the RNA targeting protein and suitable guide RNAs are selectively expressed (for example spatially or temporally under the control of a regulated promoter, for example a tissue- or cell cycle-specific promoter and/or enhancer), this can be used to protect the cells or systems (in vivo or in vitro) from RNA interference (RNAi) in those cells. This may be useful in neighboring tissues or cells where RNAi is not required or for the purposes of comparison of the cells or tissues where the CRISPR-associated proteins and suitable crRNAs are and are not expressed (i.e., where the RNAi is not controlled and where it is, respectively). The RNA targeting proteins can be used to control or bind to molecules comprising or consisting of RNAs, such as ribozymes, ribosomes, or riboswitches. In some embodiments, the guide RNAs can recruit the RNA targeting proteins to these molecules so that the RNA targeting proteins are able to bind to them. These methods are described, e.g., in WO 2016205764 and WO 2017070605, both of which are incorporated herein by reference in the entirety.

Modifying Riboswitches and Controlling Metabolic Regulations

Riboswitches are regulatory segments of messenger RNAs that bind small molecules and in turn regulate gene expression. This mechanism allows the cell to sense the intracellular concentration of these small molecules. A specific riboswitch typically regulates its adjacent gene by altering the transcription, the translation or the splicing of this gene. Thus, in some embodiments, the riboswitch activity can be controlled by the use of the RNA targeting proteins in combination with suitable guide RNAs to target the riboswitches. This may be achieved through cleavage of, or binding to, the riboswitch. Methods of using CRISPR systems to control riboswitches are described, e.g., in WO 2016205764 and WO 2017070605, both of which are incorporated herein by reference in their entireties.

RNA Modification

In some embodiments, the CRISPR-associated proteins described herein can be fused to a base-editing domain, such as ADAR1, ADAR2, APOBEC, or activation-induced cytidine deaminase (AID), and can be used to modify an RNA sequence (e.g., an mRNA). In some embodiments, the CRISPR-associated protein includes one or more mutations (e.g., in a catalytic domain), which renders the CRISPR-associated protein incapable of cleaving RNA.

In some embodiments, the CRISPR-associated proteins can be used with an RNA-binding fusion polypeptide comprising a base-editing domain (e.g., ADAR1, ADAR2, APOBEC, or AID) fused to an RNA-binding domain, such as MS2 (also known as MS2 coat protein), Qbeta (also known as Qbeta coat protein), or PP7 (also known as PP7 coat protein). The amino acid sequences of the RNA-binding domains MS2, Qbeta, and PP7 are provided below:

```
MS2 (MS2 coat protein)
                                       (SEQ ID NO: 96)
MASNFTQFVLVDNGGTGDVTVAPSNFANGVAEWISSNSRSQAYKVTCSV
RQSSAQKRKYTIKVEVPKVATQTVGGVELPVAAWRSYLNMELTIPIFAT
NSDCELIVKAMQGLLKDGNPIPSAIAANSGIY Qbeta (Qbeta coat protein)
                                       (SEQ ID NO: 97)
MAKLETVTLGNIGKDGKQTLVLNPRGVNPTNGVASLSQAGAVPALEKRV
TVSVSQPSRNRKNYKVQVKIQNPTACTANGSCDPSVTRQAYADVTFSFT
QYSTDEERAFVRTELAALLASPLLIDAIDQLNPAY PP7 (PP7 coat protein)
                                       (SEQ ID NO: 98)
MSKTIVLSVGEATRTLTEIQSTADRQIFEEKVGPLVGRLRLTASLRQNG
AKTAYRVNLKLDQADVVDCSTSVCGELPKVRYTQVWSHDVTIVANSTEA
SRKSLYDLTKSLVVQATSEDLVVNLVPLGR
```

In some embodiments, the RNA binding domain can bind to a specific sequence (e.g., an aptamer sequence) or secondary structure motifs on a crRNA of the system described herein (e.g., when the crRNA is in an effector-crRNA complex), thereby recruiting the RNA binding fusion polypeptide (which has a base-editing domain) to the effector complex. For example, in some embodiments, the CRISPR system includes a CRISPR associated protein, a crRNA having an aptamer sequence (e.g., an MS2 binding loop, a QBeta binding loop, or a PP7 binding loop), and a RNA-binding fusion polypeptide having a base-editing domain fused to an RNA-binding domain that specifically binds to the aptamer sequence. In this system, the CRISPR-associated protein forms a complex with the crRNA having the aptamer sequence. Further the RNA-binding fusion polypeptide binds to the crRNA (via the aptamer sequence) thereby forming a tripartite complex that can modify a target RNA.

Methods of using CRISPR systems for base editing are described, e.g., in International Publication No. WO 2017/219027, which is incorporated herein by reference in its entirety, and in particular with respect to its discussion of RNA modification.

RNA Splicing

In some embodiments, an inactivated CRISPR-associated protein described herein (e.g., a CRISPR associated protein having one or more mutations in a catalytic domain) can be used to target and bind to specific splicing sites on RNA transcripts. Binding of the inactivated CRISPR-associated protein to the RNA may sterically inhibit interaction of the spliceosome with the transcript, enabling alteration in the frequency of generation of specific transcript isoforms. Such method can be used to treat disease through exon skipping such that an exon having a mutation may be skipped in a mature protein. Methods of using CRISPR systems to alter splicing are described, e.g., in International Publication No. WO 2017/219027, which is incorporated herein by reference in its entirety, and in particular with respect to its discussion of RNA splicing.

Therapeutic Applications

The CRISPR systems described herein can have various therapeutic applications. Such applications may be based on one or more of the abilities below, both in vitro and in vivo, of the subject CRISPR/Cas13e or Cas13f systems: induce cellular senescence, induce cell cycle arrest, inhibit cell growth and/or proliferation, induce apoptosis, induce necrosis, etc.

In some embodiments, the new CRISPR systems can be used to treat various diseases and disorders, e.g., genetic disorders (e.g., monogenetic diseases), diseases that can be treated by nuclease activity (e.g., Pcsk9 targeting, Duchenne Muscular Dystrophy (DMD), BCL11a targeting), and various cancers, etc.

In some embodiments, the CRISPR systems described herein can be used to edit a target nucleic acid to modify the target nucleic acid (e.g., by inserting, deleting, or mutating one or more nucleic acid residues). For example, in some embodiments the CRISPR systems described herein comprise an exogenous donor template nucleic acid (e.g., a DNA molecule or a RNA molecule), which comprises a desirable nucleic acid sequence. Upon resolution of a cleavage event induced with the CRISPR system described herein, the molecular machinery of the cell will utilize the exogenous donor template nucleic acid in repairing and/or resolving the cleavage event. Alternatively, the molecular machinery of the cell can utilize an endogenous template in repairing and/or resolving the cleavage event. In some embodiments, the CRISPR systems described herein may be used to alter a target nucleic acid resulting in an insertion, a deletion, and/or a point mutation). In some embodiments, the insertion is a scarless insertion (i.e., the insertion of an intended nucleic acid sequence into a target nucleic acid resulting in no additional unintended nucleic acid sequence upon resolution of the cleavage event). Donor template nucleic acids may be double stranded or single stranded nucleic acid molecules (e.g., DNA or RNA). Methods of designing exogenous donor template nucleic acids are described, for example, in International Publication No. WO 2016/094874 A1, the entire contents of which are expressly incorporated herein by reference.

In one aspect, the CRISPR systems described herein can be used for treating a disease caused by overexpression of RNAs, toxic RNAs, and/or mutated RNAs (e.g., splicing defects or truncations). For example, expression of toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," Hum. Mol. Genet., 2009 Apr. 15; 18(8):1471-81). Myotonic dystrophy (dystrophia myotonica (DM)) is of particular interest to geneticists because it produces an extremely wide range of clinical features. The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain.

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," Cell, 136.4 (2009): 777-793, and WO 2016/205764 A1, both of which are incorporated herein by reference in the entirety. Those of skill in this field will understand how to use the new CRISPR systems to treat these diseases.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne Muscular Dystrophy (DMD), frontotemporal dementia, and Parkinsonism linked to chromosome 17 (FTDP-17), and cystic fibrosis.

The CRISPR systems described herein can further be used for antiviral activity, in particular against RNA viruses. The CRISPR-associated proteins can target the viral RNAs using suitable guide RNAs selected to target viral RNA sequences.

The CRISPR systems described herein can also be used to treat a cancer in a subject (e.g., a human subject). For example, the CRISPR-associated proteins described herein can be programmed with crRNA targeting a RNA molecule that is aberrant (e.g., comprises a point mutation or are alternatively-spliced) and found in cancer cells to induce cell death in the cancer cells (e.g., via apoptosis).

The CRISPR systems described herein can also be used to treat an autoimmune disease or disorder in a subject (e.g., a human subject). For example, the CRISPR-associated proteins described herein can be programmed with crRNA targeting a RNA molecule that is aberrant (e.g., comprises a point mutation or are alternatively-spliced) and found in cells responsible for causing the autoimmune disease or disorder.

Further, the CRISPR systems described herein can also be used to treat an infectious disease in a subject. For example, the CRISPR-associated proteins described herein can be programmed with crRNA targeting a RNA molecule expressed by an infectious agent (e.g., a bacteria, a virus, a parasite or a protozoan) in order to target and induce cell death in the infectious agent cell. The CRISPR systems may also be used to treat diseases where an intracellular infectious agent infects the cells of a host subject. By programming the CRISPR-associated protein to target a RNA molecule encoded by an infectious agent gene, cells infected with the infectious agent can be targeted and cell death induced.

Furthermore, in vitro RNA sensing assays can be used to detect specific RNA substrates. The CRISPR-associated proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S. Pat. No. 8,795,965, EP 3009511, WO 2016205764, and WO 2017070605; each of which is incorporated herein by reference in its entirety.

Cells and Progenies Thereof

In certain embodiments, the methods of the invention can be used to introduce the CRISPR systems described herein into a cell, and cause the cell and/or its progeny to alter the production of one or more cellular produces, such as antibody, starch, ethanol, or any other desired products. Such cells and progenies thereof are within the scope of the invention.

In certain embodiments, the methods and/or the CRISPR systems described herein lead to modification of the translation and/or transcription of one or more RNA products of the cells. For example, the modification may lead to increased transcription/translation/expression of the RNA product. In other embodiments, the modification may lead to decreased transcription/translation/expression of the RNA product.

In certain embodiments, the cell is a prokaryotic cell.

In certain embodiments, the cell is a eukaryotic cell, such as a mammalian cell, including a human cell (a primary human cell or an established human cell line). In certain embodiments, the cell is a non-human mammalian cell, such as a cell from a non-human primate (e.g., monkey), a cow/bull/cattle, sheep, goat, pig, horse, dog, cat, rodent (such as rabbit, mouse, rat, hamster, etc). In certain embodiments, the cell is from fish (such as salmon), bird (such as poultry bird, including chick, duck, goose), reptile, shellfish (e.g., oyster, claim, lobster, shrimp), insect, worm, yeast, etc. In certain embodiments, the cell is from a plant, such as monocot or dicot. In certain embodiment, the plant is a food crop such as barley, cassava, cotton, groundnuts or peanuts, maize, millet, oil palm fruit, potatoes, pulses, rapeseed or canola, rice, rye, sorghum, soybeans, sugar cane, sugar beets, sunflower, and wheat. In certain embodiment, the plant is a cereal (barley, maize, millet, rice, rye, sorghum, and wheat). In certain embodiment, the plant is a tuber (cassava and potatoes). In certain embodiment, the plant is a sugar crop (sugar beets and sugar cane). In certain embodiment, the plant is an oil-bearing crop (soybeans, groundnuts or peanuts, rapeseed or canola, sunflower, and oil palm fruit). In certain embodiment, the plant is a fiber crop (cotton). In certain embodiment, the plant is a tree (such as a peach or a nectarine tree, an apple or pear tree, a nut tree such as almond or walnut or pistachio tree, or a citrus tree, e.g., orange, grapefruit or lemon tree), a grass, a vegetable, a fruit, or an algae. In certain embodiment, the plant is a nightshade plant; a plant of the genus *Brassica*; a plant of the genus *Lactuca*; a plant of the genus *Spinacia*; a plant of the genus *Capsicum*; cotton, tobacco, asparagus, carrot, cabbage, broccoli, cauliflower, tomato, eggplant, pepper, lettuce, spinach, strawberry, blueberry, raspberry, blackberry, grape, coffee, cocoa, etc.

A related aspect provides cells or progenies thereof modified by the methods of the invention using the CRISPR systems described herein.

In certain embodiments, the cell is modified in vitro, in vivo, or ex vivo.

In certain embodiments, the cell is a stem cell.

7. Delivery

Through this disclosure and the knowledge in the art, the CRISPR systems described herein, or any of the components thereof described herein (Cas proteins, derivatives, functional fragments or the various fusions or adducts thereof, and guide RNA/crRNA), nucleic acid molecules thereof, and/or nucleic acid molecules encoding or providing components thereof, can be delivered by various delivery systems such as vectors, e.g., plasmids and viral delivery vectors, using any suitable means in the art. Such methods include (and are not limited to) electroporation, lipofection, microinjection, transfection, sonication, gene gun, etc.

In certain embodiments, the CRISPR-associated proteins and/or any of the RNAs (e.g., guide RNAs or crRNAs) and/or accessory proteins can be delivered using suitable vectors, e.g., plasmids or viral vectors, such as adeno-associated viruses (AAV), lentiviruses, adenoviruses, retroviral vectors, and other viral vectors, or combinations thereof. The proteins and one or more crRNAs can be packaged into one or more vectors, e.g., plasmids or viral vectors. For bacterial applications, the nucleic acids encoding any of the components of the CRISPR systems described herein can be delivered to the bacteria using a phage. Exemplary phages, include, but are not limited to, T4 phage, Mu, X phage, T5 phage, T7 phage, T3 phage, ΦD29, M13, MS2, Qβ, and ΦX174.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose, or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adenoviruses, which can be at a single dose containing at least 1-105 particles (also referred to as particle units, pu) of adenoviruses. In some embodiments, the dose preferably is at least about 1,106 particles, at least about $1 \times 10^7$ particles, at least about $1 \times 10^8$ particles, and at least about $1 \times 10^9$ particles of the adenoviruses. The delivery methods and the doses are described, e.g., in WO 2016205764 A1 and U.S. Pat. No. 8,454,972 B2, both of which are incorporated herein by reference in the entirety.

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR-associated proteins and/or an accessory protein, each operably linked to a promoter (e.g., the same promoter or a different promoter); (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofection formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in delivery RNA.

Further means of introducing one or more components of the new CRISPR systems to the cell is by using cell penetrating peptides (CPP). In some embodiments, a cell penetrating peptide is linked to the CRISPR-associated proteins. In some embodiments, the CRISPR-associated proteins and/or guide RNAs are coupled to one or more CPPs to effectively transport them inside cells (e.g., plant protoplasts). In some embodiments, the CRISPR-associated proteins and/or guide RNA(s) are encoded by one or more circular or non-circular DNA molecules that are coupled to one or more CPPs for cell delivery.

CPPs are short peptides of fewer than 35 amino acids derived either from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin 03 signal peptide sequence, polyarginine peptide Args sequence, Guanine rich-molecular transporters, and sweet arrow peptide. CPPs and methods of using them are described, e.g., in Hällbrink el al., "Prediction of cell-penetrating peptides," *Methods Mol. Biol.*, 2015; 1324:39-58; Ramakrishna et al., "Gene disruption by cell-penetrating peptide-mediated delivery of Cas9 protein and guide RNA," Genome Res., 2014 June; 24(6):1020-7; and WO 2016205764 A1; each of which is incorporated herein by reference in its entirety.

Various delivery methods for the CRISPR systems described herein are also described, e.g., in U.S. Pat. No.

8,795,965, EP 3009511, WO 2016205764, and WO 2017070605; each of which is incorporated herein by reference in its entirety.

8. Kits

Another aspect of the invention provides a kit, comprising any two or more components of the subject CRISPR/Cas system described herein, such as the Cas13e and Cas13f proteins, derivatives, functional fragments or the various fusions or adducts thereof, guide RNA/crRNA, complexes thereof, vectors encompassing the same, or host encompassing the same.

In certain embodiments, the kit further comprise an instruction to use the components encompassed therein, and/or instructions for combining with additional components that may be available elsewhere.

In certain embodiments, the kit further comprise one or more nucleotides, such as nucleotide(s) corresponding to those useful to insert the guide RNA coding sequence into a vector and operably linking the coding sequence to one or more control elements of the vector.

In certain embodiments, the kit further comprise one or more buffers that may be used to dissolve any of the components, and/or to provide suitable reaction conditions for one or more of the components. Such buffers may include one or more of PBS, HEPES, Tris, MOPS, $Na_2CO_3$, $NaHCO_3$, NaB, or combinations thereof. In certain embodiments, the reaction condition includes a proper pH, such as a basic pH. In certain embodiments, the pH is between 7-10.

In certain embodiments, any one or more of the kit components may be stored in a suitable container.

EXAMPLES

Example 1 Identification of Novel Cas13e and Cas13f Systems

A computational pipeline was used to produce an expanded database of class 2 CRISPR-Cas systems from genomic and metagenomic sources. Genome and metagenome sequences were downloaded from NCBI (Benson et al., 2013; Pruitt et al., 2012), NCBI whole genome sequencing (WGS), and DOE JGI Integrated Microbial Genomes (Markowitz et al., 2012). Proteins were predicted (Prodigal (Hyatt el al., 2010) in anon mode) on all contigs at least 5 kb in length, and de-duplicated (i.e., removing identical protein sequences) to construct a complete protein database. Proteins larger than 600 residues were considered as Large Proteins (LPs). Since the currently identified Cas13 proteins are mostly larger than 900 residues in size, in order to reduce the complexity of calculation, only Large Proteins were considered further.

CRISPR arrays were identified using Piler-CR (Edgar, PILER-CR: Fast and accurate identification of CRISPR repeats. *BMC Bioinformatics* 8:18, 2007), using all default parameters. Non-redundant Large Protein sequence-encoding ORFs located within ±10 kb from the CRISPR arrays were grouped into CRISPR-proximal Large Protein encoding clusters, and the encoded LPs were defined as Cas-LPs.

First, BLASP was used to conduct pairwise alignment between the Cas-LPs, and BLASTP alignment results with Evalue<1E-10 were obtained. MCL was then used to further cluster the Cas-LPs based on the BLASTP results to create families of Cas proteins.

Next, BLASTP was used to align Cas-LPs to all LPs and BLASP alignment results with Evalue<1E-10 were obtained. Cas-LPs families were further expanded according to the BLASTP alignment results. The Cas-LP families were obtained for further analysis with no more than double increase after expansion.

For functional characterization of the candidate Cas proteins, protein family databases Pfam (Finn el al., 2014), NR database, and Cas proteins in NCBI were used to annotate the candidate Cas proteins. Multiple sequence alignment was then conducted for each candidate Cas effector proteins using MAFFT (Katoh and Standley, 2013). JPred and HHpred were then used to analyze conserved regions in these proteins, to identify candidate Cas proteins/families having two conserved RXXXXH motifs.

This analysis led to the identification of seven novel Cas13 effector proteins falling within two new Cas13 families different from all previously identified Class 2 CRISPR-Cas systems. These include Cas13e.1 (SEQ ID NO: 1) and Cas13e.2 (SEQ ID NO: 2) of the new Cas13e family, and Cas13f.1 (SEQ ID NO: 3), Cas13f.2 (SEQ ID NO: 4), Cas13f.3 (SEQ ID NO: 5), Cas13f.4 (SEQ ID NO: 6), and Cas13f.5 (SEQ ID NO: 7) of the new Cas13f family.

(SEQ ID NO: 1)
MAQVSKQTSKKRELSIDEYQGARKWCFTIAFNKALVNRDKNDGLEVESLLRHEKYSKHDWYDEDTRALIKCSTQAAN

AKAEALRNYFSHYRHSPGCLIFTAEDELRTIMERAYERAIFECRRRETEVIIEFPSLFEGDRITTAGVVFFVSFFVE

RRVLDRLYGAVSGLKKNEGQYKLIRKALSMYCLKDSRFTKAWDKRVLLFRDILAQLGRIPAEAYEYYHGEQGDKKRA

NDNEGINPKRHKDKFIEFALHYLEAQHSEICFGRRHIVREEAGAGDEHKKHRTKGKVVVDFSKKDEDQSYYISKNNV

IVRIDKNAGPRSYRMGLNELKYLVLLSLQGKGDDAIAKLYRYRQHVENILDVVKVIDKDNHVFLPRFVLEQHGIGRK

AFKQRIDGRVKHVRGVWEKKKAATNEMILHEKARDILQYVNENCIRSENPGEYNRLLVCLVGKDVENFQAGLKRLQL

AERIDGRVYSIFAQTSTINEMHQVVCDQILNRLCRIGDQKLYDYVGLGKKDEIDYKQKVAWFKEHISIRRGFLRKKF

WYDSKKGFAKLVEEHLESGGGQRDVGLDKKYYHIDAIGRFEGANPALYETLARDRLCLMMAQYFLGSVRKELGNKIV

WSNDSIELPVEGSVGNEKSIVFSVSDYGKLYVLDDAEFLGRICEYFMPHEKGKIRYHTVYEKGFRAYNDLQKKCVEA

VLAFEEKVVKAKKMSEKEGAHYIDFREILAQTMCKEAEKTAVNKVRRAFFHHHLKEVIDEFGLFSDVMKKYGIEKEW

KFPVK*

(SEQ ID NO: 2)
MKVENIKEKSKKAMYLINHYEGPKKWCFAIVLNRACDNYEDNPHLFSKSLLEFEKTSRKDWFDEETRELVEQADTEI
QPNPNLKPNITANRKLKDIRNYFSHHYHKNECLYFKNDDPIRCIMEAAYEKSKIYIKGKQIEQSDIPLPELFESSGW
ITPAGILLLASFFVERGILHRLMGNIGGFKDNRGEYGLTHDIFITYCLKGSYSIRAQDHDAVMFRDILGYLSRVPIE
SFQRIKQPQIRKEGQLSERKTDKFITFALNYLEDYGLKDLEGCKACFARSKIVREQENVESINDKEYKPHENKKKVE
IHEDQSKEDRFYINRNNVILKIQKKDGHSNIVRMGVYELKYLVLMSLVGKAKEAVEKIDNYIQDLRDQLPYIEGKNK
EEIKEYVRFFPRFIRSHLGLLQINDEEKIKARLDYVKIKWLDKKEKSKELELHKKGRDILRYINERCDRELNRNVYN
RILELLVSKDLIGFYRELEELKRIRRIDKNIVQNLSGQKTINALHEKVCDLVLKEIESLDTENLRKYLGLIPKEEKE
VIFKEKVDRILKQPVIYKGFLRYQFFKDDKKSFVLLVEDALKEKGGGCDVPLGKEYYKIVSLDKYDKENKTLCETLA
MDRLCLMMARQYYLSLNAKLAQEAQQIEWKKEDSIELIIFILKNPDQSKQSFSIRFSVRDETKLYVTDDPEFLARLC
SYFFPVEKEIEYHKLYSEGINKYTNLQKEGIEAILELEKKLIERNRIQSAKNYLSFNEIMNKSGYNKDEQDDLKKVR
NSLLHYKLIFEKEHLKKFYEVMRGEGIEKKWSLIV*

(SEQ ID NO: 3)
MNGIELKKEEAAFYFNQAELNLKAIEDNIFDKERRKILLNNPQILAKMENFIFNFRDVIKNAKGEIDCLLLKLRELR
NFYSHYVHKRDVRELSKGEKPILEKYYQFAIESIGSENVKLEIIENDAWLADAGVLFFLCIFLKKSQANKLISGISG
FKRNDDIGQPRRNLFTYFSIREGYKVVPEMQKHFLLFSLVNHLSNQDDYIEKAHQPYDIGEGLFFHRIASTFLNISG
ILRNMKFYTYQSKRLVEQRGELKREKDIFAWEEPFQGNSYFEINGHKGVIGEDELKELCYAFLIGNQDANKVEGRIT
QFLEKFRNANSVQQVKDDEMLKPEYFPANYFAESGVGRIKDRVLNRLNKAIKSNKAKKGEIIAYDKMREVMAFINNS
LPVDEKLKPDKYRYLGMVRFWDREKDNIKREFETKEWSKYLPSNFWTAKNLERVYGLAREKNAELFNKLKADVEKM
DERELEKYQKINDAKDLANLRRLASDFGVKWEEKDWDEYSGQIKKQIIDSQKLTIMKQRITAGLKKKHGIENLNLRI
TIDINKSRKAVLNRIAIPRGFVKRHILGWQESEKVSKKIREAECEILLSKEYEELSKQFFQSKDYDKMTRINGLYEK
NKLIALMAVYLMGQLRILFKEHTKLDDITKITVDFKISDKVIVKIPFSNYPSLVYTMSSKYVDNIGNYGFSNKDKDK
PILGKIDVIEKQRMEFIKEVLGFEKYLFDDKIIDKSKFADTATHISFAEIVEELVEKGWDKDRLIKLKDARNKALHG
EILIGTSFDETKSLINELKK*

(SEQ ID NO: 4)
MSPDFIKLEKQEAAFYFNQTELNLKAIESNILDKQQRMILLNNPRILAKVGNFIFNFRDVIKNAKGEIDCLLFKLEE
LRNFYSHYVHIDNVKELSNGEKPLLERYYQIAIQATRSEDVKFELFETRNENKITDAGVLFFLCMFLKKSQANKLIS
GISGFKRNDPIGQPRRNLFTYFSAREGYKALPDMQKHFLLFTLVNYLSNQDEYISELKQYGEIGQGAFFNRIASTFL
NISGISGNIKFYSYQSKRIKEQRGELNSEKDSFEWIEPFQGNSYFEINGHKGVIGEDELKELCYALLVAKQDINAVE
GKIMQFLKKFRNIGNLQQVKDDEMLEIEYFPASYFNESKKEDIKKEILGRLDKKIRSCSAKAEKAYDKMKEVMEFIN
NSLPAEEKLKRKDYRRYLKMVRFWSREKGNIEREFRIKEWSKYFSSDFWRKNNLEDVYKLATQKNAELFKNLKAAAE
KMGETEFEKYQQINDVKDLASLRRLIQDFGLKWEEKDWEEYSEQIKKQITDRQKLTIMKQRVTAELKKKHGIENLNL
RITIDSNKSRKAVLNRIAIPRGFVKKHILGWQGSEKISKNIREAECKILLSKKYEELSRQFFEAGNFDKLIQINGLY
EKNKLTAFMSVYLMGRLNIQLNKHTELGNLKKTEVDFKISDKVIEKIPFSQYPSLVYAMSRKYVDNVDKYKFSHQDK
KKPFLGKIDSIEKERIEFIKEVLDFEEYLFKNKVIDKSKFSDTATHISFKEICDEMGKKGCNRNKLTELNNARNAAL
HGEIPSETSFREAKPLINELKK*

(SEQ ID NO: 5)
MSPDFIKLEKQEAAFYFNQTELNLKAIESNIFDKQQRVILLNNPQILAKVGDFIFNFRDVIKNAKGEIDCLLLKLRE
LRNFYSHYVYTDDVKILSNGERPLLEKYYQFAIEATGSENVKLEIIESNNRLTEAGVLFFLCMFLKKSQANKLISGI
SGFKRNDPIGQPRRNLFTYFSVREGYKVVPDMQKHFLLEVLVNHLSGQDDYIEKAQKPYDIGEGLFFHRIASTFLNI
SGILRNMEFYIYQSKRLKEQQGELKREKDIFPWIEPFQGNSYFEINGNKGIIGEDELKELCYALLVAGKDVRAVEGK
ITQFLEKEKNADNAQQVEKDEMLDRNNFPANYFAESNIGSIKEKILNRLGKIDDSYNKTGTKIKPYDMMKEVMEFIN

-continued

NSLPADEKLKRKDYRRYLKMVRIWDSEKDNIKREFESKEWSKYFSSDFWMAKNLERVYGLAREKNAELFNKLKAVVE

KMDEREFEKYRLINSAEDLASLRRLAKDFGLKWEEKDWQEYSGQIKKQISDRQKLTIMKQRITAELKKKHGIENLNL

RITIDSNKSRKAVLNRIAVPRGFVKEHILGWQGSEKVSKKTREAKCKILLSKEYEELSKQFFQTRNYDKMIQVNGLY

EKNKLLAFMVVYLMERLNILLNKPTELNELEKAEVDFKISDKVMAKIPFSQYPSLVYAMSSKYADSVGSYKFENDEK

NKPFLGKIDTIEKQRMEFIKEVLGFEEYLFEKKIIDKSEFADTATHISFDEICNELIKKGWDKDLIKLKDARNAAL

HGEIPAETSFREAKPLINGLKK*

(SEQ ID NO: 6)

MNIIKLKKEEAAFYFNQTILNLSGLDEIIEKQIPHIISNKENAKKVIDKIFNNRLLLKSVENYIYNFKDVAKNARTE

IEAILLKLVELRNFYSHYVHNDTVKILSNGEKPILEKYYQIAIEATGSKNVKLVIIENNNCLIDSGVLFLLCMFLKK

SQANKLISSVSGFKRNDKEGQPRRNLFTYYSVREGYKVVPDMQKHFLLFALVNHLSEQDDHIEKQQQSDELGKGLFF

HRIASTFLNESGIFNKMQFYTYQSNRLKEKRGELKHEKDIFTWIEPFQGNSYFTLNGHKGVISEDQLKELCYTILIE

KQNVDSLEGKIIQFLKKFQNVSSKQQVDEDELLKREYFPANYFGRAGIGILKEKILNRLDKRMDPISKVIDKAYDKM

IEVMEFINMCLPSDEKLRQKDYRRYLKMVRFWNKEKHNIKREFDSKKWIRFLPTELWNKRNLEEAYQLARKENKKKL

EDMRNQVRSLKENDLEKYQQINYVNDLENLRLLSQELGVKWQEKDWVEYSGQIKKQISDNQKLTIMKQRITAELKKM

HGIENLNLRISIDINKSRQTVMNRIALPKGFVKNHIQQNSSEKISKRIREDYCKIELSGKYEELSRQFFDKKNFDKM

TLINGLCEKNKLIAFMVIYLLERLGFELKEKTKLGELKQTRMTYKISDKVKEDIPLSYYPKLVYAMNRKYVDNIDSY

AFAAYESKKAILDKVDIIEKQRMEFIKQVLCFEEYIFENRIIEKSKENDEETHISFIQIHDELIKKGRDTEKLSKLK

HARNKALHGEIPDGTSFEKAKLLINEIKK*

(SEQ ID NO: 7)

MNAIELKKEEAAFYFNQARLNISGLDEIIEKQLPHIGSNRENAKKTVDMILDNPEVLKKMENYVFNSRDIAKNARGE

LEALLLKLVELRNFYSHYVHKDDVKILSYGEKPLLDKYYEIAIEATGSKDVRLEIIDDKNKLIDAGVLFLLCMFLKK

SEANKLISSIRGFKRNDKEGQPRRNLFTYYSVREGYKVVPDMQKHFLLFTLVNHLSNQDEYISNLRPNQEIGQGGFF

HRIASKFLSDSGILHSMKFYTYRSKRLTEQRGELKPKKDHFTWIEPFQGNSYFSVQGQKGVIGEEQLKELCYVLLVA

REDFRAVEGKVTQFLKKFQNANNVQQVEKDEVLEKEYFPANYFENRDVGRVKDKILNRLKKITESYKAKGREVKAYD

KMKEVMEFINNCLPTDENLKLKDYRRYLKMVRFWGREKENIKREFDSKKWERFLPRELWQKRNLEDAYQLAKEKNTE

LFNKLKTIVERMNELEFEKYQQINDAKDLANLRQLARDFGVKWEEKDWQEYSGQIKKQITDRQKLTIMKQRITAALK

KKQGIENLNLRITTDINKSRKVVLNRIALPKGFVRKHILKTDIKISKQIRQSQCPIILSNNYMKLAKEFFEERNFDK

MIQINGLFEKNVLIAFMIVYLMEQLNLRLGKNTELSNLKKTEVNFTITDKVIEKVQISQYPSLVFAINREYVDGISG

YKLPPKKPKEPPYIFFEKIDAIEKERMEFIKQVLGFEEHLFEKNVIDKIRFTDTATHISFNEICDELIKKGWDENKI

IKLKDARNAALHGKIPEDTSFDEAKVLINELKK*

DNA encoding the corresponding Direct Repeat (DR) sequences in the respective pre-crRNA sequences are SEQ ID NOs: 8-14, respectively.

(SEQ ID NO: 8)
GCTGGAGCAGCCCCCGATTTGTGGGGTGATTACAGC (SEQ ID NO: 9)
GCTGAAGAAGCCTCCGATTTGAGAGGTGATTACAGC (SEQ ID NO: 10)
GCTGTGATAGACCTCGATTTGTGGGGTAGTAACAGC (SEQ ID NO: 11)
GCTGTGATAGACCTCGATTTGTGGGGTAGTAACAGC (SEQ ID NO: 12)
GCTGTGATAGACCTCGATTTGTGGGGTAGTAACAGC (SEQ ID NO: 13)
GCTGTGATGGGCCTCAATTTGTGGGGAAGTAACAGC (SEQ ID NO: 14)
GCTGTGATAGGCCTCGATTTGTGGGGTAGTAACAGC

Natural (wild-type) DNA coding sequences for Cas13e.1, Cas13e.2, Cas13f.1, Cas13f.2, Cas13f.3, Cas13f.4, and Cas13f.5 proteins are SEQ ID NOs: 15-21, respectively.

(SEQ ID NO: 15)
```
ATGGCGCAAGTGTCAAAGCAGACTTCGAAAAAGAGAGAGTTGTCTATCGATGAATATCAAGGTGCTCGGAAATGGTG
TTTTACGATTGCCTTCAACAAGGCTCTTGTGAATCGAGATAAGAACGACGGGCTTTTTGTCGAGTCGCTGTTACGCC
ATGAAAAGTATTCAAAGCACGACTGGTACGATGAGGATACACGCGCTTTGATCAAGTGTAGCACACAAGCGGCCAAT
GCGAAGGCCGAGGCGTTAAGAAACTATTTCTCCCACTATCGACATTCGCCCGGGTGTCTGACATTTACAGCAGAAGA
TGAGTTGCGGACAATCATGGAAAGGGCGTATGAGCGGGCGATCTTTGAATGCAGGAGACGCGAAACTGAAGTGATCA
TCGAGTTTCCCAGCCTGTTCGAAGGCGACCGGATCACTACGGCGGGGGTTGTGTTTTTCGTTTCGTTCTTTGTTGAA
CGGCGGGTGCTGGATCGTTTGTACGGTGCGGTAAGTGGGCTTAAGAAAAACGAAGGACAGTACAAGCTGACTCGGAA
GGCGCTTTCGATGTATTGCCTGAAAGACAGTCGTTTCACGAAGGCGTGGGACAAACGCGTGCTGCTTTTCAGGGATA
TACTCGCGCAGCTTGGACGCATCCCTGCGGAGGCGTATGAATACTACCACGGAGAGCAGGGCGACAAGAAAAGAGCA
AACGACAATGAGGGGACGAATCCGAAACGCCATAAAGACAAGTTCATCGAGTTTGCACTGCATTATCTGGAGGCGCA
ACACAGTGAGATATGCTTCGGGCGGCGACACATTGTCAGGGAGGAGGCCGGGGCAGGCGACGAACACAAAAAGCACA
GGACCAAAGGCAAGGTAGTTGTCGACTTTTCAAAAAAAGACGAAGATCAGTCATACTATATCAGTAAGAACAATGTT
ATCGTCAGGATTGATAAGAATGCCGGGCCTCGGAGTTATCGCATGGGCTTAACGAATTGAAATACCTTGTATTGCT
TAGCCTTCAGGGAAAGGGCGACGATGCGATTGCAAAACTGTACAGGTATCGGCAGCATGTGGAGAACATTCTGGATG
TAGTGAAGGTCACAGATAAGGATAATCACGTCTTCCTGCCGCGATTTGTGCTGGAGCAACATGGGATTGGCAGGAAA
GCTTTTAAGCAAAGAATAGACGGCAGAGTAAAGCATGTTCGAGGGGTGTGGGAAAAGAAGAAGGCGGCGACCAACGA
GATGACACTTCACGAGAAGGCGCGGGACATTCTTCAATACGTAAATGAAAATTGCACGAGGTCTTTCAATCCCGGCG
AGTACAACCGGCTGCTGGTGTGTCTGGTTGGCAAGGATGTTGAGAATTTTCAGGCGGGACTGAAACGCCTGCAACTG
GCCGAGCGAATCGACGGGCGGGTATATTCAATTTTTGCGCAGACCTCCACAATAAACGAGATGCATCAGGTGGTGTG
TGATCAGATTCTCAACAGACTTTGCCGAATCGGCGATCAGAAGCTCTACGATTATGTGGGGCTTGGGAAGAAGGATG
AAATAGATTACAAGCAGAAGGTTGCATGGTTCAAGGAGCATATTTCTATCCGCAGGGGTTTCTTGCGCAAGAAGTTC
TGGTATGACAGCAAGAAGGGATTCGCGAAGCTTGTGGAAGAGCATTTGGAAAGCGGCGGCGGACAGAGGGACGTTGG
GCTGGATAAAAAGTATTATCATATTGATGCGATTGGGCGATTCGAGGGTGCTAATCCAGCCTTGTATGAAACGCTGG
CGCGAGACCGTTTGTGTCTGATGATGGCGCAATACTTCCTGGGGAGTGTACGCAAGGAATTGGGTAATAAAATTGTG
TGGTCGAATGATAGCATCGAGTTGCCCGTGGAGGGCTCAGTGGGTAACGAAAAAAGCATCGTCTTCTCAGTGAGTGA
TTACGGCAAGTTATATGTGTTGGATGACGCTGAGTTTCTTGGGCGGATATGTGAGTACTTTATGCCGCACGAAAAAG
GGAAGATACGGTATCATACAGTTTACGAAAAAGGGTTTAGGGCATATAATGATCTGCAGAAGAAATGTGTCGAGGCG
GTGCTGGCGTTTGAAGAGAAGGTTGTCAAAGCCAAAAAGATGAGCGAGAAGGAAGGGGCGCATTATATTGATTTTCG
TGAGATACTGGCACAAACAATGTGTAAAGAGGCGGAGAAGACCGCCGTGAATAAGGTGCGTAGAGCGTTTTTCCATC
ATCATTTAAAGTTTGTGATAGATGAATTTGGGTTGTTTAGTGATGTTATGAAGAAATATGGAATTGAAAAGGAGTGG
AAGTTTCCTGTTAAATGA
```
(SEQ ID NO: 16)
```
ATGAAGGTTGAAAATATTAAAGAAAAAAGCAAAAAAGCAATGTATTTAATCAACCATTATGAGGGACCCAAAAAATG
GTGTTTTGCAATAGTTCTGAATAGGGCATGTGATAATTACGAGGACAATCCACACTTGTTTTCCAAATCACTTTTGG
AATTTGAAAAAACAAGTCGAAAAGATTGGTTTGACGAAGAAACACGAGAGCTTGTTGAGCAAGCAGATACAGAAATA
CAGCCAAATCCTAACCTGAAACCTAATACAACAGCTAACCGAAAACTCAAAGATATAAGAAACTATTTTTCGCATCA
TTATCACAAGAACGAATGCCTGTATTTTAAGAACGATGATCCCATACGCTGCATTATGGAAGCGGCGTATGAAAAAT
CTAAAATTTATATCAAAGGAAAGCAGATTGAGCAAAGCGATATACCATTGCCCGAATTGTTTGAAAGCAGCGGTTGG
ATTACACCGGCGGGGATTTTGTTACTGGCATCCTTTTTTGTTGAACGAGGGATTCTACATCGCTTGATGGGAAATAT
CGGAGGATTTAAAGATAATCGAGGCGAATACGGTCTTACACACGATATTTTTACCACCTATTGTCTTAAGGGTAGTT
ATTCAATTCGGGCGCAGGATCATGATGCGGTAATGTTCAGAGATATTCTCGGCTATCTGTCACGAGTTCCCACTGAG
```

-continued

TCATTTCAGCGTATCAAGCAACCTCAAATACGAAAAGAAGGCCAATTAAGTGAAAGAAAGACGGACAAATTTATAAC

ATTTGCACTAAATTATCTTGAGGATTATGGGCTGAAAGATTTGGAAGGCTGCAAAGCCTGTTTTGCCAGAAGTAAAA

TTGTAAGGGAACAAGAAAATGTTGAAAGCATAAATGATAAGGAATACAAACCTCACGAGAACAAAAAGAAAGTTGAA

ATTCACTTCGATCAGAGCAAAGAAGACCGATTTTATATTAATCGCAATAACGTTATTTTGAAGATTCAGAAGAAAGA

TGGACATTCCAACATAGTTAGGATGGGAGTATATGAACTTAAATATCTCGTTCTTATGAGTTTAGTGGGAAAAGCAA

AAGAAGCAGTTGAAAAAATTGACAACTATATCCAGGATTTGCGAGACCAGTTGCCTTACATAGAGGGGAAAAATAAG

GAAGAGATTAAAGAATACGTCAGGTTCTTTCCACGATTTATACGTTCTCACCTCGGTTTACTACAGATTAACGATGA

AGAAAAGATAAAAGCTCGATTAGATTATGTTAAGACCAAGTGGTTAGATAAAAAGGAAAAATCGAAAGAGCTTGAAC

TTCATAAAAAAGGACGGGACATCCTCAGGTATATCAACGAGCGATGTGATAGAGAGCTTAACAGGAATGTATATAAC

CGTATTTTAGAGCTCCTGGTCAGCAAAGACCTCACTGGTTTTTATCGTGAGCTTGAAGAACTAAAAAGAACAAGGCG

GATAGATAAAATATTGTCCAGAATCTTTCTGGGCAAAAAACCATTAATGCACTGCATGAAAAGGTCTGTGATCTGG

TGCTGAAGGAAATCGAAAGTCTCGATACAGAAAATCTCAGGAAATATCTTGGATTGATACCCAAAGAAGAAAAAGAG

GTCACTTTCAAAGAAAAGGTCGATAGGATTTTGAAACAGCCAGTTATTTACAAAGGGTTTCTGAGATACCAATTCTT

CAAAGATGACAAAAAGAGTTTTGTCTTACTTGTTGAAGACGCATTGAAGGAAAAAGGAGGAGGTTGTGATGTTCCTC

TTGGGAAAGAGTATTATAAAATCGTGTCACTTGATAAGTATGATAAAGAAAATAAAACCCTGTGTGAAACTCTGGCG

ATGGATAGGCTTTGCCTTATGATGGCAAGACAATATTATCTCAGTCTGAATGCAAAACTTGCACAGGAAGCTCAGCA

AATCGAATGGAAGAAAGAAGATAGTATAGAATTGATTATTTTCACCTTAAAAAATCCCGATCAATCAAAGCAGAGTT

TTTCTATACGGTTTTCGGTCAGAGATTTTACGAAGTTGTATGTAACGGATGATCCTGAATTTCTGGCCCGGCTTTGT

TCCTACTTTTTCCCAGTTGAAAAAGAGATTGAATATCACAAGCTCTATTCAGAAGGGATAAATAAATACACAAACCT

GCAAAAAGAGGGAATCGAAGCAATACTCGAGCTTGAAAAAAAGCTTATTGAACGAAATCGGATTCAATCTGCAAAAA

ATTATCTCTCATTTAATGAGATAATGAATAAAAGCGGTTATAATAAAGATGAGCAGGATGATCTAAAGAAGGTGCGA

AATTCTCTTTTGCATTATAAGCTTATCTTTGAGAAAGAACATCTCAAGAAGTTCTATGAGGTTATGAGAGGAGAAGG

GATAGAGAAAAGTGGTCTTTAATAGTATGA (SEQ ID NO: 17)
ATGAATGGCATTGAATTAAAAAAAGAAGAAGCAGCATTTTATTTTAATCAGGCAGAGCTTAATTTAAAAGCCATAGA

AGACAATATTTTTGATAAAGAAAGACGAAAGACTCTGCTTAATAATCCACAGATACTTGCCAAAATGGAAAATTTCA

TTTTCAATTTCAGAGATGTAACAAAAAATGCAAAAGGGGAAATTGACTGCTTGCTGTTGAAACTAAGAGAGCTGAGA

AACTTTTACTCGCATTATGTCCACAAACGAGATGTAAGAGAATTAAGCAAGGGCGAGAAACCTATACTTGAAAGTA

TTACCAATTTGCGATTGAATCAACCGGAAGTGAAAATGTTAAACTTGAGATAATAGAAAACGACGCGTGGCTTGCAG

ATGCCGGTGTGTTGTTTTTCTTATGTATTTTTTGAAGAAATCTCAGGCAAATAAGCTTATAAGCGGTATCAGCGGT

TTTAAAAGAAACGATGATACCGGTCAGCCGAGAAGGAATTTATTTACCTATTTCAGTATAAGGGAGGGATACAAGGT

TGTTCCGGAAATGCAGAAACATTTCCTTTTGTTTTCTCTTGTTAATCATCTCTAATCAAGATGATTATATTGAAA

AAGCGCATCAGCCATACGATATAGGCGAGGGTTTATTTTTTCATCGAATAGCTTCTACATTTCTTAATATAAGTGGG

ATTTTAAGAAATATGAAATTCTATACCTATCAGAGTAAAAGGTTAGTAGAGCAGCGGGGAGAACTCAAACGAGAAAA

GGATATTTTTGCGTGGAAGAACCGTTTCAAGGAAATAGTTATTTTGAAATAAATGGTCATAAAGGAGTAATCGGTG

AAGATGAATTGAAGGAACTATGTTATGCATTTCTGATTGGCAATCAAGATGCTAATAAAGTGGAAGGCAGGATTACA

CAATTTCTAGAAAAGTTTAGAAATGCGAACAGTGTGCAACAAGTTAAAGATGATGAAATGCTAAAACCAGAGTATTT

TCCTGCAAATTATTTTGCTGAATCAGGCGTCGGAAGAATAAAGGATAGAGTGCTTAATCGTTTGAATAAAGCGATTA

AAAGCAATAAGGCCAAGAAAGGAGAGATTATAGCATACGATAAGATGAGAGAGGTTATGGCGTTCATAAATAATTCT

CTGCCGGTAGATGAAAAATTGAAACCAAAAGATTACAAACGATATCTGGGAATGGTTCGTTTCTGGGACAGGGAAAA

AGATAACATAAAGCGGGAGTTCGAGACAAAAGAATGGTCTAAATATCTTCCATCTAATTTCTGGACGGCAAAAAACC

-continued

```
TTGAAAGGGTCTATGGTCTGGCAAGAGAGAAAAACGCAGAATTATTCAATAAACTAAAAGCGGATGTAGAAAAATG

GACGAACGGGAACTTGAGAAGTATCAGAAGATAAATGATGCAAAGGATTTGGCAAATTTACGCCGGCTTGCAAGCGA

CTTTGGTGTGAAGTGGGAAGAAAAAGACTGGGATGAGTATTCAGGACAGATAAAAAAACAAATTACAGACAGCCAGA

AACTAACAATAATGAAGCAGCGGATAACCGCAGGACTAAAGAAAAAGCACGGCATAGAAAATCTTAACCTGAGAATA

ACTATCGACATCAATAAAAGCAGAAAGGCAGTTTTGAACAGAATTGCGATTCCGAGGGGTTTTGTAAAAAGGCATAT

TTTAGGATGGCAAGAGTCTGAGAAGGTATCGAAAAAGATAAGAGAGGCAGAATGCGAAATTCTGCTGTCGAAAGAAT

ACGAAGAACTATCGAAACAATTTTTCCAAAGCAAAGATTATGACAAAATGACACGGATAAATGGCCTTTATGAAAAA

AACAAACTTATAGCCCTGATGGCAGTTTATCTAATGGGGCAATTGAGAATCCTGTTTAAAGAACACACAAAACTTGA

CGATATTACGAAAACAACTGTGGATTTCAAAATATCTGATAAGGTGACGGTAAAAATCCCCTTTTCAAATTATCCTT

CGCTCGTTTATACAATGTCCAGTAAGTATGTTGATAATATAGGGAATTATGGATTTTCCAACAAAGATAAAGACAAG

CCGATTTTAGGTAAGATTGATGTAATAGAAAAACAGCGAATGGAATTTATAAAGAGGTTCTTGGTTTTGAAAAATA

TCTTTTTGATGATAAAATAATAGATAAAAGCAAATTTGCTGATACAGCGACTCATATAAGTTTTGCAGAAATAGTTG

AGGAGCTTGTTGAAAAAGGATGGGACAAAGACAGACTGACAAAACTTAAAGATGCAAGAAATAAAGCCCTGCATGGT

GAAATACTGACGGGAACCAGCTTTGATGAAACAAAATCATTGATAAACGAATTAAAAAATGA
```

(SEQ ID NO: 18)
```
ATGTCCCCAGATTTCATCAAATTAGAAAAACAGGAAGCAGCTTTTTACTTTAATCAGACAGAGCTTAATTTAAAAGC

CATAGAAAGCAATATTTTAGACAAACAACAGCGAATGATTCTGCTTAATAATCCACGGATACTTGCCAAAGTAGGAA

ATTTCATTTTCAATTTCAGAGATGTAACAAAAAATGCAAAAGGAGAAATAGACTGTCTGCTATTTAAACTGGAAGAG

CTAAGAAACTTTTACTCGCATTATGTTCATACCGACAATGTAAAGGAATTGAGTAACGGAGAAAAACCCCTACTGGA

AAGATATTATCAAATCGCTATTCAGGCAACCAGGAGTGAGGATGTTAAGTTCGAATTGTTTGAAACAAGAAACGAGA

ATAAGATTACGGATGCCGGTGTATTGTTTTTCTTATGTATGTTTTTAAAAAAATCACAGGCAAACAAGCTTATAAGC

GGTATCAGCGGCTTCAAAAGAAATGATCCAACAGGCCAGCCGAGAAGAAACTTATTTACCTATTTCAGTGCAAGAGA

AGGATATAAGGCTTTGCCTGATATGCAGAAACATTTTCTTCTTTTTACTCTGGTTAATTATTTGTCGAATCAGGATG

AGTATATCAGCGAGCTTAAACAATATGGAGAGATTGGTCAAGGAGCCTTTTTTAATCGAATAGCTTCAACATTTTTG

AATATCAGCGGGATTTCAGGAAATACGAAATTCTATTCGTATCAAAGTAAAAGGATAAAAGAGCAGCGAGGCGAACT

CAATAGCGAAAAGGACAGCTTTGAATGGATAGAGCCTTTCCAAGGAAACAGCTATTTTGAAATAAATGGGCATAAAG

GAGTAATCGGCGAAGACGAATTAAAAGAACTTTGTTATGCATTGTTGGTTGCCAAGCAAGATATTAATGCCGTTGAA

GGCAAAATTATGCAATTCCTGAAAAAGTTTAGAAATACTGGCAATTTGCAGCAAGTTAAAGATGATGAAATGCTGGA

AATAGAATATTTTCCCGCAAGTTATTTTAATGAATCAAAAAAAGAGGACATAAAGAAAGAGATTCTTGGCCGGCTGG

ATAAAAAGATTCGCTCCTGCTCTGCAAAGGCAGAAAAAGCCTATGATAAGATGAAAGAGGTGATGGAGTTTATAAAT

AATTCTCTGCCGGCAGAGGAAAAATTGAAACGCAAAGATTATAGAAGATATCTAAAGATGGTTCGTTTCTGGAGCAG

AGAAAAAGGCAATATAGAGCGGGAATTTAGAACAAAGGAATGGTCAAAATATTTTTCATCTGATTTTTGGCGGAAGA

ACAATCTTGAAGATGTGTACAAACTGGCAACACAAAAAAACGCTGAACTGTTCAAAAATCTAAAAGCGGCAGCAGAG

AAAATGGGTGAAACGGAATTTGAAAAGTATCAGCAGATAAACGATGTAAAGGATTTGGCAAGTTTAAGGCGGCTTAC

GCAAGATTTTGGTTTGAAGTGGGAAGAAAAGGACTGGGAGGAGTATTCCGAGCAGATAAAAAAACAAATTACGGACA

GGCAGAAACTGACAATAATGAAACAAAGGGTTACGGCTGAACTAAAGAAAAAGCACGGCATAGAAAATCTTAATCTG

AGAATAACCATCGACAGCAATAAAAGCAGAAAGGCGGTTTTGAACAGAATAGCAATTCCAAGAGGATTTGTAAAAAA

ACATATTTTAGGCTGGCAGGGATCTGAGAAGATATCGAAAAATATAAGGGAAGCAGAATGCAAAATTCTGCTATCGA

AAAAAATATGAAGAGTTATCAAGGCAGTTTTTTGAAGCCGGTAATTTCGATAAGCTGACGCAGATAAATGGTCTTTAT

GAAAAGAATAAACTTACAGCTTTTATGTCAGTATATTTGATGGGTCGGTTGAATATTCAGCTTAATAAGCACACAGA

ACTTGGAAATCTTAAAAAAACAGAGGTGGATTTTAAGATATCTGATAAGGTGACTGAAAAAATACCGTTTTCTCAGT
```

```
ATCCTTCGCTTGTCTATGCGATGTCTCGCAAATATGTTGACAATGTGGATAAATATAAATTTTCTCATCAAGATAAA

AAGAAGCCATTTTTAGGTAAAATTGATTCAATTGAAAAAGAACGTATTGAATTCATAAAAGAGGTTCTCGATTTTGA

AGAGTATCTTTTTAAAAATAAGGTAATAGATAAAAGCAAATTTTCCGATACAGCGACTCATATTAGCTTTAAGGAAA

TATGTGATGAAATGGGTAAAAAAGGATGTAACCGAAACAAACTAACCGAACTTAACAACGCAAGGAACGCAGCCCTG

CATGGTGAAATACCGTCGGAGACCTCTTTTCGTGAAGCAAAACCGTTGATAAATGAATTGAAAAAATGA
```
(SEQ ID NO: 19)
```
ATGTCCCCAGATTTCATCAAATTAGAAAAACAAGAAGCAGCTTTTTACTTTAATCAGACAGAGCTTAATTTAAAAGC

CATAGAAAGCAATATTTTCGACAAACAACAGCGAGTGATTCTGCTTAATAATCCACAGATACTTGCCAAAGTAGGAG

ATTTTATTTTCAATTTCAGAGATGTAACAAAAAACGCAAAAGGAGAAATAGACTGTTTGCTATTGAAACTAAGAGAG

CTGAGAAACTTTTACTCACACTATGTCTATACCGATGACGTGAAGATATTGAGTAACGGCGAAAGACCTCTGCTGGA

AAAATATTATCAATTTGCGATTGAAGCAACCGGAAGTGAAAATGTTAAACTTGAAATAATAGAAAGCAACAACCGAC

TTACGGAAGCGGGCGTGCTGTTTTTCTTGTGTATGTTTTTGAAAAAGTCTCAGGCAAATAAGCTTATAAGCGGTATC

AGCGGTTTTAAAAGAAATGACCCGACAGGTCAGCCGAGAAGGAATTTATTTACCTACTTCAGTGTAAGGGAGGGATA

CAAGGTTGTGCCGGATATGCAGAAACATTTTCTTTTGTTTGTTCTTGTCAATCATCTCTCTGGTCAGGATGATTATA

TTGAAAAGGCGCAAAAGCCATACGATATAGGCGAGGGTTTATTTTTTCATCGAATAGCTTCTACATTTCTTAATATC

AGTGGGATTTTAAGAAATATGGAATTCTATATTTACCAGAGCAAAAGACTAAAGGAGCAGCAAGGAGAGCTCAAACG

TGAAAAGGATATTTTTCCATGGATAGAGCCTTTCCAGGGAAATAGTTATTTTGAAATAAATGGTAATAAAGGAATAA

TCGGCGAAGATGAATTGAAAGAGCTTTGTTATGCGTTGCTGGTTGCAGGAAAAGATGTCAGAGCCGTCGAAGGTAAA

ATAACACAATTTTTGGAAAAGTTTAAAAATGCGGACAATGCTCAGCAAGTTGAAAAAGATGAAATGCTGGACAGAAA

CAATTTTCCCGCCAATTATTTCGCCGAATCGAACATCGGCAGCATAAAGGAAAAAATACTTAATCGTTTGGGAAAAA

CTGATGATAGTTATAATAAGACGGGGACAAAGATTAAACCATACGACATGATGAAAGAGGTAATGGAGTTTATAAAT

AATTCTCTTCCGGCAGATGAAAAATTGAAACGCAAAGATTACAGAAGATATCTAAAGATGGTTCGTATCTGGGACAG

TGAGAAAGATAATATAAAGCGGGAGTTTGAAAGCAAAGAATGGTCAAAATATTTTTCATCTGATTTCTGGATGGCAA

AAAATCTTGAAAGGGTCTATGGGTTGGCAAGAGAGAAAAACGCCGAATTATTCAATAAGCTAAAAGCGGTTGTGGAG

AAAATGGACGAGCGGGAATTTGAGAAGTATCGGCTGATAAATAGCGCAGAGGATTTGGCAAGTTTAAGACGGCTTGC

GAAAGATTTTGGCCTGAAGTGGGAAGAAAAGGACTGGCAAGAGTATTCTGGGCAGATAAAAAAACAAATTTCTGACA

GGCAGAAACTGACAATAATGAAACAAAGGATTACGGCTGAACTAAAGAAAAAGCACGGCATAGAAAATCTCAATCTT

AGAATAACCATCGACAGCAATAAAAGCAGAAAGGCAGTTTTGAACAGAATCGCAGTTCCAAGAGGTTTTGTGAAAGA

GCATATTTTAGGATGGCAGGGGTCTGAGAAGGTATCGAAAAAGACAAGAGAAGCAAAGTGCAAAATTCTGCTCTCGA

AAGAATATGAAGAATTATCAAAGCAATTTTTCCAAACCAGAAATTACGACAAGATGACGCAGGTAAACGGTCTTTAC

GAAAAGAATAAACTCTTAGCATTTATGGTCGTTTATCTTATGGAGCGGTTGAATATCCTGCTTAATAAGCCCACAGA

ACTTAATGAACTTGAAAAAGCAGAGGTGGATTTCAAGATATCTGATAAGGTGATGGCCAAAATCCCGTTTTCACAGT

ATCCTTCGCTTGTGTACGCGATGTCCAGCAAATATGCTGATAGTGTAGGCAGTTATAAATTTGAGAATGATGAAAAA

AACAAGCCGTTTTTAGGCAAGATCGATACAATAGAAAACAACGAATGGAGTTTATAAAAGAAGTCCTTGGTTTTGA

AGAGTATCTTTTTGAAAAGAAGATAATAGATAAAAGCGAATTTGCCGACACAGCGACTCATATAAGTTTTGATGAAA

TATGTAATGAGCTTATTAAAAAAGGATGGGATAAAGACAAACTAACCAAACTTAAAGATGCCAGGAACGCGGCCCTG

CATGGCGAAATACCGGCGGAGACCTCTTTTCGTGAAGCAAAACCGTTGATAAATGGATTGAAAAAATGA
```
(SEQ ID NO: 20)
```
ATGAACATCATTAAATTAAAAAAAGAAGAAGCTGCGTTTTATTTTAATCAGACGATCCTCAATCTTTCAGGGCTTGA

TGAAATTATTGAAAACAAATTCCGCACATAATCAGCAACAAGGAAAATGCAAAGAAAGTGATTGATAAGATTTTCA

ATAACCGCTTATTATTAAAAAGTGTGGAGAATTATATCTACAACTTTAAAGATGTGGCTAAAAACGCAAGAACTGAA
```

-continued

```
ATTGAGGCTATATTGTTGAAATTAGTAGAGCTACGTAATTTTTACTCACATTACGTTCATAATGATACCGTCAAGAT
ACTAAGTAACGGTGAAAAACCTATACTGGAAAAATATTATCAAATTGCTATAGAAGCAACCGGAAGTAAAAATGTTA
AACTTGTAATCATAGAAAACAACAACTGTCTCACGGATTCTGGCGTGCTGTTTTTGCTGTGTATGTTCTTAAAAAA
TCACAGGCAAACAAGCTTATAAGTTCCGTTAGTGGTTTTAAAAGGAATGATAAAGAAGGACAACCGAGAAGAAATCT
ATTCACTTATTATAGTGTGAGGGAGGGATATAAGGTTGTGCCTGATATGCAGAAGCATTTCCTTCTATTCGCTCTGG
TCAATCATCTATCTGAGCAGGATGATCATATTGAGAAGCAGCAGCAGTCAGACGAGCTCGGTAAGGGTTTGTTTTTC
CATCGTATAGCTTCGACTTTTTTAAACGAGAGCGGCATCTTCAATAAAATGCAATTTTATACATATCAGAGCAACAG
GCTAAAAGAGAAAAGAGGAGAACTCAAACACGAAAAGGATACCTTTACATGGATAGAGCCTTTTCAAGGCAATAGTT
ATTTTACGTTAAATGGACATAAGGGAGTGATTAGTGAAGATCAATTGAAGGAGCTTTGTTACACAATTTTAATTGAG
AAGCAAAACGTTGATTCCTTGGAAGGTAAAATTATACAATTTCTCAAAAAATTTCAGAATGTCAGCAGCAAGCAGCA
AGTTGACGAAGATGAATTGCTTAAAAGAGAATATTTCCCTGCAAATTACTTTGGCCGGGCAGGAACAGGGACCCTAA
AAGAAAAGATTCTAAACCGGCTTGATAAGAGGATGGATCCTACATCTAAAGTGACGGATAAAGCTTATGACAAAATG
ATTGAAGTGATGGAATTTATCAATATGTGCCTTCCGTCTGATGAGAAGTTGAGGCAAAAGGATTATAGACGATACTT
AAAGATGGTTCGTTTCTGGAATAAGGAAAAGCATAACATTAAGCGCGAGTTTGACAGTAAAAAATGGACGAGGTTTT
TGCCGACGGAATTGTGGAATAAAAGAAATCTAGAAGAAGCCTATCAATTAGCACGGAAAGAGAACAAAAAGAAACTT
GAAGATATGAGAAATCAAGTACGAAGCCTTAAAGAAAATGACCTTGAAAAATATCAGCAGATTAATTACGTTAATGA
CCTGGAGAATTTAAGGCTTCTGTCACAGGAGTTAGGTGTGAAATGGCAGGAAAAGGACTGGGTTGAATATTCCGGGC
AGATAAAGAAGCAGATATCAGACAATCAGAAACTTACAATCATGAAACAAAGGATTACCGCTGAACTAAAGAAATG
CACGGCATCGAGAATCTTAATCTTAGAATAAGCATTGACACGAATAAAAGCAGGCAGACGGTTATGAACAGGATAGC
TTTGCCCAAAGGTTTTGTGAAGAATCATATCCAGCAAAATTCGTCTGAGAAAATATCGAAAAGAATAAGAGAGGATT
ATTGTAAAATTGAGCTATCGGGAAAATATGAAGAACTTTCAAGGCAATTTTTTGATAAAAAGAATTTCGATAAGATG
ACACTGATAAACGGCCTTTGTGAAAAGAACAAACTTATCGCATTTATGGTTATCTATCTTTTGGAGCGGCTTGGATT
TGAATTAAAGGAGAAACAAAATTAGGCGAGCTTAAACAAACAAGGATGACATATAAAATATCCGATAAGGTAAAAG
AAGATATCCCGCTTTCCTATTACCCCAAGCTTGTGTATGCAATGAACCGAAAATATGTTGACAATATCGATAGTTAT
GCATTTGCGGCTTACGAATCCAAAAAAGCTATTTTGGATAAAGTGGATATCATAGAAAAGCAACGTATGGAATTTAT
CAAACAAGTTCTCTGTTTTGAGGAATATATTTTCGAAAATAGGATTATCGAAAAAGCAAATTTAATGACGAGGAGA
CTCATATAAGTTTTACACAAATACATGATGAGCTTATTAAAAAAGGACGGGACACAGAAAAACTCTCTAAACTCAAA
CATGCAAGGAATAAAGCCTTGCACGGCGAGATTCCTGATGGGACTTCTTTTGAAAAAGCAAAGCTATTGATAAATGA
AATCAAAAAATGA
                                                    (SEQ ID NO: 21)
ATGAATGCTATCGAACTAAAAAAAGAGGAAGCAGCATTTTATTTTAATCAGGCAAGACTCAACATTTCAGGACTTGA
TGAAATTATTGAAAAGCAGTTACCACATATAGGTAGTAACAGGGAGAATGCGAAAAAAACTGTTGATATGATTTTGG
ATAATCCCGAAGTCTTGAAGAAGATGGAAAATTATGTCTTTAACTCACGAGATATAGCAAAGAACGCAAGAGGTGAA
CTTGAAGCATTGTTGTTGAAATTAGTAGAACTGCGTAATTTTTATTCACATTATGTTCATAAAGATGATGTTAAGAC
ATTGAGTTACGGAGAAAAACCTTTACTGGATAAATATTATGAAATTGCGATTGAAGCGACCGGAAGTAAAGATGTCA
GACTTGAGATAATAGATGATAAAAATAAGCTTACAGATGCCGGTGTGCTTTTTTATTGTGTATGTTTTGAAAAAA
TCAGAGGCAAACAAACTTATCAGTTCAATCAGGGGCTTTAAAAGAAACGATAAAGAAGGCCAGCCGAGAAGAAATCT
ATTCACTTACTACAGTGTCAGAGAGGGATATAAGGTTGTGCCTGATATGCAGAAACATTTTCTTTTATTCACACTGG
TTAACCATTTGTCAAATCAGGATGAATACATCAGTAATCTTAGGCCGAATCAAGAAATCGGCCAAGGGGATTTTTC
CATAGAATAGCATCAAAATTTTTGAGCGATAGCGGGATTTTACATAGTATGAAATTCTACACCTACCGGAGTAAAAG
ACTAACAGAACAACGGGGGGAGCTTAAGCCGAAAAAAGATCATTTTACATGGATAGAGCCTTTTCAGGGAAACAGTT
```

-continued

```
ATTTTTCAGTGCAGGGCCAAAAAGGAGTAATTGGTGAAGAGCAATTAAAGGAGCTTTGTTATGTATTGCTGGTTGCC
AGAGAAGATTTTAGGGCCGTTGAGGGCAAAGTTACACAATTTCTGAAAAAGTTTCAGAATGCTAATAACGTACAGCA
AGTTGAAAAGATGAAGTGCTGGAAAAAGAATATTTTCCTGCAAATTATTTTGAAAATCGAGACGTAGGCAGAGTAA
AGGATAAGATACTTAATCGTTTGAAAAAAATCACTGAAAGCTATAAAGCTAAAGGGAGGGAGGTTAAAGCCTATGAC
AAGATGAAAGAGGTAATGGAGTTTATAAATAATTGCCTGCCAACAGATGAAAATTTGAAACTCAAAGATTACAGAAG
ATATCTGAAAATGGTTCGTTTCTGGGGCAGGGAAAAGGAAAATATAAAGCGGGAATTTGACAGTAAAAAATGGGAGA
GGTTTTTGCCAAGAGAACTCTGGCAGAAAAGAAACCTCGAAGATGCGTATCAACTGGCAAAAGAGAAAAACACCGAG
TTATTCAATAAATTGAAAACAACTGTTGAGAGAATGAACGAACTGGAATTCGAAAAGTATCAGCAGATAAACGACGC
AAAAGATTTGGCAAATTTAAGGCAACTGGCGCGGGACTTCGGCGTGAAGTGGGAAGAAAAGGACTGGCAAGAGTATT
CGGGGCAGATAAAAAAACAAATTACAGACAGGCAAAAACTTACAATAATGAAACAAAGGATTACTGCTGCATTGAAG
AAAAAGCAAGGCATAGAAAATCTTAATCTTAGGATAACAACCGACACCAATAAAAGCAGAAAGGTGGTATTGAACAG
AATAGCGCTACCTAAAGGTTTTGTAAGGAAGCATATCTTAAAAACAGATATAAAGATATCAAAGCAAATAAGGCAAT
CACAATGTCCTATTATACTGTCAAACAATTATATGAAGCTGGCAAAGGAATTCTTTGAGGAGAGAAATTTTGATAAG
ATGACGCAGATAAACGGGCTATTTGAGAAAAATGTACTTATAGCGTTTATGATAGTTTATCTGATGGAACAACTGAA
TCTTCGACTTGGTAAGAATACGGAACTTAGCAATCTTAAAAAAACGGAGGTTAATTTTACGATAACCGACAAGGTAA
CGGAAAAAGTCCAGATTTCGCAGTATCCATCGCTTGTTTTCGCCATAAACAGAGAATATGTTGATGGAATCAGCGGT
TATAAGTTACCGCCCAAAAAACCGAAAGAGCCTCCGTATACTTTCTTCGAGAAAATAGACGCAATAGAAAAGAACG
AATGGAATTCATAAAACAGGTCCTCGGTTTCGAAGAACATCTTTTTGAGAAGAATGTAATAGACAAAACTCGCTTTA
CTGATACTGCGACTCATATAAGTTTTAATGAAATATGTGATGAGCTTATAAAAAAAGGATGGGACGAAAACAAATA
ATAAAACTTAAAGATGCGAGGAATGCAGCATTGCATGGTAAGATACCGGAGGATACGTCTTTTGATGAAGCGAAAGT
ACTGATAAATGAATTAAAAAAATGA
```

35

Human codon-optimized coding sequences for the seven Cas13e and Cas13f proteins (i.e., Cas13e.1, Cas13e.2, Cas13f.1, Cas13f.2, Cas13f.3, Cas13f.4 and Cas13f.5), generated for further functional experiments, are SEQ ID NOs: 22-28, respectively.

(SEQ ID NO: 22)
```
ATGGCCCAGGTGAGCAAGCAGACCTCCAAGAAGAGGGAGCTGAGCATCGACGAGTACCAGGGCGCCCGGAAGTGGTG
CTTCACCATTGCCTTCAACAAGGCCCTGGTGAACCGGGACAAGAACGACGGCCTGTTCGTGGAAAGCCTGCTGAGAC
ACGAGAAGTACAGCAAGCACGACTGGTACGACGAAGATACCCGGGCCCTGATCAAGTGCAGCACCCAGGCCGCCAAC
GCCAAGGCTGAAGCCCTGCGGAACTACTTCAGTCACTACCGGCATAGCCCTGGCTGCCTGACCTTCACCGCCGAGGA
CGAACTGCGGACCATCATGGAGAGAGCCTATGAGCGGGCCATCTTCGAGTGCAGAAGAAGAGAGACAGAGGTGATCA
TCGAGTTTCCCAGCCTGTTCGAGGGCGACCGGATCACCACCGCCGGCGTGGTGTTTTCGTGAGCTTTTCGTGGAA
AGAAGAGTGCTGGATCGGCGTGTATGGAGCCGTGTCCGGCCTGAAGAAGAATGAGGGACAGTACAAGCTGACCCGGAA
GGCCCTGAGCATGTACTGCCTGAAGGACAGCAGATTCACCAAGGCCTGGGATAAGCGGGTGCTGCTGTTCAGAGACA
TCCTGGCCCAGCTGGGAAGAATCCCCGCCGAGGCCTACGAGTACTACCACGGCGAGCAGGGTGATAAGAAGAGAGCT
AACGACAATGAGGGCACAAATCCCAAGCGGCACAAGGACAAGTTCATCGAATTTGCACTGCACTACCTGGAAGCCCA
GCACAGCGAGATCTGCTTCGGCAGACGCCACATCGTGCGGGAAGAGGCCGGCGCCGGCGATGAGCACAAGAAGCACC
GGACCAAGGGAAAGGTGGTGGTGGACTTCAGCAAGAAGGACGAGGACCAGAGCTACTATATCTCCAAGAACAACGTG
ATCGTGCGGATCGACAAGAACGCCGGCCCTAGAAGCTACCGGATGGGCCTGAACGAGCTGAAGTACCTCGTGCTGCT
GAGCCTGCAGGGGAAGGGCGACGATGCCATCGCCAAGCTGTACAGATACAGACAGCACGTGGAGAACATCCTGGATG
TGGTGAAGGTGACCGATAAGGATAACCACGTGTTCCTGCCCCGCTTCGTGCTGGAGCAGCACGGCATCGGCAGAAAG
```

-continued

GCCTTCAAGCAGCGGATCGATGGACGGGTGAAGCACGTGCGGGCGTGTGGGAGAAGAAGAAGGCCGCCACCAATGA

AATGACCCTGCACGAGAAGGCCAGAGACATCCTGCAGTACGTGAACGAAAACTGCACCCGGTCCTTCAACCCTGGCG

AATACAACAGACTGCTGGTGTGCCTGGTGGGCAAGGACGTGGAGAACTTTCAGGCCGGCCTGAAGCGGCTGCAGCTG

GCCGAAAGGATCGATGGCCGGGTGTACTCCATCTTCGCCCAGACCAGCACCATCAATGAGATGCACCAGGTGGTGTG

CGACCAGATCCTGAACCGGCTGTGCAGAATCGGCGACCAGAAGCTGTACGATTACGTGGGACTGGGCAAGAAGGACG

AAATCGACTACAAGCAGAAGGTGGCCTGGTTCAAGGAGCACATCAGCATCCGGAGAGGATTCCTGAGAAAGAAGTTC

TGGTACGATAGCAAGAAGGGATTCGCAAAGCTGGTGGAGGAACACCTGGAGTCCGGCGGCGGCCAGCGCGACGTGGG

CCTGGACAAGAAGTACTACCACATCGACGCCATCGGCAGATTCGAGGGCGCCAACCCCGCCCTGTACGAGACCCTGG

CCAGAGATCGGCTGTGCCTCATGATGGCCCAGTACTTCCTGGGCAGCGTGAGAAAGGAACTGGGCAACAAGATTGTG

TGGAGCAACGACAGCATCGAACTGCCTGTGGAAGGCTCTGTGGGAAATGAGAAGAGCATCGTGTTCTCCGTGTCTGA

CTACGGCAAGCTGTACGTGCTGGACGATGCCGAATTCCTGGGCCGGATCTGCGAATACTTCATGCCCCACGAAAAGG

GCAAGATCCGGTACCACACAGTGTACGAAAAGGGCTTTAGAGCATACAACGACCTGCAGAAGAAGTGCGTGGAGGCC

GTGCTGGCTTTCGAAGAGAAGGTGGTGAAGGCCAAGAAGATGAGCGAGAAGGAAGGCGCCCACTACATCGACTTCCG

GGAGATCCTGGCCCAGACCATGTGCAAGGAGGCCGAGAAGACCGCAGTGAACAAGGTGAGACGCGCCTTCTTCCACC

ACCACCTGAAGTTCGTGATTGACGAGTTCGGCCTGTTCAGCGACGTGATGAAGAAGTACGGCATCGAGAAGGAATGG

AAGTTCCCTGTCAAGTAA (SEQ ID NO: 23)
ATGAAGGTGGAGAACATCAAGGAAAAGTCCAAGAAGGCTATGTATCTGATCAACCACTATGAAGGCCCTAAGAAGTG

GTGCTTCGCCATCGTGCTGAATAGGGCCTGCGACAACTATGAGGATAACCCCCACCTGTTCAGCAAGAGCCTGCTGG

AATTTGAAAAGACCAGCAGAAAGGACTGGTTCGACGAGGAGACCAGGGAACTGGTGGAGCAGGCCGACACCGAGATC

CAGCCCAACCCCAACCTGAAGCCTAACACCACCGCCAACAGAAAGCTGAAGGACATCCGGAACTACTTCAGCCACCA

CTACCACAAGAATGAGTGCCTGTACTTCAAGAACGACGACCCTATCCGGTGCATCATGGAGGCAGCCTACGAGAAGT

CCAAGATCTACATCAAGGGCAAGCAGATTGAGCAGTCCGACATCCCCCTCCCTGAGCTGTTTGAGTCTAGCGGCTGG

ATCACCCCAGCCGGCATCCTGCTGCTGGCCAGCTTCTTTGTGGAGAGAGGCATTCTGCACAGACTGATGGGCAACAT

CGGCGGCTTCAAGGACAACCGGGGCGAATACGGACTGACCCACGATATCTTCACCACCTACTGCCTGAAGGGCAGCT

ACTCCATCAGAGCCCAGGACCACGACGCCGTGATGTTCAGAGACATCCTGGGCTACCTGAGCAGAGTGCCGACCGAG

AGCTTTCAGCGCATCAAGCAGCCACAGATCAGAAAGGAGGGGCAGCTGAGCGAGCGGAAGACAGACAAGTTTATCAC

CTTCGCCCTGAACTACCTGGAAGATTATGGACTGAAGGATCTGGAAGGCTGCAAGGCCTGCTTCGCCCGGAGCAAGA

TCGTGAGAGAGCAGGAGAACGTGGAAAGCATCAATGACAAGGAGTACAAGCCTCACGAAAACAAGAAGAAGGTGGAA

ATCCACTTCGATCAGTCTAAGGAAGACCGGTTCTACATCAACCGGAACAACGTGATCCTGAAGATCCAGAAGAAGGA

CGGCCACAGCAACATCGTGAGAATGGGCGTGTACGAGCTGAAGTATCTGGTGCTGATGTCCCTGGTGGGCAAGGCCA

AGGAAGCCGTGGAGAAGATCGACAACTACATCCAGGATCTGAGAGACCAGCTGCCCTACATCGAGGGCAAGAACAAG

GAAGAAATCAAGGAGTACGTGAGATTCTTCCCCAGATTCATCAGATCCCACCTGGGCCTGCTGCAGATTAACGATGA

GGAGAAGATCAAGGCCCGGCTGGACTATGTGAAGACAAAGTGGCTGGACAAGAAGGAGAAGTCCAAGGAGCTGGAGC

TGCACAAGAAGGGCCGGGATATCCTGCGGTACATCAACGAGCGGTGCGACCGGGAGCTGAACCGGAACGTGTACAAC

CGGATCCTGGAGCTGCTGGTGAGCAAGGACCTGACCGGCTTCTACCGGGAGCTGGAGGAGCTGAAGCGGACCAGACG

GATCGATAAGAACATTGTGCAGAACCTGTCCGGCCAGAAGACCATCAACGCCCTGCACGAAAAGGTGTGCGATCTCG

TGCTGAAGGAGATCGAGAGCCTGGACACCGAGAACCTGCGGAAGTACCTGGGCCTGATCCCCAAGGAGGAGAAGGAA

GTGACCTTTAAGGAGAAGGTGGACAGGATCCTGAAGCAGCCGGTGATCTACAAGGGCTTCCTGCGGTACCAGTTCTT

CAAGGACGACAAGAAGAGCTTCGTGCTGCTGGTGGAAGACGCCCTGAAGGAGAAGGGAGGCGGCTGCGACGTGCCCC

TGGGCAAGGAGTACTACAAGATCGTGTCCCTGGACAAGTATGACAAGGAAAATAAGACCCTGTGCGAGACCCTGGCA

-continued

```
ATGGATAGACTGTGCCTGATGATGGCCCGGCAGTATTACCTGAGCCTGAACGCCAAGCTGGCCCAGGAGGCCCAGCA
GATCGAATGGAAGAAGGAGGATAGCATTGAGCTGATCATCTTCACACTGAAGAATCCTGACCAGTCCAAGCAGAGCT
TCTCCATCCGGTTCAGCGTGCGGGACTTCACCAAGCTGTACGTGACCGACGACCCCGAATTCCTGGCCCGGCTGTGC
AGCTACTTCTTCCCCGTGGAGAAGGAGATCGAATACCACAAGCTGTACTCTGAAGGCATTAACAAGTACACCAACCT
GCAGAAGGAGGGGATCGAAGCCATCCTGGAGCTGGAGAAGAAGCTGATCGAAAGAAACCGGATCCAGTCCGCCAAGA
ACTACCTGAGCTTTAACGAAATCATGAACAAGAGCGGCTACAACAAGGATGAGCAGGATGACCTGAAGAAGGTGAGG
AACTCCCTGCTGCACTACAAGCTGATCTTCGAAAAGGAGCACCTGAAGAAGTTCTATGAAGTGATGCGGGCGAGGG
AATCGAGAAGAAGTGGTCCCTGATCGTGTAA
```

(SEQ ID NO: 24)
```
ATGAATGGCATCGAGCTGAAGAAGGAAGAAGCCGCCTTCTACTTCAATCAGGCCGAGCTGAACCTGAAGGCCATTGA
GGACAACATCTTCGACAAGGAGAGACGGAAGACACTGCTGAACAACCCCCAGATCCTGGCCAAGATGGAGAACTTTA
TCTTCAATTTCCGGGACGTGACCAAGAACGCCAAGGGCGAAATCGACTGCCTGCTGCTGAAGCTGAGAGAGCTGCGG
AACTTTTACAGCCACTACGTGCACAAGCGGGACGTCAGAGAACTGAGCAAGGGCGAGAAGCCGATCCTGGAGAAGTA
CTACCAGTTCGCCATCGAATCCACCGGCTCTGAGAACGTGAAGCTCGAAATCATCGAAAACGACGCCTGGCTGGCCG
ACGCCGGCGTGCTGTTCTTCCTGTGCATCTTCCTGAAGAAGAGCCAGGCAAACAAGCTGATCAGCGGCATCAGCGGC
TTCAAGAGAAACGACGACACCGGCCAGCCTCGGAGAAACCTGTTCACCTACTTCTCCATCCGGGAGGGCTACAAGGT
GGTGCCCGAAATGCAGAAGCACTTCCTGCTGTTCTCCCTGGTGAACCACCTGAGCAACCAGGACGATTATATCGAAA
AGGCCCACCAGCCCTACGACATCGGCGAGGGCCTCTTCTTCCACCGGATTGCCAGCACCTTCCTGAACATCTCCGGA
ATCCTGAGAAACATGAAGTTCTACACCTATCAGAGCAAGAGACTGGTGGAGCAGAGAGGCGAGCTGAAGCGGGAAAA
GGACATCTTCGCCTGGGAAGAACCGTTTCAGGGCAATTCCTACTTTGAGATCAACGGCCACAAGGGCGTGATTGGCG
AAGACGAGCTGAAGGAGCTGTGCTACGCCTTCCTGATCGGCAACCAGGACGCCAACAAGGTGGAGGGCCGGATCACC
CAGTTCCTGGAGAAGTTCAGAAACGCCAACAGCGTGCAGCAGGTGAAGGACGACGAGATGCTGAAGCCTGAATATTT
CCCCGCCAACTACTTTGCCGAGAGCGGCGTGGGCCGGATCAAGGACCGGGTGCTGAACAGACTGAACAAGGCCATCA
AGAGCAACAAGGCCAAGAAGGGCGAGATCATCGCCTATGACAAGATGAGAGAAGTGATGGCTTTCATCAATAACTCT
CTGCCCGTGGACGAGAAGCTGAAGCCCAAGGATTACAAGAGATACCTGGGCATGGTGAGATTCTGGGATAGAGAAA
GGACAATATCAAGCGCGAGTTCGAAACGAAGGAGTGGAGCAAGTATCTGCCCTCCAACTTCTGGACCGCCAAGAACC
TGGAGAGAGTGTACGGACTGGCCCGGGAAAAGAACGCAGAGCTGTTTAACAAGCTGAAGGCCGACGTGGAGAAGATG
GACGAAAGAGAGCTGGAAAAGTATCAGAAGATCAACGACGCCAAGGATCTGGCCAACCTGCGGCGGCTGGCCAGCGA
CTTCGGAGTGAAGTGGGAGGAGAAGGATTGGGACGAGTACTCCGGCCAGATCAAGAAGCAGATCACAGATTCCCAGA
AGCTGACCATCATGAAGCAGAGAATCACAGCCGGCCTGAAGAAGAAGCACGGCATCGAAAACCTGAACCTGAGGATC
ACCATCGACATCAACAAGTCCAGAAAGGCCGTGCTGAATCGGATCGCCATCCCCAGAGGATTTGTGAAGCGGCACAT
CCTGGGCTGGCAGGAATCCGAGAAGGTGAGCAAGAAGATCAGAGAAGCCGAATGCGAGATTCTGCTGAGCAAGGAGT
ACGAGGAGCTGAGCAAGCAGTTCTTTCAGAGCAAGGACTACGACAAGATGACCCGCATCAACGGCCTGTACGAGAAG
AATAAGCTGATCGCCCTGATGGCCGTGTATCTGATGGGCAGCTGAGAATCCTGTTCAAGGAGCACACCAAGCTGGA
CGACATCACCAAGACCACCGTGGATTTCAAGATCAGCGACAAGGTGACCGTGAAGATCCCCTTCTCCAACTATCCCT
CCCTGGTGTACACCATGAGCAGCAAGTACGTGGACAATATCGGCAACTACGGCTTCAGCAACAAGGACAAGGATAAG
CCCATTCTGGGCAAGATCGACGTGATCGAGAAGCAGCCGGATGGAGTTTATCAAGGAGGTGCTGGGATTCGAGAAGTA
CCTGTTTGACGATAAGATCATCGACAAGAGCAAGTTCGCCGACACCGCCACCCACATCAGCTTTGCCGAAATCGTGG
AAGAACTGGTGGAGAAGGGCTGGGACAAGGACCGGCTGACGAAGCTGAAGGATGCCCGGAACAAGGCCCTGCACGGC
GAGATCCTGACCGGCACCAGCTTCGACGAGACAAAGTCCCTGATCAACGAGCTGAAGAAGTAA
```

(SEQ ID NO: 25)
ATGAGCCCTGATTTCATCAAGCTGGAGAAGCAGGAAGCAGCCTTCTACTTTAACCAGACCGAGCTGAACCTGAAGGC

CATCGAATCCAATATCCTGGATAAGCAGCAGAGAATGATCCTGCTGAACAACCCCAGAATCCTGGCCAAGGTGGGCA

ACTTCATCTTCAATTTCCGGGACGTGACCAAGAACGCAAAGGGCGAAATCGACTGCCTGCTGTTCAAGCTGGAGGAA

CTGCGGAACTTCTACAGCCACTACGTGCACACCGATAACGTGAAGGAACTGTCCAACGGAGAGAAGCCTCTGCTGGA

GCGGTACTACCAGATCGCCATCCAGGCCACAAGAAGCGAGGACGTGAAGTTCGAGCTGTTCGAGACCAGGAACGAGA

ACAAGATCACCGACGCAGGCGTGCTGTTCTTCCTGTGCATGTTCCTGAAGAAGAGCCAGGCTAATAAGCTGATTTCC

GGCATCAGCGGCTTCAAGCGGAACGACCCCACCGGCCAGCCCAGACGGAACCTCTTTACCTACTTCTCTGCCCGGGA

GGGCTACAAGGCCCTGCCTGACATGCAGAAGCACTTCCTGCTGTTCACCCTGGTGAACTACCTGAGCAACCAGGACG

AGTACATCTCCGAGCTGAAGCAGTACGGAGAGATCGGACAGGGAGCCTTCTTCAACAGAATCGCCAGCACCTTCCTG

AACATCAGCGGCATCAGCGGCAACACCAAGTTCTACAGCTACCAGAGCAAGAGAATCAAGGAGCAGCGGGGCGAACT

GAACAGCGAAAAGGACAGCTTCGAGTGGATCGAGCCCTTTCAGGGCAACTCTTATTTTGAGATCAACGGCCACAAGG

GCGTGATCGGCAAGACGAGCTGAAGGAGCTGTGCTACGCCCTGCTGGTGGCCAAGCAGGACATCAATGCCGTGGAG

GGAAAGATCATGCAGTTCCTGAAGAAGTTCAGGAACACCGGCAACCTGCAGCAGGTGAAGGACGACGAGATGCTGGA

AATCGAGTACTTTCCCGCCAGCTACTTCAACGAGAGCAAGAAGGAGGACATCAAGAAGGAGATCCTGGGCAGACTGG

ACAAGAAGATCCGGTCCTGCAGCGCCAAGGCCGAGAAGGCCTACGACAAGATGAAGGAGGTGATGGAGTTTATCAAT

AACAGCCTGCCCGCCGAGGAGAAGCTGAAGAGGAAGGACTACCGCAGATACCTGAAGATGGTGAGATTCTGGTCCAG

AGAAAAGGGCAACATCGAGAGAGAGTTCAGAACCAAGGAGTGGTCCAAGTACTTCAGCAGCGACTTCTGGAGAAAGA

AC+ATCTGGAGGATGTGTACAAGCTGGCCACCCAGAAGAACGCCGAGCTGTTCAAGAATCTGAAGGCCGCCGCCGAG

AAGATGGGCGAAACAGAATTCGAAAAGTACCAGCAGATCAACGATGTGAAGGACCTGGCCAGCCTGAGACGGCTGAC

CCAGGATTTCGGCCTGAAGTGGGAGGAGAAGGATTGGGAGGAGTACAGCGAACAGATCAAGAAGCAGATCACCGACC

GGCAGAAGCTGACAATCATGAAGCAGCGGGTGACCGCCGAGCTGAAGAAGAAGCACGGCATCGAGAATCTGAACCTC

AGAATTACCATCGATTCCAACAAGAGCAGAAAGGCCGTGCTGAACAGAATCGCCATTCCCCGGGGCTTCGTGAAGAA

GCACATTCTGGGCTGGCAGGGCAGCGAAAAGATCAGCAAGAATATCCGGGAGGCCGAGTGCAAGATCCTGCTGTCCA

AGAAGTATGAGGAGCTGTCTCGGCAGTTCTTTGAGGCTGGCAACTTCGACAAGCTGACCCAGATCAACGGCCTGTAC

GAAAAGAATAAGCTGACCGCCTTCATGTCCGTCTACCTGATGGGCAGACTGAACATCCAGCTGAACAAGCACACGGA

GCTGGGAAATCTGAAGAAGACCGAGGTGGACTTCAAGATTTCCGACAAGGTGACAGAAAAGATCCCCTTCTCCCAGT

ACCCTAGCCTGGTGTACGCTATGAGCCGGAAGTACGTGGACAACGTGGACAAGTACAAGTTCAGCCACCAGGACAAG

AAGAAGCCCTTCCTGGGCAAGATCGACAGCATCGAAAAGGAGAGAATCGAATTCATCAAGGAGGTGCTGGACTTCGA

AGAGTACCTGTTTAAGAACAAGGTGATCGACAAGAGCAAGTTCAGCGATACCGCCACCCATATCTCTTTCAAGGAAA

TCTGCGACGAGATGGGCAAGAAGGGCTGCAACCGCAACAAGCTGACCGAGCTGAATAACGCTAGAAACGCCGCACTG

CACGGAGAAATCCCCAGCGAGACCAGCTTCCGGGAGGCCAAGCCCCTGATCAACGAACTGAAGAAGTAA (SEQ ID NO: 26)
ATGAGCCCTGACTTCATCAAGCTGGAAAAGCAGGAAGCCGCCTTCTACTTTAATCAGACCGAGCTGAACCTGAAGGC

CATCGAGAGCAACATCTTCGACAAGCAGCAGCGGGTGATCCTGCTGAATAACCCCCAGATCCTGGCCAAGGTGGGCG

ACTTCATCTTCAACTTCCGGGACGTGACCAAGAACGCCAAGGGAGAAATCGACTGCCTGCTGCTGAAGCTGCGGGAG

CTGAGAAACTTCTACAGCCACTATGTGTACACCGACGACGTGAAGATCCTGAGCAACGGCGAGAGGCCCCTGCTGGA

GAAGTACTACCAGTTTGCCATCGAGGCCACCGGATCTGAGAATGTGAAGCTGGAGATCATCGAGAGCAACAACCGGC

TGACCGAAGCGGGCGTGCTGTTCTTCCTGTGCATGTTCCTGAAGAAGAGCCAGGCCAACAAGCTGATTTCCGGCATC

TCCGGATTCAAGCGCAACGACCCTACCGGACAGCCTCGGCGGAACCTGTTCACCTACTTTAGCGTGCGGGAGGGCTA

CAAGGTGGTGCCCGACATGCAGAAGCACTTCCTGCTGTTCGTGCTGGTGAACCACCTGTCCGGCCAGGATGACTATA

-continued

```
TTGAGAAGGCCCAGAAGCCCTACGACATCGGCGAAGGCCTGTTCTTCCACAGAATCGCCAGCACCTTTCTCAACATC

AGCGGCATCCTGAGAAACATGGAATTCTACATCTACCAGAGCAAGCGGCTGAAGGAGCAGCAGGGAGAGCTGAAGAG

AGAGAAGGACATCTTCCCTTGGATCGAGCCTTTCCAGGGCAACAGCTACTTTGAGATCAACGGAAACAAGGGCATCA

TCGGCGAGGACGAACTGAAGGAACTGTGCTACGCCCTGCTGGTGGCCGGCAAGGACGTGAGAGCCGTGGAAGGAAAG

ATCACCCAGTTCCTGGAGAAGTTCAAGAACGCCGATAACGCCCAGCAGGTGGAGAAGGATGAAATGCTGGACCGGAA

CAACTTCCCTGCCAATTACTTTGCCGAAAGCAACATCGGCAGCATCAAGGAAAAGATCCTGAATAGACTGGGCAAGA

CCGACGACTCCTACAACAAGACCGGCACCAAGATCAAGCCCTACGACATGATGAAGGAGGTGATGGAGTTCATCAAT

AATTCTCTGCCCGCCGATGAGAAGCTGAAGCGGAAGGACTACCGGAGATACCTGAAGATGGTCCGGATCGGGACAG

CGAAAAGGACAATATCAAGCGGGAGTTTGAGAGCAAGGAATGGAGCAAGTATTTCAGCAGCGACTTCTGGATGGCCA

AGAACCTGGAAAGAGTGTACGCCTGGCCAGGGAAAAGAACGCCGAGCTGTTTAACAAGCTGAAGGCCGTGGTGGAG

AAGATGGACGAGCGGGAGTTCGAAAAGTACCGGCTGATCAACAGCGCCGAAGACCTGGCCAGCCTGCGGAGACTGGC

CAAGGACTTCGGCCTGAAGTGGGAGGAGAAGGACTGGCAGGAGTATTCTGGCCAGATCAAGAAGCAGATCTCCGACA

GACAGAAGCTGACAATTATGAAGCAGCGGATCACAGCCGAACTGAAGAAGAAGCACGGAATCGAGAACCTGAATCTG

CGGATCACCATCGACAGCAACAAGTCCAGAAAGGCCGTGCTGAACCGGATCGCCGTGCCCCGGGCTTCGTGAAGGA

ACACATCCTGGGCTGGCAAGGCTCTGAAAAGGTGAGCAAGAAGACCAGAGAAGCCAAGTGCAAGATCCTGCTGAGCA

AGGAGTACGAGGAACTGAGCAAGCAGTTCTTTCAGACACGGAATTACGACAAGATGACCCAGGTGAACGGCCTGTAC

GAGAAGAACAAGCTGCTGGCCTTCATGGTGGTGTACCTGATGGAGAGACTGAACATCCTGCTGAACAAGCCCACAGA

GCTGAACGAACTGGAAAAGGCCGAAGTGGACTTCAAGATCTCCGACAAGGTGATGGCCAAGATCCCTTTCTCTCAGT

ACCCCAGCCTGGTGTATGCAATGAGCTCCAAGTACGCCGACAGCGTGGGCTCTTACAAGTTCGAAAACGACGAGAAG

AACAAGCCCTTTCTGGGCAAGATCGACACAATCGAGAAGCAGAGAATGGAGTTCATCAAGGAGGTGCTGGGCTTCGA

GGAATACCTGTTCGAGAAGAAGATCATCGATAAGAGCGAATTCGCCGACACCGCCACCCACATCAGCTTCGACGAGA

TCTGCAACGAGCTGATCAAGAAGGGCTGGGACAAGGACAAGCTGACCAAGCTGAAGGACGCCCGGAACGCCGCCCTG

CACGGCGAGATCCCCGCCGAGACCAGCTTCCGGGAGGCCAAGCCCCTGATTAACGGCCTGAAGAAGTAA
```

(SEQ ID NO: 27)
```
ATGAACATCATCAAGCTGAAGAAGGAGGAAGCCGCCTTTTACTTTAACCAGACAATCCTGAATCTGAGCGGCCTGGA

CGAGATCATCGAGAAGCAGATCCCCCACATCATCTCCAATAAGGAAAACGCCAAGAAGGTGATTGATAAGATCTTCA

ATAACAGACTGCTGCTGAAGAGCGTGGAAAACTATATCTACAACTTCAAGGACGTGGCCAAGAACGCCCGGACCGAA

ATCGAAGCCATCCTGCTGAAGCTGGTGGAGCTGAGAAACTTCTACTCCCACTACGTGCACAACGACACCGTGAAGAT

CCTGTCCAATGGCGAGAAGCCCATCCTGGAAAAGTACTACCAGATCGCCATCGAAGCCACCGGCTCTAAGAACGTGA

AGCTGGTCATTATCGAAAACAACAACTGCCTGACCGACTCCGGCGTGCTGTTCCTGCTGTGCATGTTCCTGAAGAAG

AGCCAGGCCAACAAGCTGATTAGCAGCGTGAGCGGCTTTAAGCGGAACGACAAGGAAGGCCAGCCCAGAAGGAACCT

CTTTACTTACTATAGCGTGAGGGAAGGCTACAAGGTGGTGCCAGACATGCAGAAGCACTTCCTGCTGTTCGCCCTGG

TCAACCACCTGTCCGAGCAGGACGACCACATCGAGAAGCAGCAGCAGAGCGACGAGCTGGGCAAGGGCCTGTTCTTC

CACAGAATCGCCAGCACATTCCTGAATGAAAGCGGCATCTTCAACAAGATGCAGTTTTACACCTACCAGAGCAATCG

GCTGAAGGAGAAGCGGGCGAGCTGAAGCACGAGAAGGACACCTTCACCTGGATCGAGCCTTTCCAGGGAAACAGCT

ACTTCACCCTGAACGGGCACAAGGGCGTGATCAGCGAGGATCAGCTGAAGGAACTGTGCTACACAATCCTGATCGAG

AAGCAGAACGTGGACAGCCTGGAGGGCAAGATCATTCAGTTCCTGAAGAAGTTTCAGAACGTGTCTAGCAAGCAGCA

GGTGGATGAGGACGAGCTGCTGAAGCGGGAATACTTCCCCGCCAACTACTTCGGCCGGGCCGGCACCGGCACCCTGA

AGGAGAAGATCCTGAACCGGCTGGACAAGCGGATGGACCCCACCAGCAAGGTGACCGACAAGGCCTATGACAAGATG

ATCGAGGTGATGGAGTTCATCAACATGTGCCTGCCCAGCGACGAGAAGCTGCGGCAGAAGGATTACCGGAGATATCT

GAAGATGGTCAGATTCTGGAACAAGGAGAAGCACAACATCAAGAGAGAATTCGACAGCAAGAAGTGGACCAGATTCC
```

-continued

TGCCCACCGAGCTGTGGAATAAGCGGAACCTGGAGGAAGCCTACCAGCTGGCCCGGAAGGAGAACAAGAAGAAGCTG

GAGGACATGAGGAATCAGGTGAGGAGCCTGAAGGAGAACGACCTGGAGAAGTACCAGCAGATCAACTATGTGAACGA

CCTGGAAAACCTGCGGCTGCTGTCCCAAGAGCTGGGCGTGAAGTGGCAGGAGAAGGACTGGGTGGAATACAGCGGCC

AGATCAAGAAGCAGATCAGCGATAACCAGAAGCTGACAATCATGAAGCAGAGAATCACCGCCGAGCTGAAGAAGATG

CACGGCATCGAGAACCTGAACCTGAGAATCAGCATCGACACCAACAAGTCCCGGCAGACTGTGATGAACAGAATTGC

CCTGCCCAAGGGCTTCGTGAAGAACCACATTCAGCAGAACAGCAGCGAGAAGATCAGCAAGAGAATCAGAGAGGACT

ACTGCAAGATCGAGCTGTCCGGCAAGTACGAAGAGCTGAGCAGACAGTTTTTCGACAAGAAGAACTTTGACAAGATG

ACCCTGATCAACGGACTGTGCGAGAAGAATAAGCTCATCGCCTTCATGGTGATTTACCTGCTGGAGCGGCTGGGCTT

CGAGCTGAAGGAGAAGACCAAGCTGGGCGAGCTGAAGCAGACCCGGATGACATATAAGATCAGCGACAAGGTGAAGG

AGGACATCCCCCTCTCCTACTACCCCAAGCTGGTGTACGCCATGAATCGGAAGTATGTGGACAACATCGATAGCTAC

GCCTTCGCCGCCTACGAGTCTAAGAAGGCCATCCTGGACAAGGTGGACATCATTGAGAAGCAGAGAATGGAATTCAT

CAAGCAGGTGCTGTGCTTCGAGGAATACATCTTCGAGAACAGAATCATCGAGAAGAGCAAGTTCAACGATGAGGAGA

CCCACATCAGCTTCACCCAGATCCACGACGAACTGATCAAGAAGGGCAGAGATACCGAAAAGCTGAGCAAGCTGAAG

CACGCCAGAAACAAGGCCCTGCACGGCGAGATCCCCGACGGGACCAGCTTTGAGAAGGCCAAGCTGCTGATCAACGA

AATCAAGAAGTAA (SEQ ID NO: 28)
ATGAACGCCATCGAGCTGAAGAAGGAAGAGGCCGCCTTCTACTTCAACCAGGCCAGACTGAACATCTCTGGCCTGGA

CGAAATCATCGAGAAGCAACTGCCACACATCGGCTCTAACAGAGAGAACGCCAAGAAGACTGTGGACATGATCCTGG

ATAACCCCGAGGTGCTGAAGAAGATGGAAAACTACGTGTTCAACTCCCGCGATATTGCCAAGAATGCCCGGGGCGAG

CTGGAGGCCCTGCTGCTGAAGCTGGTCGAGCTGAGAAACTTCTATAGCCACTACGTGCACAAGGACGACGTCAAGAC

ACTGAGCTACGGTGAGAAGCCTCTGCTGGATAAGTACTACGAGATCGCCATCGAAGCCACCGGATCCAAGGACGTGC

GGCTGGAGATCATTGACGACAAGAATAAGCTGACCGACGCCGGAGTGCTGTTCCTGCTGTGCATGTTCCTGAAGAAG

AGCGAGGCTAACAAGCTGATTTCCAGCATCCGGGGCTTCAAGAGGAACGACAAGGAGGGCCAGCCTAGAAGAAACCT

GTTCACCTACTACAGCGTGAGAGAGGGCTATAAGGTGGTGCCCGACATGCAGAAGCACTTTCTGCTGTTCACCCTGG

TGAACCACCTGTCCAATCAGGACGAGTACATCTCCAACCTGCGCCCAAACCAGGAAATCGGCCAGGGCGGATTTTTC

CACCGGATCGCCAGCAAGTTCCTGAGCGACAGCGGAATCCTGCACAGCATGAAGTTCTACACATACAGATCCAAGCG

GCTGACCGAGCAGCGGGGAGAGCTGAAGCCCAAGAAGGACCACTTTACATGGATCGAGCCTTTCCAGGGCAATTCCT

ACTTCAGCGTGCAGGGCCAGAAGGGCGTGATCGGAGAGGAGCAGCTCAAGGAGCTGTGCTACGTGCTGCTGGTGGCC

CGGGAGGACTTCAGAGCCGTGGAGGGCAAGGTGACCCAGTTCCTGAAGAAGTTCCAGAATGCCAATAACGTGCAGCA

GGTGGAGAAGGACGAGGTGCTGGAAAAGGAGTACTTCCCCGCCAACTACTTTGAGAACCGGGACGTGGGAAGAGTCA

AGGACAAGATCCTGAACAGACTGAAGAAGATCACCGAGAGTTATAAGGCCAAGGGTAGAGAGGTGAAGGCCTACGAC

AAGATGAAGGAAGTGATGGAGTTCATCAACAACTGCCTGCCCACCGATGAAAACCTGAAGCTGAAGGACTACCGGCG

GTACCTGAAGATGGTGAGATTCTGGGGCAGAGAGAAGGAAAACATCAAGCGGGAGTTCGACTCCAAGAAGTGGGAGC

GCTTTCTCCCCCGGGAGCTGTGGCAGAAGAGAAACCTGGAGGACGCCTACCAGCTCGCCAAGGAGAAGAACACAGAG

CTGTTCAACAAGCTGAAGACCACCGTGGAGAGAATGAACGAACTGGAGTTCGAGAAGTACCAGCAGATCAATGACGC

CAAGGACCTGGCCAACCTGAGACAGCTGGCCAGAGACTTTGGAGTGAAGTGGGAGGAAAAGGACTGGCAGGAATACT

CTGGACAGATCAAGAAGCAGATCACCGACCGGCAGAAGCTGACCATCATGAAGCAGCGGATCACCGCCGCCCTGAAG

AAGAAGCAGGGAATCGAAACCTGAACCTGAGAATCACAACAGATACGAATAAGAGCAGGAAGGTGGTGCTGAACCG

GATCGCACTGCCCAAGGGATTCGTCAGAAAGCACATCCTGAAGACCGACATCAAGATCAGCAAGCAGATCCGGCAGA

GCCAGTGCCCTATCATCCTGTCTAACAACTACATGAAGCTGGCCAAGGAGTTCTTTGAAGAGCGGAACTTCGATAAG

ATGACCCAGATCAATGGCCTGTTCGAAGAACGTGCTGATCGCCTTCATGATCGTGTACCTGATGGAGCAGCTGAA

-continued

```
CCTGAGACTGGGCAAGAACACCGAGCTGTCCAACCTGAAGAAGACCGAGGTGAACTTTACCATCACCGACAAGGTGA

CCGAGAAGGTGCAAATCTCCCAGTACCCCAGCCTGGTGTTCGCCATTAACCGGGAGTACGTGGACGGCATCAGCGGC

TACAAGCTGCCCCCCAAGAAGCCCAAGGAACCTCCCTACACCTTCTTCGAAAAGATCGACGCCATCGAAAAGGAGCG

GATGGAATTCATCAAGCAGGTGCTGGGCTTCGAGGAGCACCTCTTCGAAAAGAACGTGATCGACAAGACCCGGTTTA

CCGACACCGCCACCCACATCAGCTTCAATGAGATCTGCGATGAGCTGATCAAGAAGGGCTGGGACGAAAACAAGATC

ATCAAGCTGAAGGATGCACGGAACGCTGCCCTGCACGGCAAGATCCCTGAAGATACCTCCTTTGACGAAGCCAAGGT

GCTGATCAACGAACTGAAGAAGTAA
```

The seven CRISPR/Cas13e and Cas13f loci structures were shown in FIG. 1.

Further analysis of RNA secondary structures for the seven DR sequences in the pre-crRNA was conducted using RNAfold. The results were shown in FIG. 2. It is apparent that all shared very conserved secondary structure.

For example, in the Cas13e family, each DR sequence forms a secondary structure consisting of a 4-base pair stem (5'-GCUG-3'), followed by a symmetrical bulge of 5+5 nucleotides (excluding the 4 stem nucleotides), further followed by a 5-base pair stem (5'-GCC C/U C-3'), and a terminal 8-base loop (5'-CGAUUUGU-3', excluding the 2 stem nucleotides).

Likewise, in the Cas13f family, with one exception (Cas13f.4), each DR sequence forms a secondary structure consisting of a 5-base pair stem (5'GCUGU3'), followed by a nearly symmetrical bulge of 5+4 nucleotides (excluding the 4 stem nucleotides), further followed by a 6-base pair stem (5'A/G CCUCG3'), and a terminal 5-base loop (5'AUUUG3', excluding the 2 stem nucleotides). The only exception being the DR for Cas13f.4, in which the second step is 1 base pair shorter, and 2 additional bases were added to the first bulge to form a largely symmetrical 6+5 bulge.

Figure 3:
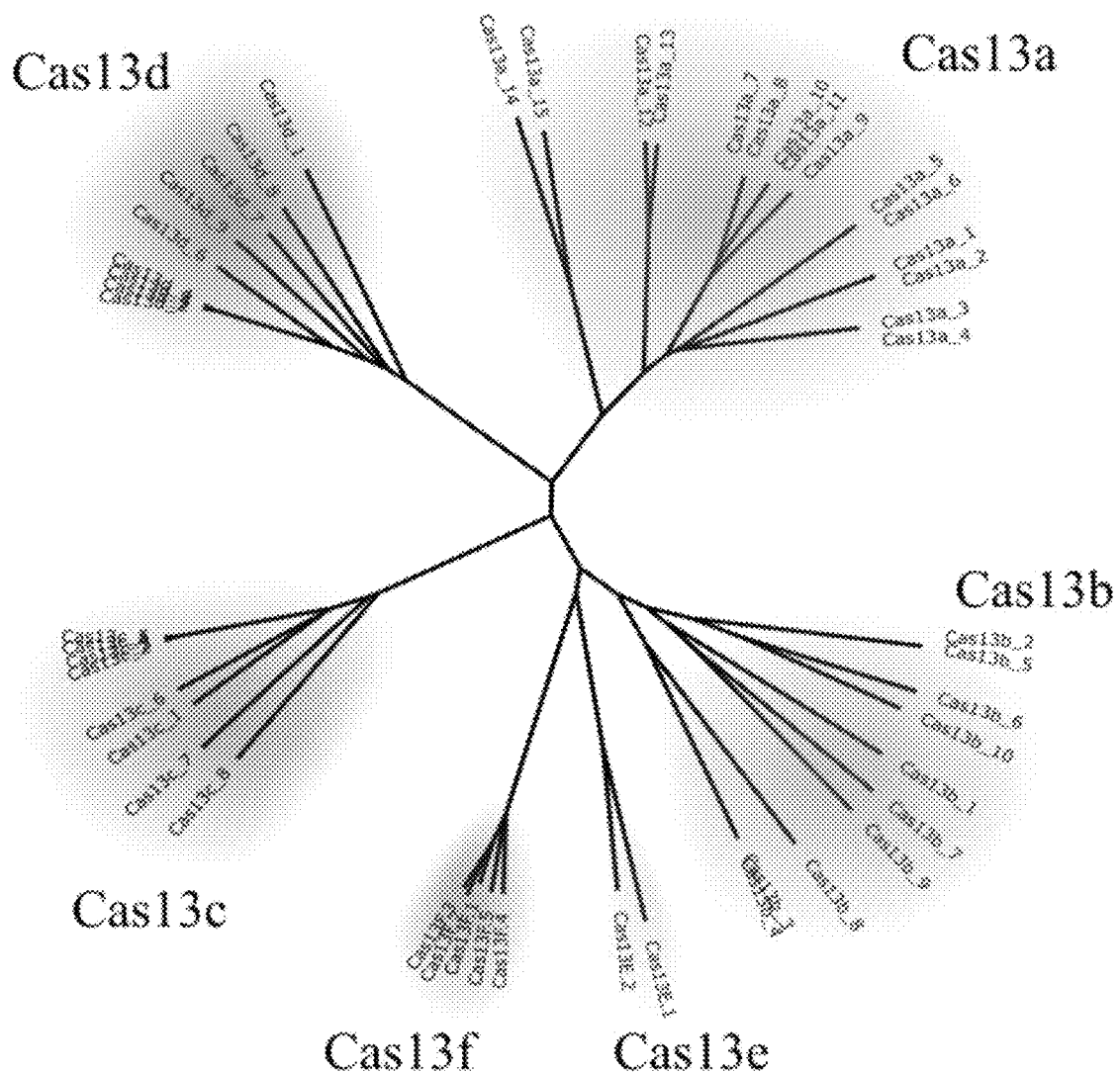
FIG. 3 shows a phylogenetic tree for the newly discovered Cas13e and Cas13f effector proteins of the invention, as well as the related previously discovered Cas13a, Cas13b, Cas13c, and Cas13d effector proteins.

Multi-sequence alignment of Cas13e and Cas13f proteins and the previously identified Cas13a, Cas13b, Cas13c, and Cas13d family proteins, using MAFFT, revealed that Cas13e and Cas13f proteins are relatively closest to the Cas13b proteins on the phylogenetic tree (FIG. 3).

Figure 4:
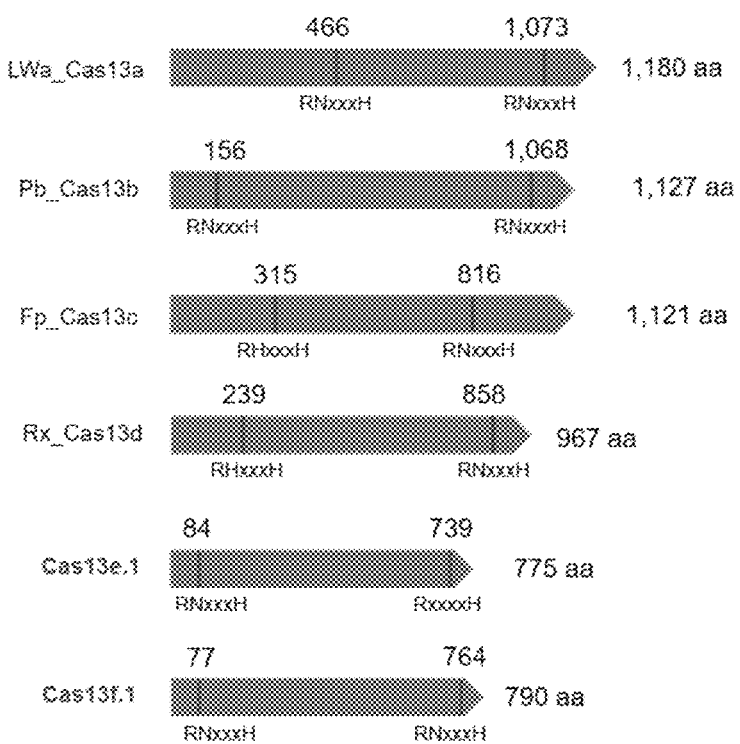
FIG. 4 shows the domain structures for the Cas13a-Cas13f proteins. The overall sizes, and the locations of the two RXXXXH motifs on each representative member of the Cas proteins are indicated.

Further, in terms of the locations of the RXXXXH motifs with respect to the N- and C-termini of the Cas proteins, Cas13e and Cas13f proteins, and to a lesser extent Cas13b proteins, have their RXXXXH motifs closer to their N- and C-termini, as compared to the Cas13a, Cas13c, and Cas13d (see FIG. 4).

Figure 5:
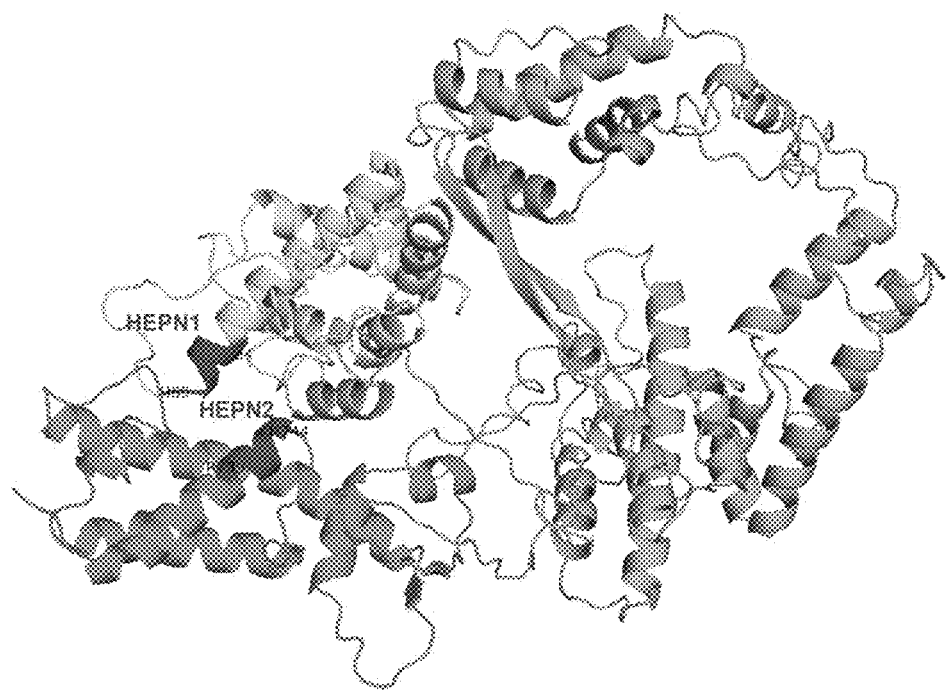
FIG. 5 shows a predicted 3D structure of the Cas13e.1 effector protein.

TASSER was then used to predict 3D structures for Cas13e proteins, followed by visualization of the predicted structures using PyMOL. Although the two RXXXXH motifs are located very close to the N- and C-termini of Cas13e.1, they are very close by in the 3D structure (FIG. 5).

Example 2 Cas13e is an Effector RNase

In order to confirm that the newly identified Cas13e proteins are effective RNase functioning in the CRISPR/Cas system, Cas13e.1 coding sequence was codon optimized for human expression (SEQ ID NO: 22), and cloned into a first plasmid with GFP gene. Meanwhile, coding sequence for guide RNA (gRNA) targeting the reporter gene (mCherry) mRNA was cloned into a second plasmid with GFP gene. The gRNA consists of a spacer coding region flanked by two direct repeat sequences for Cas13e.1 (SEQ ID NO: 29). The sequence of GFP and mCherry reporter genes are SEQ ID NO: 30-31, respectively.

(SEQ ID NO: 29)
```
GCTGGAGCAGCCCCCGATTTGTGGGGTGATTACAGCGGTCTTCGATATTCA

AGCGTCGGAAGACCTGCTGGAGCAGCCCCCGATTTGTGGGGTGATTACAGC
```

(SEQ ID NO: 30)
```
ATGGTGAGCAAGGGCGAGGAGGATAACATGGCCATCATCAAGGAGTTCATG

CGCTTCAAGGTGCACATGGAGGGCTCCGTGAACGGCCACGAGTTCGAGATC

GAGGGCGAGGGCGAGGGCCGCCCCTACGAGGGCACCCAGACCGCCAAGCTG

AAGGTGACCAAGGGTGGCCCCCTGCCCTTCGCCTGGGACATCCTGTCCCCT

CAGTTCATGTACGGCTCCAAGGCCTACGTGAAGCACCCCGCCGACATCCCC

GACTACTTGAAGCTGTCCTTCCCCGAGGGCTTCAAGTGGGAGCGCGTGATG

AACTTCGAGGACGGCGGCGTGGTGACCGTGACCCAGGACTCCTCCCTGCAG

GACGGCGAGTTCATCTACAAGGTGAAGCTGCGCGGCACCAACTTCCCCTCC

GACGGCCCCGTAATGCAGAAGAAGACCATGGGCTGGGAGGCCTCCTCCGAG

CGGATGTACCCCGAGGACGGCGCCCTGAAGGGCGAGATCAAGCAGAGGCTG

AAGCTGAAGGACGGCGGCCACTACGACGCTGAGGTCAAGACCACCTACAAG

GCCAAGAAGCCCGTGCAGCTGCCCGGCGCCTACAACGTCAACATCAAGTTG

GACATCACCTCCCACAACGAGGACTACACCATCGTGGAACAGTACGAACGC

GCCGAGGGCCGCCACTCCACCGGCGGCATGGACGAGCTGTACAAGTAA
```

(SEQ ID NO: 31)
```
ATGGTGAGCAAGGGCGAGGAGCTGTTCACCGGGGTGGTGCCCATCCTGGTC

GAGCTGGACGGCGACGTAAACGGCCACAAGTTCAGCGTGTCCGGCGAGGGC

GAGGGCGATGCCACCTACGGCAAGCTGACCCTGAAGTTCATCTGCACCACC

GGCAAGCTGCCCGTGCCCTGGCCCACCCTCGTGACCACCCTGACCTACGGC

GTGCAGTGCTTCAGCCGCTACCCCGACCACATGAAGCAGCACGACTTCTTC

AAGTCCGCCATGCCCGAAGGCTACGTCCAGGAGCGCACCATCTTCTTCAAG

GACGACGGCAACTACAAGACCCGCGCCGAGGTGAAGTTCGAGGGCGACACC

CTGGTGAACCGCATCGAGCTGAAGGGCATCGACTTCAAGGAGGACGGCAAC

ATCCTGGGGCACAAGCTGGAGTACAACTACAACAGCCACAACGTCTATATC

ATGGCCGACAAGCAGAAGAACGGCATCAAGGTGAACTTCAAGATCCGCCAC

AACATCGAGGACGGCAGCGTGCAGCTCGCCGACCACTACCAGCAGAACACC

CCCATCGGCGACGGCCCCGTGCTGCTGCCCGACAACCACTACCTGAGCACC

CAGTCCGCCCTGAGCAAAGACCCCAACGAGAAGCGCGATCACATGGTCCTG

CTGGAGTTCGTGACCGCCGCCGGGATCACTCTCGGCATGGACGAGCTGTAC

AAGTGA
```

Figure 6:
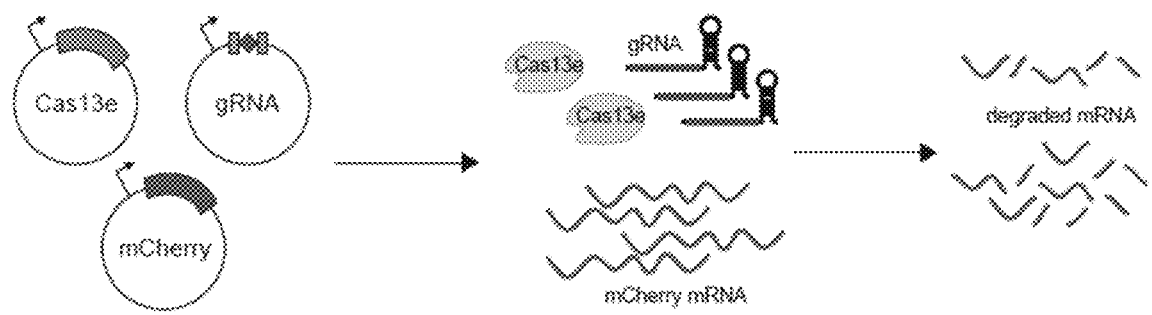
FIG. 6 is a schematic drawing showing that the three plasmids, encoding (1) a Cas13e effector protein, (2) a coding sequence for the guide RNA (gRNA) which can produce the guide RNA that is complementary to the mCherry mRNA and that can form a complex with the Cas13e effector protein, and (3) the mCherry reporter gene, respectively, can be transfected to a cell to express their respective gene products, resulting in the degradation of the reporter mCherry mRNA.

HEK293T cells were cultured in 24-well tissue culture plates according to standard protocol, and were used for triple plasmid transfection using LIPOFECTAMINE® 3000 and P3000™ reagent to introduce the three plasmids encoding the Cas13e.1 protein, the mCherry-targeting gRNA, and the mCherry coding sequence, respectively. In a negative control experiment, instead of using the plasmid encoding the mCherry-targeting gRNA, a control plasmid encoding a non-Target-gRNA was used. A GFP coding sequence was present in the Cas13e.1 and gRNA plasmid, thus expression of GFP can be used as an internal control for transfection success/efficiency. See schematic illustration in FIG. 6. Transfected HEK293T cells were then incubated at 37° C. under 5% $CO_2$ for about 24 hours, before the cells were subject to examination under the fluorescent microscope.

Figure 7:
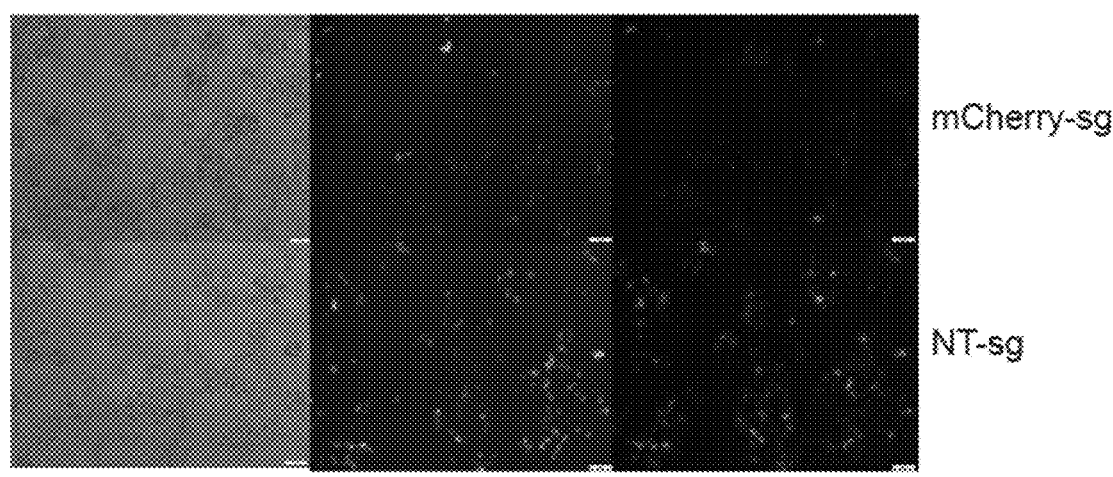
FIG. 7 shows knock-down of mCherry mRNA by guide RNA complementary to the mCherry mRNA, as evidenced by reduced mCherry expression under fluorescent microscope. As a negative control, a non-targeting (NT) guide RNA that does not hybridize with/bind to the mCherry mRNA failed to knock-down mCherry expression.
Figure 8:
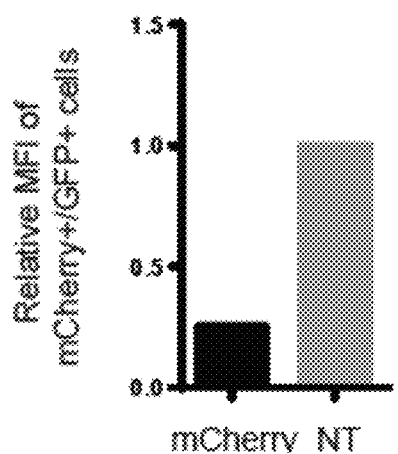
FIG. 8 shows about 75% knock-down of mCherry expression in experiments in FIG. 6.

As shown in FIG. 7, cells transfected with the mCherry-targeting gRNA, and cells transfected with the control non-targeting (NT) gRNA had equivalent growth and morphology in bright field microscope, and GFP expression in both were largely equivalent. However, RFP signal from mCherry expression was dramatically reduced by up to 75% based on flow cytometry analysis (FIG. 8). This suggests that Cas13e can utilize the mCherry-targeting gRNA to efficiently knock down mCherry mRNA level, and consequently mCherry protein expression.

Example 3 Effective Direction of sgRNA for Cas13e

Since Cas13e system can in theory utilize either the DR+Spacer (5'DR) or the Spacer+DR (3'DR) orientation, this experiment was designed to determine which is the correct orientation utilized by Cas13e.

Figure 9:
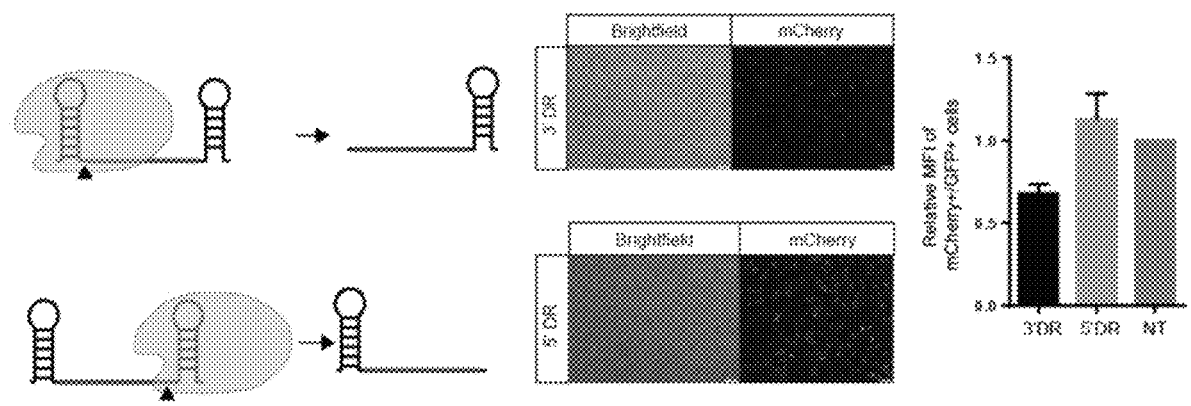
FIG. 9 shows that Cas13e utilizes a guide RNA having a DR sequence at the 3' end (as opposed to a DR sequence at the 5'-end of the guide RNA).

Using a similar triple transfection experiment setting as in Example 2, it was found that only the 3'DR orientation (Spacer+DR) supported significant mCherry knock down. This demonstrated that Cas13e utilizes its crRNA with the DR sequence at the 3'-end of the spacer. See FIG. 9.

SgRNA of DR+Spacer (5' DR) and Spacer+DR (3' DR) are SEQ ID NOs: 32 and 33, respectively.

```
                                         (SEQ ID NO: 32)
GCTGGAGCAGCCCCCGATTTGTGGGGTGATTACAGCGGTCTTCGATATTCA
AGCGTCGGAAGACCT (SEQ ID NO: 33)
GGTCTTCGATATTCAAGCGTCGGAAGACCTGCTGGAGCAGCCCCCGATTTG
TGGGGTGATTACAGC
```

Example 4 Effect of Spacer Sequence Length on Specific Activity and Collateral Activity of Cas13e.1

In order to study the effect of spacer sequence length on specific activity and collateral activity of Cas13e.1, a set of sgRNA targeting the mCherry reporter gene were designed, with spacer sequence length of 20 nt, 25 nt, 30 nt, 35 nt, 40 nt, 45 nt, or 50 nt (SEQ ID NO. 34-40).

```
                                         (SEQ ID NO: 34)
TTGGTGCCGCGCAGCTTCAC (SEQ ID NO: 35)
TTGGTGCCGCGCAGCTTCACCTTGT (SEQ ID NO: 36)
TTGGTGCCGCGCAGCTTCACCTTGTAGATG (SEQ ID NO: 37)
TTGGTGCCGCGCAGCTTCACCTTGTAGATGAACTC (SEQ ID NO: 38)
TTGGTGCCGCGCAGCTTCACCTTGTAGATGAACTCGCCGT (SEQ ID NO: 39)
TTGGTGCCGCGCAGCTTCACCTTGTAGATGAACTCGCCGTCCTGC (SEQ ID NO: 40)
TTGGTGCCGCGCAGCTTCACCTTGTAGATGAACTCGCCGTCCTGCAGGGA
```

Using a similar triple transfection experiment setting as in Example 2, the knock down efficiency of mCherry and GFP gene were analyzed by flow cytometry.

Figure 10:
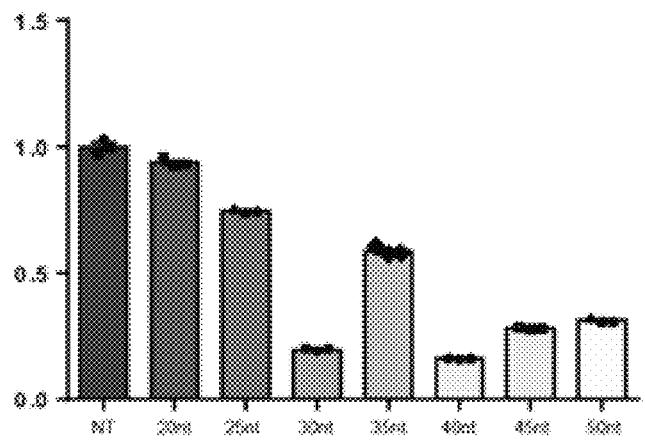
FIG. 10 shows the correlation between spacer sequence length and specific (guide RNA-dependent) RNase activity against target RNA relative to non-targeting (NT) control.

The results of mCherry and GFP knock down experiments showed the specific activity and non-specific activity (collateral activity) of Cas13e.1, respectively. It was found that Cas13e.1 has high specific activity with spacer lengths between about 30 nt to about 50 nt. See FIG. 10. Meanwhile, Cas13e.1 has highest non-specific activity when spacer length is about 30 nt. See FIG. 11.

Example 5 Single-Base RNA Editing Using dCas13e.1-ADAR2DD Fusion

In order to test whether Cas13e can be used for RNA single base editing, dCas13e.1 was generated by mutating the two RXXXXH motifs to eliminate RNase activity. Then a high fidelity ADAR2DD mutant with E488Q and T375G double mutation was fused to the (C-terminus) of dCas13e.1 to create a putative A-to-G single base RNA editor named dCas13e.1-ADAR2DD. See coding sequence in SEQ ID NO: 41.

```
                                         (SEQ ID NO: 41)
ATGCCCAAGAAGAAGCGGAAGGTGGCCCAGGTGAGCAAG

CAGACCTCCAAGAAGAGGGAGCTGAGCATCGACGAGTA

CCAGGGCGCCCGGAAGTGGTGCTTCACCATTGCCTTCAA

CAAGGCCCTGGTGAACCGGGACAAGAACGACGGCCTGT

TCGTGGAAAGCCTGCTGAGACACGAGAAGTACAGCAAGC

ACGACTGGTACGACGAAGATACCCGGGCCCTGATCAAG

TGCAGCACCCAGGCCGCCAACGCCAAGGCTGAAGCCCTG

GCGAACTACTTCAGTGCTTACCGGCATAGCCCTGGCTG

CCTGACCTTCACCGCCGAGGACGAACTGCGGACCATCAT

GGAGAGAGCCTATGAGCGGGCCATCTTCGAGTGCAGAA

GAAGAGAGACAGAGGTGATCATCGAGTTTCCCAGCCTGT

TCGAGGGCGACCGGATCACCACCGCCGGCGTGGTGTTT

TTCGTGAGCTTTTTCGTGGAAAGAAGAGTGCTGGATCGG

CTGTATGGAGCCGTGTCCGGCCTGAAGAAGAATGAGGG

ACAGTACAAGCTGACCCGGAAGGCCCTGAGCATGTACTG

CCTGAAGGACAGCAGATTCACCAAGGCCTGGGATAAGC

GGGTGCTGCTGTTCAGAGACATCCTGGCCCAGCTGGGAA
```

Figure 12:
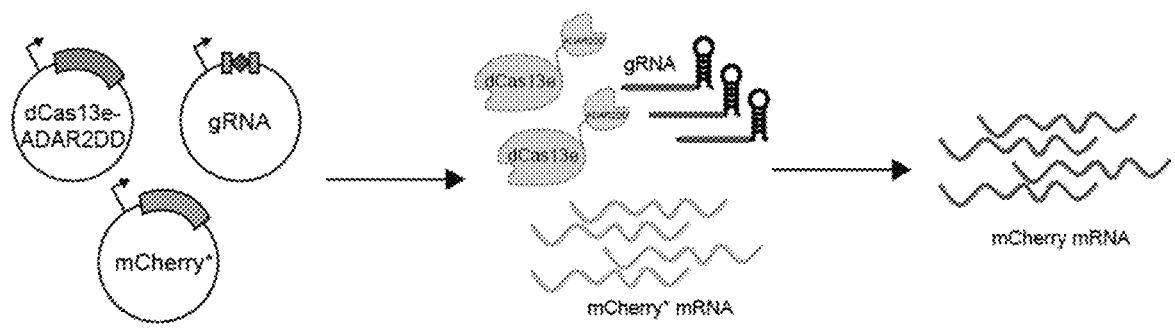
FIG. 12 shows that dCas13e.1-ADAR2DD fusion has RNA base editing activity. Specifically, three plasmids, encoding (1) a dCas13e (RNase dead) protein fused to the single-base RNA editor ADAR2DD, (2) a coding sequence for the guide RNA (gRNA) which can produce the guide RNA that is complementary to a mutant mCherry mRNA having a G-to-A point mutation and that can form a complex with the dCas13e effector protein, and (3) the mutant mCherry reporter gene encoding the mCherry mRNA having the G-to-A point mutation, respectively, can be transfected to a cell to express their respective gene products. The mutant mCherry mRNA normally cannot produced a fluorescent mCherry protein due to the point mutation. Upon guide RNA binding to the mutant mCherry mRNA, the fused ADAR2DD base editor converts A to I (G equivalent), thus restoring the ability of the mRNA to encode a fluorescent mCherry protein.
Figure 14:
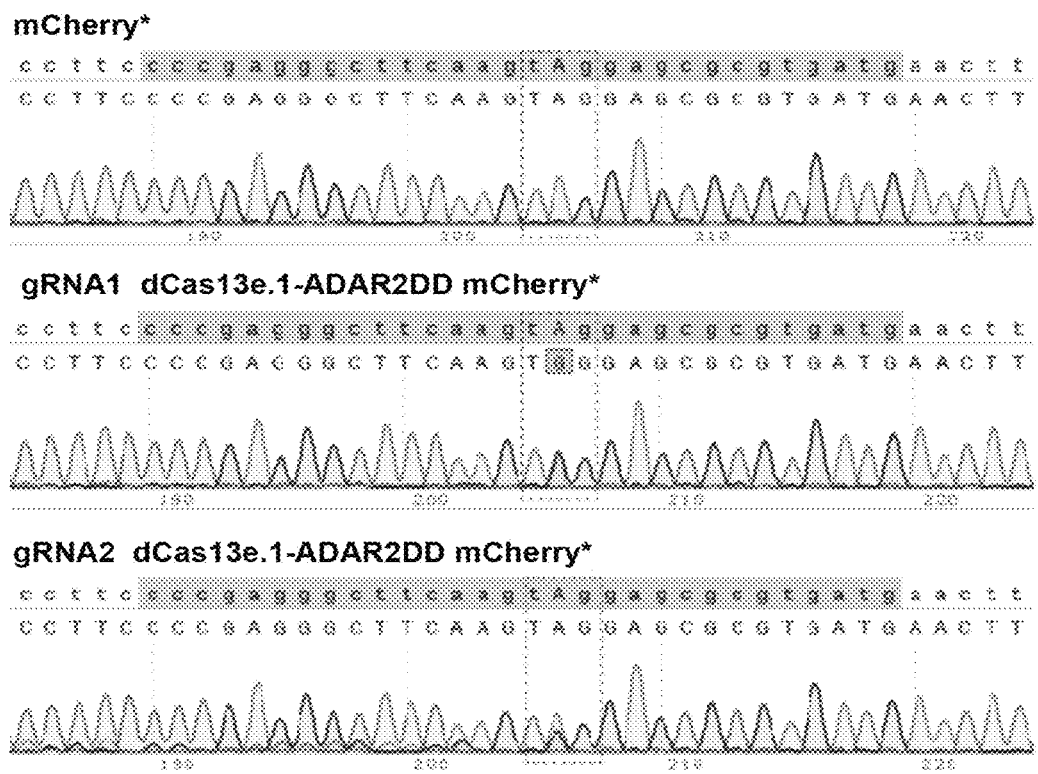
FIG. 14 shows the relevant segment of the mutant mCherry gene having the premature stop codon TAG, the sequence for the two gRNA that can be complexed with the dCas13e-ADAR2DD RNA base editor, and the "corrected" TGG codon.

-continued
GAATCCCCGCCGAGGCCTACGAGTACTACCACGGCGAG
CAGGGTGATAAGAAGAGAGCTAACGACAATGAGGGCACA
AATCCCAAGCGGCACAAGGACAAGTTCATCGAATTTGC
ACTGCACTACCTGGAAGCCCAGCACAGCGAGATCTGCTT
CGGCAGACGCCACATCGTGCGGGAAGAGGCCGGCGCCG
GCGATGAGCACAAGAAGCACCGGACCAAGGGAAAGGTGG
TGGTGGACTTCAGCAAGAAGGACGAGGACCAGAGCTAC
TATATCTCCAAGAACAACGTGATCGTGCGGATCGACAAG
AACGCCGGCCCTAGAAGCTACCGGATGGGCCTGAACGA
GCTGAAGTACCTCGTGCTGCTGAGCCTGCAGGGGAAGGG
CGACGATGCCATCGCCAAGCTGTACAGATACAGACAGC
ACGTGGAGAACATCCTGGATGTGGTGAAGGTGACCGATA
AGGATAACCACGTGTTCCTGCCCCGCTTCGTGCTGGAG
CAGCACGGCATCGGCAGAAAGGCCTTCAAGCAGCGGATC
GATGGACGGGTGAAGCACGTGCGGGCGTGTGGGAGAA
GAAGAAGGCCGCCACCAATGAAATGACCCTGCACGAGAA
GGCCAGAGACATCCTGCAGTACGTGAACGAAAACTGCA
CCCGGTCCTTCAACCCTGGCGAATACAACAGACTGCTGG
TGTGCCTGGTGGGCAAGGACGTGGAGAACTTTCAGGCC
GGCCTGAAGCGGCTGCAGCTGGCCGAAAGGATCGATGGC
CGGGTGTACTCCATCTTCGCCCAGACCAGCACCATCAA
TGAGATGCACCAGGTGGTGTGCGACCAGATCCTGAACCG
GCTGTGCAGAATCGGCGACCAGAAGCTGTACGATTACG
TGGGACTGGGCAAGAAGGACGAAATCGACTACAAGCAGA
AGGTGGCCTGGTTCAAGGAGCACATCAGCATCCGGAGA
GGATTCCTGAGAAAGAAGTTCTGGTACGATAGCAAGAAG
GGATTCGCAAAGCTGGTGGAGGAACACCTGGAGTCCGG
CGGCGGCCAGCGCGACGTGGGCCTGGACAAGAAGTACTA
CCACATCGACGCCATCGGCAGATTCGAGGGCGCCAACC
CCGCCCTGTACGAGACCCTGGCCAGAGATCGGCTGTGCC
TCATGATGGCCCAGTACTTCCTGGGCAGCGTGAGAAAG
GAACTGGGCAACAAGATTGTGTGGAGCAACGACAGCATC
GAACTGCCTGTGGAAGGCTCTGTGGGAAATGAGAAGAG
CATCGTGTTCTCCGTGTCTGACTACGGCAAGCTGTACGT
GCTGGACGATGCCGAATTCCTGGGCCGGATCTGCGAAT
ACTTCATGCCCCACGAAAAGGGCAAGATCCGGTACCACA
CAGTGTACGAAAAGGGCTTTAGAGCATACAACGACCTG
CAGAAGAAGTGCGTGGAGGCCGTGCTGGCTTTCGAAGAG
AAGGTGGTGAAGGCCAAGAAGATGAGCGAGAAGGAAGG
CGCCCACTACATCGACTTCCGGGAGATCCTGGCCCAGAC
CATGTGCAAGGAGGCCGAGAAGACCGCAGTGAACAAGG -continued
TGGCGGCTGCCTTCTTCGCTGCGCACCTGAAGTTCGTGA
TTGACGAGTTCGGCCTGTTCAGCGACGTGATGAAGAAG
TACGGCATCGAGAAGGAATGGAAGTTCCCTGTCAAGCCC
AAGAAGAAGCGGAAGGTGGGTGGAGGCGGAGGTTCTGG
GGGAGGAGGTAGTGGCGGTGGTGGTTCAGGAGGCGGCGG
AAGCCAGCTGCATTTACCGCAGGTTTTAGCTGACGCTG
TCTCACGCCTGGTCCTGGGTAAGTTTGGTGACCTGACCG
ACAACTTCTCCTCCCCTCACGCTCGCAGAAAAGTGCTG
GCTGGAGTCGTCATGACAACAGGCACAGATGTTAAAGAT
GCCAAGGTGATAAGTGTTTCTACAGGAGGCAAATGTAT
TAATGGTGAATACATGAGTGATCGTGGCCTTGCATTAAA
TGACTGCCATGCAGAAATAATATCTCGGAGATCCTTGC
TCAGATTTCTTTATACACAACTTGAGCTTTACTTAAATA
ACAAAGATGATCAAAAAAGATCCATCTTTCAGAAATCA
GAGCGAGGGGGTTTAGGCTGAAGGAGAATGTCCAGTTT
CATCTGTACATCAGCACCTCTCCCTGTGGAGATGCCAG
AATCTTCTCACCACATGAGCCAATCCTGGAAGAACCAGC
AGATAGACACCCAAATCGTAAAGCAAGAGGACAGCTAC
GGACCAAAATAGAGTCTGGTCAGGGGACGATTCCAGTGC
GCTCCAATGCGAGCATCCAAACGTGGGACGGGGTGCTG
CAAGGGGAGCGGCTGCTCACCATGTCCTGCAGTGACAAG
ATTGCACGCTGGAACGTGGTGGGCATCCAGGGATCACT
GCTCAGCATTTTCGTGGAGCCCATTTACTTCTCGAGCAT
CATCCTGGGCAGCCTTTACCACGGGGACCACCTTTCCA
GGGCCATGTACCAGCGGATCTCCAACATAGAGGACCTGC
CACCTCTCTACACCCTCAACAAGCCTTTGCTCAGTGGC
ATCAGCAATGCAGAAGCACGGCAGCCAGGGAAGGCCCCC
AACTTCAGTGTCAACTGGACGGTAGGCGACTCCGCTAT
TGAGGTCATCAACGCCACGACTGGGAAGGATGAGCTGGG
CCGCGCGTCCCGCCTGTGTAAGCACGCGTTGTACTGTC
GCTGGATGCGTGTGCACGGCAAGGTTCCCTCCCACTTAC
TACGCTCCAAGATTACCAAGCCCAACGTGTACCATGAG
TCCAAGCTGGCGGCAAAGGAGTACCAGGCCGCCAAGGCG
CGTCTGTTCACAGCCTTCATCAAGGCGGGGCTGGGGGC
CTGGGTGGAGAAGCCCACCGAGCAGGACCAGTTCTCACT
CACGTACCCATACGACGTACCAGATTACGCTTAA To serve as the target for the putative RNA base-editor, wild-type mCherry coding sequence was mutated to create a premature stop codon TAG (See bold double underlined sequence in SEQ ID NO: 42), such that no functional mCherry protein would be produced without correcting A to G by the RNA base editor. See FIGS. 12 and 14. gRNA was then designed to effect the desired A-to-G editing (FIGS. 12 and 14), and the CX530 plasmid encoding the dCas13e.1-

Figure 13:
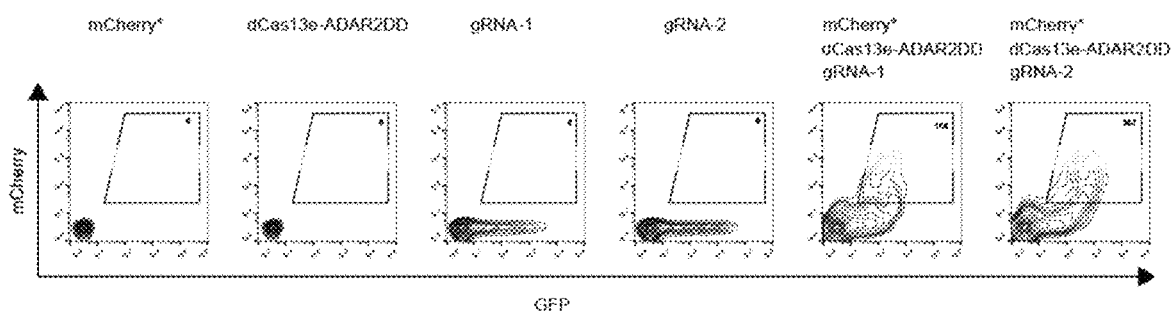
FIG. 13 shows restored expression of mCherry as a result of successful RNA base editing. In the Experiment in FIG. 12, plasmid encoding mutant mCherry (mCherry*) alone failed to express fluorescent mCherry. Plasmid encoding dCas13e-ADAR2DD base editor alone also failed to express fluorescent mCherry. Plasmid encoding either gRNA-1 or gRNA-2 alone (which also expresses a GFP reporter) also failed to express fluorescent mCherry, though GFP was expressed prominently. However, when all three plasmids were transfected into the same cell, significant fluorescent mCherry expression was observed (together with GFP reporter expression).

ADAR2DD base editor, the CX537/Cx538 plasmid encoding the sgRNA, and the CX337 plasmid encoding the mutated mCherry gene, were triple transfected into HEK293T cells using standard protocol. Transfected HEK293T cells were incubated for 24 hours at 37° C. under 5% $CO_2$, before the cells were subject to flow cytometry to isolate cells having corrected mCherry mRNA and expressing mCherry protein. See illustrative drawing FIG. 12. The results of flow cytometry analysis were shown in FIG. 13.

It is apparent that both gRNA-1 (SEQ ID NO: 43) and gRNA-2 (SEQ ID NO: 44) successfully corrected the TAG premature stop codon to generate functional mCherry proteins.

(SEQ ID NO: 42)
```
ATGGTGAGCAAGGGCGAGGAGGATAACATGGCCATCATCAAGGAGTTCA

TGCGCTTCAAGGTGCACATGGAGGGCTCCGTGAACGGCCACGAGTTCGA

GATCGAGGGCGAGGGCGAGGGCCGCCCCTACGAGGGCACCCAGACCGCC

AAGCTGAAGGTGACCAAGGGTGGCCCCCTGCCCTTCGCCTGGGACATCC

TGTCCCCTCAGTTCATGTACGGCTCCAAGGCCTACGTGAAGCACCCCGC

CGACATCCCCGACTACTTGAAGCTGTCCTTCCCCGAGGGCTTCAAG

TAGGAGCGCGTGATGAACTTCGAGGACGGCGGCGTGGTGACCGTGACC

CAGGACTCCTCCCTGCAGGACGGCGAGTTCATCTACAAGGTGAAGCTG

CGCGGCACCAACTTCCCCTCCGACGGCCCCGTAATGCAGAAGAAGACC

ATGGGCTGGGAGGCCTCCTCCGAGCGGATGTACCCCGAGGACGGCGCC

CTGAAGGGCGAGATCAAGCAGAGGCTGAAGCTGAAGGACGGCGGCCAC

TACGACGCTGAGGTCAAGACCACCTACAAGGCCAAGAAGCCCGTGCAG

CTGCCCGGCGCCTACAACGTCAACATCAAGTTGGACATCACCTCCCAC

AACGAGGACTACACCATCGTGGAACAGTACGAACGCGCCGAGGGCCGC

CACTCCACCGGCGGCATGGACGAGCTGTACAAGTAA
```

(SEQ ID NO: 43)
```
caagtagtcggggatgtcggcggggtgcttcacCtaggccttggagcc gtGCTGGAGCAGCCCCGATTTGTGGGGTGATTACAGC
```

(SEQ ID NO: 44)
```
cggggatgtcggcggggtgcttcacCtaggccttggagccgtacatga acGCTGGAGCAGCCCCGATTTGTGGGGTGATTACAGC
```

Example 6 Single-Base RNA Editing Using Shortened dCas13e.1-ADAR2DD Fusion

Figure 15:
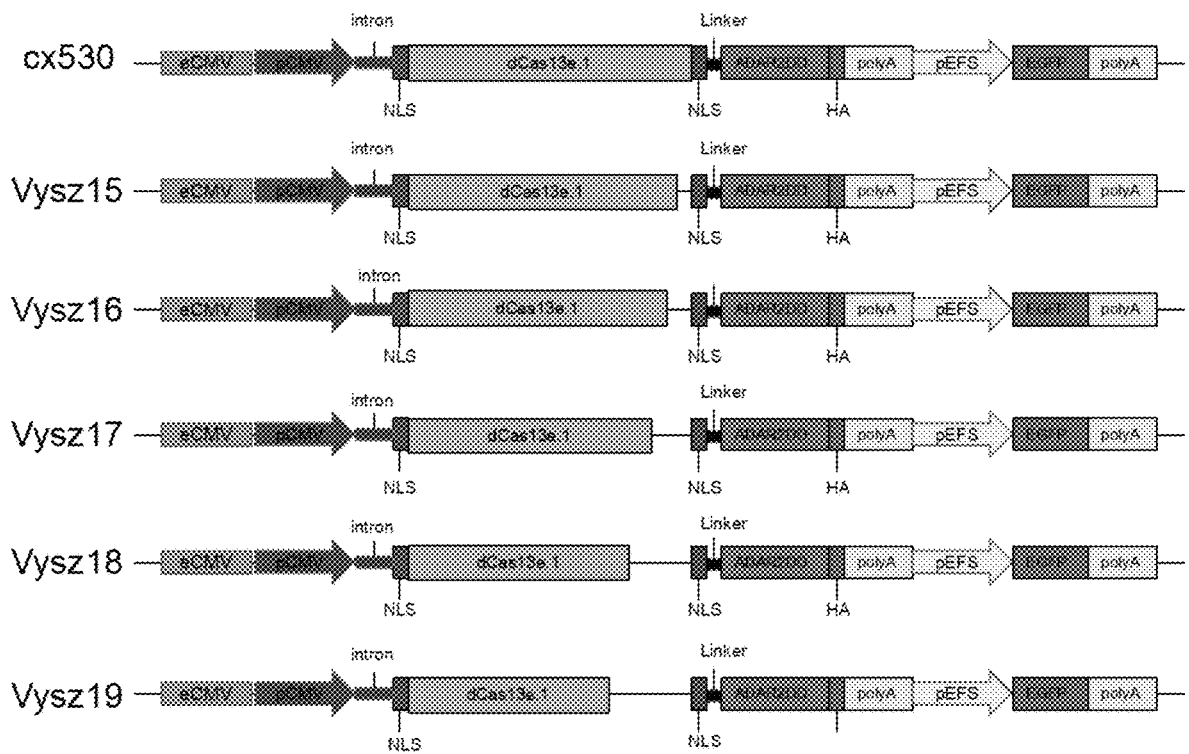
FIG. 15 is a schematic (not to scale) drawing showing the series of progressive C-terminal deletion constructs for dCas13e.1 fused to the ADAR2DD RNA base editor (shown as "ADAR2"), as well as other transcriptional control elements.

In order to determine the minimum size of the dCas13e.1 that can be used in RNA single base editing, a series of five constructs expressing progressively larger C-terminal deletions of dCas13e.1 were generated, each with 30 fewer residues from the C-terminus (i.e., 30-, 60-90-, 120, and 150-residue deletions). The resulting constructs were used to create coding sequences for dCas13e.1 fused with the high fidelity adar2 (ADAR2DD) at the respective C-terminus. These constructs were cloned into Vysz15 ("V15") to Vysz-19 ("V19") plasmids (FIG. 15) for use in experiments similar to that in Example 4. In all these constructs, the fusion proteins were expressed from the CMV promoter (pCMV) and enhancer (eCMV), and was immediately downstream of an intron that further enhances protein expression. Two Nuclear Localization Sequences (NLSs) were positioned at the N- and C-terminus of the dCas13e.1 portion of the fusion, and the ADAR2 domain (such as ADAR2DD) was fused to the C-terminal NLS through a NLS linker, and was tagged at the C-terminus by an HA-tag. An EGFP coding sequence under the independent control of the EFS promoter (pEFS) was present downstream of the polyA addition sequence for all plasmids.

Figure 16:
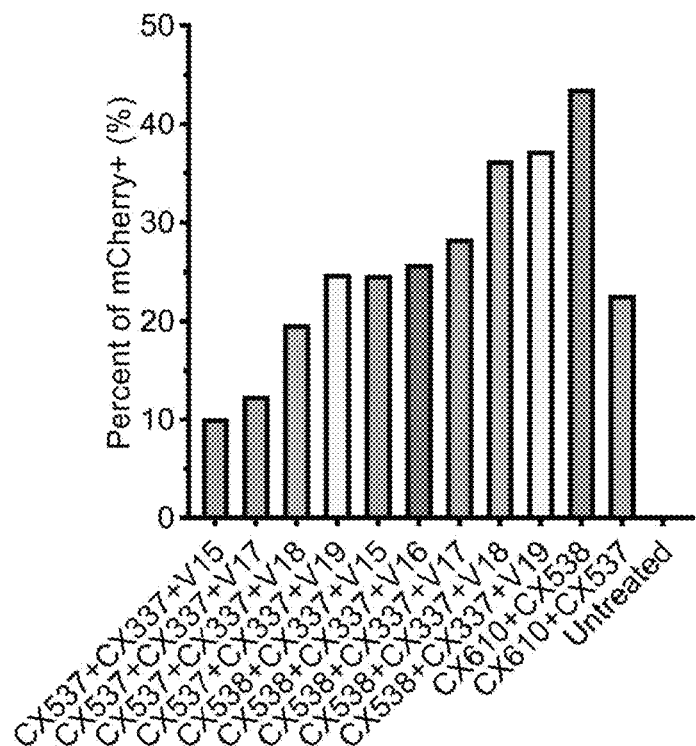
FIG. 16 shows the percentage results of mCherry mutant conversion back to wild-type mCherry, for the series of C-terminal deletion mutants in FIG. 15.

Interestingly, it was found that progressive C-terminal deletion steadily increased RNA-base editing activity in the fusion editor, such that the editor with 150 C-terminal residue deletion (in V19) exhibited the highest base editing activity. See FIG. 16. However, 180-residue deletion from the C-terminus appeared to have abolished the base editing activity, suggesting that the maximum/optimal deletion from the C-terminal end of Cas13e.1 is likely between 150-180 residues.

Figure 17:
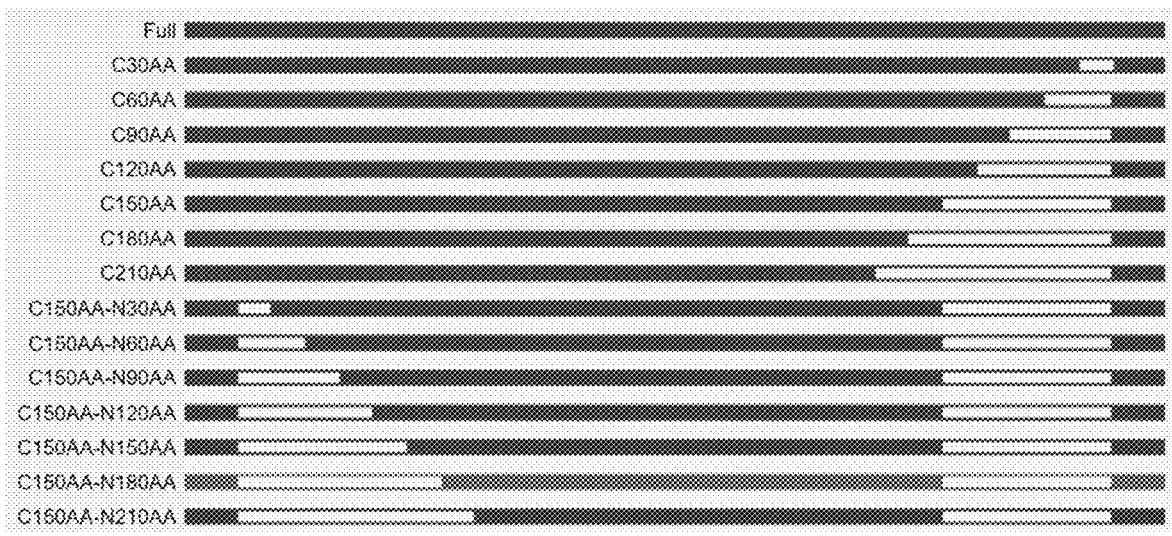
FIG. 17 is a schematic (not to scale) drawing showing the series of progressive C-terminal and optional N-terminal deletion constructs for dCas13e.1 fused to the ADAR2DD RNA base editor.
Figure 18:
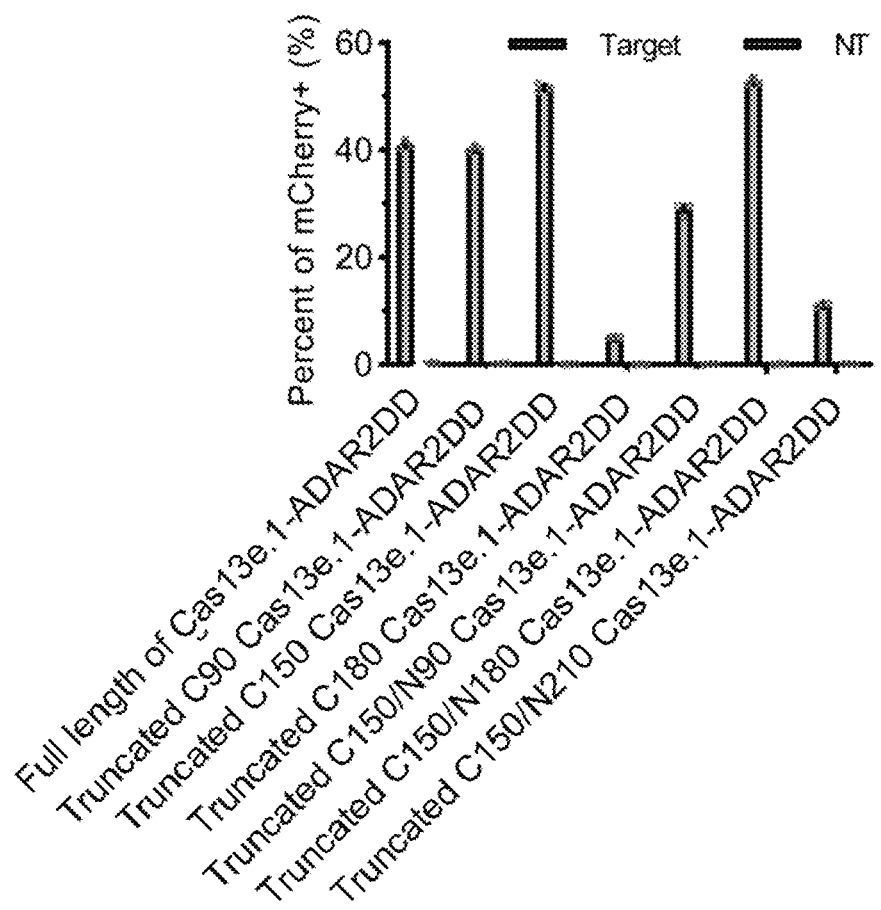
FIG. 18 shows the percentage results of mCherry mutant conversion back to wild-type mCherry, for selected C- and N-terminal deletion mutants in FIG. 17.

Based on this finding, a series of N-terminal deletion mutants were generated for the dCas13e.1 having 150 C-terminal residue deletion. Seven such N-terminal deletion mutants were generated, with 30-, 60-, 90-, 120-, 150-, 180-, and 210-residue deletions, respectively. See FIG. 17. The results in FIG. 18 showed that the best RNA editing activity was observed in the mutant with 180 N-terminal residue deletion and 150 C-terminal residue deletion, i.e., a total of 330-residue deletion from the 775-residue Cas13e.1 protein, to generate the 445-residue optimal dCas13e.1 for generating the ADAR2DD fusion.

Example 7 Mammalian Endogenous mRNA Knock-Down Efficiency Comparison Using Different Cas13 Proteins This experiment demonstrated that Cas13e and Cas13f proteins, especially Cas13f.1, were highly efficient in knocking down mammalian endogenous target mRNA, better than the previously identified Cas13 proteins.

Figure 19:
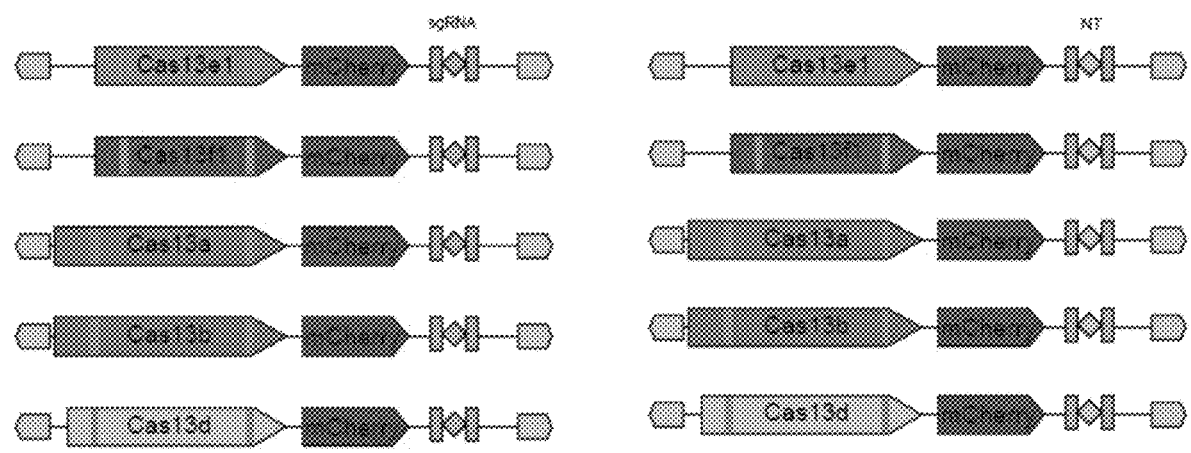
FIG. 19 shows the series of plasmids encoding Cas13a, Cas13b, Cas13d, Cas13e.1 and Cas13f.1, the mCherry reporter gene, as well as either the ANXA4-targeting gRNA coding sequence, or a non-targeting gRNA as control.

Specifically, five plasmids were constructed, each expressing one of the Cas13 proteins, namely Cas13e.1 (SEQ ID NO: 22), Cas13f.1 (SEQ ID NO: 23), LwaCas13a (SEQ ID NO: 44), PspCas13b (SEQ ID NO: 45), and RxCas13d (SEQ ID NO: 46). Each plasmid also encoded the mCherry reporter gene, as well as sgRNA/crRNA coding sequences for the respective Cas13 proteins flanked by two native DR sequences. These sgRNA's were designed to have spacer sequences targeting the ANXA4 mRNA. See SEQ ID NOs: 47-49. As negative control, 5 additional plasmids were constructed, each encoding a non-targeting sgRNA/crRNA instead of the ANXA4-targeting sgRNA/crRNA ("the control NT constructs"). See FIG. 19.

(SEQ ID NO: 51)
```
ATGCCCAAGAAGAAGCGGAAGGTGGGATCCATGAAAGTGACCAAGGTCGATGGCATCAGCCACAAGAAGTACATCGA

AGAGGGCAAGCTCGTGAAGTCCACCAGCGAGGAAAACCGGACCAGCGAGAGACTGAGCGAGCTGCTGAGCATCCGGC

TGGACATCTACATCAAGAACCCCGACAACGCCTCCGAGGAAGAGAACCGGATCAGAAGAGAGAACCTGAAGAAGTTC

TTTAGCAACAAGGTGCTGCACCTGAAGGACAGCGTGCTGTATCTGAAGAACCGGAAAGAAAAGAACGCCGTGCAGGA
```

-continued

```
CAAGAACTATAGCGAAGAGGACATCAGCGAGTACGACCTGAAAAACAAGAACAGCTTCTCCGTGCTGAAGAAGATCC
TGCTGAACGAGGACGTGAACTCTGAGGAACTGGAAATCTTTCGGAAGGACGTGGAAGCCAAGCTGAACAAGATCAAC
AGCCTGAAGTACAGCTTCGAAGAGAACAAGGCCAACTACCAGAAGATCAACGAGAACAACGTGGAAAAAGTGGGCGG
CAAGAGCAAGCGGAACATCATCTACGACTACTACAGAGAGAGCGCCAAGCGCAACGACTACATCAACAACGTGCAGG
AAGCCTTCGACAAGCTGTATAAGAAAGAGGATATCGAGAAACTGTTTTTCCTGATCGAGAACAGCAAGAAGCACGAG
AAGTACAAGATCCGCGAGTACTATCACAAGATCATCGGCCGGAAGAACGACAAAGAGAACTTCGCCAAGATTATCTA
CGAAGAGATCCAGAACGTGAACAACATCAAAGAGCTGATTGAGAAGATCCCCGACATGTCTGAGCTGAAGAAAAGCC
AGGTGTTCTACAAGTACTACCTGGACAAAGAGGAACTGAACGACAAGAATATTAAGTACGCCTTCTGCCACTTCGTG
GAAATCGAGATGTCCCAGCTGCTGAAAAACTACGTGTACAAGCGGCTGAGCAACATCAGCAACGATAAGATCAAGCG
GATCTTCGAGTACCAGAATCTGAAAAAGCTGATCGAAAACAAACTGCTGAACAAGCTGGACACCTACGTGCGGAACT
GCGGCAAGTACAACTACTATCTGCAAGTGGGCGAGATCGCCACCTCCGACTTTATCGCCCGGAACCGGCAGAACGAG
GCCTTCCTGAGAAACATCATCGGCGTGTCCAGCGTGGCCTACTTCAGCCTGAGGAACATCCTGGAAACCGAGAACGA
GAACGATATCACCGGCCGGATGCGGGCAAGACCGTGAAGAACAACAAGGGCGAAGAGAAATACGTGTCCGGCGAGG
TGGACAAGATCTACAATGAGAACAAGCAGAACGAAGTGAAAGAAAATCTGAAGATGTTCTACAGCTACGACTTCAAC
ATGGACAACAAGAACGAGATCGAGGACTTCTTCGCCAACATCGACGAGGCCATCAGCAGCATCAGACACGGCATCGT
GCACTTCAACCTGGAACTGGAAGGCAAGGACATCTTCGCCTTCAAGAATATCGCCCCCAGCGAGATCTCCAAGAAGA
TGTTTCAGAACGAAATCAACGAAAAGAAGCTGAAGCTGAAAATCTTCAAGCAGCTGAACAGCGCCAACGTGTTCAAC
TACTACGAGAAGGATGTGATCATCAAGTACCTGAAGAATACCAAGTTCAACTTCGTGAACAAAAACATCCCCTTCGT
GCCCAGCTTCACCAAGCTGTACAACAAGATTGAGGACCTGCGGAATACCCTGAAGTTTTTTGGAGCGTGCCCAAGG
ACAAAGAAGAGAAGGACGCCCAGATCTACCTGCTGAAGAATATCTACTACGGCGAGTTCCTGAACAAGTTCGTGAAA
AACTCCAAGGTGTTCTTTAAGATCACCAATGAAGTGATCAAGATTAACAAGCAGCGGAACCAGAAAACCGGCCACTA
CAAGTATCAGAAGTTCGAGAACATCGAGAAACCGTGCCCGTGGAATACCTGGCCATCATCCAGAGCAGAGAGATGA
TCAACAACCAGGACAAAGAGGAAAAGAATACCTACATCGACTTTATTCAGCAGATTTTCCTGAAGGGCTTCATCGAC
TACCTGAACAAGAACAATCTGAAGTATATCGAGAGCAACAACAACAATGACAACAACGACATCTTCTCCAAGATCAA
GATCAAAAAGGATAACAAAGAGAAGTACGACAAGATCCTGAAGAACTATGAGAAGCACAATCGGAACAAAGAAATCC
CTCACGAGATCAATGAGTTCGTGCGCGAGATCAAGCTGGGGAAGATTCTGAAGTACACCGAGAATCTGAACATGTTT
TACCTGATCCTGAAGCTGCTGAACCACAAAGAGCTGACCAACCTGAAGGGCAGCCTGGAAAAGTACCAGTCCGCCAA
CAAAGAAGAAACCTTCAGCGACGAGCTGGAACTGATCAACCTGCTGAACCTGGACAACAACAGAGTGACCGAGGACT
TCGAGCTGGAAGCCAACGAGATCGGCAAGTTCCTGGACTTCAACGAAAACAAATCAAGGACCGGAAAGAGCTGAAA
AAGTTCGACACCAACAAGATCTATTTCGACGGCGAGAACATCATCAAGCACCGGGCCTTCTACAATATCAAGAAATA
CGGCATGCTGAATCTGCTGGAAAAGATCGCCGATAAGGCCAAGTATAAGATCAGCCTGAAAGAACTGAAAGAGTACA
GCAACAAGAAGAATGAGATTGAAAAGAACTACACCATGCAGCAGAACCTGCACCGGAAGTACGCCAGACCCAAGAAG
GACGAAAAGTTCAACGACGAGGACTACAAAGAGTATGAGAAGGCCATCGGCAACATCCAGAAGTACACCCACCTGAA
GAACAAGGTGGAATTCAATGAGCTGAACCTGCTGCAGGGCCTGCTGCTGAAGATCCTGCACCGGCTCGTGGGCTACA
CCAGCATCTGGGAGCGGGACCTGAGATTCCGGCTGAAGGGCGAGTTTCCCGAGAACCACTACATCGAGGAAATTTTC
AATTTCGACAACTCCAAGAATGTGAAGTACAAAAGCGGCCAGATCGTGGAAAAGTATATCAACTTCTACAAAGAACT
GTACAAGGACAATGTGGAAAAGCGGAGCATCTACTCCGACAAGAAAGTGAAGAAACTGAAGCAGGAAAAAAAGGACC
TGTACATCCGGAACTACATTGCCCACTTCAACTACATCCCCCACGCCGAGATTAGCCTGCTGGAAGTGCTGGAAAAC
CTGCGGAAGCTGCTGTCCTACGACCGGAAGCTGAAGAACGCCATCATGAAGTCCATCGTGGACATTCTGAAAGAATA
CGGCTTCGTGGCCACCTTCAAGATCGGCGCTGACAAGAAGATCGAAATCCAGACCCTGGAATCAGAGAAGATCGTGC
```

-continued

ACCTGAAGAATCTGAAGAAAAAGAAACTGATGACCGACCGGAACAGCGAGGAACTGTGCGAACTCGTGAAAGTCATG

TTCGAGTACAAGGCCCTGGAATGA (SEQ ID NO: 45)
ATGCCCAAGAAGAAGCGGAAGGTGGTCGACAACATCCCCGCTCTGGTGGAAAACCAGAAGAAGTACTTTGGCACCTA

CAGCGTGATGGCCATGCTGAACGCTCAGACCGTGCTGGACCACATCCAGAAGGTGGCCGATATTGAGGGCGAGCAGA

ACGAGAACAACGAGAATCTGTGGTTTCACCCCGTGATGAGCCACCTGTACAACGCCAAGAACGGCTACGACAAGCAG

CCCGAGAAACCATGTTCATCATCGAGCGGCTGCAGAGCTACTTCCCATTCCTGAAGATCATGGCCGAGAACCAGAG

AGAGTACAGCAACGGCAAGTACAAGCAGAACCGCGTGGAAGTGAACAGCAACGACATCTTCGAGGTGCTGAAGCGCG

CCTTCGGCGTGCTGAAGATGTACAGGGACCTGACCAACCACTACAAGACCTACGAGGAAAAGCTGAACGACGGCTGC

GAGTTCCTGACCAGCACAGAGCAACCTCTGAGCGGCATGATCAACAACTACTACACAGTGGCCCTGCGGAACATGAA

CGAGAGATACGGCTACAAGACAGAGGACCTGGCCTTCATCCAGGACAAGCGGTTCAAGTTCGTGAAGGACGCCTACG

GCAAGAAAAAGTCCCAAGTGAATACCGGATTCTTCCTGAGCCTGCAGGACTACAACGGCGACACACAGAAGAAGCTG

CACCTGAGCGGAGTGGGAATCGCCCTGCTGATCTGCCTGTTCCTGGACAAGCAGTACATCAACATCTTTCTGAGCAG

GCTGCCCATCTTCTCCAGCTACAATGCCCAGAGCGAGGAACGGCGGATCATCATCAGATCCTTCGGCATCAACAGCA

TCAAGCTGCCCAAGGACCGGATCCACAGCGAGAAGTCCAACAAGAGCGTGGCCATGGATATGCTCAACGAAGTGAAG

CGGTGCCCCGACGAGCTGTTCACAACACTGTCTGCCGAGAAGCAGTCCCGGTTCAGAATCATCAGCGACGACCACAA

TGAAGTGCTGATGAAGCGGAGCAGCGACAGATTCGTGCCTCTGCTGCTGCAGTATATCGATTACGGCAAGCTGTTCG

ACCACATCAGGTTCCACGTGAACATGGGCAAGCTGAGATACCTGCTGAAGGCCGACAAGACCTGCATCGACGGCCAG

ACCAGAGTCAGAGTGATCGAGCAGCCCCTGAACGGCTTCGGCAGACTGGAAGAGGCCGAGACAATGCGGAAGCAAGA

GAACGGCACCTTCGGCAACAGCGGCATCCGGATCAGAGACTTCGAGAACATGAAGCGGGACGACGCCAATCCTGCCA

ACTATCCCTACATCGTGGACACCTACACACACTATCTCCTGGAAAACAACAAGGTCGAGATGTTTATCAACGACAAA

GAGGACAGCGCCCCACTGCTGCCCGTGATCGAGGATGATAGATACGTGGTCAAGACAATCCCCAGCTGCCGGATGAG

CACCCTGGAAATTCCAGCCATGGCCTTCCACATGTTTCTGTTCGGCAGCAAGAAACCGAGAAGCTGATCGTGGACG

TGCACAACCGGTACAAGAGACTGTTCCAGGCCATGCAGAAAGAAGAAGTGACCGCCGAGAATATCGCCAGCTTCGGA

ATCGCCGAGAGCGACCTGCCTCAGAAGATCCTGGATCTGATCAGCGGCAATGCCCACGGCAAGGATGTGGACGCCTT

CATCAGACTGACCGTGGACGACATGCTGACCGACACCGAGCGGAGAATCAAGAGATTCAAGGACGACCGGAAGTCCA

TTCGGAGCGCCGACAACAAGATGGGAAAGAGAGGCTTCAAGCAGATCTCCACAGGCAAGCTGGCCGACTTCCTGGCC

AAGGACATCGTGCTGTTTCAGCCCAGCGTGAACGATGGCGAGAACAAGATCACCGGCCTGAACTACCGGATCATGCA

GAGCGCCATTGCCGTGTACGATAGCGGCGACGATTACGAGGCCAAGCAGCAGTTCAAGCTGATGTTCGAGAAGGCCC

GGCTGATCGGCAAGGGCACAACAGAGCCTCATCCATTTCTGTACAAGGTGTTCGCCCGCAGCATCCCCGCCAATGCC

GTCGAGTTCTACGAGCGCTACCTGATCGAGCGGAAGTTCTACCTGACCGGCCTGTCCAACGAGATCAAGAAAGGCAA

CAGAGTGGATGTGCCCTTCATCCGGCGGGACCAGAACAAGTGGAAAACACCCGCCATGAAACCCTGGGCAGAATCT

ACAGCGAGGATCTGCCCGTGGAACTGCCCAGACAGATGTTCGACAATGAGATCAAGTCCCACCTGAAGTCCCTGCCA

CAGATGGAAGGCATCGACTTCAACAATGCCAACGTGACCTATCTGATCGCCGAGTACATGAAGAGAGTGCTGGACGA

CGACTTCCAGACCTTCTACCAGTGGAACCGCAACTACCGGTACATGGACATGCTTAAGGGCGAGTACGACAGAAAGG

GCTCCCTGCAGCACTGCTTCACCAGCGTGGAAGAGAGAGAAGGCCTCTGGAAAGAGCGGGCCTCCAGAACAGAGCGG

TACAGAAAGCAGGCCAGCAACAAGATCCGCAGCAACCGGCAGATGAGAAACGCCAGCAGCGAAGAGATCGAGACAAT

CCTGGATAAGCGGCTGAGCAACAGCCGGAACGAGTACCAGAAAAGCGAGAAAGTGATCCGGCGCTACAGAGTGCAGG

ATGCCCTGCTGTTTCTGCTGGCCAAAAAGACCCTGACCGAACTGGCCGATTTCGACGGCGAGAGGTTCAAACTGAAA

GAAATCATGCCCGACGCCGAGAAGGGAATCCTGAGCGAGATCATGCCCCATGAGCTTCACCTTCGAGAAAGGCGGCAA

GAAGTACACCATCACCAGCGAGGGCATGAAGCTGAAGAACTACGGCGACTTCTTTGTGCTGGCTAGCGACAAGAGGA

-continued

TCGGCAACCTGCTGGAACTCGTGGGCAGCGACATCGTGTCCAAAGAGGATATCATGGAAGAGTTCAACAAATACGAC

CAGTGCAGGCCCGAGATCAGCTCCATCGTGTTCAACCTGGAAAAGTGGGCCTTCGACACATACCCCGAGCTGTCTGC

CAGAGTGGACCGGGAAGAGAAGGTGGACTTCAAGAGCATCCTGAAAATCCTGCTGAACAACAAGAACATCAACAAAG

AGCAGAGCGACATCCTGCGGAAGATCCGGAACGCCTTCGATCACAACAATTACCCCGACAAAGGCGTGGTGGAAATC

AAGGCCCTGCCTGAGATCGCCATGAGCATCAAGAAGGCCTTTGGGGAGTACGCCATCATGAAGGGATCCCTTCAATG

A (SEQ ID NO: 46)
ATGCCTAAAAAGAAAAGAAAGGTGGGTTCTGGTATCGAGAAGAAGAAGAGCTTCGCCAAGGGCATGGGAGTGAAGAG

CACCCTGGTGTCCGGCTCTAAGGTGTACATGACCACATTTGCTGAGGGAAGCGACGCCAGGCTGGAGAAGATCGTGG

AGGGCGATAGCATCAGATCCGTGAACGAGGGAGAGGCTTTCAGCGCCGAGATGGCTGACAAGAACGCTGGCTACAAG

ATCGGAAACGCCAAGTTTTCCCACCCAAAGGGCTACGCCGTGGTGGCTAACAACCCACTGTACACCGGACCAGTGCA

GCAGGACATGCTGGGACTGAAGGAGACACTGGAGAAGAGGTACTTCGGCGAGTCCGCCGACGGAAACGATAACATCT

GCATCCAGGTCATCCACAACATCCTGGATATCGAGAAGATCCTGGCTGAGTACATCACAAACGCCGCTTACGCCGTG

AACAACATCTCCGGCCTGGACAAGGATATCATCGGCTTCGGAAAGTTTTCTACCGTGTACACATACGACGAGTTCAA

GGATCCAGAGCACCACCGGGCCGCTTTTAACAACAACGACAAGCTGATCAACGCCATCAAGGCTCAGTACGACGAGT

TCGATAACTTTCTGGATAACCCCAGGCTGGGCTACTTCGGACAGGCTTTCTTTTCTAAGGAGGGCAGAAACTACATC

ATCAACTACGGAAACGAGTGTTACGACATCCTGGCCCTGCTGAGCGGACTGAGGCACTGGGTGGTGCACAACAACGA

GGAGGAGTCTCGGATCAGCCGCACCTGGCTGTACAACCTGGACAAGAACCTGGATAACGAGTACATCTCCACACTGA

ACTACCTGTACGACAGGATCACCAACGAGCTGACAAACAGCTTCTCCAAGAACTCTGCCGCTAACGTGAACTACATC

GCTGAGACCCTGGGCATCAACCCAGCTGAGTTCGCTGAGCAGTACTTCAGATTTTCCATCATGAAGGAGCAGAAGAA

CCTGGGCTTCAACATCACAAAGCTGAGAGAAGTGATGCTGGACAGAAAGGATATGTCCGAGATCAGGAAGAACCACA

AGGTGTTCGATTCTATCAGAACCAAGGTGTACACAATGATGGACTTTGTGATCTACAGGTACTACATCGAGGAGGAT

GCCAAGGTGGCCGCTGCCAACAAGAGCCTGCCCGACAACGAGAAGTCTCTGAGCGAGAAGGATATCTTCGTGATCAA

CCTGAGAGGCTCCTTTAACGACGATCAGAAGGACGCTCTGTACTACGATGAGGCCAACAGGATCTGGAGAAAGCTGG

AGAACATCATGCACAACATCAAGGAGTTCCGGGGAAACAAGACCCGCGAGTACAAGAAGAAGGACGCTCCAAGGCTG

CCTAGGATCCTGCCTGCTGGAAGGGACGTGAGCGCCTTCAGCAAGCTGATGTACGCCCTGACAATGTTTCTGGACGG

AAAGGAGATCAACGATCTGCTGACCACACTGATCAACAAGTTCGACAACATCCAGTCTTTTCTGAAAGTGATGCCTC

TGATCGGCGTGAACGCTAAGTTCGTGGAGGAGTACGCCTTCTTTAAGGACAGCGCCAAGATCGCTGATGAGCTGCGG

CTGATCAAGTCCTTTGCCAGGATGGGAGAGCCAATCGCTGACGCTAGGAGAGCTATGTACATCGATGCCATCCGGAT

CCTGGGAACCAACCTGTCTTACGACGAGCTGAAGGCTCTGGCCGACACCTTCAGCCTGGATGAGAACGGCAACAAGC

TGAAGAAGGGCAAGCACGGAATGCGCAACTTCATCATCAACAACGTGATCAGCAACAAGCGGTTTCACTACCTGATC

AGATACGGCGACCCAGCTCACCTGCACGAGATCGCTAAGAACGAGGCCGTGGTGAAGTTCGTGCTGGGACGGATCGC

CGATATCCAGAAGAAGCAGGGCCAGAACGGAAAGAACCAGATCGACCGCTACTACGAGACCTGCATCGGCAAGGATA

AGGGAAAGTCCGTGTCTGAGAAGGTGGACGCTCTGACCAAGATCATCACAGGCATGAACTACGACCAGTTCGATAAG

AAGAGATCTGTGATCGAGGACACCGGAAGGGAGAACGCCGAGAGAGAAGTTTAAGAAGATCATCAGCCTGTACCT

GACAGTGATCTACCACATCCTGAAGAACATCGTGAACATCAACGCTAGATACGTGATCGGCTTCCACTGCGTGGAGC

GCGATGCCCAGCTGTACAAGGAGAAGGGATACGACATCAACCTGAAGAAGCTGGAGGAGAAGGGCTTTAGCTCCGTG

ACCAAGCTGTGCGCTGGAATCGACGAGACAGCCCCCGACAAGAGGAAGGATGTGGAGAAGGAGATGGCCGAGAGAGC

TAAGGAGAGCATCGACTCCCTGGAGTCTGCTAACCCTAAGCTGTACGCCAACTACATCAAGTACTCCGATGAGAAGA

AGGCCGAGGAGTTCACCAGGCAGATCAACAGAGAGAAGGCCAAGACCGCTCTGAACGCCTACCTGAGGAACACAAAG

TGGAACGTGATCATCCGGGAGGACCTGCTGCGCATCGATAACAAGACCTGTACACTGTTCCGGAACAAGGCTGTGCA

```
CCTGGAGGTGGCTCGCTACGTGCACGCCTACATCAACGACATCGCCGAGGTGAACTCCTACTTTCAGCTGTACCACT

ACATCATGCAGAGGATCATCATGAACGAGAGATACGAGAAGTCTAGCGGCAAGGTGTCTGAGTACTTCGACGCCGTG

AACGATGAGAAGAAGTACAACGATAGACTGCTGAAGCTGCTGTGCGTGCCTTTCGGATACTGTATCCCACGGTTTAA

GAACCTGAGCATCGAGGCCCTGTTCGACCGCAACGAGGCTGCCAAGTTTGATAAGGAGAAGAAGAAGGTGAGCGGCA

ACTCCTGA
```

(SEQ ID NO: 47)
```
ATGGCCCTTCGCAGCTCTTGCACGTCATAC
```

(SEQ ID NO: 48)
```
TTAGGCAGCCCTCATCAGTGCCGGCTCCCT
```

(SEQ ID NO: 49)
```
GGCCAGGATCTCAATTAGGCAGCCCTCATC
```

The five Cas13/sgRNA-encoding plasmids were transfected into HEK293 cells as in Example 4. After culturing for 24 hours, cells expressing mCherry were isolated through flow cytometry, and expression of ANXA4 mRNA was determined using RT-PCR to assess knock-down efficiency as compared to control cells transfected by Cas13/NT-encoding plasmids.

Figure 20:
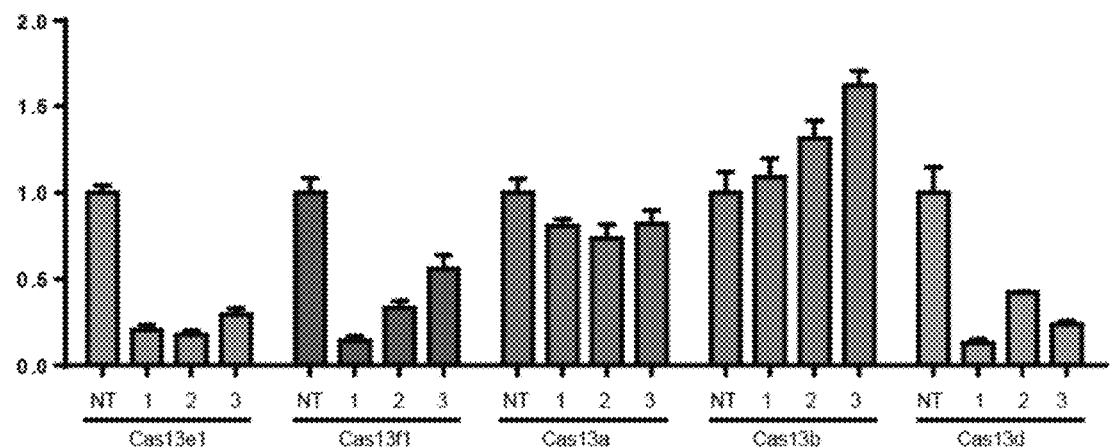
FIG. 20 shows efficient knock-down of ANXA4 expression by Cas13e.1, Cas13f.1, Cas13a, as well as Cas13d.

FIG. 20 showed that Cas13b only had marginal ANXA4 mRNA knock-down, while Cas13e.1, Cas13f.1, and Cas13d each had over 80% knock down of the target ANXA4 mRNA. Among them, Cas13e.1 appeared to have the most robust knock-down efficiency.

The invention claimed is:

1. A Clustered Regularly interspaced Short Palindromic Repeat (CRISPR)-Cas complex, comprising:
   (1) an RNA guide sequence comprising a spacer sequence capable of hybridizing to a target RNA and a direct repeat (DR) sequence 3' to the spacer sequence; and,
   (2) a CRISPR-associated protein (Cas) having;
      a) the amino acid sequence of any one of SEQ ID Nos: 2-7;
      b) an amino acid sequence at least about 90% identical to the amino acid sequence of any one of SEQ ID Nos: 2-7; or
      c) a functional fragment of the amino acid sequence of any one of SEQ ID Nos: 2-7, wherein the functional fragment consists of an N-terminal and/or a C-terminal deletion and is at least 50% Identical to any one of SEQ ID Nos: 2-7,
   wherein
      a) the amino acid sequence of any one of SEQ ID Nos: 2-7;
      b) the amino acid sequence at least about 90% identical to the amino acid sequence of any one of SEQ ID Nos: 2-7; and
      c) the functional fragment of the amino acid sequence of any one of SEQ ID Nos: 2-7,
   are capable of (i) binding to the RNA guide sequence and (ii) targeting the target RNA,
   with the proviso that the spacer sequence is not 100% complementary to a naturally-occurring bacteriophage nucleic acid when the complex comprises the Cas amino acid sequence of any one of SEQ ID Nos: 2-7.

2. The CRISPR-Cas complex of claim 1, wherein the DR sequence has substantially the same secondary structure as the secondary structure of a DR sequence encoded by a complement sequence of any one of SEQ ID NOs: 9-14.

3. The CRISPR-Cas complex of claim 1, wherein the DR sequence is encoded by a complement sequence of any one of SEQ ID NOs: 9-14.

4. The CRISPR-Cas complex of claim 1, wherein the target RNA is encoded by a eukaryotic DNA.

5. The CRISPR-Cas complex of claim 4, wherein the eukaryotic DNA is a non-human mammalian DNA, a non-human primate DNA, a human DNA, a plant DNA, an insect DNA, a bird DNA, a reptile DNA, a rodent DNA, a fish DNA, a worm/nematode DNA, or a yeast DNA.

6. The CRISPR-Cas complex of claim 1, wherein the target RNA is an mRNA.

7. The CRISPR-Cas complex of claim 1, wherein the spacer sequence is between 15-60 nucleotides, between 25-50 nucleotides, or about 30 nucleotides.

8. The CRISPR-Cas complex of claim 1, wherein the spacer sequence is 90-100% complementary to the target RNA.

9. The CRISPR-Cas complex of claim 1, wherein the amino acid sequence at least about 90% identical to the amino acid sequence of any one of SEQ ID NOs: 2-7 comprises conserved amino acid substitutions of one or more residues of any one of SEQ ID NOs. 2-7.

10. The CRISPR-Cas complex of claim 9, wherein the amino acid sequence at least about 90% identical to the amino acid sequence of any one of SEQ ID NOs: 2-7 comprises only conserved amino acid substitutions.

11. The CRISPR-Cas complex of claim 1, wherein the amino acid sequence at least about 90% identical to the amino acid sequence of any one of SEQ ID NOs: 2-7 has identical sequence to wild-type Cas of any one of SEQ ID NOs: 2-7 in an HEPN domain or an RXXXXH motif.

12. The CRISPR-Cas complex of claim 1, wherein the amino acid sequence at least about 90% identical to the amino acid sequence of any one of SEQ ID NOs: 2-7 is capable of binding to the RNA guide sequence when said RNA guide sequence is hybridized to the target RNA, and wherein said amino acid sequence at least about 90% identical to the amino acid sequence of any one of SEQ ID NOs: 2-7 has no RNase catalytic activity due to a mutation in the RNase catalytic site of the Cas.

13. The CRISPR-Cas complex of claim 1, wherein the functional fragment has an N-terminal deletion of no more than 210 residues, and/or a C-terminal deletion of no more than 180 residues.

14. The CRISPR-Cas complex of claim 13, wherein the functional fragment has an N-terminal deletion of about 180 residues, and/or a C-terminal deletion of about 150 residues.

15. The CRISPR-Cas complex of claim 14, wherein the functional fragment is fused to an RNA base-editing domain.

16. The CRISPR-Cas complex of claim 15, wherein the RNA base-editing domain comprises an adenosine deaminase; an apolipoprotein B mRNA editing enzyme; a catalytic polypeptide-like (APOBEC); or an activation-induced cytidine deaminase (AID).

17. The CRISPR-Cas complex of claim 16, wherein the adenosine deaminase is adenosine deaminase acting on RNA 2 (ADAR2) and wherein the ADAR2 has an E488Q/T375G double mutation or is ADAR2DD.

18. The CRISPR-Cas complex of claim 15, wherein the base-editing domain is further fused to an RNA-binding domain.

19. The CRISPR-Cas complex of claim 12, wherein the amino acid sequence at least about 90% identical to the amino acid sequence of any one of SEQ ID NOs: 2-7 is fused to an RNA methyltransferase, a RNA demethylase, an RNA splicing modifier, a localization factor, or a translation modification factor.

20. The CRISPR-Cas complex of claim 1, wherein
   a) the amino acid sequence of any one of SEQ ID Nos: 2-7;
   b) the amino acid sequence at least about 90% identical to the amino acid sequence of any one of SEQ ID Nos: 2-7; or
   c) the functional fragment of the amino acid sequence of any one of SEQ ID Nos: 2-7
   is fused to a nuclear localization signal (NLS) sequence or a nuclear export signal (NES).

21. The CRISPR-Cas complex of claim 1, wherein targeting of the target RNA results in a modification of the target RNA.

22. The CRISPR-Cas complex of claim 21, wherein the modification of the target RNA is a cleavage of the target RNA.

23. The CRISPR-Cas complex of claim 21, wherein the modification of the target RNA is deamination of an adenosine (A) to an inosine (I).

24. The CRISPR-Cas complex of claim 1, further comprising a target RNA comprising a sequence capable of hybridizing to the spacer sequence.

25. A fusion protein, comprising
a CRISPR-associated protein (Cas) having:
  a) the amino acid sequence of any one of SEQ ID Nos: 2-7;
  b) an amino acid sequence at least about 90% identical to the amino acid sequence of any one of SEQ ID Nos: 2-7; or
  c) afunctional fragment of the amino acid sequence of any one of SEQ ID Nos: 2-7, wherein the functional fragment consists of an N-terminal and/or a C-terminal deletion and is at least 50% identical to any one of SEQ ID Nos: 2-7, wherein the functional fragment is capable of (i) binding to an RNA guide sequence and (ii) targeting a target RNA,
and
(2) a heterologous functional domain.

26. The fusion protein of claim 25, wherein the heterologous functional domain comprises: a nuclear localization signal (NLS), a reporter protein, a detection label, a localization signal, a protein targeting moiety, a DNA binding domain, an epitope tag, a transcription activation domain, a transcription inhibition domain, a nuclease, a deamination domain, a methylase, a demethylase, a transcription release factor, an HBAC, a polypeptide having ssRNA cleavage activity, a polypeptide having dsRNA cleavage activity, a polypeptide having ssDNA cleavage activity, a polypeptide having dsDNA cleavage activity, a DNA ligase, or gi RNA ligase, or any combination thereof.

27. A method of modifying a target RNA, the method comprising contacting the target RNA with the CRISPR-Cas complex of claim 1, wherein the spacer sequence is complementary to at least 15 nucleotides of the target RNA; wherein
  a) the amino acid sequence of any one of SEQ ID Nos: 2-7;
  b) the amino acid sequence at least about 90% identical to the amino acid sequence of any one of SEQ ID Nos: 2-7; or
  c) the functional fragment of the amino acid sequence of any one of SEQ ID Nos: 2-7
associates with the RNA guide sequence to form the complex; wherein the complex binds to the target RNA; and wherein upon binding of the complex to the target RNA,
  a) the amino acid sequence of any one of SEQ ID Nos: 2-7;
  b) the amino acid sequence at least about 90% identical to the amino acid sequence of any one of SEQ ID Nos: 2-7; or
  c) the functional fragment of the amino acid sequence of any one of SEQ ID Nos: 2-7
modifies the target RNA.

28. The method of claim 27, wherein the target RNA is modified by deamination by a Double-stranded RNA-specific adenosine deaminase fused to the amino acid sequence at least about 90% identical to the amino acid sequence of any one of SEQ ID NOs: 2-7.

29. The method of claim 27, wherein the target RNA is an mRNA, a tRNA, an rRNA, a non-coding RNA, an lncRNA, or a nuclear RNA.

30. An isolated eukaryotic cell comprising a Clustered Regularly interspaced Short Palindromic Repeat (CRISPR)-Cas complex, comprising:
  (1) an RNA guide sequence comprising a spacer sequence capable of hybridizing to a target RNA and a direct repeat (DR) sequence 3' to the spacer sequence; and,
  a CRISPR-associated protein (Cas) having:
    a) the amino acid sequence of any one of SEQ ID Nos: 2-7;
    b) an amino acid sequence at least about 90% identical to the amino acid sequence of any one of SEQ ID Nos: 2-7; or
    c) a functional fragment of the amino acid sequence of any one of SEQ ID Nos: 2-7, wherein the functional fragment consists of an N-terminal and/or a C-terminal deletion and is at least 50% identical to any one of SEQ ID Nos: 2-7,
  wherein
    a) the amino acid sequence of any one of SEQ ID Nos: 2-7;
    b) the amino acid sequence at least about 90% identical to the amino acid sequence of any one of SEQ ID Nos: 2-7; and
    c) the functional fragment of the amino acid sequence of any one of SEQ ID Nos: 2-7,
  are capable of (i) binding to the RNA guide sequence and (ii) targeting the target RNA.

* * * * *

UNITED STATES PATENT AND TRADEMARK OFFICE
CERTIFICATE OF CORRECTION

PATENT NO. : 11,225,659 B2
APPLICATION NO. : 16/864982
DATED : January 18, 2022
INVENTOR(S) : Hui Yang et al.

Page 1 of 1

It is certified that error appears in the above-identified patent and that said Letters Patent is hereby corrected as shown below:

In the Claims

At Column 215, Line 11, replace "interspaced" with --Interspaced--;

At Column 215, Line 16, replace "having;" with --having:--;

At Column 215, Line 25, replace "Identical" with --identical--;

At Column 215, Line 67, replace "Nos." with --Nos:--;

At Column 216, Line 24, replace "90°/o" with --90%--;

At Column 217, Line 14, replace "a CRISPR-associated" with --(1) a CRISPR-associated--;

At Column 217, Line 20, replace "afunctional" with --a functional--;

At Column 217, Line 36, replace "HBAC" with --HDAC--;

At Column 217, Line 39, replace "gi RNA" with --an RNA--;

At Column 218, Line 24, replace "interspaced" with --Interspaced--;

At Column 218, Line 27, replace "RNA" with --RNA,--.

Signed and Sealed this
Twenty-seventh Day of February, 2024

Katherine Kelly Vidal
*Director of the United States Patent and Trademark Office*

SEQUENCE LISTING

```
<160> NUMBER OF SEQ ID NOS: 98

<210> SEQ ID NO 1
<211> LENGTH: 775
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: metagenomic

<400> SEQUENCE: 1

Met Ala Gln Val Ser Lys Gln Thr Ser Lys Lys Arg Glu Leu Ser Ile
1               5                   10                  15

Asp Glu Tyr Gln Gly Ala Arg Lys Trp Cys Phe Thr Ile Ala Phe Asn
            20                  25                  30

Lys Ala Leu Val Asn Arg Asp Lys Asn Asp Gly Leu Phe Val Glu Ser
        35                  40                  45

Leu Leu Arg His Glu Lys Tyr Ser Lys His Asp Trp Tyr Asp Glu Asp
    50                  55                  60

Thr Arg Ala Leu Ile Lys Cys Ser Thr Gln Ala Ala Asn Ala Lys Ala
65                  70                  75                  80

Glu Ala Leu Arg Asn Tyr Phe Ser His Tyr Arg His Ser Pro Gly Cys
                85                  90                  95

Leu Thr Phe Thr Ala Glu Asp Glu Leu Arg Thr Ile Met Glu Arg Ala
            100                 105                 110

Tyr Glu Arg Ala Ile Phe Glu Cys Arg Arg Arg Glu Thr Glu Val Ile
        115                 120                 125

Ile Glu Phe Pro Ser Leu Phe Glu Gly Asp Arg Ile Thr Thr Ala Gly
    130                 135                 140

Val Val Phe Phe Val Ser Phe Val Glu Arg Arg Val Leu Asp Arg
145                 150                 155                 160

Leu Tyr Gly Ala Val Ser Gly Leu Lys Lys Asn Glu Gly Gln Tyr Lys
                165                 170                 175
```

```
Leu Thr Arg Lys Ala Leu Ser Met Tyr Cys Leu Lys Asp Ser Arg Phe
            180                 185                 190

Thr Lys Ala Trp Asp Lys Arg Val Leu Leu Phe Arg Asp Ile Leu Ala
        195                 200                 205

Gln Leu Gly Arg Ile Pro Ala Glu Ala Tyr Glu Tyr His Gly Glu
    210                 215                 220

Gln Gly Asp Lys Lys Arg Ala Asn Asp Asn Glu Gly Thr Asn Pro Lys
225                 230                 235                 240

Arg His Lys Asp Lys Phe Ile Glu Phe Ala Leu His Tyr Leu Glu Ala
                245                 250                 255

Gln His Ser Glu Ile Cys Phe Gly Arg Arg His Ile Val Arg Glu Glu
            260                 265                 270

Ala Gly Ala Gly Asp Glu His Lys Lys His Arg Thr Lys Gly Lys Val
        275                 280                 285

Val Val Asp Phe Ser Lys Lys Asp Glu Asp Gln Ser Tyr Tyr Ile Ser
    290                 295                 300

Lys Asn Asn Val Ile Val Arg Ile Asp Lys Asn Ala Gly Pro Arg Ser
305                 310                 315                 320

Tyr Arg Met Gly Leu Asn Glu Leu Lys Tyr Leu Val Leu Leu Ser Leu
                325                 330                 335

Gln Gly Lys Gly Asp Asp Ala Ile Ala Lys Leu Tyr Arg Tyr Arg Gln
            340                 345                 350

His Val Glu Asn Ile Leu Asp Val Lys Val Thr Asp Lys Asp Asn
        355                 360                 365

His Val Phe Leu Pro Arg Phe Val Leu Glu Gln His Gly Ile Gly Arg
    370                 375                 380

Lys Ala Phe Lys Gln Arg Ile Asp Gly Arg Val Lys His Val Arg Gly
385                 390                 395                 400

Val Trp Glu Lys Lys Lys Ala Ala Thr Asn Glu Met Thr Leu His Glu
                405                 410                 415

Lys Ala Arg Asp Ile Leu Gln Tyr Val Asn Glu Asn Cys Thr Arg Ser
            420                 425                 430

Phe Asn Pro Gly Glu Tyr Asn Arg Leu Leu Val Cys Leu Val Gly Lys
    435                 440                 445

Asp Val Glu Asn Phe Gln Ala Gly Leu Lys Arg Leu Gln Leu Ala Glu
450                 455                 460

Arg Ile Asp Gly Arg Val Tyr Ser Ile Phe Ala Gln Thr Ser Thr Ile
465                 470                 475                 480

Asn Glu Met His Gln Val Val Cys Asp Gln Ile Leu Asn Arg Leu Cys
                485                 490                 495

Arg Ile Gly Asp Gln Lys Leu Tyr Asp Tyr Val Gly Leu Gly Lys Lys
            500                 505                 510

Asp Glu Ile Asp Tyr Lys Gln Lys Val Ala Trp Phe Lys Glu His Ile
    515                 520                 525

Ser Ile Arg Arg Gly Phe Leu Arg Lys Lys Phe Trp Tyr Asp Ser Lys
530                 535                 540

Lys Gly Phe Ala Lys Leu Val Glu His Leu Glu Ser Gly Gly Gly
545                 550                 555                 560

Gln Arg Asp Val Gly Leu Asp Lys Lys Tyr Tyr His Ile Asp Ala Ile
                565                 570                 575

Gly Arg Phe Glu Gly Ala Asn Pro Ala Leu Tyr Glu Thr Leu Ala Arg
            580                 585                 590

Asp Arg Leu Cys Leu Met Met Ala Gln Tyr Phe Leu Gly Ser Val Arg
```

```
                    595                 600                 605
Lys Glu Leu Gly Asn Lys Ile Val Trp Ser Asn Asp Ser Ile Glu Leu
            610                 615                 620

Pro Val Glu Gly Ser Val Gly Asn Glu Lys Ser Ile Val Phe Ser Val
625                 630                 635                 640

Ser Asp Tyr Gly Lys Leu Tyr Val Leu Asp Ala Glu Phe Leu Gly
            645                 650                 655

Arg Ile Cys Glu Tyr Phe Met Pro His Glu Lys Gly Lys Ile Arg Tyr
                660                 665                 670

His Thr Val Tyr Glu Lys Gly Phe Arg Ala Tyr Asn Asp Leu Gln Lys
            675                 680                 685

Lys Cys Val Glu Ala Val Leu Ala Phe Glu Glu Lys Val Val Lys Ala
            690                 695                 700

Lys Lys Met Ser Glu Lys Glu Gly Ala His Tyr Ile Asp Phe Arg Glu
705                 710                 715                 720

Ile Leu Ala Gln Thr Met Cys Lys Glu Ala Glu Lys Thr Ala Val Asn
                725                 730                 735

Lys Val Arg Arg Ala Phe Phe His His His Leu Lys Phe Val Ile Asp
            740                 745                 750

Glu Phe Gly Leu Phe Ser Asp Val Met Lys Lys Tyr Gly Ile Glu Lys
                755                 760                 765

Glu Trp Lys Phe Pro Val Lys
            770                 775

<210> SEQ ID NO 2
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: metagenomic

<400> SEQUENCE: 2

Met Lys Val Glu Asn Ile Lys Glu Lys Ser Lys Lys Ala Met Tyr Leu
1               5                   10                  15

Ile Asn His Tyr Glu Gly Pro Lys Lys Trp Cys Phe Ala Ile Val Leu
            20                  25                  30

Asn Arg Ala Cys Asp Asn Tyr Glu Asp Asn Pro His Leu Phe Ser Lys
        35                  40                  45

Ser Leu Leu Glu Phe Glu Lys Thr Ser Arg Lys Asp Trp Phe Asp Glu
    50                  55                  60

Glu Thr Arg Glu Leu Val Glu Gln Ala Asp Thr Glu Ile Gln Pro Asn
65                  70                  75                  80

Pro Asn Leu Lys Pro Asn Thr Thr Ala Asn Arg Lys Leu Lys Asp Ile
                85                  90                  95

Arg Asn Tyr Phe Ser His His Tyr His Lys Asn Glu Cys Leu Tyr Phe
            100                 105                 110

Lys Asn Asp Asp Pro Ile Arg Cys Ile Met Glu Ala Ala Tyr Glu Lys
        115                 120                 125

Ser Lys Ile Tyr Ile Lys Gly Lys Gln Ile Glu Gln Ser Asp Ile Pro
    130                 135                 140

Leu Pro Glu Leu Phe Glu Ser Ser Gly Trp Ile Thr Pro Ala Gly Ile
145                 150                 155                 160

Leu Leu Leu Ala Ser Phe Phe Val Glu Arg Gly Ile Leu His Arg Leu
```

```
            165                 170                 175
Met Gly Asn Ile Gly Gly Phe Lys Asp Asn Arg Gly Glu Tyr Gly Leu
            180                 185                 190

Thr His Asp Ile Phe Thr Thr Tyr Cys Leu Lys Gly Ser Tyr Ser Ile
            195                 200                 205

Arg Ala Gln Asp His Asp Ala Val Met Phe Arg Asp Ile Leu Gly Tyr
            210                 215                 220

Leu Ser Arg Val Pro Thr Glu Ser Phe Gln Arg Ile Lys Gln Pro Gln
225                 230                 235                 240

Ile Arg Lys Glu Gly Gln Leu Ser Glu Arg Lys Thr Asp Lys Phe Ile
                245                 250                 255

Thr Phe Ala Leu Asn Tyr Leu Glu Asp Tyr Gly Leu Lys Asp Leu Glu
                260                 265                 270

Gly Cys Lys Ala Cys Phe Ala Arg Ser Lys Ile Val Arg Glu Gln Glu
                275                 280                 285

Asn Val Glu Ser Ile Asn Asp Lys Glu Tyr Lys Pro His Glu Asn Lys
            290                 295                 300

Lys Lys Val Glu Ile His Phe Asp Gln Ser Lys Glu Asp Arg Phe Tyr
305                 310                 315                 320

Ile Asn Arg Asn Asn Val Ile Leu Lys Ile Gln Lys Lys Asp Gly His
                325                 330                 335

Ser Asn Ile Val Arg Met Gly Val Tyr Glu Leu Lys Tyr Leu Val Leu
                340                 345                 350

Met Ser Leu Val Gly Lys Ala Lys Glu Ala Val Glu Lys Ile Asp Asn
                355                 360                 365

Tyr Ile Gln Asp Leu Arg Asp Gln Leu Pro Tyr Ile Glu Gly Lys Asn
            370                 375                 380

Lys Glu Glu Ile Lys Glu Tyr Val Arg Phe Phe Pro Arg Phe Ile Arg
385                 390                 395                 400

Ser His Leu Gly Leu Leu Gln Ile Asn Asp Glu Glu Lys Ile Lys Ala
                405                 410                 415

Arg Leu Asp Tyr Val Lys Thr Lys Trp Leu Asp Lys Lys Glu Lys Ser
                420                 425                 430

Lys Glu Leu Glu Leu His Lys Lys Gly Arg Asp Ile Leu Arg Tyr Ile
            435                 440                 445

Asn Glu Arg Cys Asp Arg Glu Leu Asn Arg Asn Val Tyr Asn Arg Ile
            450                 455                 460

Leu Glu Leu Leu Val Ser Lys Asp Leu Thr Gly Phe Tyr Arg Glu Leu
465                 470                 475                 480

Glu Glu Leu Lys Arg Thr Arg Arg Ile Asp Lys Asn Ile Val Gln Asn
                485                 490                 495

Leu Ser Gly Gln Lys Thr Ile Asn Ala Leu His Glu Lys Val Cys Asp
            500                 505                 510

Leu Val Leu Lys Glu Ile Glu Ser Leu Asp Thr Glu Asn Leu Arg Lys
            515                 520                 525

Tyr Leu Gly Leu Ile Pro Lys Glu Lys Glu Val Thr Phe Lys Glu
            530                 535                 540

Lys Val Asp Arg Ile Leu Lys Gln Pro Val Ile Tyr Lys Gly Phe Leu
545                 550                 555                 560

Arg Tyr Gln Phe Phe Lys Asp Asp Lys Lys Ser Phe Val Leu Leu Val
                565                 570                 575

Glu Asp Ala Leu Lys Glu Lys Gly Gly Gly Cys Asp Val Pro Leu Gly
            580                 585                 590
```

```
Lys Glu Tyr Tyr Lys Ile Val Ser Leu Asp Lys Tyr Asp Lys Glu Asn
            595                 600                 605

Lys Thr Leu Cys Glu Thr Leu Ala Met Asp Arg Leu Cys Leu Met Met
610                 615                 620

Ala Arg Gln Tyr Tyr Leu Ser Leu Asn Ala Lys Leu Ala Gln Glu Ala
625                 630                 635                 640

Gln Gln Ile Glu Trp Lys Lys Glu Asp Ser Ile Glu Leu Ile Ile Phe
            645                 650                 655

Thr Leu Lys Asn Pro Asp Gln Ser Lys Gln Ser Phe Ser Ile Arg Phe
            660                 665                 670

Ser Val Arg Asp Phe Thr Lys Leu Tyr Val Thr Asp Asp Pro Glu Phe
            675                 680                 685

Leu Ala Arg Leu Cys Ser Tyr Phe Phe Pro Val Glu Lys Glu Ile Glu
690                 695                 700

Tyr His Lys Leu Tyr Ser Glu Gly Ile Asn Lys Tyr Thr Asn Leu Gln
705                 710                 715                 720

Lys Glu Gly Ile Glu Ala Ile Leu Glu Leu Glu Lys Lys Leu Ile Glu
            725                 730                 735

Arg Asn Arg Ile Gln Ser Ala Lys Asn Tyr Leu Ser Phe Asn Glu Ile
            740                 745                 750

Met Asn Lys Ser Gly Tyr Asn Lys Asp Glu Gln Asp Asp Leu Lys Lys
            755                 760                 765

Val Arg Asn Ser Leu Leu His Tyr Lys Leu Ile Phe Glu Lys Glu His
770                 775                 780

Leu Lys Lys Phe Tyr Glu Val Met Arg Gly Glu Gly Ile Glu Lys Lys
785                 790                 795                 800

Trp Ser Leu Ile Val
            805

<210> SEQ ID NO 3
<211> LENGTH: 790
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: metagenomic

<400> SEQUENCE: 3

Met Asn Gly Ile Glu Leu Lys Lys Glu Ala Ala Phe Tyr Phe Asn
1               5                   10                  15

Gln Ala Glu Leu Asn Leu Lys Ala Ile Glu Asp Asn Ile Phe Asp Lys
            20                  25                  30

Glu Arg Arg Lys Thr Leu Leu Asn Pro Gln Ile Leu Ala Lys Met
        35                  40                  45

Glu Asn Phe Ile Phe Asn Phe Arg Asp Val Thr Lys Asn Ala Lys Gly
50                  55                  60

Glu Ile Asp Cys Leu Leu Leu Lys Leu Arg Glu Leu Arg Asn Phe Tyr
65                  70                  75                  80

Ser His Tyr Val His Lys Arg Asp Val Arg Glu Leu Ser Lys Gly Glu
                85                  90                  95

Lys Pro Ile Leu Glu Lys Tyr Tyr Gln Phe Ala Ile Glu Ser Thr Gly
            100                 105                 110

Ser Glu Asn Val Lys Leu Glu Ile Ile Glu Asn Asp Ala Trp Leu Ala
        115                 120                 125
```

Asp Ala Gly Val Leu Phe Phe Leu Cys Ile Phe Leu Lys Lys Ser Gln
130                     135                     140

Ala Asn Lys Leu Ile Ser Gly Ile Ser Gly Phe Lys Arg Asn Asp Asp
145                 150                     155                 160

Thr Gly Gln Pro Arg Arg Asn Leu Phe Thr Tyr Phe Ser Ile Arg Glu
                165                     170                     175

Gly Tyr Lys Val Val Pro Glu Met Gln Lys His Phe Leu Leu Phe Ser
            180                     185                     190

Leu Val Asn His Leu Ser Asn Gln Asp Asp Tyr Ile Glu Lys Ala His
        195                     200                     205

Gln Pro Tyr Asp Ile Gly Glu Gly Leu Phe Phe His Arg Ile Ala Ser
210                     215                     220

Thr Phe Leu Asn Ile Ser Gly Ile Leu Arg Asn Met Lys Phe Tyr Thr
225                     230                     235                 240

Tyr Gln Ser Lys Arg Leu Val Glu Gln Arg Gly Glu Leu Lys Arg Glu
                245                     250                     255

Lys Asp Ile Phe Ala Trp Glu Glu Pro Phe Gln Gly Asn Ser Tyr Phe
            260                     265                     270

Glu Ile Asn Gly His Lys Gly Val Ile Gly Asp Glu Leu Lys Glu
        275                     280                     285

Leu Cys Tyr Ala Phe Leu Ile Gly Asn Gln Asp Ala Asn Lys Val Glu
290                     295                     300

Gly Arg Ile Thr Gln Phe Leu Glu Lys Phe Arg Asn Ala Asn Ser Val
305                     310                     315                 320

Gln Gln Val Lys Asp Asp Glu Met Leu Lys Pro Glu Tyr Phe Pro Ala
                325                     330                     335

Asn Tyr Phe Ala Glu Ser Gly Val Gly Arg Ile Lys Asp Arg Val Leu
            340                     345                     350

Asn Arg Leu Asn Lys Ala Ile Lys Ser Asn Lys Ala Lys Lys Gly Glu
        355                     360                     365

Ile Ile Ala Tyr Asp Lys Met Arg Glu Val Met Ala Phe Ile Asn Asn
370                     375                     380

Ser Leu Pro Val Asp Glu Lys Leu Lys Pro Lys Asp Tyr Lys Arg Tyr
385                     390                     395                 400

Leu Gly Met Val Arg Phe Trp Asp Arg Glu Lys Asp Asn Ile Lys Arg
                405                     410                     415

Glu Phe Glu Thr Lys Glu Trp Ser Lys Tyr Leu Pro Ser Asn Phe Trp
            420                     425                     430

Thr Ala Lys Asn Leu Glu Arg Val Tyr Gly Leu Ala Arg Glu Lys Asn
        435                     440                     445

Ala Glu Leu Phe Asn Lys Leu Lys Ala Asp Val Glu Lys Met Asp Glu
450                     455                     460

Arg Glu Leu Glu Lys Tyr Gln Lys Ile Asn Asp Ala Lys Asp Leu Ala
465                     470                     475                 480

Asn Leu Arg Arg Leu Ala Ser Asp Phe Gly Val Lys Trp Glu Glu Lys
                485                     490                     495

Asp Trp Asp Glu Tyr Ser Gly Gln Ile Lys Lys Gln Ile Thr Asp Ser
            500                     505                     510

Gln Lys Leu Thr Ile Met Lys Gln Arg Ile Thr Ala Gly Leu Lys Lys
        515                     520                     525

Lys His Gly Ile Glu Asn Leu Asn Leu Arg Ile Thr Ile Asp Ile Asn
530                     535                     540

Lys Ser Arg Lys Ala Val Leu Asn Arg Ile Ala Ile Pro Arg Gly Phe
545                 550                 555                 560

Val Lys Arg His Ile Leu Gly Trp Gln Glu Ser Glu Lys Val Ser Lys
            565                 570                 575

Lys Ile Arg Glu Ala Glu Cys Glu Ile Leu Leu Ser Lys Glu Tyr Glu
        580                 585                 590

Glu Leu Ser Lys Gln Phe Phe Gln Ser Lys Asp Tyr Asp Lys Met Thr
    595                 600                 605

Arg Ile Asn Gly Leu Tyr Glu Lys Asn Lys Leu Ile Ala Leu Met Ala
610                 615                 620

Val Tyr Leu Met Gly Gln Leu Arg Ile Leu Phe Lys Glu His Thr Lys
625                 630                 635                 640

Leu Asp Asp Ile Thr Lys Thr Thr Val Asp Phe Lys Ile Ser Asp Lys
            645                 650                 655

Val Thr Val Lys Ile Pro Phe Ser Asn Tyr Pro Ser Leu Val Tyr Thr
        660                 665                 670

Met Ser Ser Lys Tyr Val Asp Asn Ile Gly Asn Tyr Gly Phe Ser Asn
    675                 680                 685

Lys Asp Lys Asp Lys Pro Ile Leu Gly Lys Ile Asp Val Ile Glu Lys
690                 695                 700

Gln Arg Met Glu Phe Ile Lys Glu Val Leu Gly Phe Glu Lys Tyr Leu
705                 710                 715                 720

Phe Asp Asp Lys Ile Ile Asp Lys Ser Lys Phe Ala Asp Thr Ala Thr
            725                 730                 735

His Ile Ser Phe Ala Glu Ile Val Glu Glu Leu Val Lys Gly Trp
        740                 745                 750

Asp Lys Asp Arg Leu Thr Lys Leu Lys Asp Ala Arg Asn Lys Ala Leu
    755                 760                 765

His Gly Glu Ile Leu Thr Gly Thr Ser Phe Asp Glu Thr Lys Ser Leu
770                 775                 780

Ile Asn Glu Leu Lys Lys
785                 790

<210> SEQ ID NO 4
<211> LENGTH: 792
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: metagenomic

<400> SEQUENCE: 4

Met Ser Pro Asp Phe Ile Lys Leu Glu Lys Gln Glu Ala Ala Phe Tyr
1               5                   10                  15

Phe Asn Gln Thr Glu Leu Asn Leu Lys Ala Ile Glu Ser Asn Ile Leu
            20                  25                  30

Asp Lys Gln Gln Arg Met Ile Leu Leu Asn Asn Pro Arg Ile Leu Ala
        35                  40                  45

Lys Val Gly Asn Phe Ile Phe Asn Phe Arg Asp Val Thr Lys Asn Ala
    50                  55                  60

Lys Gly Glu Ile Asp Cys Leu Leu Phe Lys Leu Glu Glu Leu Arg Asn
65                  70                  75                  80

Phe Tyr Ser His Tyr Val His Thr Asp Asn Val Lys Glu Leu Ser Asn
            85                  90                  95

-continued

```
Gly Glu Lys Pro Leu Leu Glu Arg Tyr Tyr Gln Ile Ala Ile Gln Ala
            100                 105                 110

Thr Arg Ser Glu Asp Val Lys Phe Glu Leu Phe Glu Thr Arg Asn Glu
            115                 120                 125

Asn Lys Ile Thr Asp Ala Gly Val Leu Phe Phe Leu Cys Met Phe Leu
            130                 135                 140

Lys Lys Ser Gln Ala Asn Lys Leu Ile Ser Gly Ile Ser Gly Phe Lys
145                 150                 155                 160

Arg Asn Asp Pro Thr Gly Gln Pro Arg Arg Asn Leu Phe Thr Tyr Phe
                165                 170                 175

Ser Ala Arg Glu Gly Tyr Lys Ala Leu Pro Asp Met Gln Lys His Phe
            180                 185                 190

Leu Leu Phe Thr Leu Val Asn Tyr Leu Ser Asn Gln Asp Glu Tyr Ile
            195                 200                 205

Ser Glu Leu Lys Gln Tyr Gly Glu Ile Gly Gln Gly Ala Phe Phe Asn
210                 215                 220

Arg Ile Ala Ser Thr Phe Leu Asn Ile Ser Gly Ile Ser Gly Asn Thr
225                 230                 235                 240

Lys Phe Tyr Ser Tyr Gln Ser Lys Arg Ile Lys Glu Gln Arg Gly Glu
            245                 250                 255

Leu Asn Ser Glu Lys Asp Ser Phe Glu Trp Ile Glu Pro Phe Gln Gly
            260                 265                 270

Asn Ser Tyr Phe Glu Ile Asn Gly His Lys Gly Val Ile Gly Glu Asp
            275                 280                 285

Glu Leu Lys Glu Leu Cys Tyr Ala Leu Leu Val Ala Lys Gln Asp Ile
            290                 295                 300

Asn Ala Val Glu Gly Lys Ile Met Gln Phe Leu Lys Lys Phe Arg Asn
305                 310                 315                 320

Thr Gly Asn Leu Gln Gln Val Lys Asp Asp Glu Met Leu Glu Ile Glu
            325                 330                 335

Tyr Phe Pro Ala Ser Tyr Phe Asn Glu Ser Lys Lys Glu Asp Ile Lys
            340                 345                 350

Lys Glu Ile Leu Gly Arg Leu Asp Lys Lys Ile Arg Ser Cys Ser Ala
            355                 360                 365

Lys Ala Glu Lys Ala Tyr Asp Lys Met Lys Glu Val Met Glu Phe Ile
            370                 375                 380

Asn Asn Ser Leu Pro Ala Glu Glu Lys Leu Lys Arg Lys Asp Tyr Arg
385                 390                 395                 400

Arg Tyr Leu Lys Met Val Arg Phe Trp Ser Arg Glu Lys Gly Asn Ile
            405                 410                 415

Glu Arg Glu Phe Arg Thr Lys Glu Trp Ser Lys Tyr Phe Ser Ser Asp
            420                 425                 430

Phe Trp Arg Lys Asn Asn Leu Glu Asp Val Tyr Lys Leu Ala Thr Gln
            435                 440                 445

Lys Asn Ala Glu Leu Phe Lys Asn Leu Lys Ala Ala Glu Lys Met
450                 455                 460

Gly Glu Thr Glu Phe Glu Lys Tyr Gln Gln Ile Asn Asp Val Lys Asp
465                 470                 475                 480

Leu Ala Ser Leu Arg Arg Leu Thr Gln Asp Phe Gly Leu Lys Trp Glu
            485                 490                 495

Glu Lys Asp Trp Glu Glu Tyr Ser Glu Gln Ile Lys Lys Gln Ile Thr
            500                 505                 510

Asp Arg Gln Lys Leu Thr Ile Met Lys Gln Arg Val Thr Ala Glu Leu
```

```
               515                 520                 525
Lys Lys Lys His Gly Ile Glu Asn Leu Asn Leu Arg Ile Thr Ile Asp
            530                 535                 540

Ser Asn Lys Ser Arg Lys Ala Val Leu Asn Arg Ile Ala Ile Pro Arg
545                 550                 555                 560

Gly Phe Val Lys Lys His Ile Leu Gly Trp Gln Gly Ser Glu Lys Ile
                565                 570                 575

Ser Lys Asn Ile Arg Glu Ala Glu Cys Lys Ile Leu Leu Ser Lys Lys
            580                 585                 590

Tyr Glu Glu Leu Ser Arg Gln Phe Phe Glu Ala Gly Asn Phe Asp Lys
                595                 600                 605

Leu Thr Gln Ile Asn Gly Leu Tyr Glu Lys Asn Lys Leu Thr Ala Phe
            610                 615                 620

Met Ser Val Tyr Leu Met Gly Arg Leu Asn Ile Gln Leu Asn Lys His
625                 630                 635                 640

Thr Glu Leu Gly Asn Leu Lys Lys Thr Glu Val Asp Phe Lys Ile Ser
                645                 650                 655

Asp Lys Val Thr Glu Lys Ile Pro Phe Ser Gln Tyr Pro Ser Leu Val
            660                 665                 670

Tyr Ala Met Ser Arg Lys Tyr Val Asp Asn Val Asp Lys Tyr Lys Phe
                675                 680                 685

Ser His Gln Asp Lys Lys Pro Phe Leu Gly Lys Ile Asp Ser Ile
            690                 695                 700

Glu Lys Glu Arg Ile Glu Phe Ile Lys Glu Val Leu Asp Phe Glu Glu
705                 710                 715                 720

Tyr Leu Phe Lys Asn Lys Val Ile Asp Lys Ser Lys Phe Ser Asp Thr
                725                 730                 735

Ala Thr His Ile Ser Phe Lys Glu Ile Cys Asp Glu Met Gly Lys Lys
            740                 745                 750

Gly Cys Asn Arg Asn Lys Leu Thr Glu Leu Asn Asn Ala Arg Asn Ala
                755                 760                 765

Ala Leu His Gly Glu Ile Pro Ser Glu Thr Ser Phe Arg Glu Ala Lys
            770                 775                 780

Pro Leu Ile Asn Glu Leu Lys Lys
785                 790

<210> SEQ ID NO 5
<211> LENGTH: 792
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: metagenomic

<400> SEQUENCE: 5

Met Ser Pro Asp Phe Ile Lys Leu Glu Lys Gln Glu Ala Ala Phe Tyr
1               5                   10                  15

Phe Asn Gln Thr Glu Leu Asn Leu Lys Ala Ile Glu Ser Asn Ile Phe
                20                  25                  30

Asp Lys Gln Gln Arg Val Ile Leu Asn Asn Pro Gln Ile Leu Ala
            35                  40                  45

Lys Val Gly Asp Phe Ile Phe Asn Phe Arg Asp Val Thr Lys Asn Ala
        50                  55                  60

Lys Gly Glu Ile Asp Cys Leu Leu Leu Lys Leu Arg Glu Leu Arg Asn
```

-continued

```
                65                  70                  75                  80
Phe Tyr Ser His Tyr Val Tyr Thr Asp Asp Val Lys Ile Leu Ser Asn
                    85                  90                  95

Gly Glu Arg Pro Leu Leu Glu Lys Tyr Tyr Gln Phe Ala Ile Glu Ala
                    100                 105                 110

Thr Gly Ser Glu Asn Val Lys Leu Glu Ile Ile Glu Ser Asn Asn Arg
                    115                 120                 125

Leu Thr Glu Ala Gly Val Leu Phe Phe Leu Cys Met Phe Leu Lys Lys
                    130                 135                 140

Ser Gln Ala Asn Lys Leu Ile Ser Gly Ile Ser Gly Phe Lys Arg Asn
145                 150                 155                 160

Asp Pro Thr Gly Gln Pro Arg Arg Asn Leu Phe Thr Tyr Phe Ser Val
                    165                 170                 175

Arg Glu Gly Tyr Lys Val Val Pro Asp Met Gln Lys His Phe Leu Leu
                    180                 185                 190

Phe Val Leu Val Asn His Leu Ser Gly Gln Asp Asp Tyr Ile Glu Lys
                    195                 200                 205

Ala Gln Lys Pro Tyr Asp Ile Gly Glu Gly Leu Phe Phe His Arg Ile
                    210                 215                 220

Ala Ser Thr Phe Leu Asn Ile Ser Gly Ile Leu Arg Asn Met Glu Phe
225                 230                 235                 240

Tyr Ile Tyr Gln Ser Lys Arg Leu Lys Glu Gln Gln Gly Glu Leu Lys
                    245                 250                 255

Arg Glu Lys Asp Ile Phe Pro Trp Ile Glu Pro Phe Gln Gly Asn Ser
                    260                 265                 270

Tyr Phe Glu Ile Asn Gly Asn Lys Gly Ile Ile Gly Glu Asp Glu Leu
                    275                 280                 285

Lys Glu Leu Cys Tyr Ala Leu Leu Val Ala Gly Lys Asp Val Arg Ala
                    290                 295                 300

Val Glu Gly Lys Ile Thr Gln Phe Leu Glu Lys Phe Lys Asn Ala Asp
305                 310                 315                 320

Asn Ala Gln Gln Val Glu Lys Asp Glu Met Leu Asp Arg Asn Asn Phe
                    325                 330                 335

Pro Ala Asn Tyr Phe Ala Glu Ser Asn Ile Gly Ser Ile Lys Glu Lys
                    340                 345                 350

Ile Leu Asn Arg Leu Gly Lys Thr Asp Asp Ser Tyr Asn Lys Thr Gly
                    355                 360                 365

Thr Lys Ile Lys Pro Tyr Asp Met Met Lys Glu Val Met Glu Phe Ile
370                 375                 380

Asn Asn Ser Leu Pro Ala Asp Glu Lys Leu Lys Arg Lys Asp Tyr Arg
385                 390                 395                 400

Arg Tyr Leu Lys Met Val Arg Ile Trp Asp Ser Glu Lys Asp Asn Ile
                    405                 410                 415

Lys Arg Glu Phe Glu Ser Lys Glu Trp Ser Lys Tyr Phe Ser Ser Asp
                    420                 425                 430

Phe Trp Met Ala Lys Asn Leu Glu Arg Val Tyr Gly Leu Ala Arg Glu
                    435                 440                 445

Lys Asn Ala Glu Leu Phe Asn Lys Leu Lys Ala Val Val Glu Lys Met
                    450                 455                 460

Asp Glu Arg Glu Phe Glu Lys Tyr Arg Leu Ile Asn Ser Ala Glu Asp
465                 470                 475                 480

Leu Ala Ser Leu Arg Arg Leu Ala Lys Asp Phe Gly Leu Lys Trp Glu
                    485                 490                 495
```

```
Glu Lys Asp Trp Gln Glu Tyr Ser Gly Gln Ile Lys Lys Gln Ile Ser
                500                 505                 510

Asp Arg Gln Lys Leu Thr Ile Met Lys Gln Arg Ile Thr Ala Glu Leu
            515                 520                 525

Lys Lys Lys His Gly Ile Glu Asn Leu Asn Leu Arg Ile Thr Ile Asp
        530                 535                 540

Ser Asn Lys Ser Arg Lys Ala Val Leu Asn Arg Ile Ala Val Pro Arg
545                 550                 555                 560

Gly Phe Val Lys Glu His Ile Leu Gly Trp Gln Gly Ser Glu Lys Val
                565                 570                 575

Ser Lys Lys Thr Arg Glu Ala Lys Cys Lys Ile Leu Leu Ser Lys Glu
            580                 585                 590

Tyr Glu Glu Leu Ser Lys Gln Phe Phe Gln Thr Arg Asn Tyr Asp Lys
        595                 600                 605

Met Thr Gln Val Asn Gly Leu Tyr Glu Lys Asn Lys Leu Leu Ala Phe
    610                 615                 620

Met Val Val Tyr Leu Met Glu Arg Leu Asn Ile Leu Leu Asn Lys Pro
625                 630                 635                 640

Thr Glu Leu Asn Glu Leu Glu Lys Ala Glu Val Asp Phe Lys Ile Ser
                645                 650                 655

Asp Lys Val Met Ala Lys Ile Pro Phe Ser Gln Tyr Pro Ser Leu Val
            660                 665                 670

Tyr Ala Met Ser Ser Lys Tyr Ala Asp Ser Val Gly Ser Tyr Lys Phe
        675                 680                 685

Glu Asn Asp Glu Lys Asn Lys Pro Phe Leu Gly Lys Ile Asp Thr Ile
    690                 695                 700

Glu Lys Gln Arg Met Glu Phe Ile Lys Glu Val Leu Gly Phe Glu Glu
705                 710                 715                 720

Tyr Leu Phe Glu Lys Lys Ile Ile Asp Lys Ser Glu Phe Ala Asp Thr
                725                 730                 735

Ala Thr His Ile Ser Phe Asp Glu Ile Cys Asn Glu Leu Ile Lys Lys
            740                 745                 750

Gly Trp Asp Lys Asp Lys Leu Thr Lys Leu Lys Asp Ala Arg Asn Ala
        755                 760                 765

Ala Leu His Gly Glu Ile Pro Ala Glu Thr Ser Phe Arg Glu Ala Lys
    770                 775                 780

Pro Leu Ile Asn Gly Leu Lys Lys
785                 790

<210> SEQ ID NO 6
<211> LENGTH: 799
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: metagenomic

<400> SEQUENCE: 6

Met Asn Ile Ile Lys Leu Lys Lys Glu Glu Ala Ala Phe Tyr Phe Asn
1               5                   10                  15

Gln Thr Ile Leu Asn Leu Ser Gly Leu Asp Glu Ile Ile Glu Lys Gln
            20                  25                  30

Ile Pro His Ile Ile Ser Asn Lys Glu Asn Ala Lys Lys Val Ile Asp
        35                  40                  45
```

-continued

```
Lys Ile Phe Asn Asn Arg Leu Leu Lys Ser Val Glu Asn Tyr Ile
     50                  55                  60
Tyr Asn Phe Lys Asp Val Ala Lys Asn Ala Arg Thr Glu Ile Glu Ala
 65                  70                  75                  80
Ile Leu Leu Lys Leu Val Glu Leu Arg Asn Phe Tyr Ser His Tyr Val
                 85                  90                  95
His Asn Asp Thr Val Lys Ile Leu Ser Asn Gly Glu Lys Pro Ile Leu
             100                 105                 110
Glu Lys Tyr Tyr Gln Ile Ala Ile Glu Ala Thr Gly Ser Lys Asn Val
         115                 120                 125
Lys Leu Val Ile Ile Glu Asn Asn Cys Leu Thr Asp Ser Gly Val
 130                 135                 140
Leu Phe Leu Leu Cys Met Phe Leu Lys Lys Ser Gln Ala Asn Lys Leu
145                 150                 155                 160
Ile Ser Ser Val Ser Gly Phe Lys Arg Asn Asp Lys Glu Gly Gln Pro
                165                 170                 175
Arg Arg Asn Leu Phe Thr Tyr Tyr Ser Val Arg Glu Gly Tyr Lys Val
             180                 185                 190
Val Pro Asp Met Gln Lys His Phe Leu Leu Phe Ala Leu Val Asn His
         195                 200                 205
Leu Ser Glu Gln Asp Asp His Ile Glu Lys Gln Gln Gln Ser Asp Glu
 210                 215                 220
Leu Gly Lys Gly Leu Phe Phe His Arg Ile Ala Ser Thr Phe Leu Asn
225                 230                 235                 240
Glu Ser Gly Ile Phe Asn Lys Met Gln Phe Tyr Thr Tyr Gln Ser Asn
                245                 250                 255
Arg Leu Lys Glu Lys Arg Gly Glu Leu Lys His Glu Lys Asp Thr Phe
             260                 265                 270
Thr Trp Ile Glu Pro Phe Gln Gly Asn Ser Tyr Phe Thr Leu Asn Gly
         275                 280                 285
His Lys Gly Val Ile Ser Glu Asp Gln Leu Lys Glu Leu Cys Tyr Thr
 290                 295                 300
Ile Leu Ile Glu Lys Gln Asn Val Asp Ser Leu Glu Gly Lys Ile Ile
305                 310                 315                 320
Gln Phe Leu Lys Lys Phe Gln Asn Val Ser Ser Lys Gln Gln Val Asp
                325                 330                 335
Glu Asp Glu Leu Leu Lys Arg Glu Tyr Phe Pro Ala Asn Tyr Phe Gly
             340                 345                 350
Arg Ala Gly Thr Gly Thr Leu Lys Glu Lys Ile Leu Asn Arg Leu Asp
         355                 360                 365
Lys Arg Met Asp Pro Thr Ser Lys Val Thr Asp Lys Ala Tyr Asp Lys
 370                 375                 380
Met Ile Glu Val Met Glu Phe Ile Asn Met Cys Leu Pro Ser Asp Glu
385                 390                 395                 400
Lys Leu Arg Gln Lys Asp Tyr Arg Arg Tyr Leu Lys Met Val Arg Phe
                405                 410                 415
Trp Asn Lys Glu Lys His Asn Ile Lys Arg Glu Phe Asp Ser Lys Lys
             420                 425                 430
Trp Thr Arg Phe Leu Pro Thr Glu Leu Trp Asn Lys Arg Asn Leu Glu
         435                 440                 445
Glu Ala Tyr Gln Leu Ala Arg Lys Glu Asn Lys Lys Leu Glu Asp
     450                 455                 460
```

```
Met Arg Asn Gln Val Arg Ser Leu Lys Glu Asn Asp Leu Glu Lys Tyr
465                 470                 475                 480

Gln Gln Ile Asn Tyr Val Asn Asp Leu Glu Asn Leu Arg Leu Leu Ser
                485                 490                 495

Gln Glu Leu Gly Val Lys Trp Gln Glu Lys Asp Trp Val Glu Tyr Ser
            500                 505                 510

Gly Gln Ile Lys Lys Gln Ile Ser Asp Asn Gln Lys Leu Thr Ile Met
        515                 520                 525

Lys Gln Arg Ile Thr Ala Glu Leu Lys Lys Met His Gly Ile Glu Asn
    530                 535                 540

Leu Asn Leu Arg Ile Ser Ile Asp Thr Asn Lys Ser Arg Gln Thr Val
545                 550                 555                 560

Met Asn Arg Ile Ala Leu Pro Lys Gly Phe Val Lys Asn His Ile Gln
                565                 570                 575

Gln Asn Ser Ser Glu Lys Ile Ser Lys Arg Ile Arg Glu Asp Tyr Cys
            580                 585                 590

Lys Ile Glu Leu Ser Gly Lys Tyr Glu Glu Leu Ser Arg Gln Phe Phe
        595                 600                 605

Asp Lys Lys Asn Phe Asp Lys Met Thr Leu Ile Asn Gly Leu Cys Glu
    610                 615                 620

Lys Asn Lys Leu Ile Ala Phe Met Val Ile Tyr Leu Leu Glu Arg Leu
625                 630                 635                 640

Gly Phe Glu Leu Lys Glu Lys Thr Lys Leu Gly Glu Leu Lys Gln Thr
                645                 650                 655

Arg Met Thr Tyr Lys Ile Ser Asp Lys Val Lys Glu Asp Ile Pro Leu
            660                 665                 670

Ser Tyr Tyr Pro Lys Leu Val Tyr Ala Met Asn Arg Lys Tyr Val Asp
        675                 680                 685

Asn Ile Asp Ser Tyr Ala Phe Ala Ala Tyr Glu Ser Lys Lys Ala Ile
    690                 695                 700

Leu Asp Lys Val Asp Ile Ile Glu Lys Gln Arg Met Glu Phe Ile Lys
705                 710                 715                 720

Gln Val Leu Cys Phe Glu Glu Tyr Ile Phe Glu Asn Arg Ile Ile Glu
                725                 730                 735

Lys Ser Lys Phe Asn Asp Glu Glu Thr His Ile Ser Phe Thr Gln Ile
            740                 745                 750

His Asp Glu Leu Ile Lys Lys Gly Arg Asp Thr Glu Lys Leu Ser Lys
        755                 760                 765

Leu Lys His Ala Arg Asn Lys Ala Leu His Gly Glu Ile Pro Asp Gly
    770                 775                 780

Thr Ser Phe Glu Lys Ala Lys Leu Leu Ile Asn Glu Ile Lys Lys
785                 790                 795

<210> SEQ ID NO 7
<211> LENGTH: 803
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: metagenomic

<400> SEQUENCE: 7

Met Asn Ala Ile Glu Leu Lys Lys Glu Glu Ala Ala Phe Tyr Phe Asn
1               5                   10                  15
```

```
Gln Ala Arg Leu Asn Ile Ser Gly Leu Asp Glu Ile Ile Glu Lys Gln
             20                  25                  30
Leu Pro His Ile Gly Ser Asn Arg Glu Asn Ala Lys Lys Thr Val Asp
             35                  40                  45
Met Ile Leu Asp Asn Pro Glu Val Leu Lys Lys Met Glu Asn Tyr Val
 50                  55                  60
Phe Asn Ser Arg Asp Ile Ala Lys Asn Ala Arg Gly Glu Leu Glu Ala
 65                  70                  75                  80
Leu Leu Leu Lys Leu Val Glu Leu Arg Asn Phe Tyr Ser His Tyr Val
             85                  90                  95
His Lys Asp Asp Val Lys Thr Leu Ser Tyr Gly Glu Lys Pro Leu Leu
            100                 105                 110
Asp Lys Tyr Tyr Glu Ile Ala Ile Glu Ala Thr Gly Ser Lys Asp Val
            115                 120                 125
Arg Leu Glu Ile Ile Asp Asp Lys Asn Lys Leu Thr Asp Ala Gly Val
            130                 135                 140
Leu Phe Leu Leu Cys Met Phe Leu Lys Lys Ser Glu Ala Asn Lys Leu
145                 150                 155                 160
Ile Ser Ser Ile Arg Gly Phe Lys Arg Asn Asp Lys Glu Gly Gln Pro
            165                 170                 175
Arg Arg Asn Leu Phe Thr Tyr Tyr Ser Val Arg Glu Gly Tyr Lys Val
            180                 185                 190
Val Pro Asp Met Gln Lys His Phe Leu Leu Phe Thr Leu Val Asn His
            195                 200                 205
Leu Ser Asn Gln Asp Glu Tyr Ile Ser Asn Leu Arg Pro Asn Gln Glu
            210                 215                 220
Ile Gly Gln Gly Gly Phe Phe His Arg Ile Ala Ser Lys Phe Leu Ser
225                 230                 235                 240
Asp Ser Gly Ile Leu His Ser Met Lys Phe Tyr Thr Tyr Arg Ser Lys
            245                 250                 255
Arg Leu Thr Glu Gln Arg Gly Glu Leu Lys Pro Lys Lys Asp His Phe
            260                 265                 270
Thr Trp Ile Glu Pro Phe Gln Gly Asn Ser Tyr Phe Ser Val Gln Gly
            275                 280                 285
Gln Lys Gly Val Ile Gly Glu Glu Gln Leu Lys Glu Leu Cys Tyr Val
            290                 295                 300
Leu Leu Val Ala Arg Glu Asp Phe Arg Ala Val Glu Gly Lys Val Thr
305                 310                 315                 320
Gln Phe Leu Lys Lys Phe Gln Asn Ala Asn Asn Val Gln Gln Val Glu
            325                 330                 335
Lys Asp Glu Val Leu Glu Lys Glu Tyr Phe Pro Ala Asn Tyr Phe Glu
            340                 345                 350
Asn Arg Asp Val Gly Arg Val Lys Asp Lys Ile Leu Asn Arg Leu Lys
            355                 360                 365
Lys Ile Thr Glu Ser Tyr Lys Ala Lys Gly Arg Glu Val Lys Ala Tyr
            370                 375                 380
Asp Lys Met Lys Glu Val Met Glu Phe Ile Asn Asn Cys Leu Pro Thr
385                 390                 395                 400
Asp Glu Asn Leu Lys Leu Lys Asp Tyr Arg Arg Tyr Leu Lys Met Val
            405                 410                 415
Arg Phe Trp Gly Arg Glu Lys Glu Asn Ile Lys Arg Glu Phe Asp Ser
            420                 425                 430
Lys Lys Trp Glu Arg Phe Leu Pro Arg Glu Leu Trp Gln Lys Arg Asn
```

-continued

```
                    435                 440                 445
Leu Glu Asp Ala Tyr Gln Leu Ala Lys Glu Lys Asn Thr Glu Leu Phe
    450                 455                 460
Asn Lys Leu Lys Thr Thr Val Glu Arg Met Asn Glu Leu Glu Phe Glu
465                 470                 475                 480
Lys Tyr Gln Gln Ile Asn Asp Ala Lys Asp Leu Ala Asn Leu Arg Gln
                485                 490                 495
Leu Ala Arg Asp Phe Gly Val Lys Trp Glu Lys Asp Trp Gln Glu
                500                 505                 510
Tyr Ser Gly Gln Ile Lys Lys Gln Ile Thr Asp Arg Gln Lys Leu Thr
            515                 520                 525
Ile Met Lys Gln Arg Ile Thr Ala Ala Leu Lys Lys Gln Gly Ile
    530                 535                 540
Glu Asn Leu Asn Leu Arg Ile Thr Thr Asp Thr Asn Lys Ser Arg Lys
545                 550                 555                 560
Val Val Leu Asn Arg Ile Ala Leu Pro Lys Gly Phe Val Arg Lys His
                565                 570                 575
Ile Leu Lys Thr Asp Ile Lys Ile Ser Lys Gln Ile Arg Gln Ser Gln
                580                 585                 590
Cys Pro Ile Ile Leu Ser Asn Asn Tyr Met Lys Leu Ala Lys Glu Phe
            595                 600                 605
Phe Glu Glu Arg Asn Phe Asp Lys Met Thr Gln Ile Asn Gly Leu Phe
    610                 615                 620
Glu Lys Asn Val Leu Ile Ala Phe Met Ile Val Tyr Leu Met Glu Gln
625                 630                 635                 640
Leu Asn Leu Arg Leu Gly Lys Asn Thr Glu Leu Ser Asn Leu Lys Lys
                645                 650                 655
Thr Glu Val Asn Phe Thr Ile Thr Asp Lys Val Thr Glu Lys Val Gln
                660                 665                 670
Ile Ser Gln Tyr Pro Ser Leu Val Phe Ala Ile Asn Arg Glu Tyr Val
            675                 680                 685
Asp Gly Ile Ser Gly Tyr Lys Leu Pro Pro Lys Lys Pro Lys Glu Pro
    690                 695                 700
Pro Tyr Thr Phe Phe Glu Lys Ile Asp Ala Ile Glu Lys Glu Arg Met
705                 710                 715                 720
Glu Phe Ile Lys Gln Val Leu Gly Phe Glu Glu His Leu Phe Glu Lys
                725                 730                 735
Asn Val Ile Asp Lys Thr Arg Phe Thr Asp Thr Ala Thr His Ile Ser
                740                 745                 750
Phe Asn Glu Ile Cys Asp Glu Leu Ile Lys Lys Gly Trp Asp Glu Asn
            755                 760                 765
Lys Ile Ile Lys Leu Lys Asp Ala Arg Asn Ala Ala Leu His Gly Lys
    770                 775                 780
Ile Pro Glu Asp Thr Ser Phe Asp Glu Ala Lys Val Leu Ile Asn Glu
785                 790                 795                 800
Leu Lys Lys
```

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: metagenomic

<400> SEQUENCE: 8
gctggagcag cccccgattt gtggggtgat tacagc                                    36

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: metagenomic

<400> SEQUENCE: 9
gctgaagaag cctccgattt gagaggtgat tacagc                                    36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: metagenomic

<400> SEQUENCE: 10
gctgtgatag acctcgattt gtggggtagt aacagc                                    36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: metagenomic

<400> SEQUENCE: 11
gctgtgatag acctcgattt gtggggtagt aacagc                                    36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: metagenomic

<400> SEQUENCE: 12
gctgtgatag acctcgattt gtggggtagt aacagc                                    36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: metagenomic

<400> SEQUENCE: 13
```

```
gctgtgatgg gcctcaattt gtggggaagt aacagc                                 36

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: metagenomic

<400> SEQUENCE: 14
gctgtgatag gcctcgattt gtggggtagt aacagc                                 36

<210> SEQ ID NO 15
<211> LENGTH: 2328
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: metagenomic

<400> SEQUENCE: 15
atggcgcaag tgtcaaagca gacttcgaaa aagagagagt tgtctatcga tgaatatcaa        60
ggtgctcgga aatggtgttt tacgattgcc ttcaacaagg ctcttgtgaa tcgagataag       120
aacgacgggc tttttgtcga gtcgctgtta cgccatgaaa agtattcaaa gcacgactgg       180
tacgatgagg atacacgcgc tttgatcaag tgtagcacac aagcggccaa tgcgaaggcc       240
gaggcgttaa gaaactattt ctcccactat cgacattcgc ccgggtgtct gacatttaca       300
gcagaagatg agttgcggac aatcatggaa agggcgtatg agcgggcgat ctttgaatgc       360
aggagacgcg aaactgaagt gatcatcgag tttcccagcc tgttcgaagg cgaccggatc       420
actacggcgg gggttgtgtt tttcgtttcg ttctttgttg aacggcgggt gctggatcgt       480
ttgtacggtg cggtaagtgg gcttaagaaa aacgaaggac agtacaagct gactcggaag       540
gcgctttcga tgtattgcct gaaagacagt cgtttcacga aggcgtggga caaacgcgtg       600
ctgcttttca gggatatact cgcgcagctt ggacgcatcc ctgcggaggc gtatgaatac       660
taccacggag agcagggcga caagaaaaga gcaaacgaca atgaggggac gaatccgaaa       720
cgccataaag acaagttcat cgagtttgca ctgcattatc tggaggcgca acacagtgag       780
atatgcttcg ggcggcgaca cattgtcagg gaggaggccg gggcaggcga cgaacacaaa       840
aagcacagga ccaaaggcaa ggtagttgtc gacttttcaa aaaaagacga agatcagtca       900
tactatatca gtaagaacaa tgttatcgtc aggattgata agaatgccgg gcctcggagt       960
tatcgcatgg ggcttaacga attgaaatac cttgtattgc ttagccttca gggaaagggc      1020
gacgatgcga ttgcaaaact gtacaggtat cggcagcatg tggagaacat tctggatgta      1080
gtgaaggtca cagataagga taatcacgtc ttcctgccgc gatttgtgct ggagcaacat      1140
gggattggca ggaaagcttt taagcaaaga atagacggca gagtaaagca tgttcgaggg      1200
gtgtgggaaa agaagaaggc ggcgaccaac gagatgacac ttcacgagaa ggcgcgggac      1260
attcttcaat acgtaaatga aaattgcacg aggtctttca atcccggcga gtacaaccgg      1320
ctgctggtgt gtctggttgg caaggatgtt gagaattttc aggcgggact gaaacgcctg      1380
caactggccg agcgaatcga cgggcgggta tattcaattt ttgcgcagac ctccacaata      1440
aacgagatgc atcaggtggt gtgtgatcag attctcaaca gactttgccg aatcggcgat      1500
```

```
cagaagctct acgattatgt ggggcttggg aagaaggatg aaatagatta caagcagaag    1560
gttgcatggt tcaaggagca tatttctatc cgcagggggtt tcttgcgcaa gaagttctgg    1620
tatgacagca agaagggatt cgcgaagctt gtggaagagc atttggaaag cggcggcgga    1680
cagagggacg ttgggctgga taaaaagtat tatcatattg atgcgattgg gcgattcgag    1740
ggtgctaatc cagccttgta tgaaacgctg gcgcgagacc gtttgtgtct gatgatggcg    1800
caatacttcc tggggagtgt acgcaaggaa ttgggtaata aaattgtgtg gtcgaatgat    1860
agcatcgagt tgcccgtgga gggctcagtg ggtaacgaaa aaagcatcgt cttctcagtg    1920
agtgattacg gcaagttata tgtgttggat gacgctgagt tcttgggcg gatatgtgag    1980 tactttatgc cgcacgaaaa agggaagata cggtatcata cagtttacga aaaagggttt    2040 aggggcatata atgatctgca gaagaaatgt gtcgaggcgg tgctggcgtt tgaagagaag    2100
gttgtcaaag ccaaaaagat gagcgagaag gaaggggcgc attatattga ttttcgtgag    2160
atactggcac aaacaatgtg taaagaggcg gagaagaccg ccgtgaataa ggtgcgtaga    2220 gcgttttttcc atcatcattt aaagtttgtg atagatgaat ttgggttgtt tagtgatgtt    2280
atgaagaaat atggaattga aaaggagtgg aagtttcctg ttaaatga                 2328

<210> SEQ ID NO 16
<211> LENGTH: 2418
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: metagenomic

<400> SEQUENCE: 16
atgaaggttg aaaatattaa agaaaaaagc aaaaaagcaa tgtatttaat caaccattat      60
gagggaccca aaaatggtg ttttgcaata gttctgaata gggcatgtga taattacgag     120
gacaatccac acttgttttc caaatcactt ttggaatttg aaaaaacaag tcgaaaagat     180
tggtttgacg aagaaacacg agagcttgtt gagcaagcag atacagaaat acagccaaat     240
cctaacctga aacctaatac aacagctaac cgaaaactca agatataag aaactatttt      300 tcgcatcatt atcacaagaa cgaatgcctg tattttaaga cgatgatcc catacgctgc     360 attatggaag cggcgtatga aaaatctaaa atttatatca aaggaaagca gattgagcaa     420
agcgatatac cattgcccga attgtttgaa agcagcggtt ggattacacc ggcggggatt     480
ttgttactgg catccttttt tgttgaacga gggattctac atcgcttgat gggaaatatc     540
ggaggattta agataatcg aggcgaatac ggtcttacac acgatatttt taccacctat     600
tgtcttaagg gtagttattc aattcgggcg caggatcatg atgcggtaat gttcagagat     660
attctcggct atctgtcacg agttcccact gagtcatttc agcgtatcaa gcaacctcaa     720
atacgaaaag aaggccaatt aagtgaaaga agacgagaca aatttataac atttgcacta     780
aattatcttg aggattatgg gctgaaagat ttggaaggct gcaaagcctg ttttgccaga     840
agtaaaattg taagggaaca agaaaatgtt gaaagcataa atgataagga atacaaacct     900
cacgagaaca aaagaaagt tgaaattcac ttcgatcaga gcaaagaaga ccgattttat     960
attaatcgca ataacgttat tttgaagatt cagaagaaag atggacattc caacatagtt    1020
aggatgggag tatatgaact taaatatctc gttcttatga gtttagtggg aaaagcaaaa    1080
gaagcagttg aaaaaattga caactatatc caggattttgc gagaccagtt gccttacata    1140
```

```
gagggggaaaa ataaggaaga gattaaagaa tacgtcaggt tctttccacg atttatacgt    1200
tctcacctcg gtttactaca gattaacgat gaagaaaaga taaaagctcg attagattat    1260
gttaagacca agtggttaga taaaaaggaa aaatcgaaag agcttgaact tcataaaaaa    1320
ggacgggaca tcctcaggta tatcaacgag cgatgtgata gagagcttaa caggaatgta    1380
tataaccgta ttttagagct cctggtcagc aaagacctca ctggttttta tcgtgagctt    1440
gaagaactaa aaagaacaag gcggatagat aaaaatattg tccagaatct ttctgggcaa    1500
aaaaccatta atgcactgca tgaaaaggtc tgtgatctgg tgctgaagga aatcgaaagt    1560
ctcgatacag aaaatctcag gaaatatctt ggattgatac ccaaagaaga aaagagggtc    1620
actttcaaag aaaaggtcga taggattttg aaacagccag ttatttacaa agggtttctg    1680
agataccaat tcttcaaaga tgacaaaaag agttttgtct tacttgttga agacgcattg    1740
aaggaaaaag gaggaggttg tgatgttcct cttgggaaag agtattataa aatcgtgtca    1800
cttgataagt atgataaaga aaataaaacc ctgtgtgaaa ctctggcgat ggataggctt    1860
tgccttatga tggcaagaca atattatctc agtctgaatg caaaacttgc acaggaagct    1920
cagcaaatcg aatggaagaa agaagatagt atagaattga ttattttcac cttaaaaaat    1980
cccgatcaat caaagcagag ttttctata cggttttcgg tcagagattt tacgaagttg    2040
tatgtaacgg atgatcctga atttctggcc cggctttgtt cctactttt cccagttgaa    2100 aaagagattg aatatcacaa gctctattca gaagggataa ataaatacac aaacctgcaa    2160
aaagagggaa tcgaagcaat actcgagctt gaaaaaaagc ttattgaacg aaatcggatt    2220
caatctgcaa aaaattatct ctcatttaat gagataatga ataaaagcgg ttataataaa    2280
gatgagcagg atgatctaaa gaaggtgcga aattctcttt tgcattataa gcttatcttt    2340
gagaaagaac atctcaagaa gttctatgag gttatgagag gagaagggat agagaaaaag    2400
tggtctttaa tagtatga                                                  2418
```

<210> SEQ ID NO 17
<211> LENGTH: 2373
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: metagenomic

<400> SEQUENCE: 17

```
atgaatggca ttgaattaaa aaaagaagaa gcagcatttt attttaatca ggcagagctt      60
aatttaaaag ccatagaaga caatattttt gataaagaaa gacgaaagac tctgcttaat     120
aatccacaga tacttgccaa aatggaaaat ttcatttttca atttcagaga tgtaacaaaa     180
aatgcaaaag gggaaattga ctgcttgctg ttgaaactaa gagagctgag aaacttttac     240
tcgcattatg tccacaaacg agatgtaaga gaattaagca agggcgagaa acctatactt     300
gaaaagtatt accaatttgc gattgaatca accggaagtg aaaatgttaa acttgagata     360
atagaaaacg acgcgtggct tgcagatgcc ggtgtgttgt tttcttatg tatttttttg     420 aagaaatctc aggcaaataa gcttataagc ggtatcagcg gttttaaaag aaacgatgat     480
accggtcagc cgagaaggaa tttatttacc tatttcagta aaggagggg atacaaggtt     540 gttccggaaa tgcagaaaca tttccttttg ttttctcttg ttaatcatct ctctaatcaa     600
gatgattata ttgaaaaagc gcatcagcca tacgatatag gcgagggttt atttttttcat     660
```

```
cgaatagctt ctacatttct taatataagt gggattttaa gaaatatgaa attctatacc    720
tatcagagta aaaggttagt agagcagcgg ggagaactca aacgagaaaa ggatattttt    780
gcgtgggaag aaccgtttca aggaaatagt tattttgaaa taaatggtca taaaggagta    840
atcggtgaag atgaattgaa ggaactatgt tatgcatttc tgattggcaa tcaagatgct    900
aataaagtgg aaggcaggat tacacaattt ctagaaaagt ttagaaatgc gaacagtgtg    960
caacaagtta aagatgatga aatgctaaaa ccagagtatt ttcctgcaaa ttattttgct   1020
gaatcaggcg tcggaagaat aaaggataga gtgcttaatc gtttgaataa agcgattaaa   1080
agcaataagg ccaagaaagg agagattata gcatacgata agatgagaga ggttatggcg   1140
ttcataaata attctctgcc ggtagatgaa aaattgaaac caaagattta caacgatat    1200
ctgggaatgg ttcgtttctg ggacaggaa aaagataaca taaagcggga gttcgagaca    1260
aaagaatggt ctaaatatct tccatctaat ttctggacgg caaaaaacct tgaaagggtc   1320
tatggtctgg caagagagaa aaacgcagaa ttattcaata aactaaaagc ggatgtagaa   1380
aaaatggacg aacgggaact tgagaagtat cagaagataa atgatgcaaa ggatttggca   1440
aatttacgcc ggcttgcaag cgactttggt gtgaagtggg aagaaaaaga ctgggatgag   1500
tattcaggac agataaaaaa acaaattaca gacagccaga aactaacaat aatgaagcag   1560
cggataaccg caggactaaa gaaaaagcac ggcatagaaa atcttaacct gagaataact   1620
atcgacatca ataaaagcag aaaggcagtt ttgaacagaa ttgcgattcc gaggggtttt   1680
gtaaaaaggc atattttagg atggcaagag tctgagaagg tatcgaaaaa gataagagag   1740
gcagaatgcg aaattctgct gtcgaaagaa tacgaagaac tatcgaaaca attttttccaa  1800
agcaaagatt atgacaaaat gacacggata aatggccttt atgaaaaaaa caaacttata   1860
gccctgatgg cagtttatct aatggggcaa ttgagaatcc tgtttaaaga acacacaaaa   1920
cttgacgata ttacgaaaac aactgtggat ttcaaaatat ctgataaggt gacggtaaaa   1980
atccccttt caaattatcc ttcgctcgtt tatacaatgt ccagtaagta tgttgataat   2040
atagggaatt atggattttc caacaaagat aaagacaagc cgattttagg taagattgat   2100
gtaatagaaa aacagcgaat ggaatttata aaagaggttc ttggttttga aaaatatctt   2160
tttgatgata aaataataga taaaagcaaa tttgctgata cagcgactca tataagtttt   2220
gcagaaatag ttgaggagct tgttgaaaaa ggatgggaca aagacagact gacaaaactt   2280
aaagatgcaa gaaataaagc cctgcatggt gaaatactga cgggaaccag ctttgatgaa   2340
acaaaatcat tgataaacga attaaaaaaa tga                                2373
```

<210> SEQ ID NO 18
<211> LENGTH: 2379
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: metagenomic

<400> SEQUENCE: 18

```
atgtccccag atttcatcaa attagaaaaa caggaagcag cttttttactt taatcagaca    60
gagcttaatt taaaagccat agaaagcaat attttagaca aacaacagcg aatgattctg   120
cttaataatc cacggatact tgccaaagta ggaaatttca ttttcaattt cagagatgta   180
acaaaaaatg caaaaggaga aatagactgt ctgctattta aactggaaga gctaagaaac   240
```

```
ttttactcgc attatgttca taccgacaat gtaaaggaat tgagtaacgg agaaaaaccc      300
ctactggaaa gatattatca aatcgctatt caggcaacca ggagtgagga tgttaagttc      360
gaattgtttg aaacaagaaa cgagaataag attacggatg ccggtgtatt gtttttctta      420
tgtatgtttt taaaaaaatc acaggcaaac aagcttataa gcggtatcag cggcttcaaa      480
agaaatgatc caacaggcca gccgagaaga aacttattta cctatttcag tgcaagagaa      540
ggatataagg ctttgcctga tatgcagaaa cattttcttc ttttactct ggttaattat       600 ttgtcgaatc aggatgagta tatcagcgag cttaaacaat atggagagat tggtcaagga      660 gccttttta atcgaatagc ttcaacattt ttgaatatca gcgggatttc aggaaatacg       720
aaattctatt cgtatcaaag taaaaggata aaagagcagc gaggcgaact caatagcgaa      780
aaggacagct ttgaatggat agagcctttc caaggaaaca gctattttga aataaatggg      840
cataaaggag taatcggcga agacgaatta aaagaacttt gttatgcatt gttggttgcc     900
aagcaagata ttaatgccgt tgaaggcaaa attatgcaat tcctgaaaaa gtttagaaat      960
actggcaatt gcagcaagt taaagatgat gaaatgctgg aaatagaata ttttcccgca     1020
agttatttta tgaatcaaa aaagaggac ataagaaag agattcttgg ccggctggat        1080 aaaagattc gctcctgctc tgcaaaggca gaaaaagcct atgataagat gaagaggtg      1140 atggagttta taaataattc tctgccggca gaggaaaaat tgaaacgcaa agattataga     1200
agatatctaa agatggttcg tttctggagc agagaaaaag gcaatataga gcgggaattt     1260
agaacaaagg aatggtcaaa atattttca tctgattttt ggcggaagaa caatcttgaa      1320
gatgtgtaca aactggcaac acaaaaaaac gctgaactgt tcaaaaatct aaaagcggca     1380
gcagagaaaa tgggtgaaac ggaatttgaa aagtatcagc agataaacga tgtaaaggat     1440
ttggcaagtt taaggcggct tacgcaagat tttggtttga agtgggaaga aaaggactgg     1500
gaggagtatt ccgagcagat aaaaaaacaa attacggaca ggcagaaact gacaataatg     1560
aaacaagggt ttacggctga actaaagaaa aagcacggca tagaaaatct taatctgaga     1620
ataaccatcg acagcaataa aagcagaaag gcggttttga acagaatagc aattccaaga     1680
ggatttgtaa aaaacatat tttaggctgg cagggatctg agaagatatc gaaaaatata     1740
agggaagcag aatgcaaaat tctgctatcg aaaaaatatg aagagttatc aaggcagttt     1800
tttgaagccg gtaatttcga taagctgacg cagataaatg gtctttatga aaagaataaa     1860
cttacagctt ttatgtcagt atatttgatg ggtcggttga atattcagct taataagcac     1920
acagaacttg gaaatcttaa aaaacagag gtggatttta agatatctga taaggtgact     1980
gaaaaaatac cgttttctca gtatccttcg cttgtctatg cgatgtctcg caaatatgtt     2040
gacaatgtgt ataaatataa atttttctcat caagataaaa agaagccatt tttaggtaaa    2100
attgattcaa ttgaaaaaga acgtattgaa ttcataaaag aggttctcga ttttgaagag    2160
tatcttttta aaaataaggt aatagataaa agcaaatttt ccgatacagc gactcatatt    2220
agctttaagg aaatatgtga tgaaatgggt aaaaaaggat gtaaccgaaa caaactaacc    2280
gaacttaaca acgcaaggaa cgcagccctg catggtgaaa taccgtcgga gacctctttt    2340
cgtgaagcaa aaccgttgat aaatgaattg aaaaaatga                           2379
```

<210> SEQ ID NO 19
<211> LENGTH: 2379
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: metagenomic

<400> SEQUENCE: 19

```
atgtccccag atttcatcaa attagaaaaa caagaagcag ctttttactt taatcagaca      60
gagcttaatt taaaagccat agaaagcaat attttcgaca acaacagcg agtgattctg      120
cttaataatc cacagatact tgccaaagta ggagatttta ttttcaattt cagagatgta     180
acaaaaaacg caaaggaga atagactgt ttgctattga aactaagaga gctgagaaac      240
ttttactcac actatgtcta taccgatgac gtgaagatat tgagtaacgg cgaaagacct     300
ctgctggaaa atattatca atttgcgatt gaagcaaccg gaagtgaaaa tgttaaactt     360
gaaataatag aaagcaacaa ccgacttacg gaagcgggcg tgctgttttt cttgtgtatg     420
ttttgaaaa agtctcaggc aaataagctt ataagcggta tcagcggttt taaaagaaat     480
gacccgacag gtcagccgag aaggaattta tttacctact tcagtgtaag ggagggatac     540
aaggttgtgc cggatatgca gaaacatttt cttttgtttg ttcttgtcaa tcatctctct     600
ggtcaggatg attatattga aaaggcgcaa aagccatacg atataggcga gggtttattt     660
tttcatcgaa tagcttctac atttcttaat atcagtggga ttttaagaaa tatggaattc     720
tatatttacc agagcaaaag actaaaggag cagcaaggag agctcaaacg tgaaaaggat     780
attttttccat ggatagagcc tttccaggga aatagttatt ttgaaataaa tggtaataaa    840
ggaataatcg gcgaagatga attgaaagag ctttgttatg cgttgctggt tgcaggaaaa    900
gatgtcagag ccgtcgaagg taaaataaca caattttttgg aaaagtttaa aaatgcggac    960
aatgctcagc aagttgaaaa agatgaaatg ctggacagaa acaattttcc cgccaattat   1020
ttcgccgaat cgaacatcgg cagcataaag gaaaaaatac ttaatcgttt gggaaaaact   1080
gatgatagtt ataataagac ggggacaaag attaaaccat acgacatgat gaaagaggta   1140
atggagttta taaataattc tcttccggca gatgaaaaat tgaaacgcaa agattacaga   1200
agatatctaa agatggttcg tatctgggac agtgagaaag ataatataaa gcggagtttt   1260
gaaagcaaag aatggtcaaa atatttttca tctgatttct ggatggcaaa aaatcttgaa   1320
agggtctatg ggttggcaag agagaaaaac gccgaattat tcaataagct aaaagcggtt   1380
gtggagaaaa tggacgagcg ggaatttgag aagtatcggc tgataaatag cgcagaggat   1440
ttggcaagtt taagacggct tgcgaaagat tttggcctga agtgggaaga aaaggactgg   1500
caagagtatt ctgggcagat aaaaaaacaa atttctgaca ggcagaaact gacaataatg   1560
aaacaaagga ttacggctga actaaagaaa agcacggca tagaaaatct caatcttaga   1620
ataaccatcg acagcaataa aagcagaaag gcagttttga acagaatcgc agttccaaga   1680
ggttttgtga aagagcatat tttaggatgg caggggtctg agaaggtatc gaaaaagaca   1740
agagaagcaa agtgcaaaat tctgctctcg aaagaatatg aagaattatc aaagcaattt   1800
ttccaaacca gaaattacga caagatgacg caggtaaacg gtctttacga aaagaataaa   1860
ctcttagcat ttatggtcgt ttatcttatg gagcggttga atatcctgct taataagccc   1920
acagaactta tgaacttga aaagcagag gtggatttca agatatctga taaggtgatg   1980
gccaaaatcc cgttttcaca gtatccttcg cttgtgtacg cgatgtccag caaatatgct   2040
gatagtgtag gcagttataa atttgagaat gatgaaaaaa acaagccgtt tttaggcaag   2100
atcgatacaa tagaaaaaca acgaatggag tttataaaag aagtccttgg ttttgaagag   2160
```

```
tatcttttg aaaagaagat aatagataaa agcgaatttg ccgacacagc gactcatata    2220
agttttgatg aaatatgtaa tgagcttatt aaaaaaggat gggataaaga caaactaacc   2280
aaacttaaag atgccaggaa cgcggccctg catggcgaaa taccggcgga gacctctttt   2340
cgtgaagcaa aaccgttgat aaatggattg aaaaaatga                          2379
```

```
<210> SEQ ID NO 20
<211> LENGTH: 2400
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: metagenomic

<400> SEQUENCE: 20
atgaacatca ttaaattaaa aaaagaagaa gctgcgtttt attttaatca gacgatcctc     60
aatctttcag ggcttgatga aattattgaa aaacaaattc cgcacataat cagcaacaag    120
gaaaatgcaa agaaagtgat tgataagatt ttcaataacc gcttattatt aaaaagtgtg    180
gagaattata tctacaactt taaagatgtg gctaaaaacg caagaactga aattgaggct    240
atattgttga aattagtaga gctacgtaat ttttactcac attacgttca taatgatacc    300
gtcaagatac taagtaacgg tgaaaaacct atactggaaa aatattatca aattgctata    360
gaagcaaccg gaagtaaaaa tgttaaactt gtaatcatag aaaacaacaa ctgtctcacg    420
gattctggcg tgctgttttt gctgtgtatg ttcttaaaaa aatcacaggc aaacaagctt    480
ataagttccg ttagtggttt taaaaggaat gataaagaag acaaccgag aagaaatcta    540 ttcacttatt atagtgtgag ggagggatat aaggttgtgc ctgatatgca gaagcatttc    600
cttctattcg ctctggtcaa tcatctatct gagcaggatg atcatattga gaagcagcag    660
cagtcagacg agctcggtaa gggttttgttt tccatcgta tagcttcgac tttttttaaac    720 gagagcggca tcttcaataa aatgcaattt tatacatatc agagcaacag gctaaaagag    780
aaaagaggag aactcaaaca cgaaaaggat acctttacat ggatagagcc ttttcaaggc    840
aatagttatt ttacgttaaa tggacataag ggagtgatta gtgaagatca attgaaggag    900 cttttgttaca caattttaat tgagaagcaa aacgttgatt ccttggaagg taaaattata    960
caatttctca aaaatttca gaatgtcagc agcaagcagc aagttgacga agatgaattg   1020
cttaaaagag aatatttccc tgcaaattac tttggccggg caggaacagg gaccctaaaa   1080
gaaaagattc taaccggct tgataagagg atggatccta catctaaagt gacggataaa   1140
gcttatgaca aaatgattga agtgatggaa tttatcaata tgtgccttcc gtctgatgag   1200
aagttgaggc aaaaggatta tagacgatac ttaaagatgg ttcgtttctg gaataaggaa   1260
aagcataaca ttaagcgcga gtttgacagt aaaaaatgga cgaggttttt gccgacggaa   1320
ttgtggaata aagaaatct agaagaagcc tatcaattag cacggaaaga gaacaaaaag   1380
aaacttgaag atatgagaaa tcaagtacga agccttaaag aaaatgacct tgaaaaatat   1440
cagcagatta attacgttaa tgacctggag aatttaaggc ttctgtcaca ggagttaggt   1500
gtgaaatggc aggaaaagga ctgggttgaa tattccgggc agataaagaa gcagatatca   1560
gacaatcaga aacttacaat catgaaacaa aggattaccg ctgaactaaa gaaaatgcac   1620
ggcatcgaga atcttaatct tagaataagc attgacacga ataaaagcag gcagacggtt   1680
atgaacagga tagctttgcc caaaggtttt gtgaagaatc atatccagca aaattcgtct   1740
```

-continued

| | | |
|---|---|---|
| gagaaaatat cgaaaagaat aagagaggat tattgtaaaa ttgagctatc gggaaaatat | 1800 | |
| gaagaacttt caaggcaatt ttttgataaa aagaatttcg ataagatgac actgataaac | 1860 | |
| ggcctttgtg aaaagaacaa acttatcgca tttatggtta tctatctttt ggagcggctt | 1920 | |
| ggatttgaat taaggagaa acaaaatta ggcgagctta acaaacaag gatgacatat | 1980 | |
| aaaatatccg ataaggtaaa agaagatatc ccgctttcct attacccaa gcttgtgtat | 2040 | |
| gcaatgaacc gaaatatgt tgacaatatc gatagttatg catttgcggc ttacgaatcc | 2100 | |
| aaaaaagcta ttttggataa agtggatatc atagaaaagc aacgtatgga atttatcaaa | 2160 | |
| caagttctct gttttgagga atatattttc gaaaatagga ttatcgaaaa agcaaatttt | 2220 | |
| aatgacgagg agactcatat aagttttaca caaatacatg atgagcttat taaaaaagga | 2280 | |
| cgggacacag aaaaactctc taaactcaaa catgcaagga ataaagcctt gcacggcgag | 2340 | |
| attcctgatg ggacttcttt tgaaaagca agctattga taatgaaat caaaaatga | 2400 | |

<210> SEQ ID NO 21
<211> LENGTH: 2412
<212> TYPE: DNA
<213> ORGANISM: Artificial Sequence
<220> FEATURE:
<223> OTHER INFORMATION: Description of Artificial Sequence: Synthetic
  polynucleotide
<220> FEATURE:
<223> OTHER INFORMATION: metagenomic

<400> SEQUENCE: 21

| | | |
|---|---|---|
| atgaatgcta tcgaactaaa aaagaggaa gcagcatttt attttaatca ggcaagactc | 60 | |
| aacatttcag gacttgatga aattattgaa aagcagttac cacatatagg tagtaacagg | 120 | |
| gagaatgcga aaaaactgt tgatatgatt ttggataatc ccgaagtctt gaagaagatg | 180 | |
| gaaaattatg tctttaactc acgagatata gcaaagaacg caagaggtga acttgaagca | 240 | |
| ttgttgttga aattagtaga actgcgtaat ttttattcac attatgttca taaagatgat | 300 | |
| gttaagacat tgagttacgg agaaaaaccct ttactggata atattatga aattgcgatt | 360 | |
| gaagcgaccg gaagtaaaga tgtcagactt gagataatag atgataaaaa taagcttaca | 420 | |
| gatgccggtg tgcttttttt attgtgtatg ttttttgaaaa aatcagaggc aaacaaactt | 480 | |
| atcagttcaa tcaggggctt taaaagaaac gataaagaag gccagccgag aagaaatcta | 540 | |
| ttcacttact acagtgtcag agaggatat aaggttgtgc ctgatatgca gaaacatttt | 600 | |
| cttttattca cactggttaa ccatttgtca aatcaggatg aatacatcag taatcttagg | 660 | |
| ccgaatcaag aaatcggcca aggggattt ttccatagaa tagcatcaaa attttttgagc | 720 | |
| gatagcggga ttttacatag tatgaaattc tacacctacc ggagtaaaag actaacagaa | 780 | |
| caacgggggg agcttaagcc gaaaaagat cattttacat ggatagagcc ttttcaggga | 840 | |
| aacagttatt tttcagtgca gggccaaaaa ggagtaattg gtgaagagca attaaaggag | 900 | |
| ctttgttatg tattgctggt tgccagagaa gattttaggg ccgttgaggg caaagttaca | 960 | |
| caatttctga aaagtttca gaatgctaat aacgtacagc aagttgaaaa agatgaagtg | 1020 | |
| ctggaaaaag aatattttcc tgcaaattat tttgaaaatc gagacgtagg cagagtaaag | 1080 | |
| gataagatac ttaatcgttt gaaaaaaatc actgaaagct ataagctaa agggagggag | 1140 | |
| gttaaagcct atgacaagat gaagaggta atggagttta taataattg cctgccaaca | 1200 | |
| gatgaaaatt tgaaactcaa agattacaga agatatctga aatggttcg tttctggggc | 1260 | |
| agggaaaagg aaaatataaa gcgggaattt gacagtaaaa aatgggagag gttttttgcca | 1320 | |

| | |
|---|---|
| agagaactct ggcagaaaag aaacctcgaa gatgcgtatc aactggcaaa agagaaaaac | 1380 |
| accgagttat tcaataaatt gaaaacaact gttgagagaa tgaacgaact ggaattcgaa | 1440 |
| aagtatcagc agataaacga cgcaaaagat ttggcaaatt taaggcaact ggcgcgggac | 1500 |
| ttcggcgtga agtgggaaga aaaggactgg caagagtatt cggggcagat aaaaaaacaa | 1560 |
| attacagaca ggcaaaaact tacaataatg aaacaaagga ttactgctgc attgaagaaa | 1620 |
| aagcaaggca tagaaaatct taatcttagg ataacaaccg acaccaataa aagcagaaag | 1680 |
| gtggtattga acagaatagc gctacctaaa ggttttgtaa ggaagcatat cttaaaaaca | 1740 |
| gatataaaga tatcaaagca aataaggcaa tcacaatgtc ctattatact gtcaaacaat | 1800 |
| tatatgaagc tggcaaagga attctttgag gagagaaatt ttgataagat gacgcagata | 1860 |
| aacgggctat ttgagaaaaa tgtacttata gcgtttatga tagtttatct gatggaacaa | 1920 |
| ctgaatcttc gacttggtaa gaatacggaa cttagcaatc ttaaaaaaac ggaggttaat | 1980 |
| tttacgataa ccgacaaggt aacggaaaaa gtccagattt cgcagtatcc atcgcttgtt | 2040 |
| ttcgccataa acagagaata tgttgatgga atcagcggtt ataagttacc gcccaaaaaa | 2100 |
| ccgaaagagc ctccgtatac tttcttcgag aaaatagacg caatagaaaa agaacgaatg | 2160 |
| gaattcataa aacaggtcct cggtttcgaa gaacatcttt tgagaagaa tgtaatagac | 2220 |
| aaaactcgct ttactgatac tgcgactcat ataagttta tgaaatatg tgatgagctt | 2280 |
| ataaaaaaag gatgggacga aaacaaaata ataaaactta agatgcgag aatgcagca | 2340 |
| ttgcatggta agataccgga ggatacgtct tttgatgaag cgaaagtact gataaatgaa | 2400 |
| ttaaaaaaat ga | 2412 |

<210> SEQ ID NO 22
<211> LENGTH: 2328
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human codon-optimized coding sequences

<400> SEQUENCE: 22

| | |
|---|---|
| atggcccagg tgagcaagca gacctccaag aagagggagc tgagcatcga cgagtaccag | 60 |
| ggcgccccgga agtggtgctt caccattgcc ttcaacaagg ccctggtgaa ccgggacaag | 120 |
| aacgacggcc tgttcgtgga agcctgctg agacacgaga agtacagcaa gcacgactgg | 180 |
| tacgacgaag atacccgggc cctgatcaag tgcagcaccc aggccgccaa cgccaaggct | 240 |
| gaagccctgc ggaactactt cagtcactac cggcatagcc ctggctgcct gaccttcacc | 300 |
| gccgaggacg aactgcggac catcatggag agagcctatg agcgggccat cttcgagtgc | 360 |
| agaagaagag agacagaggt gatcatcgag tttcccagcc tgttcgaggg cgaccggatc | 420 |
| accaccgccg cgtggtgtt tttcgtgagc tttttcgtgg aaagaagagt gctggatcgg | 480 |
| ctgtatggag ccgtgtccgg cctgaagaag aatgagggac agtacaagct gacccggaag | 540 |
| gccctgagca tgtactgcct gaaggacagc agattcacca aggcctggga taagcgggtg | 600 |
| ctgctgttca gagacatcct ggcccagctg gaagaatcc ccgccgaggc ctacgagtac | 660 |
| taccacggcg agcagggtga taagaagaga gctaacgaca tgagggcac aaatcccaag | 720 |
| cggcacaagg acaagttcat cgaatttgca ctgcactacc tggaagccca gcacagcgag | 780 |
| atctgcttcg gcagacgcca catcgtgcgg gaagaggccg cgccggcga tgagcacaag | 840 |

```
aagcaccgga ccaagggaaa ggtggtggtg gacttcagca agaaggacga ggaccagagc    900
tactatatct ccaagaacaa cgtgatcgtg cggatcgaca agaacgccgg ccctagaagc    960
taccggatgg gcctgaacga gctgaagtac ctcgtgctgc tgagcctgca ggggaagggc   1020
gacgatgcca tcgccaagct gtacagatac agacagcacg tggagaacat cctggatgtg   1080
gtgaaggtga ccgataagga taaccacgtg ttcctgcccc gcttcgtgct ggagcagcac   1140
ggcatcggca gaaaggcctt caagcagcgg atcgatggac gggtgaagca cgtgcggggc   1200
gtgtgggaga agaagaaggc cgccaccaat gaaatgaccc tgcacgagaa ggccagagac   1260
atcctgcagt acgtgaacga aaactgcacc cggtccttca accctggcga atacaacaga   1320
ctgctggtgt gcctggtggg caaggacgtg gagaactttc aggccggcct gaagcggctg   1380
cagctggccg aaaggatcga tggccgggtg tactccatct tcgcccagac cagcaccatc   1440
aatgagatgc caccaggtggt gtgcgaccag atcctgaacc ggctgtgcag aatcggcgac   1500
cagaagctgt acgattacgt gggactgggc aagaaggacg aaatcgacta caagcagaag   1560
gtggcctggt tcaaggagca catcagcatc cggagaggat tcctgagaaa gaagttctgg   1620
tacgatagca agaagggatt cgcaaagctg gtggaggaac acctggagtc cggcggcggc   1680
cagcgcgacg tgggcctgga caagaagtac taccacatcg acgccatcgg cagattcgag   1740
ggcgccaacc ccgccctgta cgagaccctg gccagagatc ggctgtgcct catgatggcc   1800
cagtacttcc tgggcagcgt gagaaaggaa ctgggcaaca agattgtgtg gagcaacgac   1860
agcatcgaac tgcctgtgga aggctctgtg ggaaatgaga agagcatcgt gttctccgtg   1920
tctgactacg gcaagctgta cgtgctggac gatgccgaat tcctgggccg gatctgcgaa   1980
tacttcatgc cccacgaaaa gggcaagatc cggtaccaca cagtgtacga aaagggcttt   2040
agagcataca cgacctgca gaagaagtgc gtggaggccg tgctggcttt cgaagagaag   2100
gtggtgaagg ccaagaagat gagcgagaag gaaggcgccc actacatcga cttccgggag   2160
atcctggccc agaccatgtg caaggaggcc gagaagaccg cagtgaacaa ggtgagacgc   2220
gccttcttcc accaccacct gaagttcgtg attgacgagt tcggcctgtt cagcgacgtg   2280
atgaagaagt acggcatcga gaaggaatgg aagttccctg tcaagtaa              2328
```

<210> SEQ ID NO 23
<211> LENGTH: 2418
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human codon-optimized coding sequences

<400> SEQUENCE: 23

```
atgaaggtgg agaacatcaa ggaaaagtcc aagaaggcta tgtatctgat caaccactat     60
gaaggcccta agaagtggtg cttcgccatc gtgctgaata gggcctgcga caactatgag    120
gataaccccc acctgttcag caagagcctg ctggaatttg aaaagaccag cagaaggac    180 tggttcgacg aggagaccag ggaactggtg gagcaggccg acaccgagat ccagcccaac    240
cccaacctga gcctaacac caccgccaac agaaagctga aggacatccg gaactacttc    300
agccaccact accacaagaa tgagtgcctg tacttcaaga cgacgaccc tatccggtgc    360 atcatggagg cagcctacga gaagtccaag atctacatca agggcaagca gattgagcag    420
tccgacatcc ccctccctga gctgtttgag tctagcggct ggatcacccc agccggcatc    480
```

```
ctgctgctgg ccagcttctt tgtggagaga ggcattctgc acagactgat gggcaacatc      540
ggcggcttca aggacaaccg gggcgaatac ggactgaccc acgatatctt caccacctac      600
tgcctgaagg gcagctactc catcagagcc caggaccacg acgccgtgat gttcagagac      660
atcctgggct acctgagcag agtgccgacc gagagctttc agcgcatcaa gcagccacag      720
atcagaaagg aggggcagct gagcgagcgg aagacagaca gtttatcac cttcgccctg       780 aactacctgg aagattatgg actgaaggat ctggaaggct gcaaggcctg cttcgcccgg      840
agcaagatcg tgagagagca ggagaacgtg gaaagcatca atgacaagga gtacaagcct      900
cacgaaaaca gaagaaggt ggaaatccac ttcgatcagt ctaaggaaga ccggttctac       960
atcaaccgga acaacgtgat cctgaagatc agaagaagg acggccacag caacatcgtg      1020
agaatgggcg tgtacgagct gaagtatctg gtgctgatgt ccctggtggg caaggccaag     1080
gaagccgtgg agaagatcga caactacatc caggatctga gagaccagct gccctacatc     1140
gagggcaaga acaaggaaga aatcaaggag tacgtgagat cttccccag attcatcaga      1200 tcccacctgg gcctgctgca gattaacgat gaggagaaga tcaaggcccg gctggactat     1260
gtgaagacaa gtggctggaa caagaaggag aagtccaagg agctggagct gcacaagaag     1320
ggccgggata tcctgcggta catcaacgag cggtgcgacc gggagctgaa ccggaacgtg     1380
tacaaccgga tcctggagct gctggtgagc aaggacctga ccggcttcta ccgggagctg     1440
gaggagctga agcggaccag acggatcgat aagaacattg cagaacct gtccggccag       1500 aagaccatca acgccctgca cgaaaaggtg tgcgatctcg tgctgaagga gatcgagagc     1560
ctggacaccg agaacctgcg gaagtacctg gcctgatcc ccaaggagga gaaggaagtg      1620
acctttaagg agaaggtgga caggatcctg aagcagccgg tgatctacaa gggcttcctg     1680
cggtaccagt tcttcaagga cgacaagaag agcttcgtgc tgctggtgga agacgccctg     1740
aaggagaagg gaggcggctg cgacgtgccc ctgggcaagg agtactacaa gatcgtgtcc     1800
ctggacaagt atgacaagga aaataagacc ctgtgcgaga ccctggcaat ggatagactg     1860
tgcctgatga tggcccggca gtattacctg agcctgaacg ccaagctggc ccaggaggcc     1920
cagcagatca atggaagaa ggaggatagc attgagctga tcatcttcac actgaagaat      1980
cctgaccagt ccaagcagag cttctccatc cggttcagcg tgcgggactt caccaagctg     2040
tacgtgaccg acgaccccga attcctggcc cggctgtgca gctacttctt ccccgtggag     2100
aaggagatcg aataccacaa gctgtactct gaaggcatta acaagtacac caacctgcag     2160
aaggagggga tcgaagccat cctggagctg gagaagaagc tgatcgaaag aaaccggatc     2220
cagtccgcca gaactacct gagctttaac gaaatcatga acaagagcgg ctacaacaag      2280
gatgagcagg atgacctgaa gaaggtgagg aactccctgc tgcactacaa gctgatcttc     2340
gaaaaggagc acctgaagaa gttctatgaa gtgatgcggg gcgagggaat cgagaagaag     2400
tggtccctga tcgtgtaa                                                    2418
```

<210> SEQ ID NO 24
<211> LENGTH: 2373
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atgaatggca tcgagctgaa gaaggaagaa gccgccttct acttcaatca ggccgagctg      60
```

```
aacctgaagg ccattgagga caacatcttc gacaaggaga gacggaagac actgctgaac      120
aaccccccaga tcctggccaa gatggagaac tttatcttca atttccggga cgtgaccaag     180
aacgccaagg gcgaaatcga ctgcctgctg ctgaagctga gagagctgcg gaactttttac    240
agccactacg tgcacaagcg ggacgtcaga gaactgagca agggcgagaa gccgatcctg     300
gagaagtact accagttcgc catcgaatcc accggctctg agaacgtgaa gctcgaaatc     360
atcgaaaacg acgcctggct ggccgacgcc ggcgtgctgt cttcctgtg catcttcctg      420
aagaagagcc aggcaaacaa gctgatcagc ggcatcagcg gcttcaagag aaacgacgac    480
accggccagc ctcggagaaa cctgttcacc tacttctcca tccgggaggg ctacaaggtg    540
gtgcccgaaa tgcagaagca cttcctgctg ttctccctgg tgaaccacct gagcaaccag    600
gacgattata tcgaaaaggc ccaccagccc tacgacatcg gcgagggcct cttcttccac    660
cggattgcca gcaccttcct gaacatctcc ggaatcctga aaacatgaa gttctacacc     720
tatcagagca agagactggt ggagcagaga ggcgagctga gcgggaaaa ggacatcttc      780
gcctgggaag aaccgtttca gggcaattcc tactttgaga tcaacggcca agggcgtg      840
attggcgaag acgagctgaa ggagctgtgc tacgccttcc tgatcggcaa ccaggacgcc   900
aacaaggtgg agggccggat cacccagttc ctggagaagt tcagaaacgc caacagcgtg   960
cagcaggtga aggacgacga gatgctgaag cctgaatatt tcccccgccaa ctactttgcc   1020
gagagcggcg tgggccggat caaggaccgg gtgctgaaca gactgaacaa ggccatcaag   1080
agcaacaagg ccaagaaggg cgagatcatc gcctatgaca agatgagaga agtgatggct   1140
ttcatcaata actctctgcc cgtggacgag aagctgaagc caaggatta caagagatac   1200
ctgggcatgg tgagattctg ggatagagaa aaggacaata tcaagcgcga gttcgaaacg   1260
aaggagtgga gcaagtatct gccctccaac ttctggaccg ccaagaacct ggagagagtg   1320
tacggactgg cccgggaaaa gaacgcagag ctgtttaaca agctgaaggc cgacgtggag   1380
aagatggacg aaagagagct ggaaaagtat cagaagatca cgacgccaa ggatctggcc   1440
aacctgcggc ggctggccag cgacttcgga gtgaagtggg aggagaagga ttgggacgag   1500
tactccggcc agatcaagaa gcagatcaca gattcccaga agctgaccat catgaagcag   1560
agaatcacag ccggcctgaa gaagaagcac ggcatcgaaa acctgaacct gaggatcacc   1620
atcgacatca caagtccag aaaggccgtg ctgaatcgga tcgccatccc cagaggattt   1680
gtgaagcggc acatcctggg ctggcaggaa tccgagaagg tgagcaagaa gatcagagaa   1740
gccgaatgcg agattctgct gagcaaggag tacgaggagc tgagcaagca gttctttcag   1800
agcaaggact acgacaagat gacccgcatc aacggcctgt acgagaagaa taagctgatc   1860
gccctgatgg ccgtgtatct gatggggcag ctgagaatcc tgttcaagga gcacaccaag   1920
ctggacgaca tcaccaagac caccgtggat ttcaagatca gcgacaaggt gaccgtgaag   1980
atccccttct ccaactatcc ctccctggtg tacaccatga gcagcaagta cgtggacaat   2040
atcggcaact acgcttcag caacaaggac aaggataagc ccattctggg caagatcgac   2100
gtgatcgaga agcagcggat ggagtttatc aaggaggtgc tgggattcga agtacctg     2160
tttgacgata agatcatcga caagagcaag ttcgccgaca ccgccaccca catcagcttt   2220
gccgaaatcg tggaagaact ggtggagaag ggctgggaca aggaccggct gacgaagctg   2280
aaggatgccc ggaacaaggc cctgcacggc gagatcctga ccggcaccag cttcgacgag   2340
acaaagtccc tgatcaacga gctgaagaag taa                                  2373
```

<210> SEQ ID NO 25
<211> LENGTH: 2379
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human codon-optimized coding sequences

<400> SEQUENCE: 25

```
atgagccctg atttcatcaa gctggagaag caggaagcag ccttctactt taaccagacc      60
gagctgaacc tgaaggccat cgaatccaat atcctggata gcagcagag aatgatcctg      120
ctgaacaacc ccagaatcct ggccaaggtg gcaacttca tcttcaattt ccgggacgtg      180
accaagaacg caaagggcga aatcgactgc ctgctgttca gctggagga actgcggaac      240
ttctacagcc actacgtgca caccgataac gtgaaggaac tgtccaacgg agagaagcct      300
ctgctggagc ggtactacca gatcgccatc caggccacaa gaagcgagga cgtgaagttc      360
gagctgttcg agaccaggaa cgagaacaag atcaccgacg caggcgtgct gttcttcctg      420
tgcatgttcc tgaagaagag ccaggctaat aagctgattt ccggcatcag cggcttcaag      480
cggaacgacc ccaccggcca gcccagacgg aacctcttta cctacttctc tgcccgggag      540
ggctacaagg ccctgcctga catgcagaag cacttcctgc tgttcaccct ggtgaactac      600
ctgagcaacc aggacgagta catctccgag ctgaagcagt acggagagat cggacaggga      660
gccttcttca cagaatcgc cagcaccttc ctgaacatca gcggcatcag cggcaacacc      720
aagttctaca gctaccagag caagagaatc aaggagcagc ggggcgaact gaacagcgaa      780
aaggacagct tcgagtggat cgagcccttt cagggcaact cttatttga tcaacggc       840
cacaaggcgc tgatcggcga agacgagctg aaggagctgt gctacgccct gctggtggcc      900
aagcaggaca tcaatgccgt ggagggaaag atcatgcagt cctgaagaa gttcaggaac      960
accggcaacc tgcagcaggt gaaggacgac gagatgctgg aaatcgagta ctttcccgcc      1020
agctacttca cgagagcaa gaaggaggac atcaagaagg atcctggg cagactggac      1080
aagaagatcc ggtcctgcag cgccaaggcc gagaaggcct acgacaagat gaaggaggtg      1140
atggagttta caataacag cctgcccgcc gaggagaagc tgaagaggaa ggactaccgc      1200
agatacctga gatggtgag attctggtcc agagaaaagg gcaacatcga gagagagttc      1260
agaaccaagg agtggtccaa gtacttcagc agcgacttct ggagaaagaa caatctggag      1320
gatgtgtaca gctgccacc ccagaagaac gccgagctgt tcaagaatct gaaggccgcc      1380
gccgagaaga tgggcgaaac agaattcgaa agtaccagc agatcaacga tgtgaaggac      1440
ctggccagcc tgagacggct gacccaggat ttcggcctga gtgggagga aggattgg       1500
gaggagtaca gcgaacagat caagaagcag atcaccgacc ggcagaagct gacaatcatg      1560
aagcagcggg tgaccgccga gctgaagaag aagcacggca tcgagaatct gaacctcaga      1620
attaccatcg attccaacaa gagcagaaag gccgtgctga cagaatcgc cattccccgg      1680
ggcttcgtga agaagcacat tctgggctgg caggcagcg aaaagatcag caagaatatc      1740
cgggaggccg agtgcaagat cctgctgtcc aagaagtatg aggagctgtc tcggcagttc      1800
tttgaggctg gcaacttcga caagctgacc cagatcaacg gcctgtacga aaagaataag      1860
ctgaccgcct tcatgtccgt ctacctgatg ggcagactga catccagct gaacaagcac      1920
acggagctgg aaatctgaa gagaccgag gtggacttca gatttccga caggtgaca       1980
gaaaagatcc ccttctccca gtaccctagc ctggtgtacg ctatgagccg gaagtacgtg      2040
```

| | |
|---|---|
| gacaacgtgg acaagtacaa gttcagccac caggacaaga agaagcccct cctgggcaag | 2100 |
| atcgacagca tcgaaaagga gagaatcgaa ttcatcaagg aggtgctgga cttcgaagag | 2160 |
| tacctgttta agaacaaggt gatcgacaag agcaagttca gcgataccgc cacccatatc | 2220 |
| tctttcaagg aaatctgcga cgagatgggc aagaagggct gcaaccgcaa caagctgacc | 2280 |
| gagctgaata cgctagaaa cgccgcactg cacggagaaa tccccagcga ccagcttc | 2340 |
| cgggaggcca agcccctgat caacgaactg aagaagtaa | 2379 |

<210> SEQ ID NO 26
<211> LENGTH: 2379
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human codon-optimized coding sequences

<400> SEQUENCE: 26

| | |
|---|---|
| atgagccctg acttcatcaa gctggaaaag caggaagccg ccttctactt taatcagacc | 60 |
| gagctgaacc tgaaggccat cgagagcaac atcttcgaca agcagcagcg ggtgatcctg | 120 |
| ctgaataacc cccagatcct ggccaaggtg ggcgacttca tcttcaactt ccgggacgtg | 180 |
| accaagaacg ccaagggaga atcgactgc ctgctgctga agctgcggga gctgagaaac | 240 |
| ttctacagcc actatgtgta caccgacgac gtgaagatcc tgagcaacgg cgagaggccc | 300 |
| ctgctggaga gtactacca gtttgccatc gaggccaccg atctgagaa tgtgaagctg | 360 |
| gagatcatcg agagcaacaa ccggctgacc gaagcgggcg tgctgttctt cctgtgcatg | 420 |
| ttcctgaaga gagccaggc caacaagctg atttccggca tctccggatt caagcgcaac | 480 |
| gaccctaccg acagcctcg gcggaacctg ttcacctact ttagcgtgcg ggagggctac | 540 |
| aaggtggtgc ccgacatgca gaagcacttc ctgctgttcg tgctggtgaa ccacctgtcc | 600 |
| ggccaggatg actatattga aaggcccag aagccctacg acatcggcga aggcctgttc | 660 |
| ttccacagaa tcgccagcac ctttctcaac atcagcggca tcctgagaaa catggaattc | 720 |
| tacatctacc agagcaagcg gctgaaggag cagcaggag agctgaagag agagaaggac | 780 |
| atcttccctt ggatcgagcc tttccagggc aacagctact tgagatcaa cggaaacaag | 840 |
| ggcatcatcg gcgaggacga actgaaggaa ctgtgctacg ccctgctggt ggccggcaag | 900 |
| gacgtgagag ccgtggaagg aaagatcacc cagttcctgg agaagttcaa gaacgccgat | 960 |
| aacgcccagc aggtggagaa ggatgaaatg ctggaccgga caacttccc tgccaattac | 1020 |
| tttgccgaaa gcaacatcgg cagcatcaag gaaaagatcc tgaatagact gggcaagacc | 1080 |
| gacgactcct acaacaagac cggcaccaag atcaagccct acgacatgat gaaggaggtg | 1140 |
| atggagttca tcaataattc tctgcccgcc gatgagaagc tgaagcggaa ggactaccgg | 1200 |
| agatacctga gatggtccg gatctgggac agcgaaaagg acaatatcaa gcgggagttt | 1260 |
| gagagcaagg aatggagcaa gtatttcagc agcgacttct ggatggccaa gaacctggaa | 1320 |
| agagtgtacg gcctggccag ggaaaagaac gccgagctgt taacaagct gaaggccgtg | 1380 |
| gtggagaaga tggacgagcg ggagttcgaa aagtaccggc tgatcaacag cgccgaagac | 1440 |
| ctggccagcc tgcggagact ggccaaggac ttcggcctga gtgggagga aggactgg | 1500 |
| caggagtatt ctggccagat caagaagcag atctccgaca cagaagct gacaattatg | 1560 |
| aagcagcgga tcacagccga actgaagaag aagcacggaa tcgagaacct gaatctgcgg | 1620 |

```
atcaccatcg acagcaacaa gtccagaaag gccgtgctga accgatcgc cgtgccccgg    1680 ggcttcgtga aggaacacat cctgggctgg caaggctctg aaaaggtgag caagaagacc    1740
agagaagcca agtgcaagat cctgctgagc aaggagtacg aggaactgag caagcagttc    1800
tttcagacac ggaattacga caagatgacc caggtgaacg gcctgtacga agaacaag     1860 ctgctggcct tcatggtggt gtacctgatg gagagactga acatcctgct gaacaagccc    1920
acagagctga cgaactgga aaaggccgaa gtggacttca gatctccga caaggtgatg    1980 gccaagatcc ctttctctca gtaccccagc ctggtgtatg caatgagctc caagtacgcc    2040
gacagcgtgg gctcttacaa gttcgaaaac gacgagaaga caagcccctt tctgggcaag    2100
atcgacacaa tcgagaagca gagaatggag ttcatcaagg aggtgctggg cttcgaggaa    2160
tacctgttcg agaagaagat catcgataag agcgaattcg ccgacaccgc cacccacatc    2220
agcttcgacg agatctgcaa cgagctgatc aagaagggct gggacaagga caagctgacc    2280
aagctgaagg acgcccggaa cgccgccctg cacggcgaga tccccgccga gaccagcttc    2340
cgggaggcca agcccctgat aacggcctg aagaagtaa                              2379

<210> SEQ ID NO 27
<211> LENGTH: 2400
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human codon-optimized coding sequences

<400> SEQUENCE: 27
atgaacatca tcaagctgaa gaaggaggaa gccgccttt actttaaccca gacaatcctg      60 aatctgagcg gcctggacga gatcatcgag aagcagatcc cccacatcat ctccaataag     120
gaaaacgcca agaaggtgat tgataagatc ttcaataaca gactgctgct gaagagcgtg    180
gaaaactata tctacaactt caaggacgtg gccaagaacg cccggaccga aatcgaagcc    240
atcctgctga gctggtgga gctgagaaac ttctactccc actacgtgca caacgacacc     300
gtgaagatcc tgtccaatgg cgagaagccc atcctggaaa agtactacca gatcgccatc    360
gaagccaccg gctctaagaa cgtgaagctg gtcattatcg aaaacaacaa ctgcctgacc    420
gactccggcg tgctgttcct gctgtgcatg ttcctgaaga gagccaggc caacaagctg    480 attagcagcg tgagcggctt taagcggaac gacaaggaag ccagcccag aaggaacctc     540 tttacttact atagcgtgag ggaaggctac aaggtggtgc agacatgca gaagcacttc    600 ctgctgttcg ccctggtcaa ccacctgtcc gagcaggacg accacatcga gaagcagcag    660
cagagcgacg agctgggcaa gggcctgttc ttccacagaa tcgccagcac attcctgaat    720
gaaagcggca tcttcaacaa gatgcagttt tacacctacc agagcaatcg gctgaaggag    780
aagcggggcg agctgaagca cgagaaggac acccttcacct ggatcgagcc tttccaggga    840
aacagctact tcaccctgaa cgggcacaag ggcgtgatca gcgaggatca gctgaaggaa    900
ctgtgctaca atcctgat cgagaagcag aacgtggaca gcctggaggg caagatcatt    960
cagttcctga agaagtttca gaacgtgtct agcaagcagc aggtggatga ggacgagctg    1020
ctgaagcggg aatacttccc cgccaactac ttcggccggg ccggcaccgg caccctgaag    1080
gagaagatct gaaccggct ggacaagcgg atggaccca ccagcaaggt gaccgacaag    1140
gcctatgaca agatgatcga ggtgatggag ttcatcaaca tgtgcctgcc cagcgacgag    1200
```

```
aagctgcggc agaaggatta ccggagatat ctgaagatgg tcagattctg gaacaaggag      1260
aagcacaaca tcaagagaga attcgacagc aagaagtgga ccagattcct gcccaccgag      1320
ctgtggaata agcggaacct ggaggaagcc taccagctgg cccggaagga aacaagaag       1380 aagctggaga catgaggaa tcaggtgagg agcctgaagg agaacgacct ggagaagtac       1440
cagcagatca actatgtgaa cgacctggaa aacctgcggc tgctgtccca gagctgggc      1500 gtgaagtggc aggagaagga ctgggtgaa tacagcggcc agatcaagaa gcagatcagc       1560
gataaccaga agctgacaat catgaagcag agaatcaccg ccgagctgaa gaagatgcac      1620
ggcatcgaga acctgaacct gagaatcagc atcgacacca caagtcccg gcagactgtg      1680 atgaacagaa ttgccctgcc caagggcttc gtgaagaacc acattcagca gaacagcagc     1740
gagaagatca gcaagagaat cagagaggac tactgcaaga tcgagctgtc cggcaagtac     1800
gaagagctga gcagacagtt tttcgacaag aagaactttg acaagatgac cctgatcaac     1860
ggactgtgcg agaagaataa gctcatcgcc ttcatggtga tttacctgct ggagcggctg     1920
ggcttcgagc tgaaggagaa gaccaagctg ggcgagctga gcagacccg gatgacatat      1980 aagatcagcg acaaggtgaa ggaggacatc cccctctcct actacccaa gctggtgtac      2040 gccatgaatc ggaagtatgt ggacaacatc gatagctacg ccttcgccgc ctacgagtct     2100
aagaaggcca tcctggacaa ggtggacatc attgagaagc agagaatgga attcatcaag     2160
caggtgctgt gcttcgagga atacatcttc gagaacagaa tcatcgagaa gagcaagttc     2220
aacgatgagg agacccacat cagcttcacc cagatccacg acgaactgat caagaagggc     2280
agagataccg aaaagctgag caagctgaag cacgccagaa acaaggccct gcacggcgag     2340
atccccgacg ggaccagctt tgagaaggcc aagctgctga tcaacgaaat caagaagtaa     2400
```

<210> SEQ ID NO 28
<211> LENGTH: 2412
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Human codon-optimized coding sequences

<400> SEQUENCE: 28

```
atgaacgcca tcgagctgaa gaaggaagag gccgccttct acttcaacca ggccagactg       60
aacatctctg gcctggacga aatcatcgag aagcaactgc acacatcgg ctctaacaga      120 gagaacgcca agaagactgt ggacatgatc ctggataacc ccgaggtgct gaagaagatg      180
gaaaactacg tgttcaactc ccgcgatatt gccaagaatg cccggggcga gctggaggcc      240
ctgctgctga gctggtcga gctgagaaac ttctatagcc actacgtgca aaggacgac       300 gtcaagacac tgagctacgg tgagaagcct ctgctggata agtactacga gatcgccatc      360
gaagccaccg gatccaagga cgtgcggctg gagatcattg acgacaagaa taagctgacc      420
gacgccggag tgctgttcct gctgtgcatg ttcctgaaga gagcgaggc taacaagctg      480 atttccagca tccggggctt caagaggaac gacaaggagg ccagcctag aagaaacctg      540 ttcacctact acagcgtgag agagggctat aaggtggtgc ccgacatgca gaagcacttt      600
ctgctgttca ccctggtgaa ccacctgtcc aatcaggacg agtacatctc caacctgcgc      660
ccaaaccagg aaatcggcca gggcggattt ttccaccgga tcgccagcaa gttcctgagc      720
gacagcggaa tcctgcacag catgaagttc tacacataca gatccaagcg gctgaccgag      780
```

```
cagcggggag agctgaagcc caagaaggac cactttacat ggatcgagcc tttccagggc    840
aattcctact tcagcgtgca gggccagaag ggcgtgatcg gagaggagca gctcaaggag    900
ctgtgctacg tgctgctggt ggcccgggag gacttcagag ccgtggaggg caaggtgacc    960
cagttcctga agaagttcca gaatgccaat aacgtgcagc aggtggagaa ggacgaggtg   1020
ctggaaaagg agtactttcc cgccaactac tttgagaacc gggacgtggg aagagtcaag   1080
gacaagatcc tgaacagact gaagaagatc accgagagtt ataaggccaa gggtagagag   1140
gtgaaggcct acgacaagat gaaggaagtg atggagttca tcaacaactg cctgcccacc   1200
gatgaaaacc tgaagctgaa ggactaccgg cggtacctga gatggtgag attctggggc    1260 agagagaagg aaaacatcaa gcgggagttc gactccaaga agtgggagcg ctttctcccc   1320
cgggagctgt ggcagaagag aaacctggag gacgcctacc agctcgccaa ggagaagaac   1380
acagagctgt tcaacaagct gaagaccacc gtggagagaa tgaacgaact ggagttcgag   1440
aagtaccagc agatcaatga cgccaaggac ctggccaacc tgagacagct ggccagagac   1500 tttgagtga agtgggagga aaaggactgg caggaatact ctggacagat caagaagcag   1560
atcaccgacc ggcagaagct gaccatcatg aagcagcgga tcaccgccgc cctgaagaag   1620
aagcagggaa tcgaaaacct gaacctgaga atcacaacag atacgaataa gagcaggaag   1680
gtggtgctga accggatcgc actgcccaag ggattcgtca gaaagcacat cctgaagacc   1740
gacatcaaga tcagcaagca gatccggcag agccagtgcc ctatcatcct gtctaacaac   1800
tacatgaagc tggccaagga gttctttgaa gagcggaact tcgataagat gacccagatc   1860
aatggcctgt tcgagaagaa cgtgctgatc gccttcatga tcgtgtacct gatggagcag   1920
ctgaacctga gactgggcaa gaacaccgag ctgtccaacc tgaagaagac cgaggtgaac   1980
tttaccatca ccgacaaggt gaccgagaag gtgcaaatct cccagtaccc cagcctggtg   2040
ttcgccatta accgggagta cgtggacggc atcagcggct acaagctgcc ccccaagaag   2100
cccaaggaac ctccctacac cttcttcgaa aagatcgacg ccatcgaaaa ggagcggatg   2160
gaattcatca gcaggtgct gggcttcgag gagcacctct tcgaaaagaa cgtgatcgac   2220
aagacccggt ttaccgacac cgccacccac atcagcttca tgagatctg cgatgagctg   2280 atcaagaagg ctgggacga aaacaagatc atcaagctga aggatgcacg gaacgctgcc   2340
ctgcacggca gatccctga agatacctcc tttgacgaag ccaaggtgct gatcaacgaa   2400
ctgaagaagt aa                                                       2412
```

<210> SEQ ID NO 29
<211> LENGTH: 102
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: gRNA

<400> SEQUENCE: 29

```
gctggagcag cccccgattt gtggggtgat tacagcggtc ttcgatattc aagcgtcgga    60
agacctgctg gagcagcccc cgatttgtgg ggtgattaca gc                      102
```

<210> SEQ ID NO 30
<211> LENGTH: 711
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: GFP reporter genes

<400> SEQUENCE: 30
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg cccctgccc      180 ttcgcctggg acatcctgtc ccctcagttc atgtacggct ccaaggccta cgtgaagcac     240
cccgccgaca tccccgacta cttgaagctg tccttcccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tccctccga cggccccgta     420 atgcagaaga gaccatggg ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg ccgccactc caccggcggc atggacgagc tgtacaagta a              711

<210> SEQ ID NO 31
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: mCherry reporter genes

<400> SEQUENCE: 31
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtga     720

<210> SEQ ID NO 32
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SgRNA
```

```
<400> SEQUENCE: 32
gctggagcag cccccgattt gtggggtgat tacagcggtc ttcgatattc aagcgtcgga    60
agacct                                                                66

<210> SEQ ID NO 33
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SgRNA

<400> SEQUENCE: 33
ggtcttcgat attcaagcgt cggaagacct gctggagcag cccccgattt gtggggtgat    60
tacagc                                                                66

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SgRNA

<400> SEQUENCE: 34
ttggtgccgc gcagcttcac                                                 20

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SgRNA

<400> SEQUENCE: 35
ttggtgccgc gcagcttcac cttgt                                           25

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SgRNA

<400> SEQUENCE: 36
ttggtgccgc gcagcttcac cttgtagatg                                      30

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SgRNA
```

```
<400> SEQUENCE: 37
ttggtgccgc gcagcttcac cttgtagatg aactc                              35

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttggtgccgc gcagcttcac cttgtagatg aactcgccgt                         40

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SgRNA

<400> SEQUENCE: 39
ttggtgccgc gcagcttcac cttgtagatg aactcgccgt cctgc                   45

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SgRNA

<400> SEQUENCE: 40
ttggtgccgc gcagcttcac cttgtagatg aactcgccgt cctgcaggga              50

<210> SEQ ID NO 41
<211> LENGTH: 3615
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: dCas13e.1-ADAR2DD

<400> SEQUENCE: 41
atgcccaaga agaagcggaa ggtggcccag gtgagcaagc agacctccaa gaagagggag    60
ctgagcatcg acgagtacca gggcgcccgg aagtggtgct tcaccattgc cttcaacaag   120
gccctggtga accgggacaa gaacgacggc ctgttcgtgg aaagcctgct gagacacgag   180
aagtacagca agcacgactg gtacgacgaa gatacccggg ccctgatcaa gtgcagcacc   240
caggccgcca cgccaaggc tgaagccctg gcgaactact tcagtgctta ccggcatagc   300
cctggctgcc tgaccttcac cgccgaggac gaactgcgga ccatcatgga gagagcctat   360
gagcgggcca tcttcgagtg cagaagaaga gagacagagg tgatcatcga gtttcccagc   420
ctgttcgagg gcgaccggat caccaccgcc ggcgtggtgt ttttcgtgag cttttttcgtg   480 gaaagaagag tgctggatcg gctgtatgga gccgtgtccg gcctgaagaa gaatgaggga   540
```

```
cagtacaagc tgacccggaa ggccctgagc atgtactgcc tgaaggacag cagattcacc    600
aaggcctggg ataagcgggt gctgctgttc agagacatcc tggcccagct gggaagaatc    660
cccgccgagg cctacgagta ctaccacggc gagcagggtg ataagaagag agctaacgac    720
aatgagggca caaatcccaa gcggcacaag gacaagttca tcgaatttgc actgcactac    780
ctggaagccc agcacagcga gatctgcttc ggcagacgcc acatcgtgcg ggaagaggcc    840
ggcgccggcg atgagcacaa gaagcaccgg accaagggaa aggtggtggt ggacttcagc    900
aagaaggacg aggaccagag ctactatatc tccaagaaca acgtgatcgt gcggatcgac    960
aagaacgccg ccctagaag ctaccggatg ggcctgaacg agctgaagta cctcgtgctg   1020
ctgagcctgc aggggaaggg cgacgatgcc atcgccaagc tgtacagata cagacagcac   1080
gtggagaaca tcctggatgt ggtgaaggtg accgataagg ataaccacgt gttcctgccc   1140
cgcttcgtgc tggagcagca cggcatcggc agaaaggcct tcaagcagcg gatcgatgga   1200
cgggtgaagc acgtgcgggg cgtgtgggag aagaagaagg ccgccaccaa tgaaatgacc   1260
ctgcacgaga aggccagaga catcctgcag tacgtgaacg aaaactgcac ccggtccttc   1320
aaccctggcg aatacaacag actgctggtg tgcctggtgg gcaaggacgt ggagaacttt   1380
caggccggcc tgaagcggct gcagctggcc gaaaggatcg atggccgggt gtactccatc   1440
ttcgcccaga ccagcaccat caatgagatg caccaggtgg tgtgcgacca gatcctgaac   1500
cggctgtgca gaatcggcga ccagaagctg tacgattacg tgggactggg caagaaggac   1560
gaaatcgact acaagcagaa ggtggcctgg ttcaaggagc acatcagcat ccggagagga   1620
ttcctgagaa agaagttctg gtacgatagc aagaagggat tcaaagct ggtggaggaa   1680 cacctggagt ccggcggcgg ccagcgcgac gtgggcctgg acaagaagta ctaccacatc   1740
gacgccatcg gcagattcga gggcgccaac cccgccctgt acgagaccct ggccagagat   1800
cggctgtgcc tcatgatggc ccagtacttc ctgggcagcg tgagaagga actgggcaac   1860 aagattgtgt ggagcaacga cagcatcgaa ctgcctgtgg aaggctctgt gggaaatgag   1920
aagagcatcg tgttctccgt gtctgactac ggcaagctgt acgtgctgga cgatgccgaa   1980
ttcctgggcc ggatctgcga atacttcatg ccccacgaaa agggcaagat ccggtaccac   2040
acagtgtacg aaaagggctt tagagcatac aacgacctgc agaagaagtg cgtggaggcc   2100
gtgctggctt tcgaagagaa ggtggtgaag gccaagaaga tgagcgagaa ggaaggcgcc   2160
cactacatcg acttccggga gatcctggcc cagaccatgt gcaaggaggc cgagaagacc   2220
gcagtgaaca aggtggcggc tgccttcttc gctgcgcacc tgaagttcgt gattgacgag   2280
ttcggcctgt tcagcgacgt gatgaagaag tacggcatcg agaaggaatg gaagttccct   2340
gtcaagccca agaagaagcg gaaggtgggt ggaggcggag gttctggggg aggaggtagt   2400
ggcggtggtg gttcaggagg cggcggaagc cagctgcatt taccgcaggt tttagctgac   2460
gctgtctcac gcctggtcct gggtaagttt ggtgacctga ccgacaactt ctcctcccct   2520
cacgctcgca gaaaagtgct ggctggagtc gtcatgacaa caggcacaga tgttaaagat   2580
gccaaggtga taagtgtttc tacaggaggc aaatgtatta atggtgaata catgagtgat   2640 cgtgccttg cattaaatga ctgccatgca gaaataatat ctcggagatc cttgctcaga   2700
tttctttata cacaacttga gctttactta aataacaaag atgatcaaaa aagatccatc   2760
tttcagaaat cagagcgagg ggggtttagg ctgaaggaga atgtccagtt tcatctgtac   2820
atcagcacct ctccctgtgg agatgccaga atcttctcac cacatgagcc aatcctggaa   2880
gaaccagcag atagacaccc aaatcgtaaa gcaagaggac agctacggac caaaatagag   2940
```

```
tctggtcagg ggacgattcc agtgcgctcc aatgcgagca tccaaacgtg ggacggggtg    3000
ctgcaagggg agcggctgct caccatgtcc tgcagtgaca agattgcacg ctggaacgtg    3060
gtgggcatcc agggatcact gctcagcatt ttcgtggagc ccatttactt ctcgagcatc    3120
atcctgggca gcctttacca cggggaccac ctttccaggg ccatgtacca gcggatctcc    3180
aacatagagg acctgccacc tctctacacc ctcaacaagc ctttgctcag tggcatcagc    3240
aatgcagaag cacggcagcc agggaaggcc cccaacttca gtgtcaactg gacggtaggc    3300
gactccgcta ttgaggtcat caacgccacg actgggaagg atgagctggg ccgcgcgtcc    3360
cgcctgtgta agcacgcgtt gtactgtcgc tggatgcgtg tgcacggcaa ggttccctcc    3420
cacttactac gctccaagat taccaagccc aacgtgtacc atgagtccaa gctggcggca    3480
aaggagtacc aggccgccaa ggcgcgtctg ttcacagcct tcatcaaggc ggggctgggg    3540
gcctgggtgg agaagcccac cgagcaggac cagttctcac tcacgtaccc atacgacgta    3600
ccagattacg cttaa                                                     3615
```

<210> SEQ ID NO 42
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: mutated mCherry

<400> SEQUENCE: 42

```
atggtgagca agggcgagga ggataacatg gccatcatca aggagttcat gcgcttcaag     60
gtgcacatgg agggctccgt gaacggccac gagttcgaga tcgagggcga gggcgagggc    120
cgcccctacg agggcaccca gaccgccaag ctgaaggtga ccaagggtgg ccccctgccc    180
ttcgcctggg acatcctgtc ccctcagttc atgtacggct ccaaggccta cgtgaagcac    240
cccgccgaca tccccgacta cttgaagctg tccttccccg agggcttcaa gtaggagcgc    300
gtgatgaact tcgaggacgg cggcgtggtg accgtgaccc aggactcctc cctgcaggac    360
ggcgagttca tctacaaggt gaagctgcgc ggcaccaact tcccctccga cggccccgta    420
atgcagaaga gaccatgggc ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg ccgccactc caccggcggc atggacgagc tgtacaagta a              711
```

<210> SEQ ID NO 43
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gRNA

<400> SEQUENCE: 43

```
caagtagtcg gggatgtcgg cggggtgctt cacctaggcc ttggagccgt gctggagcag     60
cccccgattt gtggggtgat tacagc                                          86
```

<210> SEQ ID NO 44
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: gRNA

<400> SEQUENCE: 44
cggggatgtc ggcggggtgc ttcacctagg ccttggagcc gtacatgaac gctggagcag    60
cccccgattt gtggggtgat tacagc                                         86

<210> SEQ ID NO 45
<211> LENGTH: 3312
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
atgcccaaga agaagcggaa ggtggtcgac aacatccccg ctctggtgga aaaccagaag    60
aagtactttg gcacctacag cgtgatggcc atgctgaacg ctcagaccgt gctggaccac   120
atccagaagg tggccgatat tgagggcgag cagaacgaga caacgagaa tctgtggttt    180 caccccgtga tgagccacct gtacaacgcc aagaacggct acgacaagca gcccgagaaa   240
accatgttca tcatcgagcg gctgcagagc tacttcccat tcctgaagat catggccgag   300
aaccagagag agtacagcaa cggcaagtac aagcagaacc gcgtggaagt gaacagcaac   360
gacatcttcg aggtgctgaa gcgcgccttc ggcgtgctga gatgtacag ggacctgacc    420 aaccactaca gacctacga ggaaaagctg aacgacggct gcgagttcct gaccagcaca   480
gagcaacctc tgagcggcat gatcaacaac tactacacag tggccctgcg gaacatgaac   540
gagagatacg gctacaagac agaggacctg gccttcatcc aggacaagcg gttcaagttc   600
gtgaaggacg cctacggcaa gaaaaagtcc aagtgaata ccggattctt cctgagcctg    660
caggactaca acggcgacac acagaagaag ctgcacctga gcggagtggg aatcgccctg   720
ctgatctgcc tgttcctgga caagcagtac atcaacatct ttctgagcag gctgcccatc   780
ttctccagct acaatgccca gagcgaggaa cggcggatca tcatcagatc cttcggcatc   840
aacagcatca gctgcccaa ggaccggatc cacagcgaga gtccaacaa gagcgtggcc    900 atggatatgc tcaacgaagt gaagcggtgc cccgacgagc tgttcacaac actgtctgcc   960
gagaagcagt cccggttcag aatcatcagc gacgaccaca tgaagtgct gatgaagcgg   1020 agcagcgaca gattcgtgcc tctgctgctg cagtatatcg attacggcaa gctgttcgac  1080
cacatcaggt tccacgtgaa catgggcaag ctgagatacc tgctgaaggc cgacaagacc  1140
tgcatcgacg ccagaccag agtcagagtg atcgagcagc ccctgaacgg cttcggcaga  1200
ctggaagagg ccgagacaat gcggaagcaa gagaacggca ccttcggcaa cagcggcatc  1260
cggatcagag acttcgagaa catgaagcgg gacgacgcca tcctgccaa ctatccctac  1320 atcgtggaca cctacacaca ctacatcctg gaaaacaaca ggtcgagat gtttatcaac  1380 gacaaagagg acagcgcccc actgctgccc gtgatcgagg atgatagata cgtggtcaag  1440
acaatcccca gctgccggat gagcacccctg gaaattccag ccatggcctt ccacatgttt  1500
ctgttcggca gcaagaaaac cgagaagctg atcgtggacg tgcacaaccg gtacaagaga  1560

| | |
|---|---|
| ctgttccagg ccatgcagaa agaagaagtg accgccgaga atatcgccag cttcggaatc | 1620 |
| gccgagagcg acctgcctca gaagatcctg gatctgatca gcggcaatgc ccacggcaag | 1680 |
| gatgtggacg ccttcatcag actgaccgtg gacgacatgc tgaccgacac cgagcggaga | 1740 |
| atcaagagat tcaaggacga ccggaagtcc attcggagcg ccgacaacaa gatgggaaag | 1800 |
| agaggcttca agcagatctc cacaggcaag ctggccgact tcctggccaa ggacatcgtg | 1860 |
| ctgtttcagc ccagcgtgaa cgatggcgag aacaagatca ccggcctgaa ctaccggatc | 1920 |
| atgcagagcg ccattgccgt gtacgatagc ggcgacgatt acgaggccaa gcagcagttc | 1980 |
| aagctgatgt tcgagaaggc ccggctgatc ggcaagggca acacagagcc tcatccattt | 2040 |
| ctgtacaagg tgttcgcccg cagcatcccc gccaatgccg tcgagttcta cgagcgctac | 2100 |
| ctgatcgagc ggaagttcta cctgaccggc tgtccaacg agatcaagaa aggcaacaga | 2160 |
| gtggatgtgc ccttcatccg gcgggaccag aacaagtgga aacacccgc catgaaaacc | 2220 |
| ctgggcagaa tctacagcga ggatctgccc gtggaactgc ccagacagat gttcgacaat | 2280 |
| gagatcaagt cccacctgaa gtccctgcca cagatggaag gcatcgactt caacaatgcc | 2340 |
| aacgtgacct atctgatcgc cgagtacatg aagagagtgc tggacgacga cttccagacc | 2400 |
| ttctaccagt ggaaccgcaa ctaccggtac atggacatgc ttaagggcga gtacgacaga | 2460 |
| aagggctccc tgcagcactg cttcaccagc gtggaagaga gagaaggcct ctggaaagag | 2520 |
| cgggcctcca gaacagagcg gtacagaaag caggccagca acaagatccg cagcaaccgg | 2580 |
| cagatgagaa cgccagcag cgaagagatc gagacaatcc tggataagcg gctgagcaac | 2640 |
| agccggaacg agtaccagaa aagcgagaaa gtgatccggc gctacagagt gcaggatgcc | 2700 |
| ctgctgtttc tgctggccaa aaagaccctg accgaactgg ccgatttcga cggcgagagg | 2760 |
| ttcaaactga agaaatcat gcccgacgcc gagaagggaa tcctgagcga gatcatgccc | 2820 |
| atgagcttca ccttcgagaa aggcggcaag aagtacacca tcaccagcga gggcatgaag | 2880 |
| ctgaagaact acggcgactt ctttgtgctg gctagcgaca gaggatcgg caacctgctg | 2940 |
| gaactcgtgg gcagcgacat cgtgtccaaa gaggatatca tggaagagtt caacaaatac | 3000 |
| gaccagtgca ggcccgagat cagctccatc gtgttcaacc tggaaaagtg ggccttcgac | 3060 |
| acataccccg agctgtctgc cagagtggac cgggaagaga aggtggactt caagagcatc | 3120 |
| ctgaaaatcc tgctgaacaa caagaacatc aacaaagagc agagcgacat cctgcggaag | 3180 |
| atccggaacg ccttcgatca caacaattac cccgacaaag cgtggtgga aatcaaggcc | 3240 |
| ctgcctgaga tcgccatgag catcaagaag gcctttgggg agtacgccat catgaaggga | 3300 |
| tcccttcaat ga | 3312 |

<210> SEQ ID NO 46
<211> LENGTH: 2934
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

| | |
|---|---|
| atgcctaaaa agaaaagaaa ggtgggttct ggtatcgaga agaagaagag cttcgccaag | 60 |
| ggcatgggag tgaagagcac cctggtgtcc ggctctaagg tgtacatgac cacatttgct | 120 |
| gagggaagcg acgccaggct ggagaagatc gtggagggcg atagcatcag atccgtgaac | 180 |
| gagggagagg cttttcagcgc cgagatggct gacaagaacg ctggctacaa gatcggaaac | 240 |

```
gccaagttttt cccacccaaa gggctacgcc gtggtggcta acaacccact gtacaccgga    300
ccagtgcagc aggacatgct gggactgaag gagacactgg agaagaggta cttcggcgag    360
tccgccgacg gaaacgataa catctgcatc caggtcatcc acaacatcct ggatatcgag    420
aagatcctgg ctgagtacat cacaaacgcc gcttacgccg tgaacaacat ctccggcctg    480
gacaaggata tcatcggctt cggaaagttt tctaccgtgt acacatacga cgagttcaag    540
gatccagagc accaccgggc cgcttttaac aacaacgaca agctgatcaa cgccatcaag    600
gctcagtacg acgagttcga taactttctg gataacccca ggctgggcta cttcggacag    660
gctttctttt ctaaggaggg cagaaactac atcatcaact acggaaacga gtgttacgac    720
atcctggccc tgctgagcgg actgaggcac tgggtggtgc acaacaacga ggaggagtct    780
cggatcagcc gcacctggct gtacaacctg gacaagaacc tggataacga gtacatctcc    840
acactgaact acctgtacga caggatcacc aacgagctga caaacagctt ctccaagaac    900
tctgccgcta acgtgaacta catcgctgag accctgggca tcaacccagc tgagttcgct    960
gagcagtact tcagattttc catcatgaag gagcagaaga acctgggctt caacatcaca   1020
aagctgagag aagtgatgct ggacagaaag gatatgtccg agatcaggaa gaaccacaag   1080
gtgttcgatt ctatcagaac caaggtgtac acaatgatgg actttgtgat ctacaggtac   1140
tacatcgagg aggatgccaa ggtggccgct gccaacaaga gcctgcccga caacgagaag   1200
tctctgagcg agaaggatat cttcgtgatc aacctgagag gctcctttaa cgacgatcag   1260
aaggacgctc tgtactacga tgaggccaac aggatctgga gaaagctgga gaacatcatg   1320
cacaacatca aggagttccg gggaaacaag acccgcgagt acaagaagaa ggacgctcca   1380
aggctgccta ggatcctgcc tgctggaagg gacgtgagcg ccttcagcaa gctgatgtac   1440
gccctgacaa tgtttctgga cggaaaggag atcaacgatc tgctgaccac actgatcaac   1500
aagttcgaca catccagtc ttttctgaaa gtgatgcctc tgatcggcgt gaacgctaag   1560
ttcgtggagg agtacgcctt cttttaaggac agcgccaaga tcgctgatga gctgcggctg   1620
atcaagtcct tgccaggat gggagagcca atcgctgacg ctaggagagc tatgtacatc   1680
gatgccatcc ggatcctggg aaccaacctg tcttacgacg agctgaaggc tctggccgac   1740
accttcagcc tggatgagaa cggcaacaag ctgaagaagg gcaagcacgg aatgcgcaac   1800
ttcatcatca caacgtgat cagcaacaag cggtttcact acctgatcag atacggcgac   1860
ccagctcacc tgcacgagat cgctaagaac gaggccgtgg tgaagttcgt gctgggacgg   1920
atcgccgata tccagaagaa gcagggccag aacggaaaga accagatcga ccgctactac   1980
gagacctgca tcggcaagga taagggaaag tccgtgtctg agaaggtgga cgctctgacc   2040
aagatcatca caggcatgaa ctacgaccag ttcgataaga gagatctgt gatcgaggac   2100 accggaaggg agaacgccga gagagaagg tttaagaaga tcatcagcct gtacctgaca   2160
gtgatctacc acatcctgaa gaacatcgta aacatcaacg ctagatacgt gatcggcttc   2220
cactgcgtgg agcgcgatgc ccagctgtac aaggagaagg gatacgacat caacctgaag   2280
aagctggagg agaagggctt tagctccgtg accaagctgt gcgctggaat cgacgagaca   2340
gcccccgaca gaggaagga tgtggagaag gagatggccg agagagctaa ggagagcatc   2400
gactccctgg agtctgctaa ccctaagctg tacgccaact acatcaagta ctccgatgag   2460
aagaaggccg aggagttcac caggcagatc aacagagaga aggccaagac cgctctgaac   2520
gcctacctga ggaacacaaa gtggaacgtg atcatccggg aggacctgct gcgcatcgat   2580
```

| aacaagacct gtacactgtt ccggaacaag gctgtgcacc tggaggtggc tcgctacgtg | 2640 |
| cacgcctaca tcaacgacat cgccgaggtg aactcctact ttcagctgta ccactacatc | 2700 |
| atgcagagga tcatcatgaa cgagagatac gagaagtcta gcggcaaggt gtctgagtac | 2760 |
| ttcgacgccg tgaacgatga gaagaagtac aacgatagac tgctgaagct gctgtgcgtg | 2820 |
| cctttcggat actgtatccc acggtttaag aacctgagca tcgaggccct gttcgaccgc | 2880 |
| aacgaggctg ccaagtttga taaggagaag aagaaggtga gcggcaactc ctga | 2934 |

```
<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atggcccttc gcagctcttg cacgtcatac                                      30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttaggcagcc ctcatcagtg ccggctccct                                      30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggccaggatc tcaattaggc agccctcatc                                      30

<210> SEQ ID NO 50
<211> LENGTH: 30
<212> TYPE: DNA
<213> ORGANISM: Homo sapiens

<400> SEQUENCE: 50
ggccaggatc tcaattaggc agccctcatc                                      30

<210> SEQ ID NO 51
<211> LENGTH: 3489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
```

| atgcccaaga agaagcggaa ggtgggatcc atgaaagtga ccaaggtcga tggcatcagc | 60 |
| cacaagaagt acatcgaaga gggcaagctc gtgaagtcca ccagcgagga aaaccggacc | 120 |
| agcgagagac tgagcgagct gctgagcatc cggctggaca tctacatcaa gaaccccgac | 180 |
| aacgcctccg aggaagagaa ccggatcaga agagagaacc tgaagaagtt ctttagcaac | 240 |

```
aaggtgctgc acctgaagga cagcgtgctg tatctgaaga accggaaaga aaagaacgcc      300
gtgcaggaca agaactatag cgaagaggac atcagcgagt acgacctgaa aaacaagaac      360
agcttctccg tgctgaagaa gatcctgctg aacgaggacg tgaactctga ggaactggaa      420
atctttcgga aggacgtgga agccaagctg aacaagatca acagcctgaa gtacagcttc      480
gaagagaaca aggccaacta ccagaagatc aacgagaaca cgtggaaaaa agtgggcggc      540
aagagcaagc ggaacatcat ctacgactac tacagagaga cgccaagcg caacgactac       600
atcaacaacg tgcaggaagc cttcgacaag ctgtataaga aagaggatat cgagaaactg      660
ttttccctga tcgagaacag caagaagcac gagaagtaca agatccgcga gtactatcac      720
aagatcatcg gccggaagaa cgacaaagag aacttcgcca agattatcta cgaagagatc      780
cagaacgtga acaacatcaa agagctgatt gagaagatcc ccgacatgtc tgagctgaag      840
aaaagccagg tgttctacaa gtactacctg gacaaagagg aactgaacga caagaatatt      900
aagtacgcct tctgccactt cgtggaaatc gagatgtccc agctgctgaa aaactacgtg      960
tacaagcggc tgagcaacat cagcaacgat aagatcaagc ggatcttcga gtaccagaat     1020
ctgaaaaagc tgatcgaaaa caaactgctg aacaagctgg acacctacgt gcggaactgc     1080
ggcaagtaca actactatct gcaagtgggc gagatcgcca cctccgactt tatcgcccgg     1140
aaccggcaga acgaggcctt cctgagaaac atcatcggcg tgtccagcgt ggcctacttc     1200
agcctgagga acatcctgga aaccgagaac gagaacgata tcaccggccg gatgcgggc      1260
aagaccgtga agaacaacaa gggcgaagag aaatacgtgt ccggcgaggt ggacaagatc     1320
tacaatgaga acaagcagaa cgaagtgaaa gaaaatctga agatgttcta cagctacgac     1380
ttcaacatgg acaacaagaa cgagatcgag gacttcttcg ccaacatcga cgaggccatc     1440
agcagcatca gacacggcat cgtgcacttc aacctggaac tggaaggcaa ggacatcttc     1500
gccttcaaga tatcgccc cagcgagatc tccaagaaga tgtttcagaa cgaaatcaac     1560
gaaaagaagc tgaagctgaa aatcttcaag cagctgaaca gcgccaacgt gttcaactac     1620
tacgagaagg atgtgatcat caagtacctg aagaatacca agttcaactt cgtgaacaaa     1680
aacatcccct tcgtgcccag cttcaccaag ctgtacaaca gattgagga cctgcggaat      1740
accctgaagt ttttttggag cgtgcccaag gacaaagaag agaaggacgc ccagatctac     1800
ctgctgaaga atatctacta cggcgagttc ctgaacaagt cgtgaaaaa ctccaaggtg      1860
ttctttaaga tcaccaatga agtgatcaag attaacaagc agcggaacca gaaaaccggc     1920
cactacaagt atcagaagtt cgagaacatc gagaaaccg tgcccgtgga ataccgccc       1980
atcatccaga gcagagagat gatcaacaac caggacaaag aggaaaagaa tacctacatc     2040
gactttattc agcagatttt cctgaagggc ttcatcgact accctgaacaa gaacaatctg     2100
aagtatatcg agagcaacaa caacaatgac aacaacgaca tcttctccaa gatcaagatc     2160
aaaaaggata caaagagaa gtacgacaag atcctgaaga ctatgagaa gcacaatcgg      2220
aacaaagaaa tccctcacga gatcaatgag ttcgtgcgcg agatcaagct ggggaagatt     2280
ctgaagtaca ccgagaatct gaacatgttt tacctgatcc tgaagctgct gaaccacaaa     2340
gagctgacca acctgaaggg cagcctggaa aagtaccagt ccgccaacaa gaagaaaacc     2400
ttcagcgacg agctggaact gatcaacctg ctgaacctgg acaacaacag agtgaccgag     2460
gacttcgagc tggaagccaa cgagatcggc aagttcctgg acttcaacga aaacaaaatc     2520
aaggaccgga aagagctgaa aaagttcgac accaacaaga tctatttcga cggcgagaac     2580
```

| atcatcaagc | accgggcctt | ctacaatatc | aagaaatacg | gcatgctgaa | tctgctggaa | 2640 |
| aagatcgccg | ataaggccaa | gtataagatc | agcctgaaag | aactgaaaga | gtacagcaac | 2700 |
| aagaagaatg | agattgaaaa | gaactacacc | atgcagcaga | acctgcaccg | gaagtacgcc | 2760 |
| agacccaaga | aggacgaaaa | gttcaacgac | gaggactaca | agagtatgaa | gaggccatc | 2820 |
| ggcaacatcc | agaagtacac | ccacctgaag | aacaaggtgg | aattcaatga | gctgaacctg | 2880 |
| ctgcagggcc | tgctgctgaa | gatcctgcac | cggctcgtgg | gctacaccag | catctgggag | 2940 |
| cgggacctga | gattccggct | gaagggcgag | tttcccgaga | accactacat | cgaggaaatt | 3000 |
| ttcaatttcg | acaactccaa | gaatgtgaag | tacaaaagcg | gccagatcgt | ggaaaagtat | 3060 |
| atcaacttct | acaaagaact | gtacaaggac | aatgtggaaa | agcggagcat | ctactccgac | 3120 |
| aagaaagtga | gaaactgaa | gcaggaaaaa | aaggacctgt | acatccggaa | ctacattgcc | 3180 |
| cacttcaact | acatcccca | cgccgagatt | agcctgctgg | aagtgctgga | aaacctgcgg | 3240 |
| aagctgctgt | cctacgaccg | gaagctgaag | aacgccatca | tgaagtccat | cgtggacatt | 3300 |
| ctgaaagaat | acggcttcgt | ggccaccttc | aagatcggcg | ctgacaagaa | gatcgaaatc | 3360 |
| cagaccctgg | aatcagagaa | gatcgtgcac | ctgaagaatc | tgaagaaaaa | gaaactgatg | 3420 |
| accgaccgga | cagcgagga | actgtgcgaa | ctcgtgaaag | tcatgttcga | gtacaaggcc | 3480 |
| ctggaatga | | | | | | 3489 |

<210> SEQ ID NO 52
<211> LENGTH: 3489
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: LwaCas13a

<400> SEQUENCE: 52

| atgcccaaga | agaagcggaa | ggtgggatcc | atgaaagtga | ccaaggtcga | tggcatcagc | 60 |
| cacaagaagt | acatcgaaga | gggcaagctc | gtgaagtcca | ccagcgagga | aaaccggacc | 120 |
| agcgagagac | tgagcgagct | gctgagcatc | cggctgacta | tctacatcaa | gaaccccgac | 180 |
| aacgcctccg | aggaagagaa | ccggatcaga | gagagaacc | tgaagaagtt | ctttagcaac | 240 |
| aaggtgctgc | acctgaagga | cagcgtgctg | tatctgaaga | accggaaaga | aaagaacgcc | 300 |
| gtgcaggaca | gaactatag | cgaagaggac | atcagcgagt | acgacctgaa | aaacaagaac | 360 |
| agcttctccg | tgctgaagaa | gatcctgctg | aacgaggacg | tgaactctga | ggaactggaa | 420 |
| atctttcgga | aggacgtgga | agccaagctg | aacaagatca | acagcctgaa | gtacagcttc | 480 |
| gaagagaaca | aggccaacta | ccagaagatc | aacgagaaca | cgtgaaaaa | gtgggcggc | 540 |
| aagagcaagc | ggaacatcat | ctacgactac | tacagagaga | gcgccaagcg | caacgactac | 600 |
| atcaacaacg | tgcaggaagc | cttcgacaag | ctgtataaga | agaggatat | cgagaaactg | 660 |
| ttttcctga | tcgagaacag | caagaagcac | gagaagtaca | agatccgcga | gtactatcac | 720 |
| aagatcatcg | gccggaagaa | cgacaaagag | aacttcgcca | gattatcta | cgaagagatc | 780 |
| cagaacgtga | caacatcaa | agagctgatt | gagaagatcc | ccgacatgtc | tgagctgaag | 840 |
| aaaagccagg | tgttctacaa | gtactacctg | gacaaagagg | aactgaacga | caagaatatt | 900 |
| aagtacgcct | ctgccacctt | cgtggaaatc | gagatgtccc | agctgctgaa | aaactacgtg | 960 |
| tacaagcggc | tgagcaacat | cagcaacgat | aagatcaagc | ggatcttcga | gtaccagaat | 1020 |

```
ctgaaaaagc tgatcgaaaa caaactgctg aacaagctgg acacctacgt gcggaactgc    1080
ggcaagtaca actactatct gcaagtgggc gagatcgcca cctccgactt tatcgcccgg    1140
aaccggcaga acgaggcctt cctgagaaac atcatcggcg tgtccagcgt ggcctacttc    1200
agcctgagga acatcctgga aaccgagaac gagaacgata tcaccggccg gatgcggggc    1260
aagaccgtga agaacaacaa gggcgaagag aaatacgtgt ccggcgaggt ggacaagatc    1320
tacaatgaga acaagcagaa cgaagtgaaa gaaaatctga agatgttcta cagctacgac    1380
ttcaacatgg acaacaagaa cgagatcgag gacttcttcg ccaacatcga cgaggccatc    1440
agcagcatca gacacggcat cgtgcacttc aacctggaac tggaaggcaa ggacatcttc    1500
gccttcaaga atatcgcccc cagcgagatc tccaagaaga tgtttcagaa cgaaatcaac    1560
gaaaagaagc tgaagctgaa aatcttcaag cagctgaaca cgccaacgt gttcaactac    1620 tacgagaagg atgtgatcat caagtacctg aagaatacca agttcaactt cgtgaacaaa    1680
aacatcccct tcgtgcccag cttcaccaag ctgtacaaca gattgagga cctgcggaat    1740 accctgaagt tttttggag cgtgcccaag gacaaagaag agaaggacgc ccagatctac    1800
ctgctgaaga atatctacta cggcgagttc ctgaacaagt tcgtgaaaaa ctccaaggtg    1860
ttctttaaga tcaccaatga agtgatcaag attaacaagc agcggaacca gaaaccggc     1920 cactacaagt atcagaagtt cgagaacatc gagaaaccg tgcccgtgga atacctggcc     1980
atcatccaga gcagagagat gatcaacaac caggacaaag aggaaaagaa tacctacatc     2040
gactttattc agcagatttt cctgaagggc ttcatcgact acctgaacaa gaacaatctg    2100
aagtatatcg agagcaacaa caacaatgac aacaacgaca tcttctccaa gatcaagatc    2160
aaaaaggata caaagagaa gtacgacaag atcctgaaga actatgagaa gcacaatcgg    2220
aacaaagaaa tccctcacga gatcaatgag ttcgtgcgcg agatcaagct ggggaagatt    2280
ctgaagtaca ccgagaatct gaacatgttt tacctgatcc tgaagctgct gaaccacaaa    2340
gagctgacca acctgaaggg cagcctggaa aagtaccagt ccgccaacaa agaagaaacc    2400
ttcagcgacg agctggaact gatcaacctg ctgaacctgg acaacaacag agtgaccgag    2460
gacttcgagc tggaagccaa cgagatcggc aagttcctgg acttcaacga aaacaaaatc    2520
aaggaccgga aagagctgaa aaagttcgac accaacaaga tctatttcga cggcgagaac    2580
atcatcaagc accgggcctt ctacaatatc aagaaatacg gcatgctgaa tctgctggaa    2640
aagatcgccg ataaggccaa gtataagatc agcctgaaag aactgaaaga gtacagcaac    2700
aagaagaatg agattgaaaa gaactacacc atgcagcaga acctgcaccg gaagtacgcc    2760
agacccaaga aggacgaaaa gttcaacgac gaggactaca agagtatga aaggccatc     2820 ggcaacatcc agaagtacac ccacctgaag aacaaggtgg aattcaatga gctgaacctg    2880
ctgcagggcc tgctgctgaa gatcctgcac cggctcgtgg gctacaccag catctgggag    2940
cgggacctga gattccggct gaagggcgag tttcccgaga accactacat cgaggaaatt    3000
ttcaatttcg acaactccaa gaatgtgaag tacaaaagcg ccagatcgt ggaaaagtat     3060 atcaacttct acaaagaact gtacaaggac aatgtggaaa agcggagcat ctactccgac    3120
aagaaagtga agaaactgaa gcaggaaaaa aaggacctgt acatccggaa ctacattgcc    3180
cacttcaact acatccccca cgccgagatt agcctgctgg aagtgctgga aacctgcgg    3240 aagctgctgt cctacgaccg gaagctgaag aacgccatca tgaagtccat cgtggacatt    3300
ctgaaagaat acggcttcgt ggccaccttc aagatcggcg ctgacaagaa gatcgaaatc    3360
cagaccctgg aatcagagaa gatcgtgcac ctgaagaatc tgaagaaaaa gaaactgatg    3420
```

```
accgaccgga acagcgagga actgtgcgaa ctcgtgaaag tcatgttcga gtacaaggcc   3480
ctggaatga                                                           3489

<210> SEQ ID NO 53
<211> LENGTH: 3312
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PspCas13b

<400> SEQUENCE: 53
atgcccaaga agaagcggaa ggtggtcgac aacatccccg ctctggtgga aaaccagaag     60
aagtactttg gcacctacag cgtgatggcc atgctgaacg ctcagaccgt gctggaccac    120
atccagaagg tggccgatat tgagggcgag cagaacgaga acaacgagaa tctgtggttt    180
caccccgtga tgagccacct gtacaacgcc aagaacggct acgacaagca gcccgagaaa    240
accatgttca tcatcgagcg gctgcagagc tacttcccat tcctgaagat catggccgag    300
aaccagagag agtacagcaa cggcaagtac aagcagaacc gcgtggaagt gaacagcaac    360
gacatcttcg aggtgctgaa gcgcgccttc ggcgtgctga agatgtacag ggacctgacc    420
aaccactaca gacctacga ggaaaagctg aacgacggct gcgagttcct gaccagcaca    480
gagcaacctc tgagcggcat gatcaacaac tactacacag tggccctgcg gaacatgaac    540
gagagatacg gctacaagac agaggacctg gccttcatcc aggacaagcg gttcaagttc    600
gtgaaggacg cctacggcaa gaaaaagtcc caagtgaata ccggattctt cctgagcctg    660
caggactaca cggcgacac acagaagaag ctgcacctga gcggagtggg aatcgccctg    720
ctgatctgcc tgttcctgga caagcagtac atcaacatct ttctgagcag gctgcccatc    780
ttctccagct acaatgccca gagcgaggaa cggcggatca tcatcagatc cttcggcatc    840
aacagcatca agctgcccaa ggaccggatc cacagcgaga gtccaacaa gagcgtggcc    900 atggatatgc tcaacgaagt gaagcggtgc cccgacgagc tgttcacaac actgtctgcc    960
gagaagcagt cccggttcag aatcatcagc gacgaccaca tgaagtgct gatgaagcgg   1020 agcagcgaca gattcgtgcc tctgctgctg cagtatatcg attacggcaa gctgttcgac   1080
cacatcaggt tccacgtgaa catgggcaag ctgagatacc tgctgaaggc cgacaagacc   1140
tgcatcgacg gccagaccag agtcagagtg atcgagcagc ccctgaacgg cttcggcaga   1200
ctggaagagg ccgagacaat gcggaagcaa gagaacggca ccttcggcaa cagcggcatc   1260
cggatcagag acttcgagaa catgaagcgg gacgacgcca tcctgccaa ctatccctac   1320 atcgtggaca cctacacaca ctacatcctg gaaaacaaca aggtcgagat gttatcaac   1380 gacaaagagg acagcgcccc actgctgccc gtgatcgagg atgatagata cgtggtcaag   1440
acaatcccca gctgccggat gagcaccctg gaaattccag ccatggcctt ccacatgttt   1500
ctgttcggca gcaagaaaac cgagaagctg atcgtggacg tgcacaaccg gtacaagaga   1560
ctgttccagg ccatgcagaa agaagaagtg accgccgaga tatcgccag cttcggaatc   1620 gccgagagcg acctgcctca agatcctg gatctgatca gcggcaatgc ccacggcaag   1680
gatgtggacg ccttcatcag actgaccgtg gacgacatgc tgaccgacac cgagcggaga   1740
atcaagagat tcaaggacga ccggaagtcc attcggagcg ccgacaacaa gatgggaaag   1800
agaggcttca gcagatctc cacaggcaag ctggccgact tcctggccaa ggacatcgtg   1860
```

-continued

```
ctgtttcagc ccagcgtgaa cgatggcgag aacaagatca ccggcctgaa ctaccggatc    1920
atgcagagcg ccattgccgt gtacgatagc ggcgacgatt acgaggccaa gcagcagttc    1980
aagctgatgt tcgagaaggc ccggctgatc ggcaagggca acagagagcc tcatccattt    2040
ctgtacaagg tgttcgcccg cagcatcccc gccaatgccg tcgagttcta cgagcgctac    2100
ctgatcgagc ggaagttcta cctgaccggc ctgtccaacg agatcaagaa aggcaacaga    2160
gtggatgtgc ccttcatccg gcgggaccag aacaagtgga aaacacccgc catgaaaacc    2220
ctgggcagaa tctacagcga ggatctgccc gtggaactgc ccagacagat gttcgacaat    2280
gagatcaagt cccacctgaa gtccctgcca cagatggaag gcatcgactt caacaatgcc    2340
aacgtgacct atctgatcgc cgagtacatg aagagagtgc tggacgacga cttccagacc    2400
ttctaccagt ggaaccgcaa ctaccggtac atggacatgc ttaagggcga gtacgacaga    2460
aagggctccc tgcagcactg cttcaccagc gtggaagaga gagaaggcct ctggaaagag    2520
cgggcctcca gaacagagcg gtacagaaag caggccagca acaagatccg cagcaaccgg    2580
cagatgagaa acgccagcag cgaagagatc gagacaatcc tggataagcg gctgagcaac    2640
agccggaacg agtaccagaa aagcgagaaa gtgatccggc gctacagagt gcaggatgcc    2700
ctgctgtttc tgctggccaa aaagaccctg accgaactgg ccgatttcga cggcgagagg    2760
ttcaaactga agaaatcat gcccgacgcc gagaagggaa tcctgagcga gatcatgccc    2820
atgagcttca ccttcgagaa aggcggcaag aagtacacca tcaccagcga gggcatgaag    2880
ctgaagaact acggcgactt ctttgtgctg gctagcgaca agaggatcgg caacctgctg    2940
gaactcgtgg gcagcgacat cgtgtccaaa gaggatatca tggaagagtt caacaaatac    3000
gaccagtgca ggcccgagat cagctccatc gtgttcaacc tggaaaagtg ggccttcgac    3060 acatacccg agctgtctgc cagagtggac cgggaagaga aggtggactt caagagcatc    3120
ctgaaaatcc tgctgaacaa caagaacatc aacaaagagc agagcgacat cctgcggaag    3180
atccggaacg ccttcgatca acaattac cccgacaaag gcgtggtgga aatcaaggcc    3240
ctgcctgaga tcgccatgag catcaagaag gcctttgggg agtacgccat catgaaggga    3300
tcccttcaat ga                                                       3312
```

<210> SEQ ID NO 54  
<211> LENGTH: 2934  
<212> TYPE: DNA  
<213> ORGANISM: Artificial Sequence  
<220> FEATURE:  
<223> OTHER INFORMATION: Description of Artificial Sequence: Synthetic polynucleotide  
<220> FEATURE:  
<223> OTHER INFORMATION: RxCas13d

<400> SEQUENCE: 54

```
atgcctaaaa agaaaagaaa ggtgggttct ggtatcgaga agaagaagag cttcgccaag      60
ggcatgggag tgaagagcac cctggtgtcc ggctctaagg tgtacatgac cacatttgct    120
gagggaagcg acgccaggct ggagaagatc gtggagggcg atagcatcag atccgtgaac    180
gagggagagg ctttcagcgc cgagatggct gacaagaacg ctggctacaa gatcggaaac    240
gccaagtttt cccacccaaa gggctacgcc gtggtggcta caacccact gtacaccgga    300 ccagtgcagc aggacatgct gggactgaag gagacactgg agaagaggta cttcggcgag    360
tccgccgacg gaaacgataa catctgcatc caggtcatcc acaacatcct ggatatcgag    420
aagatcctgg ctgagtacat cacaaacgcc gcttacgccg tgaacaacat ctccggcctg    480
```

```
gacaaggata tcatcggctt cggaaagttt tctaccgtgt acacatacga cgagttcaag    540
gatccagagc accaccgggc cgcttttaac aacaacgaca agctgatcaa cgccatcaag    600
gctcagtacg acgagttcga taactttctg ataaccccca ggctgggcta cttcggacag    660
gctttctttt ctaaggaggg cagaaactac atcatcaact acggaaacga gtgttacgac    720
atcctggccc tgctgagcgg actgaggcac tgggtggtgc acaacaacga ggaggagtct    780
cggatcagcc gcacctggct gtacaacctg acaagaacc tggataacga gtacatctcc      840
acactgaact acctgtacga caggatcacc aacgagctga caaacagctt ctccaagaac    900
tctgccgcta acgtgaacta catcgctgag accctgggca tcaacccagc tgagttcgct    960
gagcagtact tcagattttc catcatgaag gagcagaaga acctgggctt caacatcaca   1020
aagctgagag aagtgatgct ggacagaaag atatgtccg agatcaggaa gaaccacaag   1080
gtgttcgatt ctatcagaac caaggtgtac acaatgatgg actttgtgat ctacaggtac   1140
tacatcgagg aggatgccaa ggtggccgct gccaacaaga gcctgcccga caacgagaag   1200
tctctgagcg agaaggatat cttcgtgatc aacctgagag gctcctttaa cgacgatcag   1260
aaggacgctc tgtactacga tgaggccaac aggatctgga gaaagctgga gaacatcatg   1320
cacaacatca aggagttccg gggaaacaag acccgcgagt acaagaagaa ggacgctcca   1380
aggctgccta ggatcctgcc tgctggaagg gacgtgagcg ccttcagcaa gctgatgtac   1440
gccctgacaa tgtttctgga cggaaaggag atcaacgatc tgctgaccac actgatcaac   1500
aagttcgaca catccagtc ttttctgaaa gtgatgcctc tgatcggcgt gaacgctaag   1560
ttcgtggagg agtacgcctt ctttaaggac agcgccaaga tcgctgatga gctgcggctg   1620
atcaagtcct tgccaggat gggagagcca atcgctgacg ctaggagagc tatgtacatc   1680
gatgccatcc ggatcctggg aaccaacctg tcttacgacg agctgaaggc tctggccgac   1740
accttcagcc tggatgagaa cggcaacaag ctgaagaagg gcaagcacgg aatgcgcaac   1800
ttcatcatca acaacgtgat cagcaacaag cggtttcact acctgatcag atacggcgac   1860
ccagctcacc tgcacgagat cgctaagaac gaggccgtgg tgaagttcgt gctgggacgg   1920
atcgccgata tccagaagaa gcagggccag aacggaaaga accagatcga ccgctactac   1980
gagacctgca tcggcaagga taagggaaag tccgtgtctg agaaggtgga cgctctgacc   2040
aagatcatca caggcatgaa ctacgaccag ttcgataaga agagatctgt gatcgaggac   2100
accggaaggg agaacgccga gagagagaag tttaagaaga tcatcagcct gtacctgaca   2160
gtgatctacc acatcctgaa gaacatcgtg aacatcaacg ctagatacgt gatcggcttc   2220
cactgcgtgg agcgcgatgc ccagctgtac aaggagaagg gatacgacat caacctgaag   2280
aagctggagg agaagggctt tagctccgtg accaagctgt cgctggaat cgacgagaca   2340 gcccccgaca gaggaagga tgtggagaag gagatggccg agagagctaa ggagagcatc   2400
gactccctgg agtctgctaa ccctaagctg tacgccaact acatcaagta ctccgatgag   2460
aagaaggccg aggagttcac caggcagatc aacagagaga aggccaagac cgctctgaac   2520
gcctacctga ggaacacaaa gtggaacgtg atcatccggg aggacctgct gcgcatcgat   2580
aacaagacct gtacactgtt ccggaacaag gctgtgcacc tggaggtggc tcgctacgtg   2640
cacgcctaca tcaacgacat cgccgaggtg aactcctact tcagctgta ccactacatc   2700 atgcagagga tcatcatgaa cgagagatac gagaagtcta gcggcaaggt gtctgagtac   2760
ttcgacgccg tgaacgatga gaagaagtac aacgatagac tgctgaagct gctgtgcgtg   2820
```

```
cctttcggat actgtatccc acggtttaag aacctgagca tcgaggccct gttcgaccgc   2880
aacgaggctg ccaagtttga taaggagaag aagaaggtga gcggcaactc ctga         2934
```

<210> SEQ ID NO 55
<211> LENGTH: 30
<212> TYPE: DNA
<213> ORGANISM: Homo sapiens

<400> SEQUENCE: 55

```
atggcccttc gcagctcttg cacgtcatac                                      30
```

<210> SEQ ID NO 56
<211> LENGTH: 30
<212> TYPE: DNA
<213> ORGANISM: Homo sapiens

<400> SEQUENCE: 56

```
ttaggcagcc ctcatcagtg ccggctccct                                      30
```

<210> SEQ ID NO 57
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57

```
gcuggagcag cccccgauuu gugggugau uacagc                                36
```

<210> SEQ ID NO 58
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58

```
gcugaagaag ccuccgauuu gagaggugau uacagc                               36
```

<210> SEQ ID NO 59
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59

```
gcugugauag accucgauuu gugggguagu aacagc                               36
```

<210> SEQ ID NO 60
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60

```
gcugugauag accucgauuu gugggguagu aacagc                               36
```

<210> SEQ ID NO 61
<211> LENGTH: 36

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gcugugauag accucgauuu guggguagu aacagc                                    36

<210> SEQ ID NO 62
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gcugugaugg gccucaauuu gugggaagu aacagc                                    36

<210> SEQ ID NO 63
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gcugugauag gccucgauuu guggguagu aacagc                                    36

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccttccccga gggcttcaag taggagcgcg tgatgaactt                                40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ccttccccga gggcttcaag taggagcgcg tgatgaactt                                40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccttccccga gggcttcaag tgggagcgcg tgatgaactt                                40

<210> SEQ ID NO 67
<211> LENGTH: 2
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 67

Gly Ser
1

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ser Gly Gly Gly Gly Ser
1               5

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Gly Gly Ser Gly Gly Gly Gly Ser Gly Gly Gly Gly Ser
1               5                   10                  15

<210> SEQ ID NO 70
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ser Leu Gly Thr Gly Asn Arg Cys Val Lys Gly Asp Ser Leu Ser Leu
1               5                   10                  15

Lys Gly Glu Thr Val Asn Asp Cys His Ala Glu Ile Ile Ser Arg Arg
            20                  25                  30

Gly Phe Ile Arg Phe Leu Tyr Ser Glu Leu Met Lys Tyr Asn Ser Gln
        35                  40                  45

Thr Ala Lys Asp Ser Ile Phe Glu Pro Ala Lys Gly Gly Glu Lys Leu
    50                  55                  60

Gln Ile Lys Lys Thr Val Ser Phe His Leu Tyr Ile Ser Thr Ala Pro
65                  70                  75                  80

Cys Gly Asp Gly Ala Leu Phe Asp Lys Ser Cys Ser Asp Arg Ala Met
                85                  90                  95

Glu Ser Thr Glu Ser Arg His Tyr Pro Val Phe Glu Asn Pro Lys Gln
            100                 105                 110

Gly Lys Leu Arg Thr Lys Val Glu Asn Gly Glu Gly Thr Ile Pro Val
        115                 120                 125

Glu Ser Ser Asp Ile Val Pro Thr Trp Asp Gly Ile Arg Leu Gly Glu
    130                 135                 140

Arg Leu Arg Thr Met Ser Cys Ser Asp Lys Ile Leu Arg Trp Asn Val
145                 150                 155                 160
```

```
Leu Gly Leu Gln Gly Ala Leu Leu Thr His Phe Leu Gln Pro Ile Tyr
            165                 170                 175

Leu Lys Ser Val Thr Leu Gly Tyr Leu Phe Ser Gln Gly His Leu Thr
        180                 185                 190

Arg Ala Ile Cys Cys Arg Val Thr Arg Asp Gly Ser Ala Phe Glu Asp
            195                 200                 205

Gly Leu Arg His Pro Phe Ile Val Asn His Pro Lys Val Gly Arg Val
        210                 215                 220

Ser Ile Tyr Asp Ser Lys Arg Gln Ser Gly Lys Thr Lys Glu Thr Ser
225                 230                 235                 240

Val Asn Trp Cys Leu Ala Asp Gly Tyr Asp Leu Glu Ile Leu Asp Gly
            245                 250                 255

Thr Arg Gly Thr Val Asp Gly Pro Arg Asn Glu Leu Ser Arg Val Ser
        260                 265                 270

Lys Lys Asn Ile Phe Leu Leu Phe Lys Lys Leu Cys Ser Phe Arg Tyr
            275                 280                 285

Arg Arg Asp Leu Leu Arg Leu Ser Tyr Gly Glu Ala Lys Lys Ala Ala
        290                 295                 300

Arg Asp Tyr Glu Thr Ala Lys Asn Tyr Phe Lys Lys Gly Leu Lys Asp
305                 310                 315                 320

Met Gly Tyr Gly Asn Trp Ile Ser Lys Pro Gln Glu Lys Asn Phe
            325                 330                 335

<210> SEQ ID NO 71
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ser Leu Gly Thr Gly Asn Arg Cys Val Lys Gly Asp Ser Leu Ser Leu
1               5                   10                  15

Lys Gly Glu Thr Val Asn Asp Cys His Ala Glu Ile Ile Ser Arg Arg
            20                  25                  30

Gly Phe Ile Arg Phe Leu Tyr Ser Glu Leu Met Lys Tyr Asn Ser Gln
        35                  40                  45

Thr Ala Lys Asp Ser Ile Phe Glu Pro Ala Lys Gly Gly Glu Lys Leu
    50                  55                  60

Gln Ile Lys Lys Thr Val Ser Phe His Leu Tyr Ile Ser Thr Ala Pro
65                  70                  75                  80

Cys Gly Asp Gly Ala Leu Phe Asp Lys Ser Cys Ser Asp Arg Ala Met
            85                  90                  95

Glu Ser Thr Glu Ser Arg His Tyr Pro Val Phe Glu Asn Pro Lys Gln
        100                 105                 110

Gly Lys Leu Arg Thr Lys Val Glu Asn Gly Gln Gly Thr Ile Pro Val
    115                 120                 125

Glu Ser Ser Asp Ile Val Pro Thr Trp Asp Gly Ile Arg Leu Gly Glu
130                 135                 140

Arg Leu Arg Thr Met Ser Cys Ser Asp Lys Ile Leu Arg Trp Asn Val
145                 150                 155                 160

Leu Gly Leu Gln Gly Ala Leu Leu Thr His Phe Leu Gln Pro Ile Tyr
            165                 170                 175

Leu Lys Ser Val Thr Leu Gly Tyr Leu Phe Ser Gln Gly His Leu Thr
        180                 185                 190
```

```
Arg Ala Ile Cys Cys Arg Val Thr Arg Asp Gly Ser Ala Phe Glu Asp
            195                 200                 205

Gly Leu Arg His Pro Phe Ile Val Asn His Pro Lys Val Gly Arg Val
            210                 215                 220

Ser Ile Tyr Asp Ser Lys Arg Gln Ser Gly Lys Thr Lys Glu Thr Ser
225                 230                 235                 240

Val Asn Trp Cys Leu Ala Asp Gly Tyr Asp Leu Glu Ile Leu Asp Gly
            245                 250                 255

Thr Arg Gly Thr Val Asp Gly Pro Arg Asn Glu Leu Ser Arg Val Ser
            260                 265                 270

Lys Lys Asn Ile Phe Leu Leu Phe Lys Lys Leu Cys Ser Phe Arg Tyr
            275                 280                 285

Arg Arg Asp Leu Leu Arg Leu Ser Tyr Gly Glu Ala Lys Lys Ala Ala
            290                 295                 300

Arg Asp Tyr Glu Thr Ala Lys Asn Tyr Phe Lys Lys Gly Leu Lys Asp
305                 310                 315                 320

Met Gly Tyr Gly Asn Trp Ile Ser Lys Pro Gln Glu Glu Lys Asn Phe
            325                 330                 335

<210> SEQ ID NO 72
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Leu His Leu Pro Gln Val Leu Ala Asp Ala Val Ser Arg Leu Val
1               5                   10                  15

Leu Gly Lys Phe Gly Asp Leu Thr Asp Asn Phe Ser Ser Pro His Ala
            20                  25                  30

Arg Arg Lys Val Leu Ala Gly Val Val Met Thr Thr Gly Thr Asp Val
            35                  40                  45

Lys Asp Ala Lys Val Ile Ser Val Ser Thr Gly Thr Lys Cys Ile Asn
50                  55                  60

Gly Glu Tyr Met Ser Asp Arg Gly Leu Ala Leu Asn Asp Cys His Ala
65                  70                  75                  80

Glu Ile Ile Ser Arg Arg Ser Leu Leu Arg Phe Leu Tyr Thr Gln Leu
            85                  90                  95

Glu Leu Tyr Leu Asn Asn Lys Asp Asp Gln Lys Arg Ser Ile Phe Gln
            100                 105                 110

Lys Ser Glu Arg Gly Gly Phe Arg Leu Lys Glu Asn Val Gln Phe His
            115                 120                 125

Leu Tyr Ile Ser Thr Ser Pro Cys Gly Asp Ala Arg Ile Phe Ser Pro
            130                 135                 140

His Glu Pro Ile Leu Glu Glu Pro Ala Asp Arg His Pro Asn Arg Lys
145                 150                 155                 160

Ala Arg Gly Gln Leu Arg Thr Lys Ile Glu Ser Gly Glu Gly Thr Ile
            165                 170                 175

Pro Val Arg Ser Asn Ala Ser Ile Gln Thr Trp Asp Gly Val Leu Gln
            180                 185                 190

Gly Glu Arg Leu Leu Thr Met Ser Cys Ser Asp Lys Ile Ala Arg Trp
            195                 200                 205

Asn Val Val Gly Ile Gln Gly Ser Leu Leu Ser Ile Phe Val Glu Pro
```

```
                210                 215                 220
Ile Tyr Phe Ser Ser Ile Ile Leu Gly Ser Leu Tyr His Gly Asp His
225                 230                 235                 240

Leu Ser Arg Ala Met Tyr Gln Arg Ile Ser Asn Ile Glu Asp Leu Pro
                245                 250                 255

Pro Leu Tyr Thr Leu Asn Lys Pro Leu Leu Ser Gly Ile Ser Asn Ala
                260                 265                 270

Glu Ala Arg Gln Pro Gly Lys Ala Pro Asn Phe Ser Val Asn Trp Thr
                275                 280                 285

Val Gly Asp Ser Ala Ile Glu Val Ile Asn Ala Thr Thr Gly Lys Asp
                290                 295                 300

Glu Leu Gly Arg Ala Ser Arg Leu Cys Lys His Ala Leu Tyr Cys Arg
305                 310                 315                 320

Trp Met Arg Val His Gly Lys Val Pro Ser His Leu Leu Arg Ser Lys
                325                 330                 335

Ile Thr Lys Pro Asn Val Tyr His Glu Ser Lys Leu Ala Ala Lys Glu
                340                 345                 350

Tyr Gln Ala Ala Lys Ala Arg Leu Phe Thr Ala Phe Ile Lys Ala Gly
                355                 360                 365

Leu Gly Ala Trp Val Glu Lys Pro Thr Glu Gln Asp Gln Phe Ser Leu
                370                 375                 380

Thr
385

<210> SEQ ID NO 73
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Leu His Leu Pro Gln Val Leu Ala Asp Ala Val Ser Arg Leu Val
1               5                   10                  15

Leu Gly Lys Phe Gly Asp Leu Thr Asp Asn Phe Ser Ser Pro His Ala
                20                  25                  30

Arg Arg Lys Val Leu Ala Gly Val Val Met Thr Thr Gly Thr Asp Val
                35                  40                  45

Lys Asp Ala Lys Val Ile Ser Val Ser Thr Gly Thr Lys Cys Ile Asn
50                  55                  60

Gly Glu Tyr Met Ser Asp Arg Gly Leu Ala Leu Asn Asp Cys His Ala
65                  70                  75                  80

Glu Ile Ile Ser Arg Arg Ser Leu Leu Arg Phe Leu Tyr Thr Gln Leu
                85                  90                  95

Glu Leu Tyr Leu Asn Asn Lys Asp Asp Gln Lys Arg Ser Ile Phe Gln
                100                 105                 110

Lys Ser Glu Arg Gly Gly Phe Arg Leu Lys Glu Asn Val Gln Phe His
                115                 120                 125

Leu Tyr Ile Ser Thr Ser Pro Cys Gly Asp Ala Arg Ile Phe Ser Pro
                130                 135                 140

His Glu Pro Ile Leu Glu Glu Pro Ala Asp Arg His Pro Asn Arg Lys
145                 150                 155                 160

Ala Arg Gly Gln Leu Arg Thr Lys Ile Glu Ser Gly Gln Gly Thr Ile
                165                 170                 175
```

```
Pro Val Arg Ser Asn Ala Ser Ile Gln Thr Trp Asp Gly Val Leu Gln
            180                 185                 190

Gly Glu Arg Leu Leu Thr Met Ser Cys Ser Asp Lys Ile Ala Arg Trp
        195                 200                 205

Asn Val Val Gly Ile Gln Gly Ser Leu Leu Ser Ile Phe Val Glu Pro
    210                 215                 220

Ile Tyr Phe Ser Ser Ile Ile Leu Gly Ser Leu Tyr His Gly Asp His
225                 230                 235                 240

Leu Ser Arg Ala Met Tyr Gln Arg Ile Ser Asn Ile Glu Asp Leu Pro
            245                 250                 255

Pro Leu Tyr Thr Leu Asn Lys Pro Leu Leu Ser Gly Ile Ser Asn Ala
        260                 265                 270

Glu Ala Arg Gln Pro Gly Lys Ala Pro Asn Phe Ser Val Asn Trp Thr
    275                 280                 285

Val Gly Asp Ser Ala Ile Glu Val Ile Asn Ala Thr Thr Gly Lys Asp
    290                 295                 300

Glu Leu Gly Arg Ala Ser Arg Leu Cys Lys His Ala Leu Tyr Cys Arg
305                 310                 315                 320

Trp Met Arg Val His Gly Lys Val Pro Ser His Leu Leu Arg Ser Lys
            325                 330                 335

Ile Thr Lys Pro Asn Val Tyr His Glu Ser Lys Leu Ala Ala Lys Glu
        340                 345                 350

Tyr Gln Ala Ala Lys Ala Arg Leu Phe Thr Ala Phe Ile Lys Ala Gly
    355                 360                 365

Leu Gly Ala Trp Val Glu Lys Pro Thr Glu Gln Asp Gln Phe Ser Leu
    370                 375                 380

Thr
385

<210> SEQ ID NO 74
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
            85                  90                  95

Phe Leu Arg Gly Asn Pro Asn Leu Ser Leu Arg Ile Phe Thr Ala Arg
        100                 105                 110

Leu Tyr Phe Cys Glu Asp Arg Lys Ala Glu Pro Glu Gly Leu Arg Arg
    115                 120                 125

Leu His Arg Ala Gly Val Gln Ile Ala Ile Met Thr Phe Lys Asp Tyr
    130                 135                 140
```

```
Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 75
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Thr Asp Ala Glu Tyr Val Arg Ile His Lys Leu Asp Ile Tyr
1               5                   10                  15

Thr Phe Lys Lys Gln Phe Phe Asn Asn Lys Ser Val Ser His Arg
                20                  25                  30

Cys Tyr Val Leu Phe Glu Leu Lys Arg Gly Glu Arg Ala Cys
            35                  40                  45

Phe Trp Gly Tyr Ala Val Asn Lys Pro Gln Ser Gly Thr Glu Arg Gly
50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
                100                 105                 110

Arg Gly Asn Gly His Thr Leu Lys Ile Trp Ala Cys Lys Leu Tyr Tyr
            115                 120                 125

Glu Lys Asn Ala Arg Asn Gln Ile Gly Leu Trp Asn Leu Arg Asp Asn
130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Ser Glu Leu Ser
            180                 185                 190

Ile Met Ile Gln Val Lys Ile Leu His Thr Thr Lys Ser Pro Ala Val
            195                 200                 205

<210> SEQ ID NO 76
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30
```

-continued

```
Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
 50                      55                  60

Asn Phe Ile Glu Lys Phe Thr Thr Glu Arg Tyr Phe Cys Pro Asn Thr
 65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
                100                 105                 110

Phe Ile Tyr Ile Ala Arg Leu Tyr His His Ala Asp Pro Arg Asn Arg
            115                 120                 125

Gln Gly Leu Arg Asp Leu Ile Ser Ser Gly Val Thr Ile Gln Ile Met
130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro Pro His Ile Leu Trp
 210                     215                 220

Ala Thr Gly Leu Lys
225

<210> SEQ ID NO 77
<211> LENGTH: 7
<212> TYPE: PRT
<213> ORGANISM: Simian virus 40

<400> SEQUENCE: 77

Pro Lys Lys Lys Arg Lys Val
1               5

<210> SEQ ID NO 78
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 78

Lys Arg Pro Ala Ala Thr Lys Lys Ala Gly Gln Ala Lys Lys Lys Lys
1               5                   10                  15

<210> SEQ ID NO 79
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 79

Pro Ala Ala Lys Arg Val Lys Leu Asp
1               5
```

```
<210> SEQ ID NO 80
<211> LENGTH: 11
<212> TYPE: PRT
<213> ORGANISM: Unknown
<220> FEATURE:
<223> OTHER INFORMATION: Description of Unknown:
      C-myc NLS sequence

<400> SEQUENCE: 80

Arg Gln Arg Arg Asn Glu Leu Lys Arg Ser Pro
1               5                   10

<210> SEQ ID NO 81
<211> LENGTH: 38
<212> TYPE: PRT
<213> ORGANISM: Homo sapiens

<400> SEQUENCE: 81

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 82
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 82

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 83
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 83

Val Ser Arg Lys Arg Pro Arg Pro
1               5

<210> SEQ ID NO 84
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 84

Pro Pro Lys Lys Ala Arg Glu Asp
1               5
```

```
<210> SEQ ID NO 85
<211> LENGTH: 8
<212> TYPE: PRT
<213> ORGANISM: Homo sapiens

<400> SEQUENCE: 85

Pro Gln Pro Lys Lys Lys Pro Leu
1               5

<210> SEQ ID NO 86
<211> LENGTH: 12
<212> TYPE: PRT
<213> ORGANISM: Mus musculus

<400> SEQUENCE: 86

Ser Ala Leu Ile Lys Lys Lys Lys Lys Met Ala Pro
1               5                   10

<210> SEQ ID NO 87
<211> LENGTH: 5
<212> TYPE: PRT
<213> ORGANISM: Influenza virus

<400> SEQUENCE: 87

Asp Arg Leu Arg Arg
1               5

<210> SEQ ID NO 88
<211> LENGTH: 7
<212> TYPE: PRT
<213> ORGANISM: Influenza virus

<400> SEQUENCE: 88

Pro Lys Gln Lys Lys Arg Lys
1               5

<210> SEQ ID NO 89
<211> LENGTH: 10
<212> TYPE: PRT
<213> ORGANISM: Hepatitis delta virus

<400> SEQUENCE: 89

Arg Lys Leu Lys Lys Lys Ile Lys Lys Leu
1               5                   10

<210> SEQ ID NO 90
<211> LENGTH: 10
<212> TYPE: PRT
<213> ORGANISM: Mus musculus

<400> SEQUENCE: 90

Arg Glu Lys Lys Lys Phe Leu Lys Arg Arg
1               5                   10

<210> SEQ ID NO 91
<211> LENGTH: 20
<212> TYPE: PRT
<213> ORGANISM: Homo sapiens

<400> SEQUENCE: 91

Lys Arg Lys Gly Asp Glu Val Asp Gly Val Asp Glu Val Ala Lys Lys
1               5                   10                  15

Lys Ser Lys Lys
            20
```

<210> SEQ ID NO 92
<211> LENGTH: 17
<212> TYPE: PRT
<213> ORGANISM: Homo sapiens

<400> SEQUENCE: 92

Arg Lys Cys Leu Gln Ala Gly Met Asn Leu Glu Ala Arg Lys Thr Lys
1               5                   10                  15

Lys

<210> SEQ ID NO 93
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
ggcccaacau gaggaucacc caugucugca ggggcc                              36

<210> SEQ ID NO 94
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ggcccaugcu gucuaagaca gcaugggcc                                      29

<210> SEQ ID NO 95
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ggcccuaagg guuuauaugg aaacccuuag ggcc                                34

<210> SEQ ID NO 96
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Lys Arg Lys Tyr Thr Ile Lys Val Glu
        50                  55                  60

Val Pro Lys Val Ala Thr Gln Thr Val Gly Gly Val Glu Leu Pro Val
65                  70                  75                  80

```
Ala Ala Trp Arg Ser Tyr Leu Asn Met Glu Leu Thr Ile Pro Ile Phe
            85                  90                  95

Ala Thr Asn Ser Asp Cys Glu Leu Ile Val Lys Ala Met Gln Gly Leu
        100                 105                 110

Leu Lys Asp Gly Asn Pro Ile Pro Ser Ala Ile Ala Ala Asn Ser Gly
    115                 120                 125

Ile Tyr
    130

<210> SEQ ID NO 97
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 98
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95
```

```
Glu Ala Ser Arg Lys Ser Leu Tyr Asp Leu Thr Lys Ser Leu Val Val
            100                 105                 110

Gln Ala Thr Ser Glu Asp Leu Val Val Asn Leu Val Pro Leu Gly Arg
            115                 120                 125
```